(12) United States Patent
Lal et al.

(10) Patent No.: US 7,884,127 B2
(45) Date of Patent: *Feb. 8, 2011

(54) INHIBITORS OF CYCLIN DEPENDENT KINASES AND THEIR USE

(75) Inventors: Bansi Lal, Mumbai (IN); Kalpana Joshi, Thane (IN); Sanjeev Kulkarni, Mumbai (IN); Malcolm Mascarenhas, Mumbai (IN); Shrikant Kamble, Mumbai (IN); Maggie Joyce Rathos, Thane (IN); Rajendrakumar Joshi, Mumbai (IN); Meenakshi Sivakumar, Mumbai (IN)

(73) Assignee: Pirimal Life Sciences Ltd. (IN)

( * ) Notice: Subject to any disclaimer, the term of this patent is extended or adjusted under 35 U.S.C. 154(b) by 921 days.

This patent is subject to a terminal disclaimer.

(21) Appl. No.: 11/530,272

(22) Filed: Sep. 8, 2006

(65) Prior Publication Data

US 2007/0015802 A1    Jan. 18, 2007

Related U.S. Application Data

(63) Continuation-in-part of application No. 10/611,539, filed on Jul. 1, 2003, now Pat. No. 7,271,193.

(30) Foreign Application Priority Data

Jul. 8, 2002    (IN)    .................. 616/MUM/2002

(51) Int. Cl.
  *A61K 31/4025*    (2006.01)
  *A61K 31/353*    (2006.01)
  *C07D 405/04*    (2006.01)
  *C07D 311/32*    (2006.01)

(52) U.S. Cl. .................. 514/422; 514/456; 549/399; 548/525

(58) Field of Classification Search .................. 514/422, 514/456; 548/525; 549/399
See application file for complete search history.

(56) References Cited

U.S. PATENT DOCUMENTS

| | | | |
|---|---|---|---|
| 4,900,727 A | 2/1990 | Kattige et al. | |
| 5,116,954 A | 5/1992 | Briet et al. | |
| 5,284,856 A | 2/1994 | Naik et al. | |
| H1427 H | 4/1995 | Briet et al. | |
| 5,723,313 A | 3/1998 | Sherr et al. | |
| 5,733,920 A | 3/1998 | Mansuri et al. | |
| 5,849,733 A | 12/1998 | Kim et al. | |
| 7,271,193 B2 * | 9/2007 | Lal et al. ............... | 514/422 |

FOREIGN PATENT DOCUMENTS

| | | |
|---|---|---|
| WO | WO 01/83469 A1 | 11/2001 |
| WO | WO 2007/148158 | 12/2007 |
| WO | WO 2008/007169 | 1/2008 |

OTHER PUBLICATIONS

Davies et al. "Structure-based design of cyclin-dependent kinase inhibitors" Pharmacology & Therapeutics, 2002, pp. 125-133.*
Toogood, Peter "Cyclin-Dependent Kinase Inhibitors for Treating Cancer" Medicinal Research Reviews, 2001, pp. 487-498.*
Senderowicz et al, "Preclinical and Clinical Development of Cyclin-Dependent Kinease Modulators"; J. Natl. Cancer Institute, vol. 92, No. 5, 2000, 376-387.
Naik et al, "An Anti-Inflammatory Cum Immunomodulatory Piperidinylbenzopyranone from *Dyoxylum binectariferum*: Isolation, Structure and Total Synthesis"; Tetrahedron, 1998, 44(7), 2081-2086.
Pérez-Roger et al, "Inhibition of Cellular Proliferation by Drug Targeting of Cyclin-Dependent Kinases"; Curr. Pharm. Biotechnol, 2000, Jul. 1 (1), 107-116.
Losiewicz et al, "Potent Inhibition of CDC2 Kinase Activity by the Flavonoid L86-8275"; Biochemical and Biophysical Research Communicaitons, 1994, 589-595.

(Continued)

*Primary Examiner*—Joseph R Kosack
(74) *Attorney, Agent, or Firm*—Frommer Lawrence & Haug LLP

(57) ABSTRACT

The present invention relates to novel compounds for the inhibition of cyclin-dependent kinases, and more particularly, to chromenone derivatives of formula (Ic)

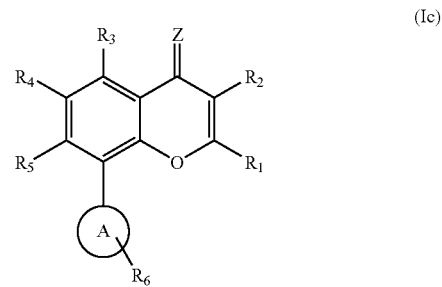

Figure 1:
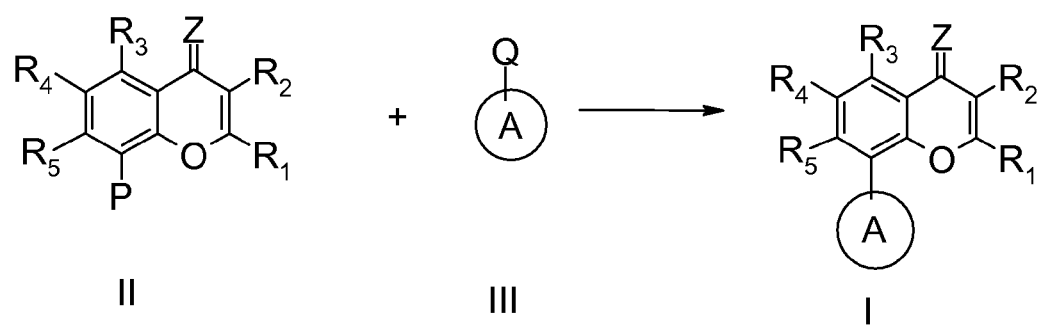

wherein $R_1$, $R_2$, $R_3$, $R_4$, $R_5$, $R_6$, $R_7$ and A have the meanings indicated in the claims. The invention also relates to processes for the preparation of the compounds of formula (Ia), to methods of inhibiting cyclin-dependent kinases and of inhibiting cell proliferation, to the use of the compounds of formula (Ic) in the treatment and prophylaxis of diseases, which can be treated or prevented by the inhibition of cyclin-dependent kinases such as cancer, to the use of the compounds of formula (Ic) in the preparation of medicaments to be applied in such diseases. The invention further relates to compositions containing a compound of formula (Ic) either alone or in combination with another active agent, in admixture or otherwise in association with an inert carrier, in particular pharmaceutical compositions containing a compound of formula (Ic) either alone or in combination with another active agent, together with pharmaceutically acceptable carrier substances and auxiliary substances.

21 Claims, 6 Drawing Sheets

OTHER PUBLICATIONS

J. Org. Chem. 1992, 57, 6321-6323.

Larget et al, "Convenient Extension of the Wessely-Moser Rearrangement for the Synthesis of substituted Alkylaminoflavones as Neuroprotective Agents in Vitro"; Bioorganic and Medicinal Chemistry Letters 10 (2000) 835-838.

Tsuritani et al; Organic Letters 2001, vol. 3, No. 17, 2709-2711.

Bang-Chi-Chen et al, "A New Facile Method for the Synthesis of 1-Arylimidazoles-5-Carboxylates", Tetrahedron Letters 41 (2000) 5453-5456.

Falb et al, "A Convenient Synthesis of Chiral Oxazolidin-2-Ones and Thiazolidin-2-Ones and an Improved Preparation of Triphosgene"; Synthetic Communications, 23(20), 2839-2844, 1993.

Hosoi et al, J. Biochem 117, 741-749 (1995).

Ongkeko et al, "Inactivation of Cdc2 Increases the Level of Apoptosis Induced by DNA Damage"; Journal of Cell Science 108, 2897-2904 (1995).

* cited by examiner

II  III  I

INHIBITORS OF CYCLIN DEPENDENT KINASES AND THEIR USE

This application is a continuation-in-part of U.S. application Ser. No. 10/611,539, filed on 1 Jul. 2003 and is still pending, which claims priority to U.S. Provisional application 60/397,326, filed on 19 Jul. 2002 and which also claims foreign priority to Indian Patent application 61/MUM/2002, filed on 8 Jul. 2002. Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to novel inhibitors of cyclin-dependent kinases (Cdks), to processes for their preparation, their use as active ingredients in pharmaceuticals, in particular for the treatment of proliferative disorders, and to pharmaceutical preparations comprising them.

BACKGROUND OF THE INVENTION

The ability of eukaryotic cells to proliferate in response to a growth signal is tightly controlled by a complex network of ordered biochemical events collectively known as the cell cycle. Mitogenic signals commit cells to entry into a series of regulated steps of the cell cycle. The synthesis of DNA (S phase), and separation of two daughter cells (M phase) are the main features of cell cycle progression. The G1 phase separates the M and S phases and prepares the cell for DNA duplication upon receiving mitogenic signals. The period between the S and M phases is known as the G2 phase during which cells repair errors that occurred during DNA duplication.

Regulators of the cell cycle have gained widespread importance in proliferative diseases. Cyclin-dependent kinases (Cdks) are a family of enzymes which become activated in specific phases of the cell cycle. Cdks consist of a catalytic subunit (the actual cyclin-dependent kinase or Cdk) and a regulatory subunit (cyclin). There are at least nine Cdks (Cdk1, Cdk2, Cdk3, Cdk4, Cdk5, Cdk6, Cdk7, Cdk8, Cdk9, etc.) and 15 different types of cyclins (cyclin A, B1, B2, D1, D2, D3, E etc.). Each step of the cell cycle is thought to be regulated by such Cdk complexes: G1/S transition (Cdk2/cyclin A, Cdk4/cyclin D1-D3, Cdk6/cyclin D3) (Senderwicz A. M. and Sausville E. A., J. Natl. Cancer Inst. 2000, 376-387), S phase (Cdk2/cyclin A), G2 phase (Cdk1/cyclin A), G2/M transition phase (Cdk1/cyclins B).

Cdks are able to phosphorylate many proteins that are involved in cell cycle events, including tumor suppressor proteins, such as the retinoblastoma gene product Rb. The Rb is involved in the G1/S transition of the cell cycle and its phosphorylation by Cdks results in its inactivation (U.S. Pat. No. 5,723,313), which in turn leads to the release of the transcriptional factor E2F and the activation of E2F-responsive genes necessary for progression to the S phase.

A wide variety of diseases are characterized by uncontrolled cell proliferation that results from some fault in the regulatory pathways in the cell cycle [e.g. overexpression of cyclins or deletions of genes encoding CKIs (Cdk inhibitory proteins)]. The overexpression of cyclinD1 leads to the deregulation of Cdk4-D1 kinase activity and thereby contributes to uncontrolled cell proliferation. With knowledge of the role of Cdks in cell cycle regulation and the discovery that approximately 90% of all neoplasias are associated with Cdk hyperactivation leading to the inactivation of the Rb pathway, Cdks are attractive targets for the development of anti-tumor drugs.

The first potent molecule to be developed as an effective Cdk inhibitor was a flavone compound, namely flavopiridol [cis-{2-(2-Chloro-phenyl)-5,7-dihydroxy-8-(3-hydroxy-1-methyl-piperidin-4-yl)-chromen-4-one hydrochloride}]. Flavopiridol is known to inhibit different Cdks and it exhibits anti-proliferative activity in vitro against a broad range of human cancer cells. Further research on flavones as a class of compounds offers a potential approach to anti-proliferative therapy. As a result, analogs of flavopiridol have been the subject of other publications. U.S. Pat. No. 5,733,920 describes novel chromone analogs as inhibitors of Cdk/Cyclin complexes. U.S. Pat. No. 5,849,733 discloses 2-thio and 2-oxo analogs of flavopiridol as protein kinase inhibitors for the treatment of proliferative diseases. WO 01/83469 discloses 3-hydroxychromen-4-one derivatives as inhibitors of cyclin dependent kinases. U.S. Pat. No. 5,116,954 and US H1427 disclose flavonoid compounds having anticancer and immunomodulatory activity. U.S. Pat. No. 5,284,856 discloses use of benzopyran-4-one derivatives for the control of tumoral diseases. U.S. Pat. No. 4,900,727 discloses benzopyran-4-one derivatives antiinflammatory agents. Anti-inflammatory benzopyran-4-one derivative from *Dysoxylum binectariferum* is described by R. G. Naik et al in Tetrahedron, 1988, 44 (7), 2081-2086.

The prominent role of Cdk/cyclin kinase complexes, in particular Cdk4/cyclin D kinase complexes, in the induction of cell proliferation and their deregulation in tumors, makes them ideal targets for developing highly specific anti-proliferative agents.

There is a clear need, however, for Cdk inhibitors which can be used as anti-proliferative agents in an efficient or more specific manner. A focused research on Cdk inhibitors by the present inventors resulted in the discovery of novel flavone analogs possessing structural features not envisaged in the prior art, as effective inhibitors of Cdks. Moreover, the compounds of the invention inhibit Cdks effectively with greater selectivity than the known Cdk inhibitors, which are under clinical trials (Curr. Pharm. Biotechnol. 2000, July (1): 107-116) and also show comparatively low cytotoxicity against various different proliferative cell lines. Therefore, the compounds of the present invention are candidate agents for the treatment of various cell proliferation related disorders.

SUMMARY OF THE INVENTION

The present invention generally relates to compounds of the general formula (Ia) or prodrugs, tautomeric forms, stereoisomers, optical isomers, pharmaceutically acceptable salts, pharmaceutically acceptable solvates or polymorphs thereof

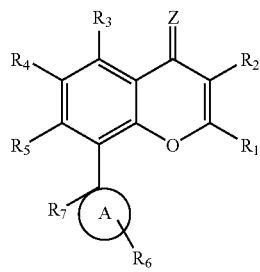

(Ia)

wherein $R_1$ is aryl, heterocycle, $NR_9R_{10}$, $OR_{11}$ or $SR_{11}$;

$R_2$ is hydrogen, alkyl, aryl, heterocycle, $OR_{11}$, halogen, cyano, nitro, $NR_9R_{10}$ or $SR_{11}$;

$R_3$, $R_4$ and $R_5$ are each independently selected from: hydrogen, alkyl, halogen, $OR_{11}$, arylalkoxy, alkylcarbonyloxy, alkoxycarbonyloxy, arylcarbonyloxy, carboxy, cyano, nitro, $NR_9R_{10}$, $SR_{11}$, arylalkylthio, —$SO_2$-alkyl, $SO_2$-aryl, $SO_2NR_9R_{10}$, aryl and heterocycle;

$R_6$ is hydrogen, alkyl, acyl, hydroxyl, $NR_9R_{10}$, alkyloxy, alkyloxycarbonyl, aryloxy,

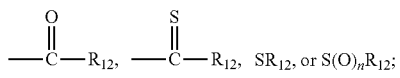

$SR_{12}$, or $S(O)_nR_{12}$;

$R_7$ is hydrogen, alkyl, alkylcarbonyl or arylcarbonyl;

$R_8$ is hydrogen, alkyl, aryl, carboxamide, sulfonamide, $NR_9R_{10}$ or $OR_{11}$;

$R_9$ and $R_{10}$ are each independently selected from: hydrogen, alkyl, aryl, acyl, heterocycle, alkoxycarbonyl, alkylcarbonyl, arylcarbonyl, heterocyclocarbonyl, carboxamide and sulfonamide; or $R_9$ and $R_{10}$, together with the nitrogen atom to which they are bonded, form a ring, which may have at least one further heteroatom selected from: nitrogen, oxygen, sulfur and phosphorus, and which is saturated, partially unsaturated or aromatic;

$R_{11}$ is hydrogen, alkyl, acyl, aryl or alkoxycarbonyl;

$R_{12}$ is hydrogen, halogen, alkyl, aryl, $NR_9R_{10}$, $OR_9$ or heterocycle;

Z is oxygen, sulfur, or $NR_8$; provided that when Z is oxygen, $R_1$ is other than $OR_{11}$ or $SR_{11}$;

n is an integer of 1 or 2;

A is a 5- to 7-membered ring; wherein:

(I) when A is a 5-membered ring it is saturated or unsaturated and represented by any one of the general structures (i) to (v);

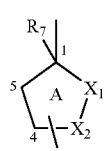

(i)

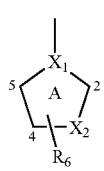

(ii)

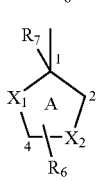

(iii)

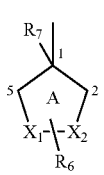

(iv)

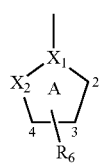

(v)

wherein $X_1$ and $X_2$ are each independently selected from: methylene and a heteroatom selected from: oxygen, sulfur, $S(O)_p$, nitrogen, provided that at least one of $X_1$ and $X_2$ is a heteroatom, and when $X_1$ or $X_2$ is nitrogen, it is at least monosubstituted by $R_{13}$, wherein $R_{13}$ is selected from: hydrogen, alkyl, alkenyl, aryl, hydroxyl, alkoxy, alkylcarbonyl, cyano, —$SO_2R_{10}$ and —CO—$(CH_2)_m$—$R_{14}$;

$R_6$ is hydrogen or a substituent as defined above on at least one carbon atom ring member;

$R_{14}$ is hydrogen, alkyl, hydroxyl, $NR_9R_{10}$, halogen, —SH, —S-alkyl, —S-aryl, heterocycle or aryl;

$R_7$, $R_9$ and $R_{10}$ are as defined above;

p is an integer of 1 or 2;

m is an integer of 0 to 6;

with the provisos that:

(a) in case of general structures (i) to (iv), when Z is oxygen, $X_2$ is $NR_{13}$, wherein $R_{13}$ is hydrogen, alkyl, $C_1$-$C_4$-alkanoyl or aryl, and $X_1$ is methylene, then $R_6$ is other than hydrogen or a substituent on the ring member at position 5 selected from: hydroxyl, $C_1$-$C_4$-alkyloxy, $C_1$-$C_4$-alkyloxycarbonyl, aryloxy and $NR_9R_{10}$;

(b) in general structure (iv), when Z is oxygen, $X_1$ is $NR_{13}$, wherein $R_{13}$ is hydrogen, alkyl, $C_1$-$C_4$ alkanoyl or aryl and $X_2$ is methylene, then $R_6$ is other than hydrogen or a substituent on the ring member at position 2 selected from: hydroxyl, $C_1$-$C_4$-alkyloxy, $C_1$-$C_4$-alkyloxycarbonyl, aryloxy and $NR_9R_{10}$;

(c) when either $X_1$ or $X_2$ is a heteroatom, or both $X_1$ and $X_2$, are heteroatoms, and A is unsaturated, there is no double bond between ring members at positions 1 and 2 or 1 and 5; or (d) in case of general structure (v), when $S(O)_p$ is at position 5, then $R_6$ is other than hydrogen;

(II) when A is a 6-membered ring, it is a saturated ring of the general structure (vi):

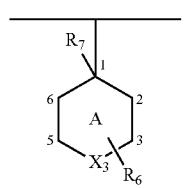

(vi)

wherein $X_3$ is oxygen, sulfur, $S(O)_p$, or nitrogen, and when $X_3$ is nitrogen, it is at least monosubstituted by $R_{13}$, wherein $R_{13}$ is selected from: hydrogen, alkyl, alkenyl, aryl, hydroxyl, alkoxy, alkylcarbonyl, cyano, —$SO_2R_{10}$ and —CO—$(CH_2)_m$—$R_{14}$;

$R_6$ is hydrogen or a substituent as defined above on at least one ring member at any of positions 2, 3, 5 or 6;

with the proviso that when Z is oxygen and $X_3$ is $NR_{13}$, wherein $R_{13}$ is hydrogen, alkyl, $C_1$-$C_4$-alkanoyl or aryl, then $R_6$ is other than hydrogen or a substituent at position 2 or 6 of the 6-membered ring A selected from: hydroxyl, $C_1$-$C_4$-alkyloxy, $C_1$-$C_4$-alkyloxycarbonyl, aryloxy and $NR_9R_{10}$;

$R_7$, $R_9$, $R_{10}$, $R_{14}$, p and m are as defined above; and (III) when A is a 7-membered ring, it is a saturated ring of the general structure (vii);

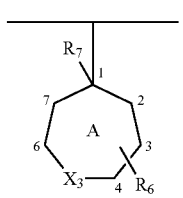

(vii)

wherein $X_3$ is oxygen, sulfur, $S(O)_p$, or nitrogen, and when $X_3$ is nitrogen, it is at least monosubstituted by $R_{13}$, wherein $R_{13}$ is selected from: hydrogen, alkyl, alkenyl, aryl, hydroxyl, alkoxy, alkylcarbonyl, cyano, —$SO_2R_{10}$ and —CO—$(CH_2)_m$—$R_{14}$;

$R_6$ is hydrogen or a substituent as defined above on at least one ring member at any of positions 2, 3, 4, 6 or 7 of the 7-membered ring A; with the proviso that when Z is oxygen and $X_3$ is $NR_{13}$, wherein $R_{13}$ is hydrogen, alkyl, $C_1$-$C_4$ alkanoyl or aryl, then $R_6$ is other than hydrogen or a substituent at position 7 of the 7-membered ring A selected from: hydroxyl, $C_1$-$C_4$-alkyloxy, $C_1$-$C_4$-alkyloxycarbonyl, aryloxy and $NR_9R_{10}$;

$R_7$, $R_9$, $R_{10}$, $R_{14}$, p and m are as defined above.

The present invention further relates to a sub-group of compounds of formula (Ib) or prodrugs, tautomeric forms, stereoisomers, optical isomers, pharmaceutically acceptable salts, pharmaceutically acceptable solvates and polymorphs thereof

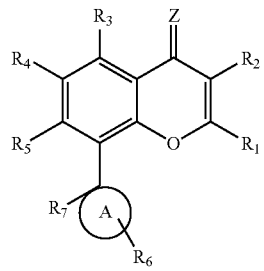

(Ib)

wherein $R_1$ is aryl, heterocycle, $NR_9R_{10}$, $OR_{11}$ or $SR_{11}$;

$R_2$ is hydrogen, alkyl, aryl, heterocycle, $OR_{11}$, halogen, cyano, nitro, $NR_9R_{10}$ or $SR_{11}$;

$R_3$, $R_4$ and $R_5$ are each independently selected from: hydrogen, alkyl, halogen, $OR_{11}$, arylalkoxy, alkylcarbonyloxy, alkoxycarbonyloxy, arylcarbonyloxy, carboxy, cyano, nitro, $NR_9R_{10}$, $SR_{11}$, arylalkylthio, —$SO_2$-alkyl, $SO_2$-aryl, $SO_2NR_9R_{10}$, aryl and heterocycle;

$R_6$ is hydrogen, alkyl, acyl, hydroxyl, $NR_9R_{10}$, alkyloxy, alkyloxycarbonyl, aryloxy,

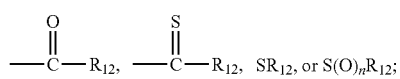

$R_7$ is hydrogen, alkyl, alkylcarbonyl or arylcarbonyl;

$R_8$ is hydrogen, alkyl, aryl, carboxamide, sulfonamide, $NR_9R_{10}$ or $OR_{11}$;

$R_9$ and $R_{10}$ are each independently selected from: hydrogen, alkyl, aryl, acyl, heterocycle, alkoxycarbonyl, alkylcarbonyl, arylcarbonyl, heterocyclocarbonyl, carboxamide and sulfonamide; or $R_9$ and $R_{10}$, together with the nitrogen atom to which they are bonded, form a 3-, 4-, 5- or 6-membered ring, which can have at least one further heteroatom selected from: nitrogen, oxygen and sulfur, and which is saturated, partially unsaturated or aromatic;

$R_{11}$ is hydrogen, alkyl, acyl, aryl, or alkoxycarbonyl;

$R_{12}$ is hydrogen, halogen, alkyl, aryl, $NR_9R_{10}$, $OR_9$ or heterocycle;

Z is oxygen, sulfur, or $NR_8$;

n is an integer of 1 or 2;

A is a saturated 5-membered ring represented by any one of the general structures (i) to (v);

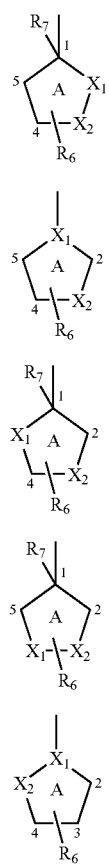

wherein $X_1$ and $X_2$ are each independently selected from: methylene and a heteroatom, wherein the heteroatom is selected from: oxygen, sulfur and nitrogen, provided that at least one of $X_1$ and $X_2$ is a heteroatom and when $X_1$ or $X_2$ is nitrogen, it is at least monosubstituted by $R_{13}$, wherein $R_{13}$ is selected from: hydrogen, alkyl, alkenyl, aryl, hydroxyl, alkoxy, alkylcarbonyl, cyano, —$SO_2R_{10}$ and —CO—$(CH_2)_m$—$R_{14}$;

$R_6$ is hydrogen or a substituent as defined above on at least one carbon atom ring member;

$R_7$, $R_9$ and $R_{10}$ are as defined above;

$R_{14}$ is hydrogen, alkyl, hydroxyl, $NR_9R_{10}$, halogen, —SH, —S-alkyl, —S-aryl, a heterocycle or aryl; and m is an integer of 0 to 6.

In one embodiment, the present compounds are inhibitors of mammalian Cdk/cyclin complexes, as well as inhibitors of insect Cdk, plant Cdk and of fungal Cdk complexes. In another embodiment the present compounds are inhibitors of the kinase activity of Cdk/cyclin complexes, e.g. the Cdk2/cyclin E and Cdk4/cyclin D1 complexes.

As described in more detail below, the present invention further relates to processes for the preparation of compounds of formula (Ia) or (Ib), use of the compounds as active ingredients in pharmaceuticals, and pharmaceutical preparations comprising them. The pharmaceutical preparations can be used to inhibit excessive proliferation of a eukaryotic cell, e.g., a mammalian cell, an insect cell, a plant cell, and/or a fungal cell, and/or prevent dedifferentiation of such cells.

Accordingly, the present compounds can be used in the treatment of proliferative disorders in mammals, especially humans, marked by unwanted proliferation of endogenous tissue.

BRIEF DESCRIPTION OF THE DRAWINGS OF THE INVENTION

FIGS. 1 to 6 represent schemes of preferred processes for the preparation of example compounds of the present invention.

DETAILED DESCRIPTION OF THE INVENTION

The present compounds are inhibitors of Cdks, particularly Cdk/cyclin complexes and find use in antiproliferative therapies for diseases characterized by excessive cell growth such as cancers, cardiovascular abnormalities, nephrological disorders, psoriasis, Alzheimer's disease, immunological disorders involving unwanted proliferation of leukocytes, restenosis and other proliferative smooth muscle disorders, viral infections, and mycotic infections.

Listed below are definitions of various terms used to describe the compounds of the present invention. These definitions apply to the terms as they are used throughout the specification (unless they are otherwise limited in specific instances) either individually or as part of a larger group. They should not be interpreted in the literal sense. They are not general definitions and are relevant only for this application.

The terms "flavone", "chromone" and "benzopyranone" or their analogs mean compounds that can be represented by the following basic structure:

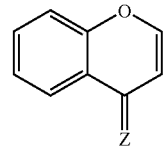

wherein Z may represent oxygen, sulfur or $NR_8$ (where $R_8$ is defined as hereinabove).

As used herein, the term "methylene" refers to a —$CH_2$— radical or a —$CH_2$— radical wherein one or both the hydrogen atoms are substituted with an alkyl residue wherein "alkyl" is defined below As used herein, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. Furthermore, unless stated otherwise, the term "alkyl" includes unsubstituted alkyl groups as well as alkyl groups, which are substituted by one or more different substituents. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure. Examples of alkyl residues containing from 1 to 20 carbon atoms are: methyl, ethyl, propyl, butyl, pentyl, hexyl, heptyl, octyl, nonyl, decyl, undecyl, dodecyl, tetradecyl, hexadecyl, octadecyl and eicosyl, the n-isomers of all these residues, iso-propyl, iso-butyl, 1-methylbutyl, iso-pentyl, neo-pentyl, 2,2-dimethylbutyl, 2-methylpentyl, 3-methylpentyl, iso-hexyl, 2,3,4-trimethylhexyl, iso-decyl, sec-butyl, or tert-butyl.

Examples of cycloalkyl residues containing 3, 4, 5, 6 or 7 ring carbon atoms are cyclopropyl, cyclobutyl, cyclopentyl, cyclohexyl or cycloheptyl which can also be substituted. The term alkyl as used herein also comprises cycloalkyl-substituted alkyl groups and alkyl-substituted cycloalkyl groups. Examples of cycloalkyl-substituted alkyl groups are: cyclopropylmethyl-, cyclobutylmethyl-, cyclopentylmethyl-, cyclohexylmethyl-, cycloheptylmethyl-, 1-cyclopropylethyl-, 1-cyclobutylethyl-, 1-cyclopentylethyl-, 1-cyclohexylethyl-, 1-cycloheptylethyl-, 2-cyclopropylethyl-, 2-cyclobutylethyl-, 2-cyclopentylethyl-, 2-cyclohexylethyl-, 2-cycloheptylethyl-, 3-cyclopropylpropyl-, 3-cyclobutylpropyl-, 3-cyclopentylpropyl-, 3-cyclohexylpropyl-, 3-cycloheptylpropyl-, etc. in which groups the cycloalkyl group as well as acyclic group can be substituted.

Of course, a cyclic alkyl group has to contain at least three carbon atoms. Thus, a group like $(C_1-C_8)$-alkyl is to be understood as comprising, among others, saturated acyclic $(C_1-C_8)$-alkyl, $(C_3-C_8)$-cycloalkyl, alkyl-cycloalkyl groups or cycloalkyl-alkyl groups like $(C_3-C_7)$-cycloalkyl-$(C_1-C_3)$-alkyl-, wherein the total number of carbon atoms can range from 4 to 8. Similarly, a group like $(C_1-C_4)$-alkyl is to be understood as comprising, among others, saturated acyclic $(C_1-C_4)$-alkyl, $(C_3-C_4)$-cycloalkyl, cyclopropyl-methyl- or methyl-cyclopropyl-.

Unless stated otherwise, the term "alkyl" preferably comprises acyclic saturated hydrocarbon residues which have from 1 to 6 carbon atoms and which can be linear or branched, and cyclic alkyl groups containing from 3 to 8 ring carbon atoms, in particular from 3 to 6 ring carbon atoms. A particular group of saturated acyclic alkyl residues is formed by $(C_1-C_4)$-alkyl residues like methyl, ethyl, n-propyl, iso-propyl, n-butyl, iso-butyl, sec-butyl and tert-butyl.

Unless stated otherwise, and irrespective of any specific substituents bonded to alkyl groups that are indicated in the definition of the compounds of the formula (Ia) or (Ib), alkyl groups can in general be unsubstituted or substituted by one or more, for example 1, 2, 3, 4 or 5 identical or different substituents. Any kind of substituents present in substituted alkyl residues can be present in any desired position provided that the substitution does not lead to an unstable molecule. A substituted alkyl refers to an alkyl residue in which one or more, for example, 1, 2, 3, 4 or 5, hydrogen atoms are replaced with substituents, for example, halogen, hydroxyl, carbonyl, alkoxyl, ester, ether, cyano, amino, amido, imino, sulfhydryl, alkylthio, thioester, sulfonyl, nitro, azido, acyloxy, heterocyclo, aralkyl, or an aryl or heteroaryl group. The carbon backbone of the alkyl group may be interrupted by heteroatoms such as oxygen, sulfur or nitrogen. Examples of substituted acyclic alkyls are hydroxymethyl, hydroxyethyl, 2-hydroxyethyl, aminoethyl or morpholinoethyl. Examples of substituted cycloalkyl groups are cycloalkyl groups which carry as substituent one or more, for example 1, 2, 3, 4 or 5, identical or different acyclic alkyl groups, for example acyclic $(C_1-C_4)$-alkyl groups like methyl groups. Examples of substituted cycloalkyl groups are 4-methylcyclohexyl, 4-tert-butylcyclohexyl or 2,3-dimethylcyclopentyl.

It will be understood by those skilled in the art that the moieties substituted on the hydrocarbon chain can themselves be substituted, if appropriate. For example, the substituents of a substituted alkyl may include substituted and unsubstituted forms of amino, imino, amido, sulfonyl (including sulfonate and sulfonamide), as well as ether, alkylthio, carbonyl (including ketones, aldehydes, carboxylates, and esters), trifluoromethyl, cyano and the like. Cycloalkyls can be further substituted with alkyl, alkenyl, alkoxyl, alkylthio, aminoalkyls, carbonyl-substituted alkyl, trifluoromethyl, cyano, and the like.

The terms "alkoxyl" or "alkoxy" as used herein refers to an alkyl group, as defined above, having an oxygen radical attached thereto. Representative alkoxyl groups include methoxy, ethoxy, propoxy, tert-butoxy and the like.

The term "aralkyl" as used herein refers to an alkyl group, as defined above, substituted with an aryl or heteroaryl group (defined below). Exemplary aralkyl groups include benzyl, —(CH$_2$)-pyridyl, etc.

The terms "alkenyl" and "alkynyl" refer to unsaturated aliphatic groups analogous in length and possible substitution to the alkyls described above, but that contain at least one double or triple bond, respectively, for example 1, 2 or 3 double bonds and/or triple bonds, provided that the double bonds are not located within a cyclic alkyl group in such a manner that an aromatic system results. Examples of alkenyl groups include vinyl, 1-propenyl, 2-propenyl, 2-butenyl, 2-methyl-1-propenyl or 3-methyl-2-butenyl. Examples of alkynyl groups include ethynyl, 2-propynyl, 2-butynyl or 3-butynyl. Alkyl groups can also be unsaturated when they are substituted.

Furthermore, unless otherwise stated, the terms "alkenyl" and "alkynyl" include unsubstituted alkenyl and alkynyl groups as well as alkenyl and alkynyl groups which are substituted by one or more, for example 1, 2, 3, 4 or 5, identical or different groups mentioned above for alkyl, for example, aminoalkenyl, aminoalkynyl, amidoalkenyl, amidoalkynyl, iminoalkenyl, iminoalkynyl, thioalkenyl, thioalkynyl, carbonyl-substituted alkenyl or alkynyl, alkenoxyl or alkynoxyl.

The term "aryl" as used herein refers to monocyclic or polycyclic hydrocarbon groups having up to 14 ring carbon atoms in which at least one carbocyclic ring is present that has a conjugated pi electron system. Examples of $(C_6-C_{14})$-aryl residues are phenyl, naphthyl, biphenyl, fluorenyl or anthracenyl. Examples of $(C_6-C_{10})$-aryl residues are phenyl or naphthyl. Unless stated otherwise, and irrespective of any specific substituents bonded to aryl groups which are indicated in the definition of the compounds of formula (Ia) or (Ib), aryl residues, for example phenyl, naphthyl or fluorenyl, can in general be unsubstituted or substituted by one or more, for example 1, 2, 3, 4 or 5, identical or different substituents. Unless stated otherwise, substituents that can be present in substituted aryl groups are: fluorine, chlorine, bromine, iodine, alkyl, alkenyl, alkynyl, trifluoromethyl, hydroxyl, aryloxy, amino, cyano, nitro, thiol, imine, amide or carbonyl (such as carboxyl, formate, carbamide, an ester, ketone or aldehyde), sulfhydryl, silyl ether, thiocarbonyl (such as thioester, thioacetate or thioformate), sulfonyl, aminoacid ester, or a heterocyclo group which is saturated, partially unsaturated or aromatic. Aryl residues can be bonded via any desired position, and in substituted aryl residues the substituents can be located in any desired position. For example, in monosubstituted phenyl residues the substituent can be located in the 2-position, the 3-position, the 4-position or the 5-position, with the 2-position being preferred. If the phenyl group carries two substituents, they can be located in 2,3-position, 2,4-position, 2,5-position, 2,6-position, 3,4-position or 3,5-position.

The terms "heterocycle" and "heterocyclo" refer to a saturated, partially unsaturated or aromatic monocyclic or polycyclic heterocyclic ring system containing 3, 4, 5, 6, 7, 8, 9, 10, 11, 12, 13 or 14 ring atoms of which 1, 2, 3 or 4 are identical or different heteroatoms selected from the series consisting of nitrogen, oxygen, sulfur and phosphorus. The heterocyclo group may, for example, have 1 or 2 oxygen atoms and/or 1 or 2 sulfur atoms, 1 to 4 nitrogen atoms and/or 1 or 2 phosphorus atoms in the ring. In monocyclic groups, heterocyclo preferably is a 3-membered, 4-membered, 5-membered, 6-membered or 7-membered ring, particularly preferably a 5-membered or 6-membered ring. Examples of such heterocyclo groups are pyrrolidinyl, piperazinyl and piperidinyl. In polycyclic groups, heterocyclo may comprise either fused rings in which two or more carbons are common to two adjoining rings, or bridged rings in which rings are joined through non-adjacent atoms. In polycyclic groups, heterocyclo preferably comprises two fused rings (bicyclic) one of which is a 5-membered or 6-membered heterocyclic ring and the other of which is a 5-membered or 6-membered heterocyclic ring. Exemplary bicyclic and tricyclic heterocyclic groups include benzoxazolyl, quinolyl, isoquinolyl, carbazolyl, indolyl, isoindolyl, phenoxazinyl, benzothiazolyl, benzimidazolyl, benzoxadiazolyl and benzofurazanyl.

The ring heteroatoms can be present in any desired number and in any position with respect to each other provided that the resulting heterocyclic system is known in the art and is stable and suitable as a subgroup in a drug substance. Preferred are heterocyclo groups having 1 or 2 identical or different heteroatoms from the group consisting of: nitrogen, oxygen and sulfur. Examples of such heterocyclo groups are: pyrrolyl, furyl, thiophenyl, imidazolyl, oxazolyl, isoxazolyl thiazolyl, isothiazolyl triazolyl, pyrazolyl, pyridinyl, pyrazinyl, pyridazinyl, pyrimidinyl, azepinyl, tetrahydrothiophenyl, tetrahydrofuranyl, morpholinyl, thiomorpholinyl, tetrahydropyranyl, lactams, pyrrolidinyl, azetidinyl.

The heterocyclo group may be bonded via any ring carbon atom, and in the case of nitrogen heterocycles via any suitable ring nitrogen atom. Thus, for example, a pyrrolyl residue can be 1-pyrrolyl, 2-pyrrolyl or 3-pyrrolyl, a pyrrolidinyl residue can be 1-pyrrolidinyl (=pyrrolidino), 2-pyrrolidinyl or 3-pyrrolidinyl, and imidazolyl can be 1-imidazolyl, 2-imidazolyl, 4-imidazolyl or 5-imidazolyl.

In the group —$NR_9R_{10}$, $R_9$ and $R_{10}$ may, together with the nitrogen atom to which they are attached form a heterocyclic ring having one or more heteroatoms. Suitable examples of heterocyclic rings formed by $R_9$ and $R_{10}$, together with the nitrogen to which they are attached, are piperidine, pyrrolidine, morpholine, piperazinyl or imidazole, which can be unsubstituted or substituted as indicated below.

Heterocyclo comprises saturated heterocyclic ring systems which do not contain any double bonds within the rings, as well as mono-unsaturated and poly-unsaturated heterocyclic ring systems which contain one or more, for example 1, 2, 3, 4 or 5, double bonds within the rings provided that the resulting system is stable. Unsaturated rings may be non-aromatic or aromatic. Aromatic heterocyclo groups may also be referred to by the customary term "heteroaryl" for which all the definitions and explanations above and below relating to heterocyclo apply.

Unless stated otherwise, and irrespective of any substituents bonded to heterocyclo groups which are indicated in the definition of the compounds of formula (Ia) or (Ib), the heterocyclo group can be unsubstituted or substituted on ring carbon atoms with one or more, for example 1, 2, 3, 4 or 5 identical or different substituents. Each suitable ring nitrogen atom in a heterocyclo group can independently of each other be unsubstituted, i.e. carry a hydrogen atom, or can be substituted. Examples of substituents for the ring carbon and ring nitrogen atoms are: $(C_1-C_8)$-alkyl, in particular $(C_1-C_4)$-alkyl, alkoxy, halogen, hydroxyl, hydroxy-$(C_1-C_4)$-alkyl such as, for example, hydroxymethyl or 1-hydroxyethyl or 2-hydroxyethyl, alkenyl, alkynyl, trifluoromethyl, aryloxy, amino, cyano, nitro, thiol, imine, amide or carbonyl (such as carboxyl, formate, carbamide, an ester, ketone or aldehyde), silyl ether, thiocarbonyl (such as thioesters, a thioacetate or a thioformate), sulfonyl, aminoacid ester, heterocyclo, aryl or the like. The substituents can be present at one or more positions provided that a stable molecule results.

The term "heteroatom" as used herein means an atom of any element other than carbon or hydrogen. Preferred heteroatoms are nitrogen, oxygen, sulfur and phosphorous.

Halogen is fluorine, chlorine, bromine or iodine, preferably fluorine, chlorine or bromine.

It will be understood that "substitution" or "substituted with" includes the implicit proviso that such substitution is in accordance with permitted valence of the substituted atom and the substituent, as well as represents a stable compound, which does not readily undergo transformation such as by rearrangement, cyclization, elimination, etc.

It should be noted that any heteroatom with unsatisfied valences is assumed to have the hydrogen atom to satisfy the valences.

"Specific inhibitors" or "specific inhibition" implies the selectivity of the drug for its inhibitory effect towards a particular Cdk-cyclin complex.

The term "prodrug" refers to a compound form which is transformed in vivo to the parent compound according to the invention, for example, by hydrolysis in blood. Thus, prodrug is a compound bearing groups which are removed by biotransformation prior to exhibiting its pharmacological action. Such groups include moieties which are readily cleaved in vivo from the compound bearing it, which compound after cleavage remains or becomes pharmacologically active. Such metabolically cleavable groups form a class well known to practitioners of the art.

Certain compounds of the present invention may exist in particular geometric or stereoisomeric forms. Centers of asymmetry that are present in the compounds of formula (Ia) or (Ib) all independently of one another have S configuration or R configuration. The present invention includes all possible enantiomers and diastereomers in pure or substantially pure form and mixtures of two or more stereoisomers, for example mixtures of enantiomers and/or diastereomers, in all ratios. Thus, compounds according to the present invention which can exist as enantiomers can be present in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods. For example, the racemic forms can be resolved by physical methods, such as fractional crystallization or separation by chiral column chromatography. The individual optical isomers can be synthesized in the optically pure form by the use of enzymes or through asymmetric synthesis. A particular enantiomer of a compound of the present invention may be prepared by derivatization with a chiral auxiliary whereby the resulting diastereomeric mixture is separated and the auxillary group cleaved to provide the pure desired enantiomer. Alternatively, where the compound contains a basic functional group such as an amino or an acidic functional group such as a carboxyl, diastereomeric salts are formed by reacting the compound with an appropriate optically active acid or base, respectively. The diastereomeric salts thus formed are separated by fractional crystallization or chromatographic means well known in the art and the pure enantiomers are subsequently isolated from the diastereomeric salts. The separation of a mixture of stereoisomers can be carried out at the stage of the compounds of formula (Ia) or (Ib) or at the stage of an intermediate during the synthesis. The present invention also includes all tautomeric forms of the compounds of formula (Ia) or (Ib). Additional asymmetric carbon atoms may be present in a substituent such as an alkyl group. All such isomers, as well as mixtures thereof, are intended to be included in this invention.

In case the compounds according to formula (Ia) or (Ib) contain one or more acidic or basic groups, the invention also comprises their corresponding pharmaceutically or toxicologically acceptable salts, in particular their pharmaceutically utilizable salts.

Compounds of formula (Ia) or (Ib) which contain one or more basic groups, i.e. groups which can be protonated, can be present and can be used according to the invention in the form of their addition salts with non-toxic inorganic or organic acids. Examples of suitable inorganic acids include: boric acid, perchloric acid, hydrochloric acid, hydrobromic acid, sulfuric acid, sulfamic acid, phosphoric acid, nitric acid and other inorganic acids known to the person skilled in the art. Examples of suitable organic acids include: acetic acid, propionic acid, succinic acid, glycolic acid, gluconic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxybenzoic acid, fumaric acid, toluenesulfonic acid, methanesulfonic acid, ethane disulfonic acid, oxalic acid, isethionic acid, ketoglutaric acid, benzenesulfonic acid, glycerophosphoric acid and other organic acids known to the person skilled in the art. The compounds of formula (Ia) or (Ib) which contain acidic groups can be used according to the invention, for example, as alkali metal salts like Li, Na, and K salts. The pharmaceutically acceptable salts of the present invention can be synthesized from the subject compound which contains a basic or acidic moiety by conventional chemical methods. Generally the salts are prepared by contacting the free base or acid with stoichiometric amounts or with an excess of the desired salt-forming inorganic or organic acid or base in a suitable solvent or dispersant or by anion exchange or cation exchange with other salts. Suitable solvents are, for example, ethyl acetate, ether, alcohols, acetone, THF, dioxane or mixtures of these solvents.

The present invention furthermore includes all solvates of compounds of formula (Ia) or (Ib), for example hydrates or adducts with alcohols and also derivatives and prodrugs of the compounds of formula (Ia) or (Ib) which contain physiologically tolerable and cleavable groups, for example esters and amides.

Various polymorphs of compounds of general formula (Ia) or (Ib) forming part of this invention may be prepared by crystallization of compounds of formula (Ia) or (Ib) under different conditions. For example, using different commonly used solvents or their mixtures for crystallization; crystallization at different temperatures; various modes of cooling, ranging from very fast to very slow cooling during crystallizations. Polymorphs may also be obtained by heating or melting the compound followed by gradual or fast cooling. The presence of polymorphs may be determined by IR spectroscopy, solid probe NMR spectroscopy, differential scanning calorimetry, powder X-ray diffraction or such other techniques.

Preferred compounds are those in which one or more of the groups contained therein have the meanings given below, with all the combinations of preferred substituent definitions being a subject of the present invention. With respect to all preferred compounds of formula (Ia) or (Ib) the present invention also includes all stereoisomeric forms and mixtures thereof in all ratios and their pharmaceutically acceptable salts. Further, also all preferred compounds of formula (Ia) or (Ib) are a subject of the present invention in the form of their prodrugs and other derivatives, for example in the form of their esters and amides.

In a first preferred embodiment, the present invention relates to compounds of general formula (Ic) or prodrugs, tautomeric forms, stereoisomers, optical isomers, pharmaceutically acceptable salts, pharmaceutically acceptable solvates or polymorphs thereof.

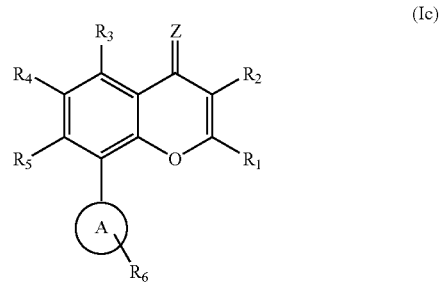

(Ic)

wherein $R_1$ is aryl, unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl; or a saturated, partially unsaturated or aromatic heterocycle having 1, 2, 3 or 4 identical or different heteroatoms selected from: nitrogen, oxygen, sulfur and phosphorus, wherein the heterocycle is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$ trifluoromethyl, hydroxyl, cyano, carboxy, $C_1$-$C_4$-alkoxycarbonyl and $C_1$-$C_4$-alkylenehydroxyl; $OR_{11}$; or $R_2$ is hydrogen; $C_1$-$C_6$-alkyl; aryl, which is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl; or saturated, partially unsaturated or aromatic heterocycle having 1, 2, 3 or 4 identical or different heteroatoms selected from: nitrogen, oxygen, sulfur and phosphorus and which is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl, —$C_1$-$C_4$-alkylenehydroxyl and $OR_{11}$;

$R_3$, $R_4$ and $R_5$ are each independently selected from: hydrogen; $C_1$-$C_6$-alkyl; halogen; $OR_{11}$; aryl, $C_1$-$C_4$-alkoxy; $C_1$-$C_4$-alkylcarbonyloxy; $C_1$-$C_4$-alkoxycarbonyloxy; arylcarbonyloxy; carboxy; cyano; nitro; $NR_9R_{10}$; $SR_{11}$; aryl-$C_1$-$C_4$-alkylthio; $SO_2$—$C_1$-$C_4$-alkyl; $SO_2$-aryl; $SO_2NR_9R_{10}$; aryl; and saturated, partially unsaturated or aromatic heterocycle having 1, 2, 3 or 4 identical or different heteroatoms selected from: nitrogen, oxygen, sulfur and phosphorus;

$R_6$ is —$C_1$-$C_4$-alkyleneOR$_{11}$;

Z is oxygen; a sulfur; or $NR_8$;

$R_8$ is hydrogen; $C_1$-$C_4$-alkyl; aryl; carboxamide; sulfonamide; $NR_9R_{10}$; or $OR_{11}$;

$R_9$ and $R_{10}$ are each independently selected from: hydrogen; $C_1$-$C_6$-alkyl; aryl; $C_1$-$C_4$-alkanoyl; heterocycle, which contains 1, 2, 3 or 4 heteroatoms selected from: nitrogen, oxygen, sulfur and phosphorus; $C_1$-$C_4$-alkoxycarbonyl; $C_1$-$C_4$-alkylcarbonyl; arylcarbonyl; heterocyclocarbonyl, wherein the heterocyclo-contains 1, 2, 3 or 4 heteroatoms selected from: nitrogen, oxygen, sulfur and phosphorus; carboxamide; and sulfonamide; wherein the aryl and heterocycle or heterocyclo- are either unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl; or $R_9$ and $R_{10}$, together with the nitrogen atom to which they are bonded, form a heterocyclic ring which can have at least one further heteroatom selected from: nitrogen, oxygen and sulfur and which is saturated, partially unsaturated or aromatic, the heterocyclic ring being either unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl;

$R_{11}$ is hydrogen; $C_1$-$C_6$-alkyl; $C_1$-$C_4$-alkanoyl; aryl, which is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl, and —$C_1$-$C_4$-alkylenehydroxyl; or $C_1$-$C_4$-alkoxycarbonyl;

A is a 5-, 6- or 7-membered ring; wherein:

(I) the 5-membered ring is saturated or unsaturated and represented by any one of the general structures (i) to (v);

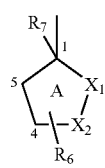

(i)

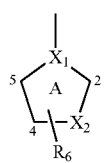

(ii)

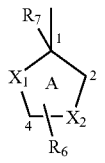

(iii)

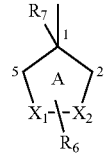

(iv)

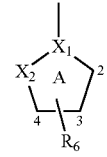

(v)

wherein $X_1$ and $X_2$ are each independently selected from: methylene and a heteroatom selected from: oxygen, sulfur, $S(O)_p$, and nitrogen, provided that at least one of $X_1$ and $X_2$ is a heteroatom, and when $X_1$ or $X_2$ is nitrogen, it is at least monosubstituted by $R_{13}$, wherein $R_{13}$ is selected from: hydrogen; unsubstituted $C_1$-$C_6$-alkyl or $C_1$-$C_6$-alkyl substituted by at least one substituent selected from: halogen, hydroxyl, carboxyl, $C_1$-$C_4$-alkoxy, amino, nitro, $C_1$-$C_4$-alkylthio, sulfhydryl, or sulfonyl; unsubstituted $C_2$-$C_6$-alkenyl, or $C_2$-$C_6$-alkenyl substituted by at least one substituent selected from: halogen, hydroxyl, carboxyl, $C_1$-$C_4$-alkoxy, amino, nitro, $C_1$-$C_4$-alkylthio, sulfhydryl or sulfonyl; hydroxyl; $C_1$-$C_4$-alkoxy; $C_1$-$C_4$-alkylcarbonyl; cyano; —$SO_2R_{10}$; —CO—$(CH_2)_m$—$R_{14}$; and aryl which is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl;

$R_6$ is a substituent as defined above on at least one carbon atom ring member;

$R_7$ is hydrogen; $C_1$-$C_4$-alkyl; $C_1$-$C_4$-alkylcarbonyl; or arylcarbonyl;

$R_{14}$ is hydrogen; $C_1$-$C_4$-alkyl; hydroxyl; $NR_9R_{10}$; halogen; —SH; —S—$C_1$-$C_4$-alkyl; —S-aryl; aryl which is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl; a heterocycle containing 1, 2, 3 or 4 heteroatoms selected from: nitrogen, oxygen, sulfur and phosphorus, the heterocycle is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl;

p is an integer of 1 or 2; and m is an integer of 0 to 6;

(II) the 6-membered ring is a saturated ring of the general structure (vi):

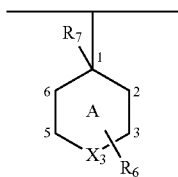

(vi)

wherein $X_3$ is selected from oxygen, sulfur, $S(O)_p$, or nitrogen, and when $X_3$ is nitrogen, it is at least monosubstituted by $R_{13}$, wherein $R_{13}$ is as defined above;

$R_6$ is a substituent as defined above on at least one ring member at any of positions 2, 3, 5 or 6 of the 6-membered ring A;

$R_7$ is hydrogen; $C_1$-$C_4$-alkyl; $C_1$-$C_4$-alkylcarbonyl; or arylcarbonyl; and (III) the 7-membered ring is a saturated ring of the general structure (vii);

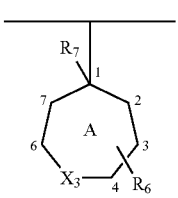

(vii)

wherein $X_3$ is selected from oxygen, sulfur, $S(O)_p$, or nitrogen, when $X_3$ is nitrogen, it is at least monosubstituted by $R_{13}$, wherein $R_{13}$ is as defined above;

$R_6$ is a substituent as defined above on at least one ring member at any of positions 2, 3, 4, 6 or 7 of the 7-membered ring A; and $R_7$ is hydrogen; $C_1$-$C_4$-alkyl; $C_1$-$C_4$-alkylcarbonyl; or arylcarbonyl.

In a second preferred embodiment of the compounds of the formula (Ic) above, the groups $R_1$ to $R_5$, $R_7$, $R_9$ to $R_{11}$, $R_{13}$, $R_{14}$, Z and A, independently from each other, have the preferred meanings given below:

$R_1$ is phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl, or is a heterocycle, which is a saturated, partially unsaturated or aromatic ring containing 5 or 6 ring atoms of which 1, 2 or 3 are identical or different heteroatoms selected from: nitrogen, oxygen, sulfur, and phosphorus, and where the heterocycle is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl;

$R_2$ is hydrogen; $C_1$-$C_6$-alkyl; phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl; $OR_{11}$; halogen; cyano; nitro; $NR_9R_{10}$ or $SR_{11}$;

$R_3$, $R_4$ and $R_5$ are each independently selected from: hydrogen, $C_1$-$C_4$-alkyl, halogen, $OR_{11}$, $C_1$-$C_4$-alkylcarbonyloxy, $NR_9R_{10}$, $SO_2NR_9R_{10}$, carboxyl, cyano and nitro;

Z is oxygen or sulfur;

A is a 5- or 6-membered ring; wherein:

(i) the 5-membered ring is a saturated or unsaturated ring represented by any one of the general structures (i) to (v), wherein $X_1$ and $X_2$ are each independently selected from: methylene and a heteroatom selected from: oxygen, sulfur, and nitrogen, provided that at least one of $X_1$ and $X_2$ is a heteroatom, and when $X_1$ or $X_2$ is nitrogen, it is at least monosubstituted by $R_{13}$, wherein $R_{13}$ is selected from: hydrogen; $C_1$-$C_6$-alkyl which is unsubstituted or substituted by halogen, hydroxyl or carboxyl; $C_2$-$C_6$-alkenyl; hydroxyl; $C_1$-$C_6$-alkoxy; $C_1$-$C_4$-alkylcarbonyl; toluenesulfonyl; cyano; $SO_2R_{10}$; —$CO(CH_2)_mR_{14}$; and phenyl, which is unsubstituted or substituted by at least one substituent selected from: halogen, $C_1$-$C_4$-alkyl, $C_1$-$C_4$-alkoxy, nitro, $NR_9R_{10}$, $SR_{11}$ trifluoromethyl, hydroxyl, cyano, carboxy, $C_1$-$C_4$-alkoxycarbonyl and —$C_1$-$C_4$-alkylenehydroxyl; and $R_7$ is hydrogen;

(ii) the 6-membered ring is a saturated ring represented by the general structure (vi), wherein $X_3$ is a heteroatom selected from: oxygen, sulfur, or nitrogen, and when $X_3$ is nitrogen, it is at least monosubstituted by $R_{13}$, wherein $R_{13}$ is selected from: hydrogen; unsubstituted $C_1$-$C_6$-alkyl or $C_1$-$C_6$-alkyl substituted by halogen, hydroxyl, or carboxyl; $C_2$-$C_6$-alkenyl; hydroxyl; $C_1$-$C_6$-alkoxy; $C_1$-$C_4$-alkylcarbonyl; toluenesulfonyl; cyano; $SO_2R_{10}$, —$CO(CH_2)_mR_{14}$; and phenyl, which is unsubstituted or substituted by at least one substituent selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl; and $R_7$ is hydrogen;

$R_9$ and $R_{10}$ are each independently selected from: hydrogen, $C_1$-$C_4$-alkyl, $C_1$-$C_4$-alkanoyl, $C_1$-$C_4$-alkoxycarbonyl, $C_1$-$C_4$-alkylcarbonyl, carboxamide and sulfonamide, or $R_9$ and $R_{10}$, together with the nitrogen atom to which they are bonded, form a 3-, 4-, 5- or 6-membered heterocyclic ring which can have at least one further heteroatom selected from: nitrogen, oxygen and sulfur, which heterocyclic ring is saturated, partially unsaturated or aromatic, and either unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl;

$R_{11}$ is hydrogen, $C_1$-$C_4$-alkyl, $C_1$-$C_4$-alkanoyl, or $C_1$-$C_4$-alkoxycarbonyl; and $R_{14}$ is hydrogen, $C_1$-$C_4$-alkyl, hydroxyl, $NR_9R_{10}$, halogen, —SH, or —S—$C_1$-$C_4$-alkyl.

In a third preferred embodiment of compounds of the general formula (Ic), A is a 5-membered saturated or unsaturated ring represented by any one of the general structures (i) to (iv);

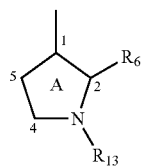
(i)

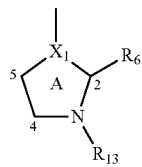
(ii)

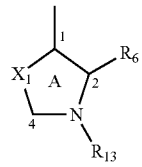
(iii)

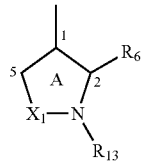
(iv)

wherein $X_1$ is either methylene or a heteroatom selected from: oxygen, sulfur, and nitrogen, except that in structures (ii) and (iv) $X_1$ is either methylene or nitrogen; and $R_6$ and $R_{13}$ are as defined above;

or a 6-membered saturated ring represented by the general structure (vi):

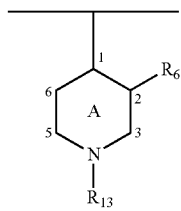
(vi)

wherein $R_6$ and $R_{13}$ are as defined above.

In a fourth embodiment of the compounds of the formula (Ic), $R_1$ is phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl, or is a heterocycle, which is a saturated, partially unsaturated or an aromatic ring containing 5 or 6 ring atoms of which 1, 2 or 3 are identical or different heteroatoms selected from: nitrogen, oxygen and sulfur, and where the heterocycle is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl $R_2$ and $R_4$ are hydrogen; and $R_3$ and $R_5$ are each independently selected from: hydroxyl, $C_1$-$C_4$-alkoxyl and $C_1$-$C_4$-alkylcarbonyloxy.

In a fifth embodiment of the compounds of the formula (Ic), A is a 5-membered saturated ring represented by the general structure (i), (iii) or (iv), wherein $X_1$ is methylene, $X_2$ is $NR_{13}$, wherein $R_{13}$ is hydrogen or $C_1$-$C_4$-alkyl, $R_7$ is hydrogen, and $R_6$ is $C_1$-$C_4$-alkylenehydroxy.

In a first alternative embodiment, the present invention relates to compounds of general formula (Ig) or prodrugs, tautomeric forms, stereoisomers, optical isomers, pharmaceutically acceptable salts, pharmaceutically acceptable solvates or polymorphs thereof

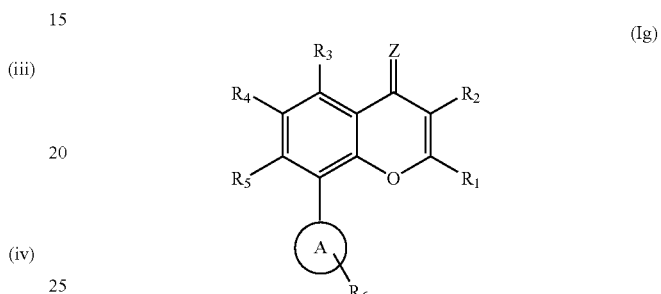
(Ig)

wherein $R_1$ is aryl, which is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl; saturated, partially unsaturated or aromatic heterocycle having 1, 2, 3 or 4 identical or different heteroatoms selected from: nitrogen, oxygen, sulfur and phosphorus, wherein the heterocycle is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl; $NR_9R_{10}$; $OR_{11}$; or $SR_{11}$;

$R_2$ is hydrogen; $C_1$-$C_6$-alkyl; aryl, which is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl; saturated, partially unsaturated or aromatic heterocycle having 1, 2, 3 or 4 identical or different heteroatoms selected from: nitrogen, oxygen, sulfur and phosphorus, wherein the heterocycle is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl, and $C_1$-$C_4$-alkylenehydroxyl; $OR_{11}$ halogen; cyano; nitro; $NR_9R_{10}$; or $SR_{11}$;

$R_3$, $R_4$ and $R_5$ are each independently selected from: hydrogen; $C_1$-$C_6$-alkyl; halogen; $OR_{11}$; aryl; $C_1$-$C_4$-alkoxy; $C_1$-$C_4$-alkylcarbonyloxy; $C_1$-$C_4$-alkoxycarbonyloxy; arylcarbonyloxy; carboxy; cyano; nitro; $NR_9R_{10}$; $SR_{11}$; aryl-$C_1$-$C_4$-alkylthio; $SO_2$—$C_1$-$C_4$-alkyl; $SO_2$-aryl; $SO_2NR_9R_{10}$; aryl; and saturated, partially unsaturated or aromatic heterocycle having 1, 2, 3 or 4 identical or different heteroatoms selected from: nitrogen, oxygen, sulfur and phosphorus;

$R_6$ is hydrogen, $C_1$-$C_4$-alkyl, $C_1$-$C_4$-alkanoyl, hydroxyl, $C_1$-$C_4$-alkoxyl, —$C_1$-$C_4$-alkoxycarbonyl, —$C_1$-$C_4$-alkyleneOR$_{11}$, —$C_1$-$C_4$-alkylenehalo, —$C_1$-$C_4$-alkyleneNR$_9$R$_{10}$, —$C_1$-$C_4$-alkyleneC(O)OR$_9$, phenoxy, —NR$_9$R$_{10}$, SR$_{12}$, S(O)$_n$R$_{12}$, —C(O)R$_{12}$ or —C(S)R$_{12}$;

Z is oxygen; sulfur; or NR$_8$;

$R_8$ is hydrogen; $C_1$-$C_4$-alkyl, aryl, $C_1$-$C_4$-alkoxylcarbonyl, carboxamide, sulfonamide, NR$_9$R$_{10}$, or OR$_{11}$;

$R_9$ and $R_{10}$ are each independently selected from: hydrogen; $C_1$-$C_6$-alkyl; aryl; $C_1$-$C_4$-alkanoyl; heterocycle, which has 1, 2, 3 or 4 heteroatoms selected from: nitrogen, oxygen, sulfur and phosphorus; $C_1$-$C_4$-alkoxycarbonyl; $C_1$-$C_4$-alkylcarbonyl; arylcarbonyl; heterocyclocarbonyl, wherein the heterocyclo- has 1, 2, 3 or 4 heteroatoms selected from: nitrogen, oxygen, sulfur and phosphorus; carboxamide, and sulfonamide; wherein the aryl and heterocycle or heterocyclo- are either unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, NR$_9$R$_{10}$, SR$_{11}$, trifluoromethyl, hydroxyl, cyano, carboxy, $C_1$-$C_4$-alkoxycarbonyl and $C_1$-$C_4$-alkylenehydroxyl; or $R_9$ and $R_{10}$, together with the nitrogen atom to which they are bonded, form a heterocyclic ring which can have at least one further heteroatom selected from: nitrogen, oxygen and sulfur and which is saturated, partially unsaturated or aromatic, the heterocyclic ring being either unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, NR$_9$R$_{10}$, SR$_{11}$, trifluoromethyl, hydroxyl, cyano, carboxy, $C_1$-$C_4$-alkoxycarbonyl and $C_1$-$C_4$-alkylenehydroxyl;

$R_{11}$ is hydrogen; $C_1$-$C_6$-alkyl; $C_1$-$C_4$-alkanoyl; aryl, which is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, NR$_9$R$_{10}$, SR$_{11}$, trifluoromethyl, hydroxyl, cyano, carboxy, $C_1$-$C_4$-alkoxycarbonyl, and —$C_1$-$C_4$-alkylenehydroxyl;

$R_{12}$ is hydrogen; halogen; $C_1$-$C_6$-alkyl; NR$_9$R$_{10}$; OR$_9$, aryl, which is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, NR$_9$R$_{10}$, SR$_{11}$, trifluoromethyl, hydroxyl, cyano, carboxy, $C_1$-$C_4$-alkoxycarbonyl, and $C_1$-$C_4$-alkylenehydroxyl; or a heterocycle, unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, NR$_9$R$_{10}$, SR$_{11}$, trifluoromethyl, hydroxyl, cyano, carboxy, $C_1$-$C_4$-alkoxycarbonyl and $C_1$-$C_4$-alkylenehydroxyl;

A is a 5-membered saturated or unsaturated ring represented by any one of the general structures (i) to (v);

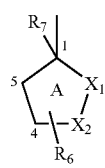
(i)

-continued

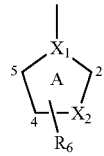
(ii)

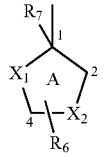
(iii)

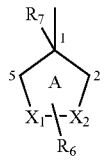
(iv)

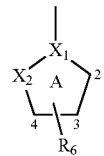
(v)

wherein $X_1$ and $X_2$ are each independently selected from: methylene and a heteroatom selected from: oxygen, sulfur, S(O)$_p$, and nitrogen, provided that at least one of $X_1$ and $X_2$ is a heteroatom, and when $X_1$ or $X_2$ is nitrogen, it is at least monosubstituted by $R_{13}$, wherein $R_{13}$ is selected from: hydrogen; $C_1$-$C_6$-alkyl, which is unsubstituted or substituted by at least one substituent selected from: halogen, hydroxyl, carboxyl, $C_1$-$C_4$-alkoxy, amino, nitro, $C_1$-$C_4$-alkylthio, sulfhydryl and sulfonyl; $C_2$-$C_6$-alkenyl, which is unsubstituted or substituted by at least one substituent selected from: halogen, hydroxyl, carboxyl, $C_1$-$C_4$-alkoxy, amino, nitro, $C_1$-$C_4$-alkylthio, sulfhydryl and sulfonyl; aryl, which is unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, NR$_9$R$_{10}$, SR$_{11}$, trifluoromethyl, hydroxyl, cyano, carboxy, $C_1$-$C_4$-alkoxycarbonyl and $C_1$-$C_4$-alkylenehydroxyl; hydroxyl; $C_1$-$C_4$-alkoxy; $C_1$-$C_4$-alkylcarbonyl; cyano; —SO$_2$R$_{10}$; and —CO—(CH$_2$)$_m$—R$_{14}$;

$R_6$ is a substituent as defined above on at least one carbon atom ring member;

$R_{14}$ is hydrogen, $C_1$-$C_4$-alkyl, hydroxyl, NR$_9$R$_{10}$, halogen, —SH, and —S—$C_1$-$C_4$-alkyl;

p is an integer of 1 or 2;

m is an integer of 0 to 6; and n is an integer of 1 or 2.

In a second embodiment of compounds of general formula (Ig), $R_1$ is phenyl, which is unsubstituted or substituted by 1, 2, or 3 identical or different substituents selected from: halogen, $C_1$-$C_4$-alkyl, $C_1$-$C_4$-alkoxy, nitro, NR$_9$R$_{10}$, SR$_{11}$, trifluoromethyl, hydroxyl, cyano, carboxy, $C_1$-$C_4$-alkoxycarbonyl and $C_1$-$C_4$-alkylenehydroxyl, or is a heterocycle, which is a saturated, partially unsaturated or aromatic ring containing 5 or 6 ring atoms of which 1, 2 or 3 are identical or different heteroatoms selected from: nitrogen, oxygen, sulfur and phosphorus, and where the heterocycle is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl;

$R_2$ is hydrogen; $C_1$-$C_6$-alkyl; phenyl, unsubstituted or substituted by at least one substituent selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl; $OR_{11}$; halogen; cyano; nitro; $NR_9R_{10}$ or $SR_{11}$;

$R_3$, $R_4$ and $R_5$ are each independently selected from: hydrogen, $C_1$-$C_4$-alkyl, halogen, $OR_{11}$, $C_1$-$C_4$-alkylcarbonyloxy, $NR_9R_{10}$, $SO_2NR_9R_{10}$, carboxyl, cyano and nitro;

A is a 5-membered saturated ring represented by any one of the general structures (i) to (v);

(i)
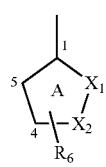

(ii)
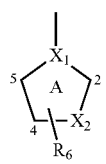

(iii)
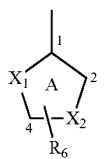

(iv)
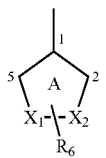

(v)
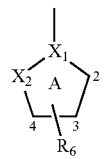

wherein $X_1$ and $X_2$ are each independently selected from: methylene and a heteroatom selected from: oxygen, sulfur, and nitrogen, provided that at least one of $X_1$ and $X_2$ is a heteroatom, and when $X_1$ or $X_2$ is nitrogen, it is at least monosubstituted by $R_{13}$, wherein $R_{13}$ is selected from: hydrogen; $C_1$-$C_6$-alkyl, which is unsubstituted or substituted by halogen, hydroxyl, or carboxyl; $C_2$-$C_6$-alkenyl; hydroxyl; $C_1$-$C_6$-alkoxy; $C_1$-$C_4$-alkylcarbonyl; toluenesulfonyl; cyano; $SO_2R_{10}$; —$CO(CH_2)_mR_{14}$; and phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl;

$R_9$ and $R_{10}$ are each independently selected from: hydrogen, $C_1$-$C_4$-alkyl, $C_1$-$C_4$-alkanoyl, $C_1$-$C_4$-alkoxycarbonyl, $C_1$-$C_4$-alkylcarbonyl, carboxamide and sulfonamide; or $R_9$ and $R_{10}$, together with the nitrogen atom to which they are bonded, form a 3-, 4-, 5- or 6-membered heterocyclic ring which can have at least one further heteroatom selected from: nitrogen, oxygen and sulfur, which ring is saturated, partially unsaturated or aromatic and either unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl;

$R_{11}$ is hydrogen, $C_1$-$C_4$-alkyl, $C_1$-$C_4$-alkanoyl or $C_1$-$C_4$-alkoxycarbonyl;

$R_{12}$ is hydrogen, halogen, $C_1$-$C_4$-alkyl, —$NR_9R_{10}$, or $OR_9$;

$R_{14}$ is hydrogen, $C_1$-$C_4$-alkyl, hydroxyl, —$NR_9R_{10}$, halogen, —SH, or —S—$C_1$-$C_4$-alkyl; and Z is oxygen or sulfur.

In a third embodiment of compounds of formula (Ig), $R_1$ is phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, —$C_1$-$C_4$-alkoxycarbonyl and —$C_1$-$C_4$-alkylenehydroxyl; or a heterocycle, which is a saturated, partially unsaturated or aromatic ring containing 6 ring atoms of which 1, 2 or 3 are identical or different heteroatoms selected from: nitrogen, oxygen and sulfur, and where the heterocycle is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl $R_2$ and $R_4$ are hydrogen; and $R_3$ and $R_5$ are each independently selected from: hydroxyl, $C_1$-$C_4$-alkoxyl and $C_1$-$C_4$-alkylcarbonyloxy.

In a fourth embodiment of compounds of the formula (Ig), A is represented by any one of the general structures (i) to (iv):

(i)
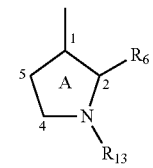

(ii)
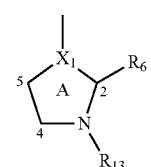

(iii)
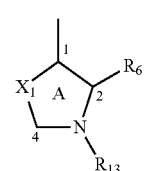

-continued

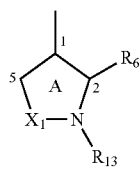

(iv)

wherein $X_1$ is either a methylene or a heteroatom selected from: oxygen, sulfur, and nitrogen, except that in structures (ii) and (iv) $X_1$ is either a methylene or nitrogen, and wherein $R_{13}$ is selected from: hydrogen; unsubstituted $C_1$-$C_6$-alkyl; or $C_1$-$C_6$-alkyl substituted by halogen, hydroxyl, or carboxyl; $C_2$-$C_6$-alkenyl; hydroxyl; $C_1$-$C_6$-alkoxy; $C_1$-$C_4$-alkylcarbonyl; toluenesulfonyl; cyano; $SO_2R_{10}$; —$CO(CH_2)_mR_{14}$; and phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$ trifluoromethyl, hydroxyl, cyano, carboxy, $C_1$-$C_4$-alkoxycarbonyl and —$C_1$-$C_4$-alkylenehydroxyl.

In a fifth embodiment of compounds of the formula (Ig), $R_6$ is selected from: $C_1$-$C_4$-alkyleneOR$_{11}$, $C_1$-$C_4$-alkylenehalo, $C_1$-$C_4$-alkyleneNR$_9$R$_{10}$, and $C_1$-$C_4$-alkyleneC(O)OR$_9$, where $R_9$, $R_{10}$ and $R_{11}$ are as defined.

In a further embodiment, the present invention relates to compounds of the general formula (Ic) or (Ig), wherein $R_1$ is phenyl or pyridinyl, substituted by 1, 2 or 3 identical or different substituents selected from: halogen and nitro, $R_2$ and $R_4$ are hydrogen, $R_3$ and $R_5$ are hydroxyl, A is a saturated 5-membered ring represented by any one of the general structures (i) to (v), wherein $X_1$, $X_2$, $R_6$ and $R_{13}$ are as defined. More particularly $X_1$ is methylene, $X_2$ is nitrogen, $R_6$ is —$C_1$-$C_4$-alkylenehydroxyl, $R_{13}$ is $C_1$-$C_4$-alkyl and Z is oxygen.

In alternative compounds of the formula (Ia) or (Ib), the substituents $R_1$ to $R_7$, A and Z and the groups aryl and heterocyclo or heterocycle, independently from each other, have the following meanings. Hence, one or more of the substituents $R_1$ to $R_7$ and A and Z have the preferred or particularly preferred meanings given below.

$R_1$ is selected from: aryl and heterocyclo, each of which is unsubstituted, mono- or polysubstituted by halogen, $C_1$-$C_4$-alkyl, $C_1$-$C_4$-alkoxy, hydroxyl, carboxyl, COO-alkyl, $CONH_2$, CONHOH, CONH-alkyl, CON(alkyl)$_2$, nitro, trifluoromethyl, amino, $C_1$-$C_4$-alkylamino, di-$C_1$-$C_4$alkylamino, or phenyl. In one embodiment, the heterocyclo is an unsaturated 5 or 6-membered ring containing 1 or 2 nitrogen atoms, unsubstituted or mono- or polysubstituted as indicated above. In another embodiment, $R_1$ is selected from: phenyl; which is unsubstituted or mono- or polysubstituted by halogen, $C_1$-$C_4$-alkyl, $C_1$-$C_4$-alkoxy, hydroxyl, carboxyl, COO-alkyl, $CONH_2$, CONH-alkyl, CON(alkyl)$_2$, nitro, trifluoromethyl, amino, $C_1$-$C_4$-alkylamino, di-$C_1$-$C_4$-alkylamino or phenyl; and pyridyl mono- or polysubstituted by the substituents indicated above for phenyl.

In yet another embodiment, $R_1$ is selected from: phenyl, chlorophenyl, dichlorophenyl, chlorofluorophenyl, dichlorofluorophenyl, chlorohydroxylphenyl, chlorocarboxyphenyl, chloronitrophenyl, chloromethoxyphenyl, aminochlorophenyl, N-hydroxycarboxychlorophenyl, cyanochlorophenyl, bromophenyl, dibromophenyl, bromofluorophenyl, bromohydroxylphenyl, bromocarboxyphenyl, bromonitrophenyl, bromomethoxyphenyl, aminobromophenyl, N-hydroxycarboxybromophenyl, bromocyanophenyl fluorophenyl, difluorophenyl, fluorohydroxylphenyl, pyridyl, chloropyridyl, dichloropyridyl, chlorofluoropyridyl, chlorohydroxylpyridyl, bromopyridyl, dibromopyridyl, bromofluoropyridyl, bromohydroxylpyridyl, fluoropyridyl, difluoropyridyl, fluorohydroxylpyridyl, and bis-trifluoromethylphenyl, dichlorofluorophenyl, $R_2$ is selected from: hydrogen, $C_1$-$C_6$-alkyl, $C_1$-$C_6$-alkoxyl, hydroxyl, nitro, amino and a halogen.

$R_3$, $R_4$ and $R_5$ are selected from: hydrogen; $C_1$-$C_4$-alkyl, unsubstituted or substituted by: halogen, hydroxyl, or carboxyl; $C_1$-$C_4$-alkoxyl; hydroxyl; carboxyl; nitro; amino; and —O-acyl. In one embodiment, $R_3$ and $R_5$ are hydroxyl or $C_1$-$C_4$ alkylcarbonyloxy, and $R_4$ is hydrogen.

$R_6$ is selected from: hydrogen; hydroxyl; unsubstituted $C_1$-$C_6$-alkyl; $C_1$-$C_6$-alkyl substituted by halogen, hydroxyl or carboxy; $C_1$-$C_6$-alkoxyl; $C_1$-$C_6$-alkoxycarbonyl; aryloxy; amino; $C_1$-$C_6$-alkylamino; di $C_1$-$C_6$-alkylamino; and —$C_1$-$C_4$-alkylene-O—$C_1$-$C_4$-alkyl. $R_6$ is —$C_1$-$C_4$-alkylene-OH, and is preferably —$CH_2OH$.

$R_7$ is hydrogen.

Z is oxygen.

In formula (Ia) or (Ic), A is a saturated or unsaturated 5-membered ring or a saturated 6-membered ring containing at least one heteroatom selected from: nitrogen, oxygen and sulfur, the ring is unsubstituted or at least monosubstituted by $R_6$. The unsaturated 5-membered ring can have one or two double bonds in its ring structure. In formula (Ia), (Ib), (Ic) or (Ig), A in particular is a saturated 5-membered ring containing 1 or 2 nitrogen atoms, and in formula (Ia) or (Ic) is a saturated 6-membered ring containing 1 nitrogen atom, wherein in both cases the ring is unsubstituted or at least monosubstituted by $R_6$.

When A is a 5-membered ring of general structures (i) to (v) and both $X_1$ and $X_2$ independently represent a heteroatom selected from nitrogen, oxygen and sulfur, the following conditions apply:

(a) A can be unsaturated as valence and stability may permit, (b) $X_1$ can only be the heteroatom nitrogen in the general structures (ii) and (v) and $X_2$ can be any one of the heteroatoms indicated above, (c) $R_6$ can be attached to the carbon ring member at position 4 or 5 when A is of general structure (i), (d) $R_6$ can be attached to the carbon ring member at position 2, 4 or 5 when A is of general structure (ii), (e) $R_6$ can be attached to the carbon ring member at position 2 or 4 when A is of general structure (iii), (f) $R_6$ can be attached to the carbon ring member at position 2 or 5 when A is of general structure (iv), and (g) $R_6$ can be attached to the carbon ring member at position 2, 3 or 4 when A is of general structure (v).

In another embodiment, compounds of formula (Ia), (Ib) or (Ig) are compounds in which ring A is a saturated 5-membered ring, $X_2$ is $NR_{13}$, where $R_{13}$ is hydrogen, $C_1$-$C_6$-alkyl or acyl, $X_1$ is methylene, $R_6$ is selected from: hydrogen, unsubstituted $C_1$-$C_6$-alkyl, or $C_1$-$C_6$-alkyl substituted by halogen, hydroxyl or carboxyl, and $R_7$ is hydrogen.

In yet another embodiment, compounds of formula (Ia) are compounds in which A is a 6-membered ring, $X_3$ is $NR_{13}$, where $R_{13}$ is hydrogen, $C_1$-$C_6$-alkyl or acyl, $R_6$ is selected from: hydrogen, unsubstituted $C_1$-$C_6$-alkyl, or $C_1$-$C_6$-alkyl substituted by halogen, hydroxyl or carboxyl, and $R_7$ is hydrogen.

In a further embodiment, compounds of formula (Ia) are compounds in which A is a 7-membered ring, $X_3$ is $NR_{13}$, where $R_{13}$ is hydrogen, $C_1$-$C_6$-alkyl or acyl, $R_6$ is selected from: hydrogen, unsubstituted $C_1$-$C_6$-alkyl, or $C_1$-$C_6$-alkyl substituted by halogen, hydroxyl or carboxyl, and $R_7$ is hydrogen.

$R_6$ is —$C_1$-$C_4$-alkylene-OH.

$R_{13}$ is —$CH_3$.

In yet a further embodiment, compounds of formula (Ia) or (Ib) are compounds in which $R_2$ is hydrogen, halogen, nitro, cyano, $NR_9R_{10}$, wherein $R_9$ and $R_{10}$ are as defined above, or $OR_{11}$, wherein $R_{11}$ is hydrogen or alkyl; $R_3$ and $R_5$ are each independently selected from: hydrogen and $OR_{11}$, wherein $R_{11}$ is hydrogen, alkyl or aryl; $R_4$ is hydrogen; Z is oxygen, sulfur, or $NR_8$, wherein $R_8$ is hydrogen, alkyl, aryl, carboxamide, $NR_9R_{10}$ or $OR_{11}$, wherein $R_9$ and $R_{10}$ are each independently selected from: hydrogen, alkyl, acyl, heterocycle, alkoxycarbonyl, carboxamide and sulfonamide, and $R_{11}$ is selected from: hydrogen, alkyl and acyl.

In a still further embodiment, compounds of formula (Ia) or (Ib) are compounds in which $R_1$ is aryl, or a heterocycle; $R_2$ is hydrogen; at least one of $R_3$ and $R_5$ is $OR_{11}$, wherein $R_{11}$ is hydrogen or alkyl; $R_4$ is hydrogen; $R_6$ is hydroxymethyl, alkoxymethyl or alkylcarbonyloxymethyl; $R_7$ is hydrogen; and Z is oxygen.

Examples of preferred compounds according to the present invention are listed below:

(±)-trans-2-(2-chloro-phenyl)-8-(2-hydroxymethyl-1-methyl-pyrrolidin-3-yl)-5,7-dimethoxy-chromen-4-one,
(±)-trans-2-(2-chloro-phenyl)-5,7-dihydroxy-8-(2-hydroxymethyl-1-methyl-pyrrolidin-3-yl)-chromen-4-one,
(+)-trans-2-(2-chloro-phenyl)-8-(2-hydroxymethyl-1-methyl-pyrrolidin-3-yl)-5,7-dimethoxy-chromen-4-one,
(+)-trans-2-(2-chloro-phenyl)-5,7-dihydroxy-8-(2-hydroxymethyl-1-methyl-pyrrolidin-3-yl)-chromen-4-one,
(−)-trans-2-(2-chloro-phenyl)-8-(2-hydroxymethyl-1-methyl-pyrrolidin-3-yl)-5,7-dimethoxy-chromen-4-one,
(−)-trans-2-(2-chloro-phenyl)-5,7-dihydroxy-8-(2-hydroxymethyl-1-methyl-pyrrolidin-3-yl)-chromen-4-one,
(+)-trans-2-(2-bromo-phenyl)-8-(2-hydroxymethyl-1-methyl-pyrrolidin-3-yl)-5,7-dimethoxy-chromen-4-one,
(+)-trans-2-(2-bromo-phenyl)-5,7-dihydroxy-8-(2-hydroxymethyl-1-methyl-pyrrolidin-3-yl)-chromen-4-one,
(+)-trans-8-(2-hydroxymethyl-1-methyl-pyrrolidin-3-yl)-2-(2-iodo-phenyl)-5,7-dimethoxy-chromen-4-one,
(+)-trans-5,7-dihydroxy-8-(2-hydroxymethyl-1-methyl-pyrrolidin-3-yl)-2-(2-iodo-phenyl)-chromen-4-one,
(+)-trans-2-(2-fluoro-phenyl)-8-(2-hydroxymethyl-1-methyl-pyrrolidin-3-yl)-5,7-dimethoxy-chromen-4-one,
(+)-trans-2-(2-fluoro-phenyl)-5,7-dihydroxy-8-(2-hydroxymethyl-1-methyl-pyrrolidin-3-yl)-chromen-4-one,
(±)-trans-2-(2-chloro-5-fluoro-phenyl)-8-(2-hydroxymethyl-1-methyl-pyrrolidin-3-yl)-5,7-dimethoxy-chromen-4-one,
(±)-trans-2-(2-chloro-5-fluoro-phenyl)-5,7-dihydroxy-8-(2-hydroxymethyl-1-methyl-pyrrolidin-3-yl)-chromen-4-one,
(+)-trans-2-(2-chloro-5-fluoro-phenyl)-8-(2-hydroxymethyl-1-methyl-pyrrolidin-3-yl)-5,7-dimethoxy-chromen-4-one,
(+)-trans-2-(2-chloro-5-fluoro-phenyl)-5,7-dihydroxy-8-(2-hydroxymethyl-1-methyl-pyrrolidin-3-yl)-chromen-4-one,
(+)-trans-2-(2-bromo-5-fluoro-phenyl)-8-(2-hydroxymethyl-1-methyl-pyrrolidin-3-yl)-5,7-dimethoxy-chromen-4-one,
(+)-trans-2-(2-bromo-5-fluoro-phenyl)-5,7-dihydroxy-8-(2-hydroxymethyl-1-methyl-pyrrolidin-3-yl)-chromen-4-one,
(±)-trans-2-(2-bromo-5-methoxy-phenyl)-8-(2-hydroxymethyl-1-methyl-pyrrolidin-3-yl)-5,7-dimethoxy-chromen-4-one,
(±)-trans-2-(2-bromo-5-methoxy-phenyl)-5,7-dihydroxy-8-(2-hydroxymethyl-1-methyl-pyrrolidin-3-yl)-chromen-4-one,
(±)-trans-2-(2-bromo-5-hydroxy-phenyl)-5,7-dihydroxy-8-(2-hydroxymethyl-1-methyl-pyrrolidin-3-yl)-chromen-4-one,
(+)-trans-2-(2-bromo-5-methoxy-phenyl)-8-(2-hydroxymethyl-1-methyl-pyrrolidin-3-yl)-5,7-dimethoxy-chromen-4-one,
(+)-trans-2-(2-bromo-5-methoxy-phenyl)-5,7-dihydroxy-8-(2-hydroxymethyl-1-methyl-pyrrolidin-3-yl)-chromen-4-one,
(+)-trans-2-(2-bromo-5-hydroxy-phenyl)-8-(2-hydroxymethyl-1-methyl-pyrrolidin-3-yl)-5,7-dihydroxy-chromen-4-one,
(+)-trans-2-(2-chloro-5-methyl-phenyl)-8-(2-hydroxymethyl-1-methyl-pyrrolidin-3-yl)-5,7-dimethoxy-chromen-4-one
(+)-trans-2-(2-chloro-5-methyl-phenyl)-5,7-dihydroxy-8-(2-hydroxymethyl-1-methyl-pyrrolidin-3-yl)-chromen-4-one,
(+)-trans-2-(2-bromo-5-nitro-phenyl)-8-(2-hydroxymethyl-1-methyl-pyrrolidin-3-yl)-5,7-dimethoxy-chromen-4-one,
(+)-trans-2-(2-bromo-5-nitro-phenyl)-8-(2-hydroxymethyl-1-methyl-pyrrolidin-3-yl)-5,7-dihydroxy-chromen-4-one,
(+)-trans-2-(2-bromo-4-nitro-phenyl)-8-(2-hydroxymethyl-1-methylpyrrolidin-3-yl)-5,7-dimethoxy-chromen-4-one,
(+)-trans-2-(2-bromo-4-nitro-phenyl)-5,7-dihydroxy-8-(2-hydroxymethyl-1-methyl-pyrrolidin-3-yl)-chromen-4-one,
(+)-trans-2-(2,4-dichloro-5-fluoro-phenyl)-8-(2-hydroxymethyl-1-methyl-pyrrolidin-3-yl)-5,7-dimethoxy-chromen-4-one,
(+)-trans-2-(2,4-dichloro-5-fluoro-phenyl-5,7-dihydroxy-8-(2-hydroxymethyl-1-methyl-pyrrolidin-3-yl)-chromen-4-one,
(+)-trans-8-(2-hydroxymethyl-1-methyl-pyrrolidin-3-yl)-5,7-dimethoxy-2-phenyl-chromen-4-one,
(+)-trans-5,7-dihydroxy-8-(2-hydroxymethyl-1-methyl-pyrrolidin-3-yl)-2-phenyl-chromen-4-one,
(+)-trans-4-[8-(2-hydroxymethyl-1-methyl-pyrrolidin-3-yl)-5,7-dimethoxy-4-oxo-4H-chromen-2-yl]-3-methyl-benzonitrile,
(+)-trans-4-[5,7-dihydroxy-8-(2-hydroxymethyl-1-methyl-pyrrolidin-3-yl)-4-oxo-4H-chromen-2-yl]-3-methyl-benzonitrile,
(±)-trans-8-(2-hydroxymethyl-1-methyl-pyrrolidin-3-yl)-5,7-dimethoxy-2-(4-trifluoromethyl-phenyl)-chromen-4-one,
(±)-trans-5,7-dihydroxy-8-(2-hydroxymethyl-1-methyl-pyrrolidin-3-yl)-2-(4-trifluoromethyl-phenyl)-chromen-4-one,
(+)-trans-8-(2-hydroxymethyl-1-methyl-pyrrolidin-3-yl)-5,7-dimethoxy-2-(4-trifluoromethyl-phenyl)-chromen-4-one,
(+)-trans-5,7-dihydroxy-8-(2-hydroxymethyl-1-methyl-pyrrolidin-3-yl)-2-(4-trifluoromethyl-phenyl)-chromen-4-one,
(−)-trans-8-(2-hydroxymethyl-1-methyl-pyrrolidin-3-yl)-5,7-dimethoxy-2-(4-trifluoromethyl-phenyl)-chromen-4-one, (−)-trans-5,7-dihydroxy-8-(2-hydroxymethyl-1-methyl-pyrrolidin-3-yl)-2-(4-trifluoromethyl-phenyl)-chromen-4-one,
(+)-trans-8-(2-hydroxymethyl-1-methyl-pyrrolidin-3-yl)-5,7-dimethoxy-2-thiophen-2-yl-chromen-4-one,
(+)-trans-5,7-dihydroxy-8-(2-hydroxymethyl-1-methyl-pyrrolidin-3-yl)-2-thiophen-2-yl-chromen-4-one,
(+)-trans-2-(2-chloro-5-methoxy-phenyl)-8-(2-hydroxymethyl-1-methyl-pyrrolidin-3-yl)-5,7-dimethoxy-chromen-4-one,
(+)-trans-2-(2-chloro-5-methoxy-phenyl)-5,7-dihydroxy-8-(2-hydroxymethyl-1-methyl-pyrrolidin-3-yl)-chromen-4-one,
(+)-trans-2-(2-chloro-5-hydroxy-phenyl)-5,7-dihydroxy-8-(2-hydroxymethyl-1-methyl-pyrrolidin-3-yl)-chromen-4-one,
(+)-trans-2-(3-chloro-phenyl)-8-(2-hydroxymethyl-1-methyl-pyrrolidin-3-yl)-5,7-dimethoxy-chromen-4-one,
(+)-trans-2-(3-chloro-phenyl)-5-hydroxy-8-(2-hydroxymethyl-1-methyl-pyrrolidin-3-yl)-7-methoxy-chromen-4-one
(+)-trans-2-(3-chloro-phenyl)-5,7-dihydroxy-8-(2-hydroxymethyl-1-methyl-pyrrolidin-3-yl)-chromen-4-one,
(+)-trans-2-(3-fluoro-phenyl)-5,7-dimethoxy-8-(2-hydroxymethyl-1-methyl-pyrrolidin-3-yl)-chromen-4-one,
(+)-trans-2-(3-fluoro-phenyl)-5,7-dihydroxy-8-(2-hydroxymethyl-1-methyl-pyrrolidin-3-yl)-chromen-4-one,
(+)-trans-2-(4-bromo-phenyl)-8-(2-hydroxymethyl-1-methyl-pyrrolidin-3-yl)-5,7-dimethoxy-chromen-4-one,
(+)-trans-2-(4-bromo-phenyl)-5-hydroxy-8-(2-hydroxymethyl-1-methyl-pyrrolidin-3-yl)-7-methoxy-chromen-4-one,
(+)-trans-2-(4-bromo-phenyl)-5,7-dihydroxy-8-(2-hydroxymethyl-1-methyl-pyrrolidin-3-yl)-chromen-4-one,
(+)-trans-2-(2,6-difluoro-phenyl)-8-(2-hydroxymethyl-1-methyl-pyrrolidin-3-yl)-5,7-dimethoxy-chromen-4-one,
(+)-trans-2-(2,6-difluoro-phenyl)-5,7-dihydroxy-8-(2-hydroxymethyl-1-methyl-pyrrolidin-3-yl)-chromen-4-one,
(±)-trans-4-[8-(2-hydroxymethyl-1-methyl-pyrrolidin-3-yl)-5,7-dimethoxy-4-oxo-4H-chromen-2-yl]-benzonitrile,
(±)-trans-4-[5-hydroxy-8-(2-hydroxymethyl-1-methyl-pyrrolidin-3-yl)-7-methoxy-4-oxo-4H-chromen-2-yl]-benzonitrile,
(±)-trans-4-[5,7-dihydroxy-8-(2-hydroxymethyl-1-methyl-pyrrolidin-3-yl)-4-oxo-4H-chromen-2-yl]-benzonitrile,
(+)-trans-4-[8-(2-hydroxymethyl-1-methyl-pyrrolidin-3-yl)-5,7-dimethoxy-4-oxo-4H-chromen-2-yl]-benzonitrile,
(+)-trans-4-[5-hydroxy-8-(2-hydroxymethyl-1-methyl-pyrrolidin-3-yl)-7-methoxy-4-oxo-4H-chromen-2-yl]-benzonitrile,
(+)-trans-4-[5,7-dihydroxy-8-(2-hydroxymethyl-1-methyl-pyrrolidin-3-yl)-4-oxo-4H-chromen-2-yl]-benzonitrile,
(±)-trans-2-[(3,5-bis-trifluoromethyl)-phenyl]-8-(2-hydroxymethyl-1-methylpyrrolidin-3-yl)-5,7-dimethoxy-chromen-4-one,
(±)-trans-2-[(3,5-bis-trifluoromethyl)-phenyl]-5,7-dihydroxy-8-(2-hydroxymethyl-1-methylpyrrolidin-3-yl)-chromen-4-one,
(±)-trans-2-(2-chloro-pyridin-3-yl)-8-(2-hydroxymethyl-1-methyl-pyrrolidin-3-yl)-5,7-dimethoxy-chromen-4-one,
(±)-trans-2-(2-chloro-pyridin-3-yl)-5,7-dihydroxy-8-(2-hydroxymethyl-1-methyl-pyrrolidin-3-yl)-chromen-4-one,
(+)-trans-2-(2-chloro-pyridin-3-yl)-8-(2-hydroxymethyl-1-methyl-pyrrolidin-3-yl)-5,7-dimethoxy-chromen-4-one,
(+)-trans-2-(2-chloro-pyridin-3-yl)-5,7-dihydroxy-8-(2-hydroxymethyl-1-methyl-pyrrolidin-3-yl)-chromen-4-one,
(+)-trans-8-(2-hydroxymethyl-1-methyl-pyrrolidin-3-yl)-5,7-dimethoxy-2-(4-nitro-phenyl)-chromen-4-one,
(+)-trans-5,7-dihydroxy-8-(2-hydroxymethyl-1-methyl-pyrrolidin-3-yl)-2-(4-nitro-phenyl)-chromen-4-one,
(+)-trans-2-(4-amino-phenyl)-5,7-dihydroxy-8-(2-hydroxymethyl-1-methyl-pyrrolidin-3-yl)-chromen-4-one,
(±)-trans-8-(2-hydroxymethyl-1-methyl-pyrrolidin-3-yl)-5,7-dimethoxy-2-(2-methoxy-phenyl)-chromen-4-one,
(±)-trans-5,7-dihydroxy-8-(2-hydroxymethyl-1-methyl-pyrrolidin-3-yl)-2-(2-hydroxy-phenyl)-chromen-4-one,
(+)-trans-3-chloro-4-[8-(2-hydroxymethyl-1-methyl-pyrrolidin-3-yl)-5,7-dimethoxy-4-oxo-4H-chromen-2-yl]-benzonitrile,
(+)-trans-3-chloro-4-[5,7-dihydroxy-8-(2-hydroxymethyl-1-methyl-pyrrolidin-3-yl)-4-oxo-4H-chromen-2-yl]-benzonitrile,
(+)-trans-2-(4-bromo-2-chloro-phenyl)-8-(2-hydroxymethyl-1-methyl-pyrrolidin-3-yl)-5,7-dimethoxy-chromen-4-one,
(+)-trans-2-(4-bromo-2-chloro-phenyl)-5,7-dihydroxy-8-(2-hydroxymethyl-1-methyl-pyrrolidin-3-yl)-chromen-4-one,
(±)-trans-2-(2-chloro-5-dimethylamino-phenyl)-8-(2-hydroxymethyl-1-methyl-pyrrolidin-3-yl)-5,7-dimethoxy-chromen-4-one,
(±)-trans-2-(2-chloro-5-methylamino-phenyl)-5,7-dihydroxy-8-(2-hydroxymethyl-1-methyl-pyrrolidin-3-yl)-chromen-4-one,
(±)-trans-2-(2-chloro-4-methoxy-phenyl)-8-(2-hydroxymethyl-1-methyl-pyrrolidin-3-yl)-5,7-dimethoxy-chromen-4-one,
(±)-trans-2-(2-chloro-4-hydroxy-phenyl)-5,7-dihydroxy-8-(2-hydroxymethyl-1-methyl-pyrrolidin-3-yl)-chromen-4-one,
(±)-trans-2-(2-chloro-phenyl)-8-(3-hydroxy-1-methyl-piperidin-4-yl)-5,7-dimethoxy-chromen-4-one,
(±)-trans-8-(2-azidomethyl-1-methyl-pyrrolidin-3-yl)-2-(2-chloro-phenyl)-5,7-dimethoxy-chromen-4-one,
(±)-trans-8-(2-aminomethyl-1-methyl-pyrrolidin-3-yl)-2-(2-chloro-phenyl)-5,7-dimethoxy-chromen-4-one,
(±)-trans-8-(2-aminomethyl-1-methyl-pyrrolidin-3-yl)-2-(2-chloro-phenyl)-5,7-dihydroxy-chromen-4-one,
(±)-trans-{3-[2-(2-chloro-phenyl)-5,7-dimethoxy-4-oxo-4H-chromen-8-yl]-1-methyl-pyrrolidin-2-yl}-acetonitrile,
(±)-trans-{3-[2-(2-chloro-phenyl)-5,7-dihydroxy-4-oxo-4H-chromen-8-yl]-1-methyl-pyrrolidin-2-yl}-acetonitrile,
(±)-trans-2-(2-chloro-phenyl)-8-(2-imidazol-1-yl methyl-1-methyl-pyrrolidin-3-yl)-5,7-dimethoxy-chromen-4-one,
(±)-trans-2-(2-chloro-phenyl)-5,7-dihydroxy-8-(2-imidazol-1-ylmethyl-1-methyl-pyrrolidin-3-yl)-chromen-4-one,
(±)-trans-2-[2-chloro-phenyl-8-(2-mercaptomethyl-1-methyl-pyrrolidin-3-yl)]-5,7-dimethoxy-chromen-4-one,
(±)-trans-2-(2-chloro-phenyl)-5,7-dihydroxy-8-(2-mercaptomethyl-1-methyl-pyrrolidin-3-yl)-chromen-4-one,
(±)-trans-2-(2-chloro-phenyl)-8-[2-hydroxymethyl-1-(4-methoxy-phenyl)-pyrrolidin-3-yl]-5,7-dimethoxy-chromen-4-one,
(±)-trans-2-(2-chloro-phenyl)-5,7-dihydroxy-8-[2-hydroxymethyl-1-(4-hydroxyphenyl)-pyrrolidin-3-yl]-chromen-4-one,
(±)-trans-2-(2-chloro-phenyl)-8-(3-hydroxy-piperidin-4-yl)-5,7-dimethoxy-chromen-4-one,
(±)-trans-2-(2-chloro-phenyl)-8-(3-hydroxy-1-propyl-piperidin-4-yl)-5,7-dimethoxy-chromen-4-one,
(±)-trans-2-(2-chloro-phenyl)-8-(2-hydroxymethyl-1-propyl-pyrrolidin-3-yl)-5,7-dimethoxy-chromen-4-one, (±)-trans-2-(2-chloro-phenyl)-5,7-dihydroxy-8-(2-hydroxymethyl-1-propyl-pyrrolidin-3-yl)-chromen-4-one,
(+)-trans-2-(2-chloro-3-fluoro-phenyl)-8-(2-hydroxymethyl-1-methyl-pyrrolidin-3-yl)-5,7-dimethoxy-chromen-4-one,
(+)-trans-2-(2-chloro-3-fluoro-phenyl)-5,7-dihydroxy-8-(2-hydroxymethyl-1-methyl-pyrrolidin-3-yl)-chromen-4-one,
(+)-trans-2-(2-bromo-3-fluoro-phenyl)-8-(2-hydroxymethyl-1-methyl-pyrrolidin-3-yl)-5,7-dimethoxy-chromen-4-one,
(+)-trans-2-(2-bromo-3-fluoro-phenyl)-5,7-dihydroxy-8-(2-hydroxymethyl-1-methyl-pyrrolidin-3-yl)-chromen-4-one,
(+)-trans-2-(2-chloro-5-iodo-phenyl)-8-(2-hydroxymethyl-1-methyl-pyrrolidin-3-yl)-5,7-dimethoxy-chromen-4-one,
(+)-trans-2-(2-chloro-5-iodo-phenyl)-5,7-dihydroxy-8-(2-hydroxymethyl-1-methyl-pyrrolidin-3-yl)-chromen-4-one,
(+)-trans-2-(2-bromo-5-chloro-phenyl)-8-(2-hydroxymethyl-1-methyl-pyrrolidin-3-yl)-5,7-dimethoxy-chromen-4-one,
(+)-trans-2-(2-bromo-5-chloro-phenyl)-5,7-dihydroxy-8-(2-hydroxymethyl-1-methyl-pyrrolidin-3-yl)-chromen-4-one,
(±)-trans-3-[2-(2-chloro-phenyl)-5,7-dimethoxy-4-oxo-4H-chromen-8-yl]-1-methyl-pyrrolidine-2-carbaldehyde,
(±)-trans-3-[2-(2-chloro-phenyl)-5,7-dimethoxy-4-oxo-4H-chromen-8-yl]-1-methyl-1-oxy-pyrrolidine-2-carboxylic acid,
(±)-trans-3-[2-(2-chloro-phenyl)-5,7-dimethoxy-4-oxo-4H-chromen-8-yl]-1-methyl-pyrrolidine-2-carboxylic acid,
(±)-trans-3-[2-(2-chloro-phenyl)-5,7-dihydroxy-4-oxo-4H-chromen-8-yl]-1-methyl-pyrrolidine-2-carboxylic acid,
(±)-trans-2-(2-chloro-phenyl)-5,7-dihydroxy-8-(2-hydroxymethyl-1-methyl-1-oxy-pyrrolidin-3-yl)-chromen-4-one,
(+)-trans-2-(4-amino-2-bromo-phenyl)-8-(2-hydroxymethyl-1-methyl-pyrrolidin-3-yl)-5,7-dimethoxy-chromen-4-one,
(+)-trans-2-(4-amino-2-bromo-phenyl)-5,7-dihydroxy-8-(2-hydroxymethyl-1-methyl-pyrrolidin-3-yl)-chromen-4-one,
(+)-trans-2-(2-bromo-4-methoxy-phenyl)-8-(2-hydroxymethyl-1-methyl-pyrrolidin-3-yl)-5,7-dimethoxy-chromen-4-one,
(+)-trans-2-(2-bromo-4-methoxy-phenyl)-5,7-dihydroxy-8-(2-hydroxymethyl-1-methyl-pyrrolidin-3-yl)-chromen-4-one, and
(+)-trans-2-(2-bromo-4-hydroxy-phenyl)-5,7-dihydroxy-8-(2-hydroxymethyl-1-methyl-pyrrolidin-3-yl)-chromen-4-one.

The present invention further relates to a pharmaceutically acceptable salt of a compound of general formula (Ia), (Ib), (Ic) or (Ig), wherein the pharmaceutically acceptable salt is selected from: an inorganic or organic acid salt, where the inorganic acid is selected from, for example, boric acid, perchloric acid, hydrochloric acid, hydrobromic acid, sulfuric acid, sulfamic acid, phosphoric acid and nitric acid, and where the organic acid is selected from, for example, acetic acid, propionic acid, succinic acid, glycolic acid, gluconic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxybenzoic acid, fumaric acid, toluenesulfonic acid, methanesulfonic acid, ethane disulfonic acid, oxalic acid, isethionic acid, ketoglutaric acid, benzenesulfonic acid and glycerophosphoric acid; an alkali metal salt, like a Li, Na or K salt. Preferably, the pharmaceutically acceptable salt is a hydrochloric acid salt, citric acid salt, tartaric acid salt, maleic acid salt, methane sulfonic acid salt, acetic acid salt, sulfuric acid salt or nitric acid salt.

Examples of preferred salts of compounds of general formula (Ia), (Ib), (Ic) or (Ig) according to the present invention are listed below:
(±)-trans-2-(2-chloro-phenyl)-5,7-dihydroxy-8-(2-hydroxymethyl-1-methyl-pyrrolidin-3-yl chromen-4-one hydrochloride,
(+)-trans-2-(2-chloro-phenyl)-5,7-dihydroxy-8-(2-hydroxymethyl-1-methyl-pyrrolidin-3-yl)-chromen-4-one hydrochloride,
(−)-trans-2-(2-chloro-phenyl)-5,7-dihydroxy-8-(2-hydroxymethyl-1-methyl-pyrrolidin-3-yl)-chromen-4-one hydrochloride,
(±)-trans-2-(2-chloro-5-fluoro-phenyl)-5,7-dihydroxy-8-(2-hydroxymethyl-1-methyl-pyrrolidin-3-yl)-chromen-4-one hydrochloride,
(±)-trans-2-(2-chloro-5-fluoro-phenyl)-5,7-dihydroxy-8-(2-hydroxymethyl-1-methyl-pyrrolidin-3-yl)-chromen-4-one methane sulfonate,
(+)-trans-2-(2-chloro-5-fluoro-phenyl)-5,7-dihydroxy-8-(2-hydroxymethyl-1-methyl-pyrrolidin-3-yl)-chromen-4-one hydrochloride,
(+)-trans-2-(2-bromo-5-fluoro-phenyl)-5,7-dihydroxy-8-(2-hydroxymethyl-1-methyl-pyrrolidin-3-yl)-chromen-4-one hydrochloride,
(+)-trans-2-(2-bromo-5-fluoro-phenyl)-5,7-dihydroxy-8-(2-hydroxymethyl-1-methyl-pyrrolidin-3-yl)-chromen-4-one methane sulfonate,
(+)-trans-2-(2-bromo-4-nitro-phenyl)-5,7-dihydroxy-8-(2-hydroxymethyl-1-methyl-pyrrolidin-3-yl)-chromen-4-one hydrochloride,
(+) acetic acid 3-[2-(2-bromo-4-nitro-phenyl)-5,7-dihydroxy-4-oxo-4H-chromen-8-yl]-1-methyl-pyrrolidin-2-ylmethyl ester hydrochloride,
(+)-trans-2-(2,4-dichloro-5-fluoro-phenyl-5,7-dihydroxy-8-(2-hydroxymethyl-1-methyl-pyrrolidin-3-yl)-chromen-4-one hydrochloride,
(+)-trans-2-(2,4-dichloro-5-fluoro-phenyl)-5,7-dihydroxy-8-(2-hydroxymethyl-1-methyl-pyrrolidin-3-yl)-chromen-4-one methane sulfonate,
(+)-trans-2-(2,4-dichloro-5-fluoro-phenyl)-5,7-dihydroxy-8-(2-hydroxymethyl-1-methyl-pyrrolidin-3-yl)-chromen-4-one citrate,
(+)-trans-2-(2,4-dichloro-5-fluoro-phenyl)-5,7-dihydroxy-8-(2-hydroxymethyl-1-methyl-pyrrolidin-3-yl)-chromen-4-one tartrate,
(+)-trans-2-(2,4-dichloro-5-fluoro-phenyl)-5,7-dihydroxy-8-(2-hydroxymethyl-1-methyl-pyrrolidin-3-yl)-chromen-4-one maleate,
(+)-trans-2-(2,4-dichloro-5-fluoro-phenyl)-5,7-dihydroxy-8-(2-hydroxymethyl-1-methyl-pyrrolidin-3-yl)-chromen-4-one acetate,
(+)-trans-2-(2,4-dichloro-5-fluoro-phenyl)-5,7-dihydroxy-8-(2-hydroxymethyl-1-methyl-pyrrolidin-3-yl)-chromen-4-one sulfate,
(+)-trans-2-(2,4-dichloro-5-fluoro-phenyl)-5,7-dihydroxy-8-(2-hydroxymethyl-1-methyl-pyrrolidin-3-yl)-chromen-4-one nitrate.
(+)-trans-5,7-dihydroxy-8-(2-hydroxymethyl-1-methyl-pyrrolidin-3-yl)-2-phenyl-chromen-4-one hydrochloride, (+)-trans-4-[5,7-dihydroxy-8-(2-hydroxymethyl-1-methyl-pyrrolidin-3-yl)-4-oxo-4H-chromen-2-yl]-3-methyl-benzonitrile hydrochloride, (+)-trans-5,7-dihydroxy-8-(2-hydroxymethyl-1-methyl-pyrrolidin-3-yl)-2-(4-trifluoromethyl-phenyl)-chromen-4-one hydrochloride, (+)-trans-5,7-dihydroxy-8-(2-hydroxymethyl-1-methyl-pyrrolidin-3-yl)-2-thiophen-2-yl-chromen-4-one hydrochloride, and (+)-trans-2-(2-chloro-5-hydroxy-phenyl)-5,7-dihydroxy-8-(2-hydroxymethyl-1-methyl-pyrrolidin-3-yl)-chromen-4-one hydrochloride, The present invention also relates to processes for the preparation of compounds of formula (Ia), (Ib), (Ic) or (Ig) or pharmaceutically acceptable salts thereof. One such process comprises reacting a benzopyranone of formula (II):

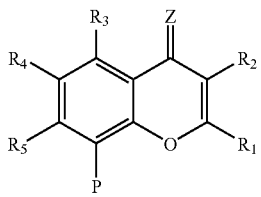

II wherein $R_1$, $R_2$, $R_3$, $R_4$, $R_5$ and Z have the meaning defined above and P is a functional group, with a compound of formula (III),

III wherein A is substituted by $R_6$ and $R_7$, and A, $R_6$ and $R_7$ have the meaning defined above, except that A is other than a 5-membered ring of the general structure (ii) and (v) above, wherein $X_1$ is nitrogen; Q is a functional group bound to a saturated or unsaturated carbon atom in the A, P and Q being capable of forming a carbon-carbon coupling between the respective carbon atoms to which they are attached, and i) where Q is bound to an unsaturated carbon atom, carrying out the reaction in the presence of a metal catalyst, an organic or inorganic base and an organic or inorganic solvent, and followed by treatment with a reducing agent to reduce any double bond between members at positions 1 and 2 or 1 and 5 of 5-membered ring A, between members at positions 1 and 6 or 1 and 2 of 6-membered ring A and between members at positions 1 and 2 or 1 and 7 of 7-membered ring A to a single bond, and ii) where Q is bound to a saturated carbon atom, carrying out the reaction in the presence of a suitable ligand or catalyst and a leaving group, and optionally converting the resultant compound of formula (Ia), (Ib), (Ic) or (Ig) into a pharmaceutically acceptable salt.

In another process for the preparation of compounds of formula (Ia), (Ib), (Ic) or (Ig) or pharmaceutically acceptable salts thereof, a benzopyranone of formula (II):

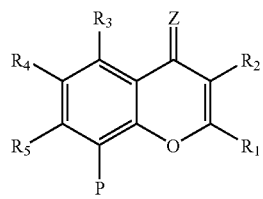

II wherein $R_1$, $R_2$, $R_3$, $R_4$, $R_5$ and Z are as defined and P is a functional group, is reacted with a compound of formula (IIIA),

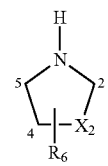

IIIA wherein $X_2$ and $R_6$ are as defined, in the presence of a metal catalyst, an organic or inorganic base and an organic or inorganic solvent, to form a nitrogen-carbon coupling between the carbon of the compound of formula (II) to which P is attached and the nitrogen of the compound of formula (IIIA), and, optionally, converting the resultant compound of formula (Ia), (Ib), (Ic) or (Ig) into a pharmaceutically acceptable salt.

Alternatively, a compound of formula (Ia), (Ib), (Ic) or (Ig) or a pharmaceutically acceptable salt thereof can be prepared by reacting a compound of formula (XA):

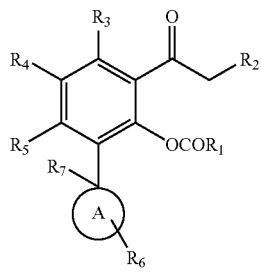

XA wherein in each case $R_1$, $R_2$, $R_3$, $R_4$, $R_5$, $R_6$ and A are as defined, with an organic or inorganic base, subsequently adding an acid capable of effecting cyclization to the reaction mixture, followed by adding an organic or inorganic base, and, optionally, converting the compound of formula (Ia), (Ib) (Ic) or (Ig) into a pharmaceutically acceptable salt, or reacting a compound of formula (XIIA):

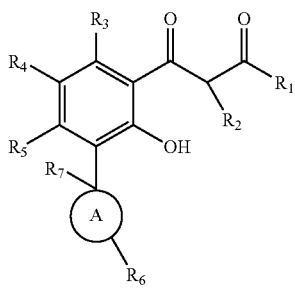

XIIA wherein in each case $R_1$, $R_2$, $R_3$, $R_4$, $R_5$, $R_6$, $R_7$ and A are as defined, with an acid capable of effecting cyclization, and then adding an organic or inorganic base to the reaction mixture and, optionally, converting the resultant compound of formula (Ia), (Ib), (Ic) or (Ig) into a pharmaceutically acceptable salt.

Compound of formula (XIIA) is obtained from compound of formula (XIA)

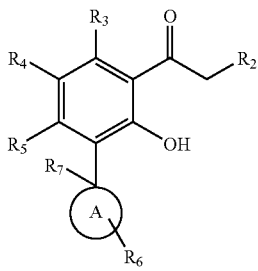

XIA by treatment with an appropriate carboxylic acid ester such as $R_1COOMe$, $R_1COOEt$ etc. or with an acid halide like $R_1COX$ wherein X is a halogen, such as chlorine, or with an activated ester such as an anhydride in the presence of a base such as NaH in a solvent such as DMF, THF or 1,4-dioxane.

In the process, ring A can be selected from:

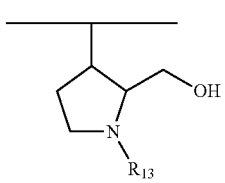

(a)

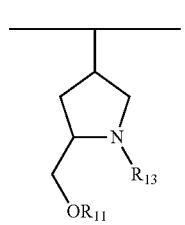

(b)

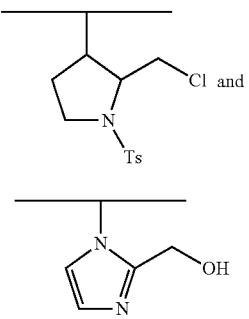

(c)

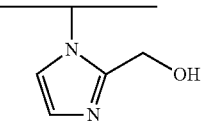

(d)

$R_{11}$ can be hydrogen and/or $R_{13}$ can be methyl.

A process for the preparation of a compound of formula (XIIIA) or a pharmaceutically acceptable salt thereof

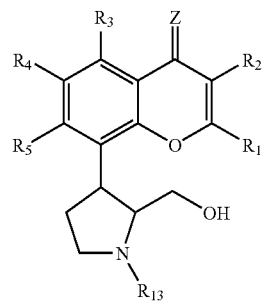

XIIIA wherein $R_1$, $R_2$, $R_3$, $R_4$, $R_5$, $R_{13}$ and Z are as defined above, comprises reacting a compound of formula (VIIA)

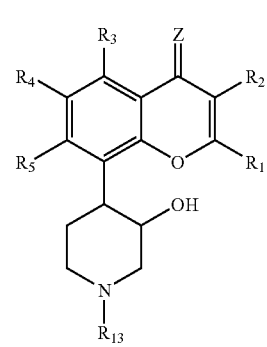

VIIA wherein $R_1$, $R_2$, $R_3$, $R_4$, $R_5$, $R_{13}$ and Z are as defined above, with a reagent suitable to effect replacement of the —OH group on the piperidino ring by a good leaving group, in the presence of an organic or inorganic base, followed by adding a suitable organic base in the presence of a suitable organic solvent to effect contraction of the piperidino ring and, if appropriate, converting the resultant compound of formula (XIIIA) into a pharmaceutically acceptable salt.

A process for the preparation of a compound of formula (XXXIA) or a pharmaceutically acceptable salt thereof

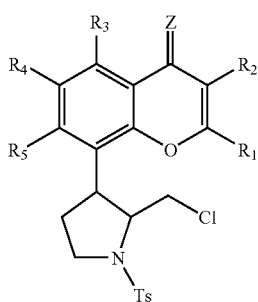

XXXIA wherein $R_1$, $R_2$, $R_3$, $R_4$, $R_5$ and Z are as defined above, comprises reacting a benzopyranone of formula (XXXA):

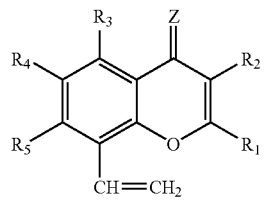

XXXA wherein $R_1$, $R_2$, $R_3$, $R_4$, $R_5$ and Z are as defined above, with N-allyl-N-chlorotosylamide in the presence of an alkylborane and, optionally, converting the resultant compound of formula (XXXIA) into a pharmaceutically acceptable salt.

A process for the preparation of a compound of formula (XXXVII):

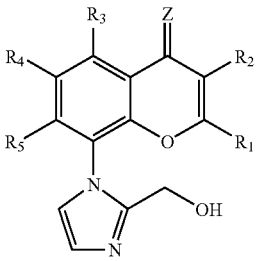

XXXVII wherein $R_1$, $R_2$, $R_3$, $R_4$, $R_5$ and Z are as defined, comprises reacting a compound of formula (XXXVI):

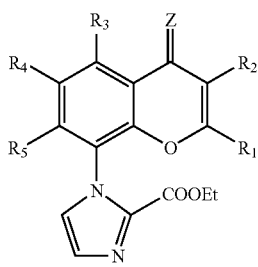

XXXVI wherein $R_1$, $R_2$, $R_3$, $R_4$, $R_5$ and Z are as defined above, with a suitable reducing agent capable of converting the ester group —C(O)OEt on the imidazolyl ring into the group —CH$_2$OH and, if appropriate, converting the resultant compound of formula (XXXVII) into a pharmaceutically acceptable salt. The compound of formula (XXXVI) above is prepared by reacting a compound of formula (XXXV):

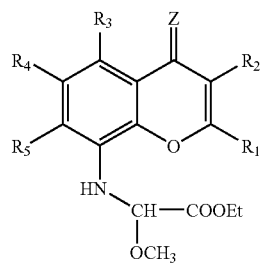

XXXV wherein $R_1$, $R_2$, $R_3$, $R_4$, $R_5$ and Z are as defined, with an isocyanide in the presence of an inorganic base in an organic solvent.

The present invention also relates to a process for the resolution of a compound of general formula (VIII A) or a pharmaceutically acceptable salt thereof:

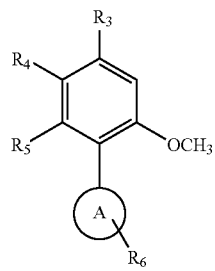

VIIIA wherein $R_3$, $R_4$, $R_5$, $R_6$ and A are as defined, which process comprises reacting the racemic compound of formula (VIIIA) with a chiral auxiliary in the presence of a solvent, crystallising out the required diastereomeric salt and subsequently treating with base to obtain the desired enantiomer of the compound of formula (VIII A).

The present invention also relates to a process for the preparation of a compound of the formula (1f), or a pharmaceutically acceptable salt thereof:

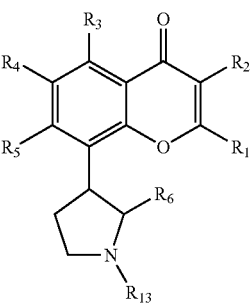

(If)

wherein $R_1$, $R_2$, $R_3$, $R_4$, $R_5$, and $R_{13}$ are as defined, $R_6$ is $CH_2OH$, comprising reacting a racemic compound of the formula (VIII):

VIII

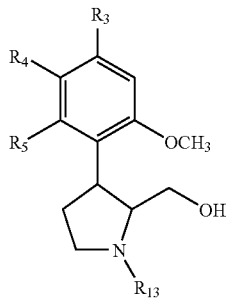

wherein $R_3$, $R_4$, $R_5$ and $R_{13}$ are as defined, with a chiral auxiliary in the presence of a solvent to form a diastereomeric salt of the compound of formula (VIII), crystallising out the required diastereomeric salt and subsequently treating with a base to obtain the desired enantiomer of the compound of formula (VIII), treating the compound of formula (VIII) with an acylating agent or an activated form of an acid in the presence of a Lewis acid catalyst to obtain the acylated compound of formula (IX):

IX

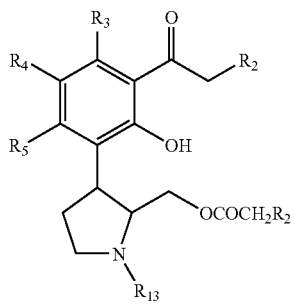

wherein $R_2$, $R_3$, $R_4$, $R_5$ and $R_{13}$ are as defined, treating the compound of formula (IX) with either:
  (a) an acid chloride of formula $R_1COCl$, an anhydride of formula $(R_1CO)_2O$ or an ester of formula $R_1COOCH_3$, where $R_1$ is as defined,
  (b) an acid of formula $R_1COOH$, where $R_1$ is as defined, and phosphorus oxychloride, in the presence of an acid scavenger to obtain an acid chloride in situ under neutral conditions, or
  (c) a combination of $R_1COOH$, (wherein $R_1$ is as defined), and polyphoshoric acid, to form the compound of formula (X)

X

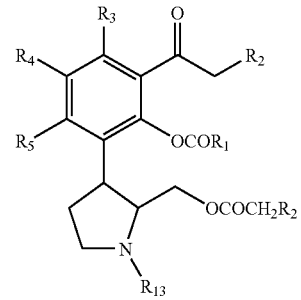

wherein $R_1$, $R_2$, $R_3$, $R_4$, $R_5$ and $R_{13}$ are as defined, treating the compound of formula (X) with an acid capable of effecting cyclization and subsequently with a base to form the subject compound of formula (If), and, optionally, converting the subject compound into a pharmaceutically acceptable salt;

alternatively, subjecting the compound of formula (IX) above to ester hydrolysis by treating with a base in aqueous ethanol or methanol to form a compound of formula (XI)

XI

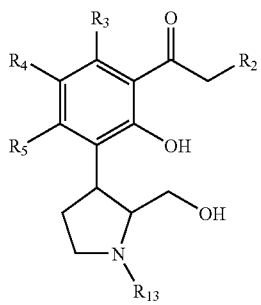

wherein $R_2$, $R_3$, $R_4$, $R_5$ and $R_{13}$ are as defined, treating the compound of formula (XI) with a carboxylic acid ester, an acid chloride or an activated ester, in the presence of a base in a solvent to form a compound of the formula (XII).

XII

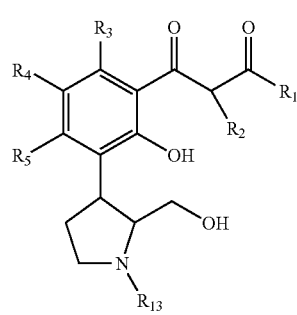

wherein $R_1$, $R_2$, $R_3$, $R_4$, $R_5$ and $R_{13}$ are as defined, and treating the compound of formula (XII) with an acid capable of effecting cyclization and subsequently treating with a base to form the subject compound of formula (1f), and, optionally, converting the subject compound into a pharmaceutically acceptable salt.

Compounds of general formula (Ia), (Ib), (Ic) or (Ig) and intermediates thereof may be prepared by any of the general schemes outlined below and illustrated in FIGS. 1-6. Unless otherwise specified, the groups A, Z, $R_1$, $R_2$, $R_3$, $R_4$, $R_5$, $R_{11}$ and $R_{13}$ are as defined in respect of general formula (Ia), (Ib), (Ic) or (Ig) above.

Scheme 1 (FIG. 1)

The compounds of the present invention are formed in scheme 1 by a metal catalyzed, for example nickel or palladium catalyzed, C—C bond coupling reaction well known in the art. In the compound of formula (II), P is a functional group, for example, a halogen such as Cl, Br, I or a triflate. In the compounds of formulae (I) and (III), A may be an optionally substituted 5-, 6- or 7-membered ring as defined above. In the compound of formula (III), Q is an appropriately chosen organometallic reagent, for example, organostannane, organozinc, organosilicon, organoborane or Grignard reagent.

Where ring A is a 5-membered ring having the general structure (ii) or (v), wherein $X_1$ is N, the 5-membered heterocycle may be coupled directly with the compound of formula (II) using a suitable catalyst such as $Pd(OAc)_2$, $PdCl_2(PhCN)_2$, $Pd(Ph_3P)_4$ and CuI. Coupling is carried out in presence of a base such as sodium carbonate, potassium carbonate, piperidine and pyrrolidine using solvents such as DMF.

Figure 2:
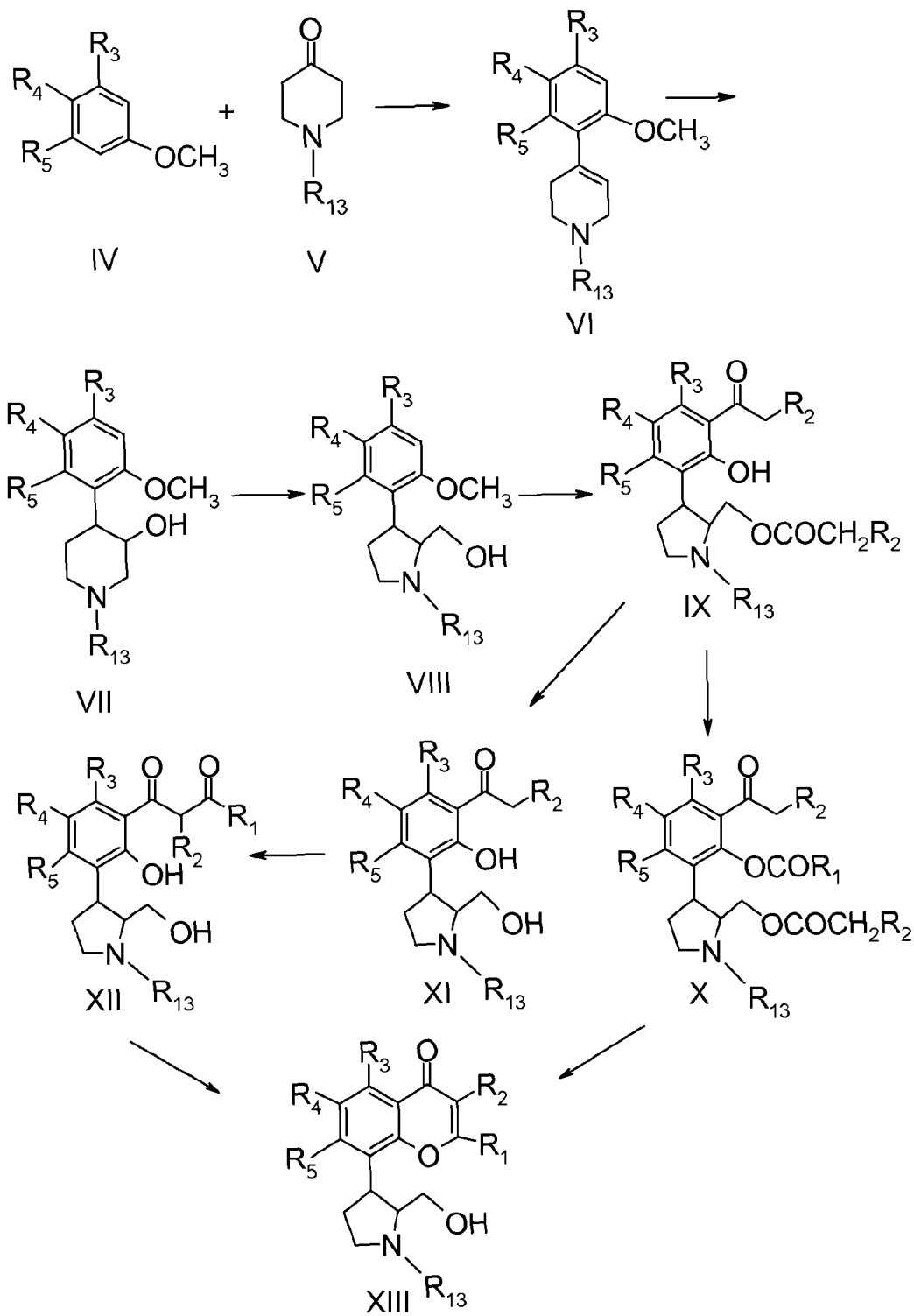

Scheme 2 (FIG. 2)

Alternatively, the preparation of compounds of general formula (Ia), (Ib), (Ic) or (Ig) (denoted as compounds of formula (XIII)) wherein Z is O, A is a 5-membered ring corresponding to general structures (i), (iii) or (iv) wherein $X_1$ is methylene, $X_2$ is $NR_{13}$, $R_6$ is alkyl and $R_7$ is hydrogen (wherein both $R_6$ and $R_7$ are substitutions on A as defined hereinabove) can be carried out in accordance with the steps shown in the scheme in FIG. 2.

In compounds of the formulae (VI) to (XIII), the group $R_{13}$ as depicted in Scheme 2 is preferably alkyl. As outlined in Scheme 2, the preparation steps up to compounds of formula (VII) starting from the compound of general formula (IV) are described in U.S. Pat. No. 4,900,727, which is incorporated herein by reference. In the conversion of the compound of formula (VII) to that of formula (VIII) in Scheme 2, the hydroxyl function on the piperidine ring may be converted to a good leaving group such as tosyl, mesyl, triflate or halide by treatment with appropriate reagents like p-toluenesulfonylchloride, methanesulfonylchloride, triflic anhydride or $PCl_5$ in the presence of an appropriate organic or inorganic base like triethylamine, pyridine, $K_2CO_3$ or $Na_2CO_3$, followed by ring contraction using a base such as sodium acetate in a solvent such as isopropanol. The ring contraction involved in this step may be effected before flavone formation as depicted in Scheme 2 or it may be done after building the flavone with desired substitutions. The compound of general formula (VIII) may be resolved by reacting it with a chiral auxiliary such as (+)-dibenzoyl tartaric acid, (+)-dibutyl tartaric acid, (+)-ketopinic acid, (+)-camphor-10-sulfonic acid or (+) camphoric acid in the presence of a solvent such as methanol, isopropanol, diisopropyl ether, ethyl acetate or chloroform, crystallising out the required diastereomeric salt and subsequently treating with base such as $NaHCO_3$, $Na_2CO_3$ or $K_2CO_3$ to obtain the desired enantiomer of compound of formula (VIII). The compound of formula (VIII) may then be treated with an acylating agent such as a carboxylic acid, an acid chloride, an acid anhydride or any activated form of an acid, in the presence of a Lewis acid catalyst such as $BF_3.Et_2O$, $ZnCl_2$, $AlCl_3$ or $TiCl_4$ to obtain the corresponding acylated compound of formula (IX). Subsequently the compound of formula (IX) can be converted to the compound of formula (X) by treating it with a reagent like an acid chloride of formula $R_1COCl$, an anhydride of formula $(R_1CO)_2O$, an ester of formula $R_1COOCH_3$ or any like reagent wherein $R_1$ is as defined hereinabove. The said conversion can also be brought about by treating the compound of formula (IX) with an acid of formula $R_1COOH$ and phosphorus oxychloride in presence of an acid scavenger such as pyridine to obtain an acid chloride in situ. Conversion of the compound of formula (IX) to the compound of formula (X) can also be brought about by a combination of $R_1COOH$ and polyphosphoric acid. The compound of the formula (IX) may be converted to that of the formula (XI) by standard ester hydrolysis using bases like KOH or NaOH in aqueous ethanol or methanol. The resultant alcohol of formula (XI) may be converted to a β-diketone of formula (XII) by treatment with an appropriate carboxylic acid ester such as $R_1COOMe$, $R_1COOEt$ etc. or with an acid halide like $R_1COX$ wherein X is a halogen or with an activated ester such as an anhydride in the presence of a base such as NaH in a solvent such as DMF, THF or 1,4-dioxane. The β-diketone of formula (XII) may finally be converted into the required flavone of formula (XIII) by treatment with a strong acid such as concentrated HCl and subsequent treatment with a mild base such as $Na_2CO_3$, $NaHCO_3$ or $K_2CO_3$. Alternatively, the intermediate of formula (X) may be converted into the flavone of formula (XIII) by treatment with a base such as NaH followed by cyclization using a strong acid like concentrated HCl and subsequent treatment with a mild base like $Na_2CO_3$, $NaHCO_3$ or $K_2CO_3$.

Figure 6:
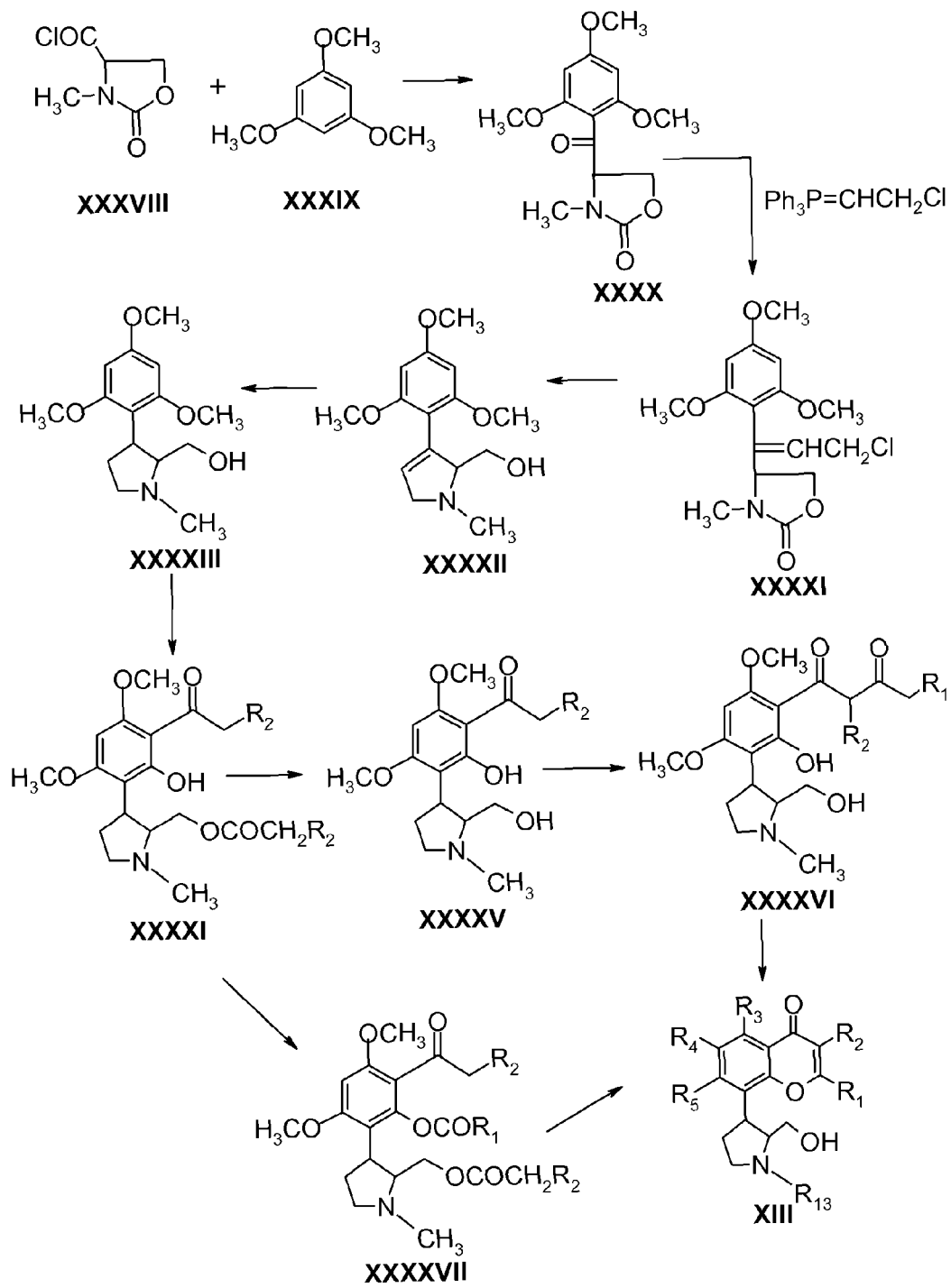

An alternative method for preparing the compound of formula (VIII), which is a key intermediate in the preparation of a compound of general formula (Ia), (Ib), (Ic) or (Ig), is represented in FIG. 6 (compound of formula (XXXXIII)).

Figure 3:
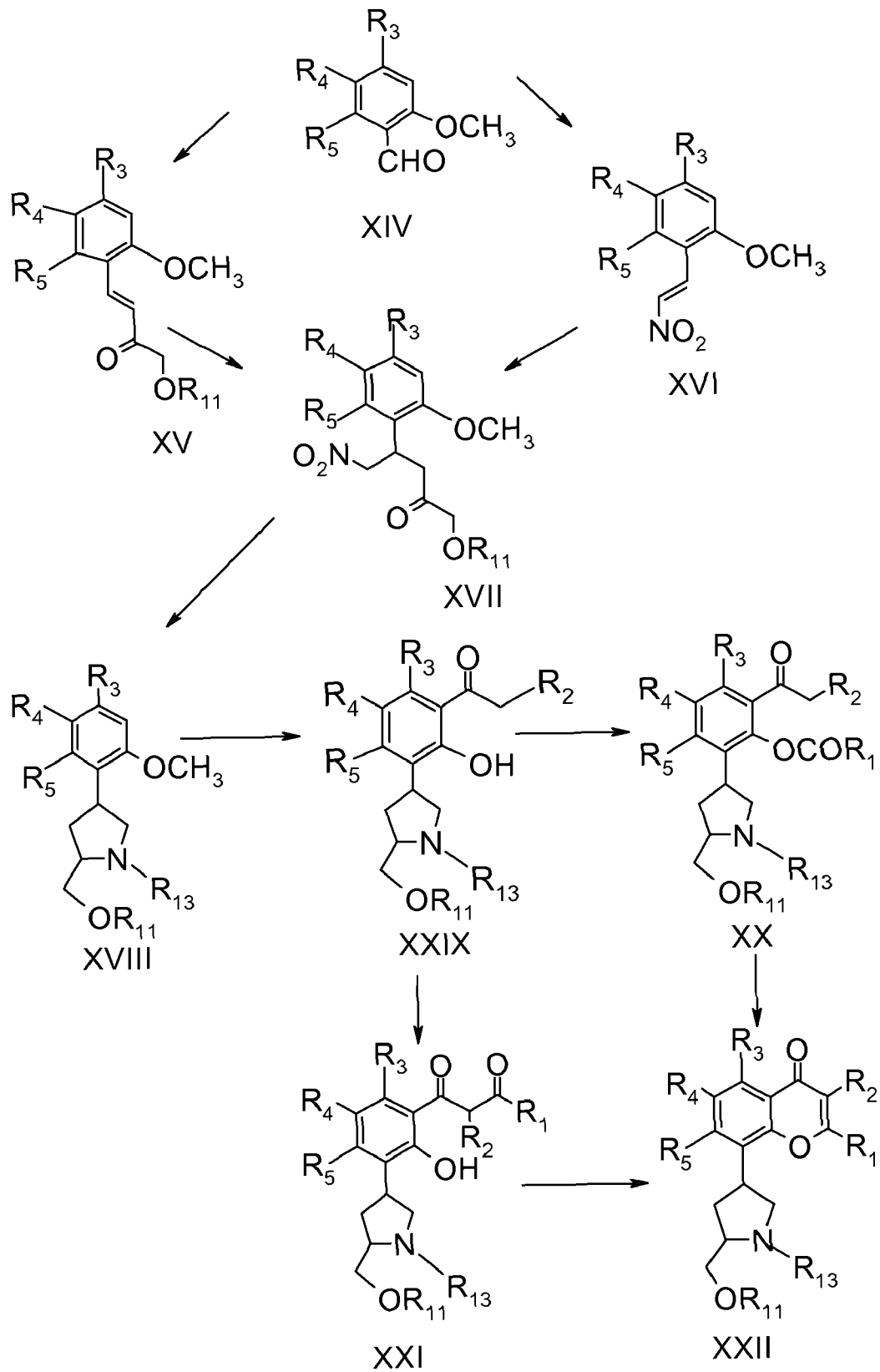

Scheme 3 (FIG. 3)

Scheme 3 outlines the preparation of the intermediate compound represented by formula (XVIII), which is subsequently converted to a compound of formula (XXII) by following similar process steps as described in Scheme 2 for the conversion of the compound of formula (VIII) to the compound of formula (XIII). The compound of formula (XXII) as prepared herein is a compound of general formula (Ia), (Ib), (Ic) or (Ig) above wherein Z is O, A is a 5-membered ring corresponding to general structure (i), (iii) or (iv) wherein $X_1$ is methylene and $X_2$ is $NR_{13}$, and the substitutions $R_6$ and $R_7$ on ring A are —$CH_2$—$OR_{11}$ and H, respectively.

As outlined in scheme 3, the compound of formula (XVIII) is prepared in three steps starting from an aldehyde of formula (XIV). The compound of formula (XIV) is first converted into the compound of formula (XVII) in two steps involving condensation of the compound of formula (XIV) with an appropriate ketone using a Knoevenagel reaction, followed by a Michael reaction of the resulting intermediate of formula (XV) with nitromethane in the presence of base to obtain the compound of formula (XVII). The Michael reaction in the presence of a chiral base such as proline leads to chiral compound of formula (XVII). Alternatively, the compound of formula (XVII) can be obtained by first converting the aldehyde (XIV) into the nitrostyrene derivative of formula (XVI) which in turn is reacted with an appropriate ketone by a Michael reaction, using base as described above.

The resulting compound of formula (XVII) is then subjected to a sequence of reactions involving selective reduction of the nitro group by known methods such as treatment with Sn/HCl or Fe/HCl followed by in situ cyclization or sequential cyclization and subsequent reduction to yield the compound of formula (XVIII). Alternatively, reductive cyclization of the compound of formula (XVII) using a catalyst like Raney nickel directly gives the compound of formula (XVIII). This pivotal intermediate is then converted to the compound of formula (XXII) as described in scheme 3. Process steps from the compound of formula (XVIII) to the compound of formula (XXII) are as described for the conversion of the compound of formula (VIII) to the compound of formula (XIII) in scheme 2.

Figure 4:
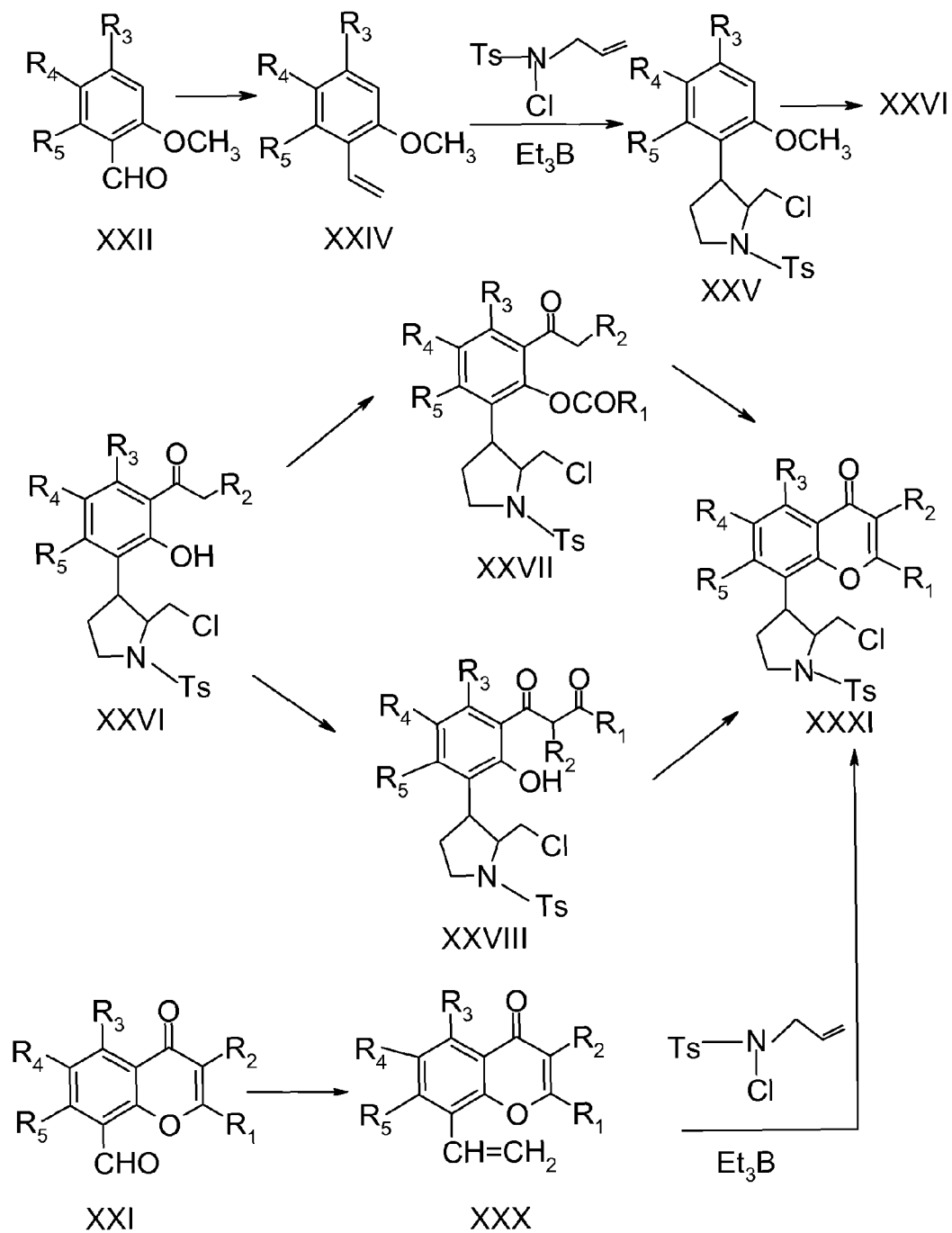

Scheme 4 (FIG. 4)

Another method of obtaining a compound of general formula (Ia), (Ib), (Ic) or (Ig) (denoted as formula XXXI), wherein Z is O, A is a 5-membered ring represented by general structure (i), (iii) or (iv) wherein $X_1$ is methylene and $X_2$ is $NR_{13}$, wherein $R_{13}$ represents p-toluenesulfonyl (Ts), $R_6$ is a haloalkyl group, with the halo preferably being Cl, and $R_7$ is H, is described in scheme 4.

As outlined in scheme 4, the compound of formula (XXXI) is prepared starting from the aldehyde of formula (XXIII). The compound of formula (XXIII) is converted using a Wittig reaction to the corresponding styrene compound of formula (XXIV) which in turn is converted into the compound of formula (XXV) by a [3+2] cycloaddition with N-allyl-N-chlorotosylamide in the presence of alkylboranes such as triethyl borane ($Et_3B$) (Oshima et. al. Org. Lett., 2001, 3, 2709-2711). The compound of formula (XXV) is then converted into the compound of formula (XXXI) via the compounds of formulae (XXVI), (XXVII) and (XXVIII) as described in scheme 2. The use of an alternative intermediate of formula (XXIX) also leads to the compound of formula (XXXI) by following the above cycloaddition route.

Figure 5:
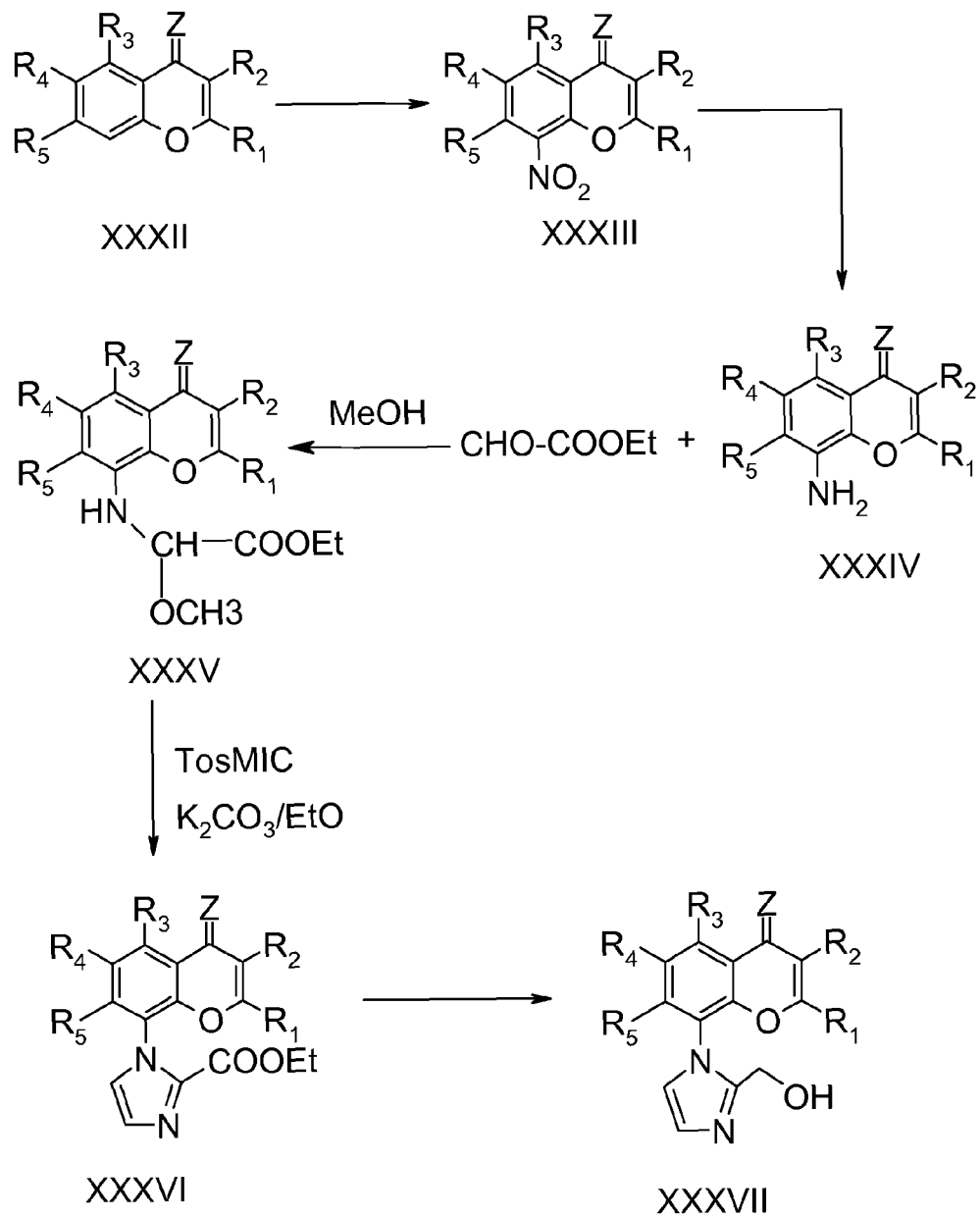

Scheme 5 (FIG. 5)

Preparation of the preferred compound of general formula (Ia) or (Ic) (denoted as the compound of formula (XXXVII)), wherein A is a 5-membered ring corresponding to general structure (ii), wherein $X_1$ is N, $X_2$ is N, A is an unsaturated ring and the substitution $R_6$ on ring A is $-CH_2OH$, is depicted in Scheme 5.

As outlined in scheme 5, the compound of formula (XXXVI) is prepared starting from the compound of formula (XXXII). The compound of formula (XXXII) on nitration provides the compound of formula (XXXIII) which on reduction gives the corresponding amino compound of formula (XXXIV) (Larget et al, Bioorg. Med. Chem. Lett., 2000, 10, 835). Conversion of amino flavone of formula (XXXIV) to the compound of formula (XXXV) by treatment with ethyl glyoxylate in methanol followed by conversion of the intermediate of formula (XXXV) to that of formula (XXXVI) by employing the method described in the literature (Tetrahedron Lett., 2000, 41, 5453) using tosylmethylisocyanide (TosMIC) in presence of a base such as $Na_2CO_3$ or $K_2CO_3$ in a solvent such as ethanol or methanol. The compound of formula (XXXVI) may then be converted to the required final compound of the formula (XXXVII) by reduction using a reagent like lithium aluminum hydride.

Scheme 6 (FIG. 6)

As stated herein above in respect of scheme 2, the key intermediate of formula (VIII), which corresponds to the compound of formula (XXXXIII) in FIG. 6, may be prepared by the alternative process steps illustrated in scheme 6. The compound of formula (XXXXIII) may be prepared starting from the chiral compound of formula (XXXVIII), which in turn is prepared in accordance with the procedure described in (Synth. Commun., 1993, 23(20), 2839-2844). The compound of formula (XXXVIII) on reacting with trimethoxybenzene (formula (XXXIX)) under Friedel-Crafts conditions gives the resulting ketone of formula (XXXX), which on treatment with $Ph_3P=CHCH_2Cl$ using Wittig conditions leads to the compound of formula (XXXXI). Ring opening using a mild aqueous base followed by cyclization in the presence of a base such as sodium hydride leads to the compound of formula (XXXXII). Subsequent hydrogenation of the double bond in the 5-membered ring in the presence of a chiral catalyst gives the corresponding compound of formula (XXXXIII) (corresponding to the compound of formula (VIII) in scheme 2), which may be further converted to the compound of formula (XIII) (corresponding to the compound of general formula (Ia), (Ib), (Ic) or (Ig)) by following the same process steps as described in scheme 2 for the conversion of the compound of formula (VIII) to the compound of formula XIII.

Intermediates of this invention may also be prepared by a process disclosed in the prior art or by a modification of the procedure described in U.S. Pat. No. 4,900,727, which is incorporated as reference herein.

The compounds according to the general formula (Ia), (Ib), (Ic) or (Ig) can be used to inhibit the activity of various cyclin-dependent kinases and are useful pharmaceutical compounds for the treatment of various diseases. In the context of the present invention, treatment includes the therapy as well as the prophylaxis of the respective diseases.

In one embodiment, the compounds of the present invention are for use in regulating cell proliferation. The compounds of the present invention are capable of inhibiting cell proliferation and therefore, are useful in treating diseases which are caused due to an excessive or abnormal cell growth.

There are a wide variety of pathological conditions with excessive or abnormal cell proliferation against which the compounds of the invention can act to provide therapeutic benefits. Examples of such pathological conditions include:

a. various cancers and leukemias including (but not limited to) the following:
  i. carcinoma, including that of bladder, breast, colon, kidney, liver, lung, ovary, pancreas, stomach, cervix, thyroid, prostate, and skin;
  ii. hematopoietic tumors of lymphoid lineage, including acute lymphocytic leukemia, B-cell lymphoma, and Burkett's lymphoma;
  iii. hematopoietic tumors of myeloid lineage, including acute and chronic myelogenous leukemias and promyelocytic leukemia;
  iv. tumors of mesenchymal origin, including fibrosarcoma and rhabdomysarcoma; and
  v. other tumors including melanoma, seminoma, teratocarcinoma, osteosarcoma, neuroblastoma and glioma,
b. chemotherapy- and/or radiation therapy induced epithelial cytotoxicity side-effects such as alopecia;
c. dermatology (psoriasis);
d. bone diseases;
e. inflammation and arthritis;
f. fibroproliferative disorders such as those involving connective tissues, atherosclerosis and other smooth muscle proliferative disorders, as well as chronic inflammation;
g. cardiovascular abnormalities (restenosis, tumoral angiogenesis, atherosclerosis);
h. nephrology (glomerulonephritis);
i. parasitology (unicellular parasites such as *Plasmodium, Trypanosoma, Toxoplasma*, etc);
j. neurology (Alzheimer's disease, stroke);
k. viral infections (cytomegalovirus, human immunodeficiency virus, herpes); and
l. mycotic infections.

In addition to proliferative disorders, the present compounds can be used in the treatment of differentiative disorders which result from, for example, de-differentiation of tissue, optionally accompanied by abortive reentry into mitosis. Such degenerative disorders include chronic neurodegenerative diseases of the nervous system, including Alzheimers's disease as suggested by the finding that Cdk5 is involved in the phosphorylation of tau protein (J. BioChem. 1995, 117, 741-749), Parkinson's disease, Huntington's chorea, amylotrophic lateral sclerosis and the like, as well as spinocerebellar degenerations. Other differentiative disorders include, for example, disorders associated with connective tissue, such as those that may occur due to de-differentiation of chondrocytes or osteocytes, as well as vascular disorders which involve de-differentiation of endothelial tissue and smooth muscle cells, gastric ulcers characterized by degenerative changes in glandular cells, and renal conditions marked by failure to differentiate, e.g. Wilm's tumors.

In addition to therapeutic applications (e.g., for both human and veterinary uses) it will be apparent that the compounds of the present invention can be used as a cell culture additive for controlling proliferative and/or differentiation states of cells in vitro and can also be used for ex vivo tissue generation as for example, to enhance the generation of prosthetic tissue devices for implantation such as described in U.S. Pat. No. 5,733,920 which is incorporated herein by reference.

Differential screening assays known in the art can be used to select those compounds of the present invention which have specificity for non-human Cdk enzymes. Thus, compounds which act specifically on eukaryotic pathogens, e.g., anti-fungal or anti-parasitic agents, can be selected from the subject compounds of general formula (Ia), (Ib), (Ic) or (Ig). Such inhibitors are useful in patients where fungal infection is a particular problem such as in patients with leukemias and lymphomas, diabetes mellitus, AIDS, or in people who are receiving immunosuppressive therapy.

When selected for anti-mycotic uses the formulations of the inhibitors can be provided with those inhibitors which inhibit a cyclin-dependent kinase complex of the human pathogen with an $IC_{50}$ at least an order of magnitude less than an $IC_{50}$ for inhibition of a human cyclin-dependent kinase complex, though more preferably at least two or three orders of magnitude less.

In a similar manner, certain of the present compounds can be selected on the basis of inhibitory specificity for insect or plant Cdk's relative to the mammalian enzyme in a differential screen. Such insect or plant Cdk inhibitors of the present invention find use in insecticides and agricultural applications, respectively.

The present invention therefore also relates to the compounds of the formula (Ia), (Ib), (Ic) or (Ig) and/or their pharmaceutically acceptable salts and/or their prodrugs for use as pharmaceuticals (or medicaments), to the use of the compounds of the formula (Ia), (Ib), (Ic) or (Ig) and/or their physiologically tolerable salts and/or their prodrugs for the production of pharmaceuticals for the inhibition of cell proliferation or for the therapy or prophylaxis of the diseases mentioned above, for example for the production of pharmaceuticals for the therapy and prophylaxis of cancer, inflammation and arthritis, psoriasis, bone diseases, mycotic or viral infections, cardiovascular disorders, Alzheimers's disease, etc., and to methods of treatment aiming at such purposes including methods for said therapies and prophylaxes. The present invention furthermore relates to pharmaceutical composition that contains an effective amount of at least one compound of the formula (Ia), (Ib), (Ic) or (Ig) and/or its physiologically tolerable salts and/or its prodrugs in addition to a customary pharmaceutically acceptable carrier, optionally, with other active anti-proliferative agents, and to a process for the production of a pharmaceutical, which comprises bringing at least one compound of formula (Ia), (Ib), (Ic) or (Ig) into a suitable administration form using a pharmaceutically suitable and physiologically tolerable carrier and, if appropriate, further suitable active compounds and/or additives. These compositions can be prepared by applying known techniques in the art such as those taught in "*Remington's Pharmaceutical Sciences*", published by Mack Publishing Co. or "*Pharmaceutical Dosage Form and Drug Delivery Systems*" (Sixth Edition), published by Williams & Wilkins, (1995), each of which is hereby incorporated by reference. The pharmaceutical composition comprises the compound of formula (Ia), (Ib), (Ic) or (Ig) in an amount adequate to inhibit proliferation of a eukaryotic cell, which may be a mammalian cell, a human pathogen, such as *Candida albicans, Aspergillus fumigatus, Rhizopus arrhizus, Mucor pusillus*, an insect cell or a plant cell.

The present invention also relates to a method for the preparation of a medicament for the treatment or prevention of disorders associated with excessive cell proliferation, characterized in that at least one compound of the general formula (Ia), (Ib), (Ic) or (Ig) is used as the pharmaceutically active substance.

The pharmaceutical composition normally contains about 1 to 99%, preferably about 5 to 70%, most preferably from about 10 to about 30% by weight of the compound of the formula (Ia), (Ib), (Ic) or (Ig) and/or its physiologically tolerable salt and/or its prodrug. The amount of the active ingredient of the formula (Ia), (Ib), (Ic) or (Ig) and/or its physiologically tolerable salt and/or its prodrug in the pharmaceutical composition normally is from about 5 to 500 mg. The dose of the compound of this invention, which is to be administered, can cover a wide range. The dose to be administered daily is to be selected to suit the desired effect. About 20 to 1,000 mg are preferably administered daily per patient. If required, higher or lower daily doses can also be administered. Actual dosage levels of the active ingredient in the pharmaceutical composition of this invention may be varied so as to obtain an amount of the active ingredient which is effective to achieve the desired therapeutic response for a particular patient, composition, and mode of administration without being toxic to the patient.

The selected dosage level will depend upon a variety of factors including the activity of the particular compound of the present invention employed, or the ester or salt thereof, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

The pharmaceuticals can be administered orally, including sublingually, for example in the form of pills, tablets, coated tablets, capsules, granules, powders, syrups or elixirs. Administration, however, can also be carried out: rectally or vaginally, for example in the form of suppositories; parentally, for example intravenously, intramuscularly or subcutaneously, including by the use of infusion techniques, in the form of injectable sterile solutions or suspensions; topically, for example in the form of creams, ointments, lotions, foams, gels, emulsions, solutions, tinctures, magmas or transdermal patches; or by other routes, for example ophthalmically, optically, nasally, or in other forms, for example, aerosols, inhalants or nasal sprays.

The pharmaceutical compositions according to the invention are prepared in a manner known per se and familiar to one skilled in the art. Pharmaceutically acceptable inert inorganic and/or organic carriers and/or additives can be used in addition to the compound(s) of the formula (Ia), (Ib), (Ic) or (Ig) and/or its (their) physiologically tolerable salt(s) and/or its (their) prodrug(s). For the production of pills, tablets, coated tablets and hard gelatin capsules it is possible to use, for example, lactose, corn starch or derivatives thereof, gum arabic, magnesia or glucose, etc. Carriers for soft gelatin capsules and suppositories are, for example, fats, wax, natural or hardened oils, etc. Suitable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned. Additives that may be used are, for example, fillers, antioxidants, dispersants, emulsifiers, defoamers, flavor corrigants, preservatives, solubilizers or colorants.

Commonly used pharmaceutically acceptable carriers and additives which can be used as appropriate to formulate the composition for its intended route of administration include: acidifying agents (examples include but are not limited to acetic acid, citric acid, fumaric acid, hydrochloric acid, nitric acid); alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine); adsorbents (examples include but are not limited to powdered cellulose and activated charcoal); aerosol propellants (examples include but are not limited to carbon dioxide, $CCl_2F_2$, $F_2ClC$—$CClF_2$ and $CClF_3$); air displacement agents (examples include but are not limited to nitrogen and argon); antifungal preservatives (examples include but are not limited to benzoic acid, butylparaben, ethylparaben, methylparaben, propylparaben, sodium benzoate); antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal); antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite); binding materials (examples include but are not limited to block polymers, natural and synthetic rubber, polyacrylates, polyurethanes, silicones and styrene-butadiene copolymers); buffering agents (examples include but are not limited to potassium metaphosphate, potassium phosphate monobasic, sodium acetate, sodium citrate anhydrous and sodium citrate dihydrate); carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection); chelating agents (examples include but are not limited to edetate disodium and edetic acid); colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red); clarifying agents (an example includes but is not limited to bentonite); emulsifying agents (examples include but are not limited to acacia, cetomacrogol, cetyl alcohol, glyceryl monostearate, lecithin, sorbitan monooleate, polyethylene 50 stearate); encapsulating agents (examples include but are not limited to gelatin and cellulose acetate phthalate); flavorants (examples include but are not limited to anise oil, cinnamon oil, cocoa, menthol, orange oil, peppermint oil and vanillin); humectants (examples include but are not limited to glycerin, propylene glycol and sorbitol); levigating agents (examples include but are not limited to mineral oil and glycerin); oils (examples include but are not limited to arachis oil, mineral oil, olive oil, peanut oil, sesame oil and vegetable oil); ointment bases (examples include but are not limited to lanolin, hydrophilic ointment, polyethylene glycol ointment, petrolatum, hydrophilic petrolatum, white ointment, yellow ointment, and rose water ointment); penetration enhancers (transdermal delivery) (examples include but are not limited to monohydroxy or polyhydroxy alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas); plasticizers (examples include but are not limited to diethyl phthalate and glycerin); solvents (examples include but are not limited to alcohol, corn oil, cottonseed oil, glycerin, isopropyl alcohol, mineral oil, oleic acid, peanut oil, purified water, water for injection, sterile water for injection and sterile water for irrigation); stiffening agents (examples include but are not limited to cetyl alcohol, cetyl esters wax, microcrystalline wax, paraffin, stearyl alcohol, white wax and yellow wax); suppository bases (examples include but are not limited to cocoa butter and polyethylene glycols (mixtures)); surfactants (examples include but are not limited to benzalkonium chloride, nonoxynol 10, oxtoxynol 9, polysorbate 80, sodium lauryl sulfate and sorbitan monopalmitate); suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum); sweetening agents (examples include but are not limited to aspartame, dextrose, glycerin, mannitol, propylene glycol, saccharin sodium, sorbitol and sucrose); tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, povidone and pregelatinized starch); tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac); tablet direct compression excipients (examples include but are not limited to dibasic calcium phosphate); tablet disintegrants (examples include but are not limited to alginic acid, carboxymethylcellulose calcium, microcrystalline cellulose, polacrillin potassium, sodium alginate, sodium starch glycollate and starch); tablet glidants (examples include but are not limited to colloidal silica, corn starch and talc); tablet lubricants (examples include but are not limited to calcium stearate, magnesium stearate, mineral oil, stearic acid and zinc stearate); tablet/capsule opaquants (examples include but are not limited to titanium dioxide); tablet polishing agents (examples include but are not limited to carnuba wax and white wax); thickening agents (examples include but are not limited to beewax, cetyl alcohol and paraffin); tonicity agents (examples include but are not limited to dextrose and sodium chloride);

viscosity increasing agents (examples include but are not limited to alginic acid, bentonite, carbomers, carboxymethylcellulose sodium, methylcellulose, povidone, sodium alginate and tragacanth); and wetting agents (examples include but are not limited to heptadecaethylene oxycetanol, lecithins, polyethylene sorbitol monooleate, polyoxyethylene sorbitol monooleate, polyoxyethylene stearate).

The pharmaceutical composition can contain the compound of the formula (Ia), (Ib), (Ic) or (Ig) and/or its physiologically tolerable salt and/or their prodrug either alone or in combination. Furthermore, in addition to at least one compound of the formula (Ia), (Ib), (Ic) or (Ig) and/or its physiologically tolerable salt and/or its prodrug, the pharmaceutical composition can also contain one or more other therapeutically or prophylactically active ingredients. Thus, the compounds of the present invention may be used as drugs in the treatment of proliferative disorders either alone or as part of combined therapies. For instance, the compounds of the present invention may be used in combination with one or more known anti-proliferative agents such as an anti-cancer or a cytostatic or a cytotoxic agent. If formulated as a fixed dose, such a combination product employ the compounds of the present invention within the dosage range described above and the other pharmaceutically active agent within its approved dosage range. For example, the Cdk inhibitor olomoucine has been found to act synergistically with known cytotoxic agents in inducing apoptosis (J. Cell Sci., 1995, 108, 2897). The compound of general formula (Ia), (Ib), (Ic) or (Ig) may be used sequentially with known anti-proliferative agents such as anticancer or cytotoxic agents when a combination formulation is inappropriate.

Optional anti-proliferative agents which can be added to the composition include but are not limited to compounds listed on the cancer chemotherapy drug regimens in the 13th Edition of the Merck Index, (2000), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin, epirubicin, etoposide, fluorouracil, hexamethylmelamine, hydroxyurea, ifosfamide, leucovorin, lomustine, mechlorethamine, 6-mercaptopurine, mesna, methotrexate, mitomycin C, mitoxantrone, prednisolone, prednisone, procarbazine, streptozocin, tamoxifen, thioguanine, vinblastine, vincristine, vindesine.

Other anti-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference such as aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, vinorelbine.

Optional cyclin-dependent kinase (Cdk) inhibiting agents which can be added to the composition include but are not limited to alsterpaullone, butyrolactone I, Cdk2 inhibitor, Cdk2/Cyclin Inhibitory Peptide I, Cdk2/Cyclin Inhibitory peptide II, 2-(2-hydroxyethylamino)-6-(3-chloroanilino)-9-isopropylpurine, indirubin-3'-monoxime, kenpaullone, olomoucine, iso-olomoucine, $N^9$-isopropyl-olomoucine, purvalanol A, roscovitine, (S)-isomer roscovitine and WHI-P180 [4-(3'-hydroxyphenyl)amino-6,7-dimethoxyquinazoline] (from Calbiochem Signal Transduction Catalog & Technical Resource 2001).

It is understood that modifications that do not substantially affect the activity of the various embodiments of this invention are included within the invention disclosed herein. Accordingly, the following examples are intended to illustrate but not to limit the present invention.

The following abbreviations are used herein:

Conc.: Concentrated

THF: Tetrahydofuran

EtOAc: Ethyl acetate

MeOH: Methanol

IPA: Isopropanol

DBTA: Dibenzoyl tartaric acid

DMF: Dimethyl formamide.

All NMR data was aquired on 300 MHz Bruker instrument and IR data was recorded using KBr pellets.

EXAMPLE 1

1-Methyl-4-(2,4,6-trimethoxy-phenyl)-1,2,3,6-tetrahydro-pyridine 1-methyl-4-piperidone (340 g, 3.0 mol) was added slowly, to a solution of 1,3,5-trimethoxybenzene (500 g, 2.97 mol) in glacial acetic acid (600 mL), maintaining the temperature of the reaction mixture below 40° C. Conc. HCl (450 mL) was added over 20 min. The temperature was raised to 85-90° C. and the reaction mixture was stirred for 3.5 h. It was allowed to cool to 40° C., poured over crushed ice (4 kg) and stirred for 20 min. The precipitate of unreacted 1,3,5-trimethoxybenzene was filtered off. The filtrate was basified, below 10° C., to pH 11-12 using a 50% aqueous NaOH solution. The off white solid obtained was filtered, washed with water and dried to obtain the compound, 1-Methyl-4-(2,4,6-trimethoxy-phenyl)-1,2,3,6-tetrahydro-pyridine.

Yield: 580 g (74%); mp: 112-114° C.

IR $cm^{-1}$: 3045, 2900, 2837, 1600, 1585.

$^1$H NMR (CDCl$_3$): δ 6.15 (s, 2H), 5.55 (s, 1H), 3.85 (s, 3H), 3.75 (s, 6H), 3.10 (d, 2H), 2.55 (t, 2H), 2.40 (s, 3H), 2.35 (m, 2H).

MS (EI): m/z 263 (M$^+$).

EXAMPLE 2

(±)-trans-1-Methyl-4-(2,4,6-trimethoxy-phenyl)-piperidin-3-ol

Boron trifluoride diethyl etherate (300 mL, 2.37 mol) was added slowly with stirring, under an atmosphere of nitrogen, at 0° C., to a solution of the compound of example (1) (300 g, 1.14 mol) and NaBH$_4$ (75 g, 1.97 mol) in dry THF (2.25 L). The temperature of the reaction mixture was slowly raised to 55° C. and stirred for 1.5 h. It was cooled to 30° C. Ice cold water (100 mL) was slowly added followed by acidification with conc. HCl (375 mL). The reaction mixture was stirred for 1 h. at 50-55° C. It was cooled to 30° C. and basified using 50% aqueous NaOH solution to pH 11-12. Hydrogen peroxide (30%, 225 mL) was added over 0.5 h. The reaction mixture was stirred at 55-60° C. for 1.5 h. It was cooled to 30° C. and sufficient water added to dissolve the precipitated salts. The organic layer was separated and the aqueous portion extracted with EtOAc (2×1 L). The organic extracts were dried (anhydrous $Na_2SO_4$) and concentrated. The crude viscous brown oil obtained was treated with 4N HCl (1.2 L) and extracted with EtOAc (2×500 mL). The aqueous portion was cooled, basified with 50% aqueous NaOH solution and extracted using EtOAc (2×1 L). The organic extract was dried (anhydrous $Na_2SO_4$) and concentrated to obtain the title compound.

Yield: 210 g (65.6%); mp: 96-97° C.
IR $cm^{-1}$: 3582, 3374, 3017.
$^1$H NMR ($CDCl_3$): δ 6.15 (s, 2H), 4.40 (m, 1H), 3.79 (s, 3H), 3.74 (s, 6H), 3.20 (dd, 1H), 3.00 (m, 1H), 2.80 (m, 1H), 2.40 (m, 1H), 2.37 (s, 3H), 2.00 (m, 1H), 1.90 (t, 1H), 1.52 (m, 1H).
MS (CI): m/z 282 (M+1).

EXAMPLE 3

(±)-trans-Acetic acid 1-methyl-3-(2,4,6-trimethoxy-phenyl)-pyrrolidin-2-ylmethyl ester Method A:

Distilled triethyl amine (344 mL, 2.49 mol) was added slowly to a solution of compound of example 2 (350 g, 1.25 mol) in dry $CH_2Cl_2$ (2.5 L). To the reaction mixture methanesulfonyl chloride (122 mL, 171.1 g, 1.49 mol) was added with stirring, at 0° C., under an atmosphere of $N_2$ and over a period of 20 min. The reaction mixture was further stirred for 1 h at 0° C. It was poured over saturated aqueous $NaHCO_3$ solution (1.5 L). The organic layer was separated, washed with brine, dried (anhydrous$Na_2SO_4$) and concentrated to obtained a residue. This was dissolved in distilled isopropyl alcohol (1.5 L), anhydrous sodium acetate (408 g, 4.97 mmol) was added and the reaction mixture was refluxed for 1 h. It was cooled to room temperature. Sodium acetate was filtered off and washed with $CHCl_3$. The filtrate was concentrated to obtain the title compound, which was purified using a silica gel column and 60% EtOAc+petroleum ether 60-80° C. as eluant.

Yield: 241 g (60%).
$^1$H NMR ($CDCl_3$): δ 6.13 (s, 2H), 4.00 (m, 2H), 3.81 (m, 1H), 3.79 (s, 3H), 3.74 (s, 6H), 3.20 (m, 1H), 2.75 (m, 1H), 2.69 (m, 1H), 2.47 (s, 3H), 2.00 (m, 2H), 1.99 (s, 3H).

Method B:

Methanesulfonyl chloride (44.8 g, 0.4 mol) was added dropwise to a cooled and stirred solution of compound of example 2 (100 g, 0.35 mol) and triethylamine (71.88 g, 0.7 mol) in dry THF (1.0 L). The reaction mixture was further stirred for 45 min. at 0° C. The precipitate of triethylamine HCl was filtered and washed with dry THF (2×100 mL). The filtrate was added dropwise to a refluxing suspension of sodium acetate (115 g, 1.42 mol) in 2-propanol (1.0 L). The reaction mixture was refluxed for a further 15 min., diluted with EtOAc (1.0 L) and salts were filtered. The mixture of salts was washed with EtOAc (2×100 mL). The combined filtrate was concentrated to give a gum. Water (50 mL) was added to the gum with stirring to obtain a solid which was filtered and dried to yield the title compound.

Yield: 90 g (81%); mp: 74-77° C.
$^1$H NMR ($CDCl_3$): δ 6.13 (s, 2H), 4.00 (m, 2H), 3.81 (m, 1H), 3.79 (s, 3H), 3.76 (s, 6H), 3.20 (m, 1H), 2.75 (m, 1H), 2.69 (m, 1H), 2.47 (s, 3H), 2.00 (m, 2H), 1.99 (s, 3H).

EXAMPLE 4

(±)-trans-[1-Methyl-3-(2,4,6-trimethoxy-phenyl)-pyrrolidin-2-yl]-methanol

A 10% aqueous NaOH solution (596 mL) was added to a solution of the compound of example 3 (241 g, 0.75 mol) in methanol (596 mL). The reaction mixture was stirred at 50° C. for 45 min. It was concentrated to a gum and then poured into ice-cold water (2 L). The resulting solid was filtered to obtain the title compound.

Yield: 198 g (94%); mp: 82-85° C.
IR $cm^{-1}$: 3421, 3009, 1607.
$^1$H NMR ($CDCl_3$): δ 6.15 (s, 2H), 3.92 (m, 1H), 3.80 (s, 9H), 3.60 (dd, 1H), 3.45 (d, 1H), 3.20 (m, 1H), 2.78 (m, 1H), 2.50 (m, 1H), 2.42 (s, 3H), 2.00 (m, 1H), 1.92 (m, 1H).
MS (ES+): m/z 282 (M+1).

EXAMPLE 5

(±)-trans-Acetic acid 3-(3-acetyl-2-hydroxy-4,6-dimethoxy-phenyl)-1-methyl-pyrrolidin-2-yl methyl ester $BF_3$-etherate (32.5 mL, 250 mmol) was added dropwise, with stirring, at 0° C., under $N_2$ atmosphere to a solution of compound of example 4 (14.4 g, 51 mmol) in acetic anhydride (26 mL, 250 mmol). The reaction mixture was stirred at room temperature for 2 h. It was poured over crushed ice (1 kg), basified using a saturated aqueous $Na_2CO_3$ solution and extracted using EtOAc (3×200 mL). The organic extract was washed with brine, dried (anhydrous $Na_2SO_4$) and concentrated to get title compound.

Yield: 11.5 g (64%).
$^1$H NMR ($CDCl_3$): δ 14.00 (s, 1H), 5.94 (s, 1H), 4.01 (m, 2H), 3.89 (s, 3H), 3.85 (s, 3H), 3.74 (m, 1H), 3.14 (m, 1H), 2.75 (m, 1H), 2.70 (m, 1H), 2.60 (s, 3H), 2.42 (s, 3H), 2.07 (m, 1H), 2.03 (s, 3H), 1.85 (m, 1H).
MS (CI): m/z 352 (M+1).

EXAMPLE 6

(±)-trans-1-[2-Hydroxy-3-(2-hydroxymethyl-1-methyl-pyrrolidin-3-yl)-4,6-dimethoxy-phenyl]-ethanone To a solution of compound of example 5 (11 g, 31 mmol) in methanol (25 mL) was added with stirring, at room temperature, a 10% aqueous NaOH (25 mL) solution. The temperature of the reaction mixture was raised to 50° C. for 45 min. It was cooled to room temperature, acidified using conc. HCl and concentrated to remove methanol. It was basified using a saturated aqueous $Na_2CO_3$ solution. The precipitated title compound was filtered, washed with water and dried.

Yield: 8.5 g (87%).
$^1$H NMR ($CDCl_3$): δ 5.92 (s, 1H), 3.90 (m, 1H), 3.81 (s, 3H), 3.79 (s, 3H), 3.32 (d, 1H), 3.10 (m, 1H), 2.83 (m, 1H), 2.74 (m, 1H), 2.56 (s, 3H), 2.52 (m, 1H), 2.32 (s, 3H), 1.94 (m, 2H).

EXAMPLE 7

(±)-trans-2-(2-Chloro-phenyl)-8-(2-hydroxymethyl-1-methyl-pyrrolidin-3-yl)-5,7-dimethoxy-chromen-

53

4-one

Sodium hydride (50%, 2.17 g, 45.3 mmol) was added in portions to a solution of compound of example 6 (2.8 g, 9 mmol) in dry DMF (30 mL) at 0° C., under nitrogen atmosphere and with stirring. After 10 min., methyl 2-chlorobenzoate (5.09 g, 29.9 mmol) was added. The reaction mixture was stirred at 25° C. for 2 h. Methanol was added carefully below 20° C. The reaction mixture was poured over crushed ice (300 g), acidified with 1:1 HCl (pH 2) and extracted using EtOAc (2×100 mL). The aqueous layer was basified using a saturated $Na_2CO_3$ (pH 10) and extracted using $CHCl_3$ (3×200 mL). The organic layer was dried (anhydrous $Na_2SO_4$) and concentrated. To the residue, conc. HCl (25 mL) was added and stirred at room temperature for 2 h. The reaction mixture was poured over crushed ice (300 g) and made basic using a saturated aqueous $Na_2CO_3$ solution. The mixture was extracted using $CHCl_3$ (3×200 mL). The organic extract was washed with water, dried (anhydrous $Na_2SO_4$) and concentrated to obtain the title compound.

Yield: 2.5 g (64.6%); mp: 95-97° C.

IR $cm^{-1}$: 3431, 1648, 1598, 1571.

$^1H$ NMR ($CDCl_3$): δ 7.70 (dd, 1H), 7.55 (m, 1H), 7.45 (m, 2H), 6.55 (s, 1H), 6.45 (s, 1H), 4.17 (m, 1H), 4.05 (s, 3H), 3.95 (s, 3H), 3.65 (dd, 1H), 3.37 (dd, 1H), 3.15 (m, 1H), 2.77 (d, 1H), 2.50 (m, 1H), 2.30 (s, 3H), 2.05 (m, 2H).

MS (ES+): m/z 430 (M+1).

EXAMPLE 8

(±)-trans-2-(2-Chloro-phenyl)-5,7-dihydroxy-8-(2-hydroxymethyl-1-methyl-pyrrolidin-3-yl)-chromen-4-one Molten pyridine hydrochloride (2.5 g, 21 mmol, 10×w/w) was added to compound of example 7 (0.25 g, 0.58 mmol) and heated at 180° C. for 1.5 h. The reaction mixture was cooled to 25° C., diluted with MeOH (10 mL) and basified using $Na_2CO_3$ to pH 10. The mixture was filtered and the organic layer was concentrated. The residue was suspended in water (10 mL), stirred for 30 min., filtered and dried to obtain the title compound.

Yield: 0.166 g (70%); mp: 228-230° C.

IR $cm^{-1}$: 3422, 3135, 1664, 1623, 1559.

$^1H$ NMR ($CDCl_3$): δ 12.60 (s, 1H), 7.50 (m, 4H), 6.45 (s, 1H), 6.30 (s, 1H), 4.15 (m, 1H), 3.90 (m, 2H), 3.29 (m, 2H), 2.92 (m, 1H), 2.78 (s, 3H), 2.48 (m, 1H), 1.98 (m, 1H).

MS (ES+): m/z 402 (M+1).

Analysis: $C_{21}H_{20}ClNO_5 \cdot H_2O$ C, 59.45 (60.00); H, 5.17 (5.24); N, 3.68 (3.33); Cl, 8.84 (8.44).

EXAMPLE 9

(±)-trans-2-(2-Chloro-phenyl)-5,7-dihydroxy 8-(2-hydroxymethyl-1-methyl-pyrrolidin-3-yl-chromen-4-one hydrochloride Compound of example 8 (1 g, 2.4 mmol) was suspended in methanol (5 mL) and ethereal HCl (25 mL) was added. The suspension was stirred to get a clear solution. The solution was concentrated and dried to obtain the title compound.

Yield: 1.0 g (95.5%).

IR $cm^{-1}$: 3383, 1654, 1618, 1570.

$^1H$ NMR ($CD_3OD$): δ 7.80 (d, 1H), 7.55 (m, 3H), 6.53 (s, 1H), 6.37 (s, 1H), 4.23 (m, 1H), 3.89 (m, 2H), 3.63 (m, 1H), 3.59 (m, 1H), 3.38 (m, 1H), 2.90 (s, 3H), 2.45 (m, 1H), 2.35 (m, 1H).

MS (ES+): m/z 402 (M−36.5).

EXAMPLE 10

(−)-trans-[1-Methyl-3-(2,4,6-trimethoxy-phenyl)-pyrrolidin-2-yl]-methanol

Method A:

Compound of example 4 (27.3 g, 97.1 mmol), was dissolved in methanol (100 mL) and heated to 70° C. To this hot solution was added (+) DBTA (36.51 g, 101.9 mmol) and the heating was continued for 10 min. It was concentrated to get a solid (63.81 g), which was crystallized using methanol (45 mL) and isopropanol (319 mL). Filtration and an isopropanol wash with subsequent drying afforded the crystalline tartarate salt (13.14 g), $[\alpha]_D^{25}=+55.34°$ (c=1.14, methanol). This product was then recrystallized using methanol (10 mL) and isopropanol (40 mL). It was isolated as described above, yield: 9.04 g, $[\alpha]_D^{25}=+49.67°$ (c=1.248, methanol). The free base was obtained from this product as follows.

The salt (9 g) was suspended in ethyl acetate (100 mL). To this suspension 5% aqueous $NaHCO_3$ solution (100 mL) was added and the mixture was stirred for 30 minutes. The organic portion was separated and the aqueous portion was further extracted using ethyl acetate (2×50 mL). The organic portions were combined and concentrated to obtain the title compound.

Yield: 3.6 g (26.3%).

$[\alpha]_D^{25}=-17.6°$ (c=1.1, methanol).

$^1H$ NMR ($CDCl_3$): δ 6.13 (s, 2H), 3.90 (m, 1H), 3.79 (s, 3H), 3.74 (s, 6H), 3.51 (dd, 1H), 3.38 (d, 1H), 3.13 (m, 1H), 2.69 (m, 1H), 2.47 (m, 1H), 2.34 (s, 3H), 2.00 (m, 1H), 1.93 (m, 1H).

MS (ES+): m/z 282 (M+1).

Method B:

Compound of example 4 (27.3 g, 97.1 mmol), was dissolved in methanol (100 mL) and heated to 70° C. To this hot solution was added (+)-DBTA (36.51 g, 101.9 mmol) and the heating was continued for 10 min. It was concentrated to get a solid (63.81 g), which was crystallized using methanol (63 mL) and IPA (630 mL). Filtration and an IPA wash with subsequent drying afforded the crystalline tartarate salt (22.05 g), $[\alpha]_D^{25}=+55.34°$ (c=0.7, methanol). This product was then recrystallized using methanol (22 mL) and IPA (220 mL). It was isolated as described above, yield: 13.04 g (20.4%), $[\alpha]_D^{25}=+50.1°$ (c=0.7, methanol). The free base was obtained from this product as follows.

The salt (13.04 g) was suspended in ethyl acetate (100 mL). To this suspension 5% aqueous $NaHCO_3$ solution (100 mL) was added and the mixture was stirred for 30 min. The organic portion was separated and the aqueous portion was further extracted using ethyl acetate (2×50 mL). The organic portions were combined and concentrated to obtain the title compound.

Yield: 5.5 g (96.5%).

$[\alpha]_D^{25}=19.9°$ (c=0.7, methanol).

$^1H$ NMR ($CDCl_3$): δ 6.13 (s, 2H), 3.90 (m, 1H), 3.79 (s, 9H), 3.51 (dd, 1H), 3.38 (d, 1H), 3.13 (m, 1H), 2.69 (m, 1H), 2.47 (m, 1H), 2.34 (s, 3H), 2.00 (m, 1H), 1.93 (m, 1H).

MS (ES+): m/z 282 (M+1).

EXAMPLE 11

(−)-trans-Acetic acid 3-(3-acetyl-2-hydroxy-4,6-dimethoxy-phenyl)-1-methyl-pyrrolidin-2-yl methyl ester 11A. Compound of example 10, method A (14.4 g, 51 mmol) was subjected to Friedel Crafts acylation using $BF_3$-etherate (32.5 mL, 250 mmol) and acetic anhydride (26 mL, 250 mmol) as described in example 23, to obtain the title compound.

Yield: 12 g (66.8%)

$^1$H NMR (CDCl$_3$): δ 14.20 (s, 1H), 5.96 (s, 1H), 4.10 (d, 2H), 3.90 (s, 3H), 3.89 (s, 3H), 3.85 (m, 1H), 3.26 (m, 1H), 2.82 (m, 1H), 2.74 (m, 1H), 2.66 (s, 3H), 2.52 (s, 3H), 2.21 (m, 2H), 2.10 (s, 3H).

11B. Compound of example 10, method B (10 g, 35.58 mmol) was subjected to Friedel Crafts acylation using $BF_3$-etherate (25.2 g, 178 mmol) and acetic anhydride (18 g, 178 mmol) as described in example 5, to obtain the title compound.

Yield: 10 g (83%).

$^1$H NMR (CDCl$_3$): δ 14.20 (s, 1H), 5.96 (s, 1H), 4.10 (d, 2H), 3.90 (s, 3H), 3.89 (s, 3H), 3.85 (m, 1H), 3.26 (m, 1H), 2.82 (m, 1H), 2.74 (m, 1H), 2.66 (s, 3H), 2.52 (s, 3H), 2.21 (m, 2H), 2.10 (s, 3H).

EXAMPLE 12

(−)-trans-1-[2-Hydroxy-3-(2-hydroxymethyl-1-methyl-pyrrolidin-3-yl)-4,6-dimethoxy-phenyl)-ethanone 12A. Compound of example 11A (11 g, 31 mmol) in MeOH (25 mL) was subjected to hydrolysis using 10% aqueous NaOH (25 mL) solution as described in the example 6, to obtain the title compound.

Yield: 8 g (81.8%)

IR cm$^{-1}$: 3400, 3121, 3001, 1629, 1590.

$^1$H NMR (CDCl$_3$): δ 5.96 (s, 1H), 3.93 (m, 1H), 3.90 (s, 3H), 3.88 (s, 3H), 3.59 (dd, 1H), 3.37 (d, 1H), 3.13 (m, 1H), 2.75 (m, 1H), 2.61 (s, 3H), 2.59 (m, 1H), 2.37 (s, 3H), 2.00 (m, 2H).

MS (ES+): m/z 310 (M+1).

12B. Compound of example 1b (10 g, 28.4 mmol) in MeOH (25 mL) was subjected to hydrolysis using 10% aqueous NaOH (25 mL) solution as described in the example 6, to obtain the title compound.

Yield: 7.14 g (82%).

IR cm$^{-1}$: 3400, 3121, 3001, 1629, 1590.

$^1$H NMR (CDCl$_3$): δ 5.96 (s, 1H), 3.93 (m, 1H), 3.90 (s 3H), 3.88 (s, 3H), 3.59 (dd, 1H), 3.37 (d, 1H), 3.13 (m, 1H), 2.75 (m, 1H), 2.61 (s, 3H), 2.59 (m, 1H), 2.37 (s, 3H), 2.00 (m, 2H).

MS (ES+): m/z 310 (M+1).

EXAMPLE 13

(+)-trans-2-(2-Chloro-phenyl)-8-(2-hydroxymethyl-1-methyl-pyrrolidin-3-yl)-5,7-dimethoxy-chromen-4-one 13A. Compound of example 12A (0.75 g, 2.4 mmol), was reacted with methyl 2-chlorobenzoate (1.36 g, 7.9 mmol) in dry DMF (15 mL) in the presence of NaH (50%, 0.582 g, 12.9 mmol), using the procedure described in example 8 to get the title compound.

Yield: 0.67 g (64%); mp: 95-97° C.

IR cm$^{-1}$: 3400, 1660.

$^1$HNMR (CDCl$_3$): δ 7.7 (dd, 1H), 7.55 (m, 1H), 7.45 (m, 2H), 6.55 (s, 1H), 6.45 (s, 1H), 4.17 (m, 1H), 4.05 (s, 3H), 3.95 (s, 3H), 3.65 (dd, 1H), 3.37 (dd, 1H), 3.15 (m, 1H), 2.77 (d, 1H), 2.5 (m, 1H), 2.3 (s, 3H), 2.05 (m, 2H).

MS: m/e 430 (M+1).

13B. Compound of example 12b (0.7 g., 2.2 mmol) was reacted with methyl 2-chlorobenzoate (1.15 g, 6.75 mmol) in dry DMF (15 mL) in the presence of NaH (50%, 0.54 g, 11.25 mmol), using the procedure described in example 7 to afford the title compound.

Yield: 0.67 g (64%); mp: 91-93° C.

IR cm$^{-1}$: 3431, 1648, 1598, 1571.

$[α]_D^{25}$=+5.8° (c=0.7, methanol).

$^1$H NMR (CDCl$_3$): δ 7.70 (dd, 1H), 7.52 (m, 1H), 7.45 (m, 2H), 6.50 (s, 1H), 6.44 (s, 1H), 4.17 (m, 1H), 4.00 (s, 3H), 3.97 (s, 3H), 3.64 (dd, 1H), 3.40 (d, 1H), 3.15 (m, 1H), 2.74 (d, 1H), 2.52 (m, 1H), 2.32 (s, 3H), 2.00 (m, 2H).

MS (ES+): m/z 430 (M+1).

EXAMPLE 14

(+)-trans-2-(2-Chloro-phenyl)-5,7-dihydroxy-8-(2-hydroxymethyl-1-methyl-pyrrolidin-3-yl)-chromen-4-one 14A. Compound of example 13A (0.4 g, 0.9 mmol) subjected to demethylation using pyridine hydrochloride (4.1 g, 35.4 mmol) as described in example 9, afforded the title compound.

Yield: 0.2 g, (56%); mp: 228-230° C.

$^1$H NMR (CDCl$_3$): δ 12.6 (s, 1H), 7.5 (m, 4H), 6.45 (s, 1H), 6.3 (s, 1H), 4.15 (m, 1H), 3.9 (m, 2H), 3.29 (m, 2H), 2.92 (m, 1H), 2.78 (s, 3H), 2.48 (m, 1H), 1.98 (m, 1H).

MS: m/e 402 (M+1), 384 (M−18), 370 (M-31).

$[α]_D^{25}$=+12.12° (c=0.132, methanol:CHCl$_3$, 40:60).

14B. Compound of example 13B (0.4 g, 0.9 mmol) subjected to demethylation using pyridine hydrochloride (4.1 g, 35.4 mmol) as described in example 8, afforded the title compound.

Yield: 0.25 g (70%).

IR cm$^{-1}$: 3422, 3135, 1664, 1623, 1559.

$^1$H NMR (CDCl$_3$): δ 7.56 (d, 1H), 7.36 (m, 3H), 6.36 (s, 1H), 6.20 (s, 1H), 4.02 (m, 1H), 3.70 (m, 2H), 3.15 (m, 2H), 2.88 (m, 1H), 2.58 (s, 3H), 2.35 (m, 1H), 1.88 (m, 1H.

MS (ES+): m/z 402 (M+1).

Analysis: $C_{21}H_{20}ClNO_5$C, 62.24 (62.71); H, 5.07 (4.97); N, 3.60 (3.48); Cl, 9.01 (8.83).

EXAMPLE 15

(+)-trans-2-(2-Chloro-phenyl)-5,7-dihydroxy-8-(2-hydroxymethyl-1-methyl-pyrrolidin-3-yl)-chromen-4-one hydrochloride 15A. Compound of example 14A (1 g, 2.4 mmol) was suspended in methanol (5 mL) and ethereal HCl (10 mL) was added. The suspension was stirred to get a clear solution. The solution was concentrated and dried to obtain the title compound.

Yield: 1.0 g (95.5%).

IR cm$^{-1}$: 3383, 1654, 1618, 1570.

$^1$H NMR (CD$_3$OD): δ 7.80 (d, 1H), 7.55 (m, 3H), 6.53 (s, 1H), 6.37 (s, 1H), 4.23 (m, 1H), 3.89 (m, 2H), 3.63 (m, 1H), 3.59 (m, 1H), 3.38 (m, 1H), 2.90 (s, 3H), 2.45 (m, 1H), 2.35 (m, 1H).

MS (ES+): m/z 402 (M−36.5).

15B. Compound of example 14b (0.2 g, 0.48 mmol) was suspended in IPA (2 mL) and 3.5% HCl (5 mL) was added. The suspension was heated to get a clear solution. The solution was cooled and solid filtered to obtain the title compound.

Yield: 0.21 g (97%); mp: 188-192° C.
$[\alpha]_D^{25}$=+21.3° (c=0.2, methanol).
$^1$H NMR (CD$_3$OD): δ 7.80 (d, 1H), 7.60 (m, 3H), 6.53 (s, 1H), 6.37 (s, 1H), 4.23 (m, 1H), 3.89 (m, 2H), 3.63 (m, 1H), 3.59 (dd, 1H), 3.38 (m, 1H), 2.90 (s, 3H), 2.45 (m, 1H), 2.35 (m, 1H).
MS (ES+): m/z 402 (M−36.5).

EXAMPLE 16

(+)-trans-2-(2-Bromo-phenyl)-8-(2-hydroxymethyl-1-methyl-pyrrolidin-3-yl)-5,7-dimethoxy-chromen-4-one Sodium hydride (50%, 0.54 g, 11.3 mmol) was added in portions to a solution of compound of example 12A (0.7 g, 2.26 mmol) in dry DMF (10 mL) at 0° C., under nitrogen atmosphere and with stirring. After 10 min. methyl 2-bromobenzoate (1.6 g, 7.44 mmol) was added. The reaction mixture was stirred at room temperature for 2 h. Methanol was added carefully at below 20° C. followed by, addition of concentrated HCl (10 mL) and passage of a strong stream of HCl gas for 2 h. The reaction mixture was poured over crushed ice (75 g) and made basic using a saturated aqueous Na$_2$CO$_3$ solution. The mixture was extracted using CHCl$_3$ (3×50 mL). The organic extract was washed with water, dried (anhydrous Na$_2$SO$_4$) and concentrated to obtain the title compound which was purified using a silica gel column and a mixture of 2% methanol+1% liquor ammonia in CHCl$_3$ as eluant.

Yield: 0.4 g (37.3%).
$^1$H NMR (CDCl$_3$): δ 7.70 (d, 1H), 7.60 (d, 1H), 7.40 (m, 2H), 6.45 (s, 1H), 6.40 (s, 1H), 4.15 (m, 1H), 4.00 (s, 3H), 3.98 (s, 3H), 3.65 (dd, 1H), 3.38 (d, 1H), 3.08 (m, 1H), 2.68 (d, 1H), 2.45 (m, 1H), 2.27 (s, 3H), 2.05 (m, 2H).
MS (EI): m/z 474 (M$^+$).

EXAMPLE 17

(+)-trans-2-(2-Bromo-phenyl)-5,7-dihydroxy-8-(2-hydroxymethyl-1-methyl-pyrrolidin-3-yl)-chromen-4-one A mixture of compound of example 16 (0.36 g, 0.76 mmol) and dry pyridine hydrochloride (3.6 g, 31.6 mmol) was heated at 180° C. for 1.5 h. The reaction mixture was cooled to room temperature, treated with water (50 mL) and basified using an aqueous saturated Na$_2$CO$_3$ solution. It was extracted using CHCl$_3$ (3×100 mL). The organic extract was washed with water, dried (anhydrous Na$_2$SO$_4$) and concentrated. Traces of pyridine were removed using high vacuum. Purification was carried out using a silica gel column and a mixture of 5% methanol+1% liquor ammonia in CHCl$_3$ as eluant to obtain title compound.

Yield: 0.182 g (54%); mp: 235-237° C.
IR cm$^{-1}$: 3450, 1660.
MS (ES+): m/z 447 (M+1).

Analysis: C$_{21}$H$_{20}$BrNO$_5$, C, 56.53 (56.52); H, 4.65 (4.52); N, 3.17 (3.14); Br, 17.75 (17.90).

EXAMPLE 18

(+)-trans-8-(2-Hydroxymethyl-1-methyl-pyrrolidin-3-yl)-2-(2-iodo-phenyl)-5,7-dimethoxy-chromen-4-one Compound of example 12A (0.45 g, 1.46 mmol) in dry DMF (10 mL) reacted with methyl 2-iodobenzoate (2.5 g, 9.54 mmol) in the presence of NaH (50%, 0.35 g, 7.29 mmol) as described in example 16, afforded the title compound.

Yield: 0.29 g (38%).
$^1$H NMR (CDCl$_3$): δ 7.98 (d, 1H), 7.50 (m, 2H), 7.30 (s, 1H), 6.45 (s, 1H), 6.35 (s, 1H), 4.15 (m, 1H), 4.02 (s, 3H), 3.99 (s, 3H), 3.70 (dd, 1H), 3.55 (m, 1H), 3.25 (m, 1H), 3.05 (m, 1H), 2.57 (m, 1H), 2.40 (s, 3H), 2.15 (m, 2H).
MS (ES+): m/z 522 (M+1).

EXAMPLE 19

(+)-trans-5,7-Dihydroxy-8-(2-hydroxymethyl-1-methyl-pyrrolidin-3-yl)-2-(2-iodo-phenyl)-chromen-4-one Compound of example 18 (0.29 g, 0.588 mmol) subjected to demethylation using pyridine hydrochloride (3 g, 25.97 mmol) as described in example 17, afforded the title compound.

Yield: 0.145 g (50%); mp: 233-235° C.
IR cm$^{-1}$: 3400, 1660.
$^1$H NMR (DMSO d$_6$): δ 12.80 (s, 1H), 8.08 (d, 1H), 7.65 (m, 2H), 7.35 (m, 1H), 6.48 (s, 1H), 6.18 (s, 1H), 3.80 (m, 1H), 3.55 (m, 2H), 2.92 (m, 2H), 2.74 (m, 1H), 2.45 (s, 3H), 2.20 (m, 1H), 1.85 (m, 1H).
MS (CI): m/z 494 (M+1).
Analysis: C$_{21}$H$_{20}$INO$_5$.H$_2$OC, 49.5 (49.33); H, 4.05 (4.33); N, 2.84 (2.73); I, 24.48 (24.81).

EXAMPLE 20

(+)-trans-2-(2-Fluoro-phenyl)-8-(2-hydroxymethyl-1-methyl-pyrrolidin-3-yl)-5,7-dimethoxy-chromen-4-one Compound of example 12A (0.8 g, 2.5 mmol) in dry DMF (10 mL) treated with methyl 2-fluorobenzoate (1.76 g, 11.42 mmol) in the presence of NaH (50%, 0.62 g, 12.9 mmol) as described in example 16, afforded the title compound.

Yield: 0.68 g (65%).
$^1$H NMR (CDCl$_3$): δ 8.13 (t, 1H), 7.45 (m, 1H), 7.30 (m, 1H), 7.18 (m, 1H), 6.80 (s, 1H) 6.45 (s, 1H), 4.30 (m, 1H), 4.00 (s, 3H), 3.98 (s, 3H), 3.68 (dd, 1H), 3.38 (d, 1H), 3.25 (t, 1H), 2.75 (m, 2H), 2.40 (s, 3H), 2.10 (m, 2H).
MS (ES+): m/z 414 (M+1).

EXAMPLE 21

(+)-trans-2-(2-Fluoro-phenyl)-5,7-dihydroxy-8-(2-hydroxymethyl-1-methyl-pyrrolidin-3-yl)-chromen-4-one Compound of example 20 (0.07 g, 0.169 mmol) subjected to demethylation with pyridine hydrochloride (1 g, 8.65 mmol) as described in example 17 afforded the title compound.

Yield: 0.017 g (26%); mp: 206-208° C.
IR cm$^{-1}$: 3400, 1660.
$^1$H NMR (DMSO d$_6$): δ 8.08 (m, 1H), 7.65 (m, 1H), 7.40 (m, 2H), 6.68 (s, 1H), 6.18 (s, 1H), 4.20 (m, 1H), 3.85 (dd, 1H), 3.70 (m, 1H), 3.58 (m, 1H), 3.48 (m, 1H), 3.30 (m, 1H), 2.85 (s, 3H), 2.35 (m, 2H).
MS (CI): m/z 386 (M+1).
Analysis: C$_{21}$H$_{20}$FNO$_5$.H$_2$O C, 63.09 (62.53); H, 5.5 (4.99); N, 3.4 (3.4).

EXAMPLE 22

(±)-trans-2-(2-Chloro-5-fluoro-phenyl)-8-(2-hydroxymethyl-1-methyl-pyrrolidin-3-yl)-5,7-dimethoxy-chromen-4-one Compound of example 6 (1.0 g, 3.2 mmol) in dry DMF (25 mL) was reacted with methyl 2-chloro-5-fluorobenzoate (1.22 g, 6.4 mmol) in the presence of NaH (50%, 0.776 g, 16 mmol) as described in example 16, to obtain the title compound.
Yield: 0.9 g (63%).
$^1$H NMR (CDCl$_3$): δ 7.55 (m, 1H), 7.46 (m, 1H), 7.15 (m, 1H), 6.60 (s, 1H), 6.45 (s 1H), 4.25 (m, 1H), 4.05 (s, 3H), 4.03 (s, 3H), 3.70 (d, 1H), 3.40 (d, 1H), 3.30 (m, 1H), 2.60 (m, 1H), 2.58 (m, 1H), 2.30 (s, 3H), 2.00 (m, 2H).
MS (ES+): m/z 448 (M+1).

EXAMPLE 23

(±)-trans-2-(2-Chloro-5-fluoro-phenyl)-5,7-dihydroxy-8-(2-hydroxymethyl-1-methyl-pyrrolidin-3-yl)-chromen-4-one Compound of example 22 (0.8 g, 1.78 mmol) was demethylated using pyridine hydrochloride (8.0 g, 69.0 mmol) as described in example 17 to obtain the title compound.
Yield: 0.45 g (60%); mp: 253-254° C.
IR cm$^{-1}$: 3450, 1665.
$^1$H NMR (DMSO d$_6$): δ 7.72 (m, 2H), 7.49 (m, 1H), 6.53 (s, 1H), 6.12 (s, 1H), 3.85 (m, 1H), 3.47 (m, 2H), 2.91 (m, 2H), 2.76 (m, 1H), 2.47 (s, 3H), 2.20 (m, 1H), 1.80 (m, 1H).
MS (ES+): m/z 420 (M+1).
Analysis: C$_{21}$H$_{19}$ClFNO$_5$C, 60.2 (60.08); H, 4.53 (4.56); N, 3.86 (3.34); Cl, 8.17 (8.44).

EXAMPLE 24

(±)-trans-2-(2-Chloro-5-fluoro-phenyl)-5,7-dihydroxy-8-(2-hydroxymethyl-1-methyl-pyrrolidin-3-yl)-chromen-4-one hydrochloride Compound of example 23 (0.1 g, 0.244 mmol) was converted to its hydrochloride salt using the procedure described in example 9.
Yield: 0.108 g (100%).
$^1$H NMR (CD$_3$OD): δ 7.67 (m, 2H), 7.37 (m, 1H), 6.60 (s, 1H), 6.37 (s, 1H), 4.20 (m, 1H), 3.90 (m, 2H), 3.69 (m, 1H), 3.60 (dd, 1H), 3.45 (m, 1H), 2.98 (s, 3H), 2.52 (s, 1H), 2.29 (s, 1H).
MS (ES+): m/z 420 (M−36.5).

EXAMPLE 25

(±)-trans-2-(2-Chloro-5-fluoro-phenyl)-5,7-dihydroxy-8-(2-hydroxymethyl-1-methyl-pyrrolidin-3-yl)-chromen-4-one methane sulfonate (Compound No. 39)

Compound of example 23 (0.70 g, 1.66 mmol) in methanol (5 mL) was treated with methane sulfonic acid solution in methanol (5%, 3.2 mL, 1.66 mmol). A clear solution obtained was concentrated to obtain the title compound.
Yield: 0.750 g (87.6%); mp: 192-193° C.
$^1$H NMR (D$_2$O): δ 7.30 (m, 3H), 6.32 (s, 1H), 6.05 (s, 1H), 4.03 (m, 1H), 3.65 (m, 4H), 3.30 (m, 1H), 2.90 (s, 3H), 2.70 (s, 3H), 2.25 (m, 2H).
MS (ES+): m/z 420 (M−96).
Analysis: C$_{22}$H$_{23}$ClFNO$_8$S.2H$_2$O C, 47.52 (47.87); H, 4.94 (4.93); N, 2.66 (2.53); Cl, 6.49 (6.42); S, 6.18 (5.81).

EXAMPLE 26

(+)-trans-2-(2-Chloro-5-fluoro-phenyl)-8-(2-hydroxymethyl-1-methyl-pyrrolidin-3-yl)-5,7-dimethoxy-chromen-4-one Compound of example 12A (1.0 g, 3.2 mmol) in dry DMF (25 mL) was reacted with methyl 2-chloro-5-fluorobenzoate (1.22 g, 6.4 mmol) in the presence of NaH (50%, 0.776 g, 16 mmol) as described in example 16, to obtain the title compound.
Yield: 0.9 g (63%).
$^1$H NMR (CDCl$_3$): δ 7.57 (m, 1H), 7.46 (m, 1H), 7.16 (m, 1H), 6.58 (s, 1H), 6.45 (s 1H), 4.15 (m, 1H), 4.00 (s, 3H), 3.97 (s, 3H), 3.63 (dd, 1H), 3.32 (d, 1H), 3.13 (m, 1H), 2.61 (m, 1H), 2.53 (m, 1H), 2.29 (s, 3H), 2.00 (m, 2H).
MS (CI): m/z 448 (M+1).

EXAMPLE 27

(+)-trans-2-(2-Chloro-5-fluoro-phenyl)-5,7-dihydroxy-8-(2-hydroxymethyl-1-methyl-pyrrolidin-3-yl)-chromen-4-one Compound of example 26 (0.8 g, 1.78 mmol) was demethylated using pyridine hydrochloride (8.0 g, 69.0 mmol) as described in example 17 to obtain the title compound.
Yield: 0.45 g (60%); mp: 253-254° C.
IR cm$^{-1}$: 3450, 1665.
$^1$H NMR (DMSO d$_6$): δ 12.70 (s, 1H), 7.75 (m, 2H), 7.54 (m, 1H), 6.55 (s, 1H), 6.14 (s, 1H), 3.80 (m, 1H), 3.51 (m, 3H), 2.94 (m, 2H), 2.46 (s, 3H), 2.15 (m, 1H), 1.86 (m, 1H).
MS (ES+): m/z 420 (M+1).
Analysis: C$_{21}$H$_{19}$ClFNO$_5$C, 60.2 (60.08); H, 4.53 (4.56); N, 3.86 (3.34); Cl, 8.17 (8.44).

EXAMPLE 28

(+)-trans-2-(2-Chloro-5-fluoro-phenyl)-5,7-dihydroxy-8-(2-hydroxymethyl-1-methyl-pyrrolidin-3-yl)-chromen-4-one hydrochloride Compound of example 27 (0.1 g, 0.244 mmol) was converted to its hydrochloride salt using procedure as described in example 9.
Yield: 0.108 g (100%).
$[α]_D^{25}$=+18.05° (c=0.7, methanol).
$^1$H NMR (CD$_3$OD): δ 7.67 (m, 2H), 7.37 (m, 1H), 6.60 (s, 1H), 6.37 (s, 1H), 4.25 (m, 1H), 3.90 (m, 2H), 3.69 (m, 1H), 3.60 (dd, 1H), 3.45 (m, 1H), 2.98 (s, 3H), 2.52 (m, 1H), 2.29 (m, 1H).

MS (ES+): m/z 420 (M−36.5).

EXAMPLE 29

(+)-trans-2-(2-Bromo-5-fluoro-phenyl)-8-(2-hydroxymethyl-1-methyl-pyrrolidin-3-yl)-5,7-dimethoxy-chromen-4-one Compound of example 12A (6 g, 19.42 mmol) in dry DMF (60 mL) was reacted with methyl 2-bromo-5-fluorobenzoate (6.7 g, 28.75 mmol) in the presence of NaH (50%, 3.88 g, 80.8 mmol) as detailed in example 16, to obtain the title compound.

Yield: 3.94 g (41.2%).

$^1$H NMR (CDCl$_3$): δ 7.65 (m, 1H), 7.45 (m, 1H), 7.10 (m, 1H), 6.47 (s, 1H), 6.45 (s, 1H), 4.15 (m, 1H), 4.00 (s, 3H), 3.97 (s, 3H), 3.64 (dd, 1H), 3.35 (d, 1H), 3.10 (m, 1H), 2.64 (m, 1H), 2.45 (m, 1H), 2.27 (s, 3H), 2.00 (m, 2H).

MS (ES+): m/z 493 (M+1).

EXAMPLE 30

(+)-trans-2-(2-Bromo-5-fluoro-phenyl)-5,7-dihydroxy-8-(2-hydroxymethyl-1-methyl-pyrrolidin-3-yl)-chromen-4-one Compound of example 29 (3.9 g, 7.92 mmol) was subjected to demethylation using pyridine hydrochloride (39 g, 337.6 mmol) as described in example 17, to obtain the title compound.

Yield: 1.4 g (38.14%); mp: 145-147° C.

IR cm$^{-1}$: 3650, 1640.

$^1$H NMR (CDCl$_3$+TFA): δ 12.40 (s, 1H), 7.55 (m, 1H), 7.28 (m, 1H), 7.00 (m, 1H), 6.31 (s, 1H), 6.28 (s, 1H), 3.98 (m, 1H), 3.68 (m, 2H), 3.50 (m, 2H), 3.15 (m, 1H), 2.80 (s, 3H), 2.30 (m, 1H), 2.08 (m, 1H).

MS (ES+): m/z 465 (M+1).

EXAMPLE 31

(+)-trans-2-(2-Bromo-5-fluoro-phenyl)-5,7-dihydroxy-8-(2-hydroxymethyl-1-methyl-pyrrolidin-3-yl)-chromen-4-one hydrochloride Compound of example 30 (1.0 g) was converted to its hydrochloride salt using procedure as described in example 9.

Yield: 1.0 g (93%).

MS (ES+): m/z 465 (M−36.5).

EXAMPLE 32

(+)-trans-2-(2-Bromo-5-fluoro-phenyl)-5,7-dihydroxy-8-(2-hydroxymethyl-1-methyl-pyrrolidin-3-yl)-chromen-4-one methane sulfonate Compound of example 30 (1.97 g, 4.25 mmol) was converted to its methane sulfonate salt using the procedure as described in example 25.

Yield: 2.3 g (96.63%).

$^1$H NMR (D$_2$O): δ 7.58 (m, 1H), 7.20 (m, 1H), 7.11 (m, 1H), 6.30 (s, 1H), 6.02 (s, 1H), 4.02 (m, 1H), 3.85 (m, 2H), 3.45 (m, 2H), 3.35 (m, 1H), 2.83 (s, 3H), 2.70 (s, 3H), 2.20 (m, 2H).

Analysis: C$_{22}$H$_{23}$BrNFO$_8$S.H$_2$O, C, 46.08 (45.68); H, 4.61 (4.35); N, 2.63 (2.42), Br, 14.73 (13.81); S, 4.99 (5.54).

MS (ES+): m/z 465 (M−96).

EXAMPLE 33

(±)-trans-2-(2-Bromo-5-methoxy-phenyl)-8-(2-hydroxymethyl-1-methyl-pyrrolidin-3-yl)-5,7-dimethoxy-chromen-4-one Compound of example 6 (1.5 g, 4.85 mmol) in dry DMF (25 mL) was reacted with methyl 2-bromo-5-methoxybenzoate (3.11 g, 12.69 mmol) in the presence of NaH (50%, 1.16 g, 24.17 mmol) as described in example 16, to obtain the title compound.

Yield: 1.8 g (73.6%).

$^1$H NMR (CDCl$_3$): δ 7.55 (d, 1H), 7.12 (d, 1H), 6.90 (dd, 1H), 6.42 (s, 1H), 6.38 (s, 1H), 4.15 (m, 1H), 4.00 (s, 3H), 3.98 (s, 3H), 3.85 (s, 3H), 3.65 (dd, 1H), 3.35 (d, 1H), 3.15 (m, 1H), 2.75 (d, 1H), 2.50 (m, 1H), 2.34 (s, 3H), 2.05 (m, 2H).

MS (EI): m/z 504 (M$^+$).

EXAMPLE 34

(±)-trans-2-(2-Bromo-5-methoxy-phenyl)-5,7-dihydroxy-8-(2-hydroxymethyl-1-methyl-pyrrolidin-3-yl)-chromen-4-one (Compound A) and (±)-trans-2-(2-Bromo-5-hydroxy-phenyl)-5,7-dihydroxy-8-(2-hydroxymethyl-1-methyl-pyrrolidin-3-yl)-chromen-4-one (Compound B)

Compound of example 33 (0.97 g, 1.92 mmol) was demethylated using pyridine hydrochloride (15 g, 129.87 mmol) as described in example 17 to obtain the title compounds (A) & (B) respectively.

Compound (A):

Yield: 0.2 g (21.8%); mp: 233-235° C.

$^1$H NMR (DMSO d$_6$): δ 12.80 (s, 1H), 7.80 (d, 1H), 7.35 (s, 1H), 7.15 (d, 1H), 6.50 (s, 1H), 6.15 (s, 1H), 3.88 (m, 1H), 3.80 (s, 3H), 3.55 (m, 2H), 2.98 (m, 2H), 2.88 (m, 1H), 2.40 (s, 3H), 2.10 (m, 1H), 1.90 (m, 1H). MS (EI): m/z 476 (M$^+$).

Compound (B):

Yield: 0.14 g (15.7%); mp: 256-258° C.

$^1$H NMR (DMSO d$_6$): δ 12.80 (s, 1H), 7.75 (d, 1H), 7.15 (d, 1H), 6.90 (m, 1H), 6.50 (s, 1H), 6.15 (s, 1H), 3.78 (m, 1H), 3.45 (m, 2H), 3.00 (m, 2H), 2.80 (m, 1H) 2.45 (s, 3H), 2.15 (m, 1H), 1.95 (m, 1H).

MS (ES+): m/z 463 (M+1).

EXAMPLE 35

(+)-trans-2-(2-Bromo-5-methoxy-phenyl)-8-(2-hydroxymethyl-1-methyl-pyrrolidin-3-yl)-5,7-dimethoxy-chromen-4-one Compound of example 12A (1.9 g, 6.12 mmol) in dry DMF (25 mL) was reacted with methyl 2-bromo-5-methoxybenzoate (4.3 g, 17.55 mmol) in the presence of NaH (50%, 1.92 g, 40 mmol) as described in example 16, to obtain the title compound.

Yield: 2.0 g (66%).

$^1$H NMR (CDCl$_3$): δ 7.58 (d, 1H), 7.10 (d, 1H), 6.92 (dd, 1H), 6.48 (s, 1H), 6.38 (s, 1H), 4.15 (m, 1H), 4.00 (s, 3H), 3.98 (s, 3H), 3.85 (s, 3H), 3.62 (dd, 1H), 3.35 (d, 1H), 3.10 (t, 1H), 2.70 (d, 1H), 2.50 (m, 1H), 2.28 (s, 3H), 1.90 (m, 2H).

MS (EI): m/z 504 (M+).

EXAMPLE 36

(+)-trans-2-(2-Bromo-5-methoxy-phenyl)-5,7-dihydroxy-8-(2-hydroxymethyl-1-methyl-pyrrolidin-3-yl)-chromen-4-one (Compound A) and (+)-trans-2-(2-Bromo-5-hydroxy-phenyl)-8-(2-hydroxymethyl-1-methylpyrrolidin-3-yl)-5,7-dihydroxy-chromen-4-one (Compound B)

Compound of example 35 (1.7 g, 3.37 mmol) was demethylated using pyridine hydrochloride (24 g, 236 mmol) as described in example 17 to obtain the title compounds (A) & (B) respectively.

Compound (A):
Yield: 0.4 g (25%); mp: 233-235° C.
IR cm$^{-1}$: 3400, 1663.
MS (EI): m/z 476 (M+).
Analysis: $C_{22}H_{22}BrNO_6.0.5H_2O$, C, 54.21 (54.44); H, 4.76 (4.77); N, 2.42 (2.88); Br, 16.12 (16.49).

Compound (B):
Yield: 0.23 g (15%); mp: 256-258° C.
$^1$H NMR (DMSO d$_6$): δ 12.80 (s, 1H), 7.75 (d, 1H), 7.10 (d, 1H), 6.90 (m, 1H), 6.50 (s, 1H), 6.20 (s, 1H), 3.80 (s, 1H), 3.55 (m, 2H), 2.98 (m, 2H), 2.80 (m, 1H), 2.48 (s, 3H), 2.22 (m, 1H), 1.85 (m, 1H).
MS (ES−): m/z 461 (M−1).

EXAMPLE 37

(+)-trans-2-(2-Chloro-5-methyl-phenyl)-8-(2-hydroxymethyl-1-methyl-pyrrolidin-3-yl)-5,7-dimethoxy-chromen-4-one Compound of example 12A (1 g, 3.2 mmol) in dry DMF (30 mL) was reacted with methyl 2-chloro-5-methylbenzoate (3.97 g, 21.5 mmol) in the presence of NaH (50%, 0.776 g, 16.2 mmol)) as described in example 16, to get the title compound.
Yield: 0.537 g (37.4%).
$^1$H NMR (CDCl$_3$): δ 7.58 (s, 1H), 7.40 (d, 1H), 7.20 (d, 1H), 6.55 (s, 1H), 6.45 (s, 1H), 4.20 (m, 1H), 4.00 (s, 3H), 3.97 (s, 3H), 3.65 (dd, 1H), 3.40 (d, 1H), 3.18 (m, 1H), 2.75 (d, 1H), 2.55 (m, 1H), 2.40 (s, 3H), 2.35 (s, 3H), 2.05 (m, 2H).
MS (ES+): m/z 444 (M+1).

EXAMPLE 38

(+)-trans-2-(2-Chloro-5-methyl-phenyl)-5,7-dihydroxy-8-(2-hydroxymethyl-1-methyl-pyrrolidin-3-yl)-chromen-4-one Compound of example 37 (0.48 g, 1.1 mmol) was reacted with pyridine hydrochloride (5 g, 43.3 mmol) as described in example 17 to obtain the title compound.
Yield: 0.31 g (68%); mp: 206-208° C.
$^1$H NMR (CDCl$_3$): δ 12.59 (s, 1H), 7.35 (m, 2H), 7.18 (d, 1H), 6.35 (s, 1H), 6.20 (s, 1H), 4.05 (d, 1H), 3.72 (m, 2H), 3.15 (m, 2H), 2.90 (m, 1H), 2.60 (s, 3H), 2.35 (s, 3H), 2.30 (m, 1H), 1.90 (m, 1H).
MS (EI): m/z 415 (M+).

EXAMPLE 39

(+)-trans-2-(2-Bromo-5-nitro-phenyl)-8-(2-hydroxymethyl-1-methyl-pyrrolidin-3-yl)-5,7-dimethoxy-chromen-4-one 2-Bromo-5-nitrobenzoic acid (2.85 g, 12.5 mmol) was added to a solution of compound of example 11A (2.2 g, 6.27 mmol) in dry pyridine (25 mL), with stirring, under N$_2$ atmosphere at 0° C. POCl$_3$ (5.2 mL, 8.73 g, 57.32 mmol) was added dropwise and the reaction mixture stirred for 1.5 h. at 0-5° C. It was then poured over crushed ice, treated with saturated aqueous Na$_2$CO$_3$ solution and extracted with chloroform (3×200 mL). The organic extract was washed with brine, dried (anhydrous Na$_2$SO$_4$) and concentrated. Traces of pyridine were removed under high vacuum to obtain (+)-trans-2-Bromo-5-nitro-benzoic acid 2-(2-acetoxymethyl-1-methyl-pyrrolidin-3-yl)-6-acetyl-3,5-dimethoxy-phenyl ester (3.62 g, 6.25 mmol) a viscous oil, which was converted to the title compound using NaH (50%, 1.5 g, 31.2 mmol) in dry 1,4-dioxane (50 mL) followed by treatment with HCl as described in example 16.
Yield: 0.36 g (10%).
$^1$H NMR (CDCl$_3$): δ 8.50 (d, 1H), 8.22 (dd, 1H), 7.90 (d, 1H), 6.48 (s, 1H), 6.46 (s, 1H), 4.18 (m, 1H), 4.02 (s, 3H), 3.98 (s, 3H), 3.65 (dd, 1H), 3.35 (d, 1H), 3.15 (m, 1H), 2.72 (m, 1H), 2.50 (m, 1H), 2.32 (s, 3H), 2.02 (m, 2H).
MS (EI): m/z 519 (M+).

EXAMPLE 40

(+)-trans-2-(2-Bromo-5-nitro-phenyl)-8-(2-hydroxymethyl-1-methylpyrrolidin-3-yl)-5,7-dihydroxy-chromen-4-one Compound of example 39 (0.12 g, 0.23 mmol) was demethylated using pyridine hydrochloride (1.2 g, 10.39 mmol) as described in example 17 to obtain the title compound.
Yield: 0.07 g (61%).
IR cm$^{-1}$: 3350, 1660.
$^1$H NMR (DMSO d$_6$): δ 12.70 (s, 1H), 8.65 (d, 1H), 8.45 (dd, 1H), 8.00 (d, 1H), 6.65 (s, 1H), 6.25 (s, 1H), 3.75 (m, 1H), 3.48 (m, 2H), 2.98 (m, 2H), 2.85 (m, 1H), 2.50 (s, 3H), 2.15 (m, 1H), 1.86 (m, 1H).
MS (EI): m/z 491 (M+).

EXAMPLE 41

(+)-trans-2-(2-Bromo-4-nitro-phenyl)-8-(2-hydroxymethyl-1-methylpyrrolidin-3-yl)-5,7-dimethoxy-chromen-4-one 2 Bromo-4-nitrobenzoic acid (3.70 g, 15 mmol) was reacted with compound of example 11A (2.12 g, 6 mmol) in dry pyridine (25 mL) using POCl$_3$ (7 g, 45.8 mmol) as described in example 53 to obtain (+)-trans-2-Bromo-4 nitrobenzoic acid 2-(2-acetoxymethyl-1-methyl-pyrrolidin-3-yl)-6-acetyl-3,5-dimethoxy-phenyl ester (3.4 g, 5.9 mmol) a viscous oil, which was converted to the title using NaH (50%, 2.8 g, 50 mmol) in dry 1,4-dioxane (100 mL) followed by treatment with HCl as described in example 16.
Yield: 11%
IR cm$^{-1}$: 3400, 1660, 1525, 1350.
$^1$HNMR (CDCl$_3$): δ 8.6 (s, 1H), 8.32 (d, 1H), 7.95 (d, 1H), 6.6 (s, 1H), 6.44 (s, 1H), 4.2 (m, 1H), 4.02 (s, 3H), 3.98 (s, 3H), 3.65 (dd, 1H), 3.2 (m, 1H), 2.75 (d, 1H), 2.6 (d, 1H), 2.45 (s, 3H), 2.1 (m, 2H).
MS (ES+): m/z 520 (M+1).

EXAMPLE 42

(+)-trans-2-(2-Bromo-4-nitro-phenyl)-5,7-dihydroxy-8-(2-hydroxymethyl-1-methyl-pyrrolidin-3-yl)-chromen-4-one Compound of example 41 (0.3 g, 0.6 mmol) was demethylated using pyridine hydrochloride (3 g, 26 mmol) as described in example 17 to obtain the title compound.

Yield: 0.153 g (52%); mp: 186° C.
IR cm$^{-1}$: 3421, 1665, 1627, 1524.
$^1$H NMR (CDCl$_3$+DMSO d$_6$): δ 12.20 (s, 1H), 8.54 (s, 1H), 8.27 (dd, 1H), 7.75 (d, 1H), 6.39 (s, 1H), 6.23 (s, 1H), 3.96 (m, 1H), 3.72 (m, 2H), 3.34 (m, 1H), 3.18 (m, 2H), 2.61 (s, 3H), 2.37 (m, 1H), 2.00 (m, 1H).
MS (EI): m/z 491 (M$^+$).
Analysis: C$_{21}$H$_{19}$BrN$_2$O$_7$.0.5H$_2$O. C, 46.96 (46.94); H, 4.3 (3.91); N, 5.38 (5.21), Br, 21.21 (21.51).

EXAMPLE 43

(+)-trans-2-(2-Bromo-4-nitro-phenyl)-5,7-dihydroxy-8-(2-hydroxymethyl-1-methyl-pyrrolidin-3-yl)-chromen-4-one hydrochloride Compound of example 42 (0.1 g 0.2 mmol) was converted to its hydrochloride salt using procedure described in example 9.

Yield: 0.1 g (94.7%).
$^1$H NMR (CD$_3$OD): δ 8.65 (s, 1H), 8.38 (dd, 1H), 8.00 (dd, 1H), 6.59 (s, 1H), 6.38 (s, 1H), 4.21 (m, 1H), 3.90 (m, 2H), 3.63 (m, 2H), 3.42 (m, 1H), 2.98 (s, 3H), 2.50 (m, 1H), 2.29 (m, 1H).
IR cm$^{-1}$: 3421, 1665, 1627, 1524.
MS (EI): m/z 491 (M−36.5).
Analysis: C$_{21}$H$_{20}$BrClN$_2$O$_7$.2H$_2$O. C, 44.58 (44.7); H, 4.12 (4.25); N, 4.76 (4.96), Halogens (Cl+Br), 20.39 (20.48).

EXAMPLE 44

(+) Acetic acid 3-[2-(2-bromo-4-nitro-phenyl)-5,7-dihydroxy-4-oxo-4H-chromen-8-yl]-1-methyl-pyrrolidin-2-ylmethyl ester Compound of example 42 (0.1 g, 0.2 mmol) was stirred in dry dichloromethane (10 mL) with acetic anhydride (0.3 mL, 1 mmol) and catalytic amount of dimethylaminopyridine at 25° C. After 1 h. saturated sodium carbonate solution (8 mL) was added to the reaction mixture and stirred for 15 min. The organic layer was separated and aqueous layer was extracted with CHCl$_3$ (3×50 mL). The combined organic layer was concentrated and product obtained was purified by column chromatography and 10% CH$_3$CN in CHCl$_3$+1% liquor NH$_3$ as eluant to obtain the title compound.

Yield: 0.078 g (62%).
$^1$H NMR (CDCl3): δ 12.43 (s, 1H), 8.61 (s, 1H), 8.32 (d, 1H), 7.74 (d, 1H), 6.43 (s, 1H), 6.32 (s, 1H), 4.28 (m, 2H), 3.95 (dd, 1H), 3.42 (m, 1H), 3.40 (m, 1H), 2.80 (m, 1H), 2.63 (s, 3H), 2.43 (m, 1H), 2.00 (m, 1H), 1.99 (s, 3H).
MS (EI): m/z 533.5 (M$^+$).

EXAMPLE 45

(+) Acetic acid 3-[2-(2-bromo-4-nitro-phenyl)-5,7-dihydroxy-4-oxo-4H-chromen-8-yl]-1-methyl-pyrrolidin-2-yl methyl ester hydrochloride Compound of example 44 (0.05 g 0.09 mmol) was converted to its hydrochloride salt using procedure described in example 9.

Yield: 0.05 g, (83%).
MS (EI): m/z 533 (M−36.5).
Analysis: C$_{23}$H$_{22}$BrClN$_2$O$_8$ 2.5H$_2$O. C, 44.91 (44.81); H, 4.31 (4.39); N, 4.11 (4.55).

EXAMPLE 46

(+)-trans-2-(2,4-Dichloro-5-fluoro-phenyl)-8-(2-hydroxymethyl-1-methyl-pyrrolidin-3-yl)-5,7-dimethoxy-chromen-4-one Compound of example 12A (0.8 g, 2.58 mmol) in dry DMF (10 mL) was reacted with 2,4-dichloro-5-fluoro-benzoyl chloride (0.887 g, 3.9 mmol) in the presence of NaH (50%, 0.62 g, 12.5 mmol) as detailed in example 16, to obtain the title compound.

Yield: 0.54 g (43.4%).
$^1$H NMR (CDCl$_3$): δ 7.75 (d, 1H), 7.57 (d, 1H), 6.60 (s, 1H), 6.45 (s, 1H), 4.20 (m, 1H), 3.99 (s, 3H), 3.97 (s, 3H), 3.65 (dd, 1H), 3.36 (d, 1H), 3.20 (m, 1H), 2.65 (m, 2H), 2.38 (s, 3H), 2.10 (m, 2H).
MS (ES+): m/z 482 (M+1).

EXAMPLE 47

(+)-trans-2-(2,4-Dichloro-5-fluoro-phenyl)-5,7-dihydroxy-8-(2-hydroxymethyl-1-methyl-pyrrolidin-3-yl)-chromen-4-one Compound of example 46 (0.53 g, 1.1 mmol) was subjected to demethylation using pyridine hydrochloride (5.5 g, 47.6 mmol) as described in example 17 to obtain the title compound.

Yield: 0.29 g (58%).
IR cm$^{-1}$: 3422, 1664, 1618, 1401.
$^1$H NMR (CDCl$_3$+DMSO d$_6$): δ 7.50 (m, 2H), 6.42 (s, 1H), 6.19 (s, 1H), 4.04 (m, 1H), 3.71 (m, 2H), 3.16 (m, 2H), 2.88 (m, 1H), 2.58 (s, 3H), 2.36 (m, 1H), 1.92 (m, 1H).
MS (ES+): m/z 454 (M+1).

EXAMPLE 48

(+)-trans-2-(2,4-Dichloro-5-fluoro-phenyl)-5,7-dihydroxy-8-(2-hydroxymethyl-1-methyl-pyrrolidin-3-yl)-chromen-4-one hydrochloride Compound of example 47 (0.89 g, 1.96 mmol) was converted to its hydrochloride salt using procedure as described in example 9.

Yield: 0.91 g (92%).
$^1$H NMR (CD$_3$OD): δ 7.86 (m, 2H), 6.65 (s, 1H), 6.38 (s, 1H), 4.26 (q, 1H), 3.87 (m, 2H), 3.71 (m, 1H), 3.60 (dd, 1H), 3.56 (q, 1H), 2.99 (s, 3H), 2.55 (m, 1H), 2.28 (m, 1H).
IR cm$^{-1}$: 3386, 1657.
MS (ES+): m/z 454 (M−36.5).
Analysis: C$_{21}$H$_{19}$Cl$_3$FNO$_5$, C, 51.08 (51.35); H, 4.26 (3.87); N, 3.13 (2.85), Cl, 21.99 (21.70).

EXAMPLE 49

(+)-trans-2-(2,4-Dichloro-5-fluoro-phenyl)-5,7-dihydroxy-8-(2-hydroxymethyl-1-methyl-pyrrolidin-3-yl)-chromen-4-one methane sulfonate Methanesulfonic acid (0.012 g, 0.125 mmol) was added to the suspension of compound of example 47 (0.05 g, 0.11 mmol) in methanol (2 mL). It was stirred for 5 min. at 25° C. to obtain clear solution. The solvent was removed under reduced pressure to obtain residue. The residue was washed twice with dry ether (2×5 mL) and dried under high vacuum (0.1 mm) to obtain the title compound.

Yield: 0.054 g (90%).

Analysis: $C_{22}H_{22}Cl_2FNO_8S.2.5H_2O$ C, 44.26 (44.34); H, 4.42 (4.53); N, 2.58 (2.35); Cl, 12.11 (11.92).

EXAMPLE 50

(+)-trans-2-(2,4-Dichloro-5-fluoro-phenyl)-5,7-dihydroxy-8-(2-hydroxymethyl-1-methyl-pyrrolidin-3-yl)-chromen-4-one citrate Citric acid monohydrate (0.023 g, 0.11 mmol) was added to the suspension of compound of example 47 (0.05 g, 0.11 mmol) in methanol (2 mL). It was stirred for 10 min. at 50-55° C. The reaction mixture was concentrated and solid was dried to obtain the title compound.

Yield: 0.065 g (91.5%).

Analysis: $C_{27}H_{26}Cl_2FNO_{12}$ C, 49.75 (50.17); H, 4.25 (4.05); N, 2.60 (2.17); Cl, 10.69 (10.97).

EXAMPLE 51

(+)-trans-2-(2,4-Dichloro-5-fluoro-phenyl)-5,7-dihydroxy-8-(2-hydroxymethyl-1-methyl-pyrrolidin-3-yl)-chromen-4-one tartrate Tartaric acid (0.016 g, 0.11 mmol) was added to the suspension of compound of example 47 (0.05 g, 0.11 mmol) in methanol (2 mL). It was stirred for 10 min. at 50-55° C. The reaction mixture was concentrated and solid was dried to obtain the title compound.

Yield: 0.06 g (90.19%).

Analysis: $C_{25}H_{24}Cl_2FNO_{11}.2.0H_2O$ C, 47.43 (46.84); H, 4.13 (4.37); N, 2.40 (2.18); Cl, 10.77 (11.08).

EXAMPLE 52

(+)-trans-2-(2,4-Dichloro-5-fluoro-phenyl)-5,7-dihydroxy-8-(2-hydroxymethyl-1-methyl-pyrrolidin-3-yl)-chromen-4-one maleate Maleic acid (0.0127 g, 0.11 mmol) was added to the suspension of compound of example 47 (0.05 g, 0.11 mmol) in methanol (2 mL). It was stirred for 5 min. at 50° C. to get clear solution. The reaction mixture was concentrated and solid was dried to obtain the title compound.

Yield: 0.059 g (90.19%).

Analysis: $C_{25}H_{22}Cl_2FNO_9.1.5H_2O$ C, 50.54 (50.23); H, 4.08 (4.18); N, 2.31 (2.34); Cl, 11.83 (11.88).

EXAMPLE 53

(+)-trans-2-(2,4-Dichloro-5-fluoro-phenyl)-5,7-dihydroxy-8-(2-hydroxymethyl-1-methyl-pyrrolidin-3-yl)-chromen-4-one acetate Acetic acid (0.0068 g, 0.11 mmol) was added to the suspension of compound of example 47 (0.05 g, 0.11 mmol) in methanol (2 mL). It was stirred for 5 min. at 50-55° C. to get clear solution. The reaction mixture was concentrated and solid was dried to obtain the title compound.

Yield: 0.05 g (88.33%).

Analysis: $C_{23}H_{22}Cl_2FNO_9$ C, 53.67 (53.71); H, 4.63 (4.31); N, 3.08 (2.72); Cl, 13.93 (13.79).

EXAMPLE 54

(+)-trans-2-(2,4-Dichloro-5-fluoro-phenyl)-5,7-dihydroxy-8-(2-hydroxymethyl-1-methyl-pyrrolidin-3-yl)-chromen-4-one sulfate $H_2SO_4$ solution (55 µL, 5% methanolic solution, 0.055 mmol) was added to the suspension of compound of example 47 (0.025 g, 0.055 mmol) in methanol (2 mL). It was stirred for 5 min at 50-55° C. The reaction mixture was concentrated and solid was dried to obtain the title compound.

Yield: 0.025 g (82.24%).

MS (ES−): m/z 550 (M−1).

EXAMPLE 55

(+)-trans-2-(2,4-Dichloro-5-fluoro-phenyl)-5,7-dihydroxy-8-(2-hydroxymethyl-1-methyl-pyrrolidin-3-yl)-chromen-4-one nitrate $HNO_3$ solution (55 µL, 6.9% methanolic solution, 0.055 mmol) was added to the suspension of compound of example 47 (0.025 g, 0.055 mmol) in methanol (2 mL). It was stirred for 5 min. at 50-55° C. to get clear solution. The reaction mixture was concentrated and solid was dried to obtain the title compound.

Yield: 0.025 g (87.81%).

MS (ES−): m/z 515 (M−1).

EXAMPLE 56

(+)-trans-8-(2-Hydroxymethyl-1-methyl-pyrrolidin-3-yl)-5,7-dimethoxy-2-phenyl-chromen-4-one Compound of example 12A (1 g, 3.23 mmol) in dry DMF (15 mL) was reacted with methyl benzoate (2.29 g, 16.84 mmol) in the presence of NaH (50%, 0.77 g, 16.04 mmol) as described in example 16 to obtain the title compound.

Yield: 0.49 g (38.3%).

$^1$H NMR (CDCl$_3$): δ 8.00 (m, 2H), 7.50 (m, 3H), 6.68 (s, 1H), 6.45 (s, 1H), 4.40 (m, 1H), 4.02 (s, 3H), 3.99 (s, 3H), 3.72 (dd, 1H), 3.45 (d, 1H), 3.35 (m, 1H), 2.82 (m, 2H), 2.48 (s, 3H), 2.10 (m, 2H).

MS (EI): m/z 395 (M$^+$).

EXAMPLE 57

(+)-trans-5,7-Dihydroxy-8-(2-hydroxymethyl-1-methyl-pyrrolidin-3-yl)-2-phenyl-chromen-4-one Compound of example 56 (0.5 g, 1.27 mmol) was treated with dry pyridine hydrochloride (5 g, 43.29 mmol) as described in the example 17, to obtain the title compound.

Yield: 0.3 g (64%); mp: 212-215° C.

IR cm$^{-1}$: 3420, 1660.

$^1$H NMR (DMSO d$_6$): δ 12.90 (s, 1H), 8.10 (d, 2H), 7.62 (m, 3H), 6.95 (s, 1H), 6.18 (s, 1H), 4.05 (m, 1H), 3.55 (m, 2H), 3.00 (m, 3H), 2.52 (s, 3H), 2.25 (m, 1H), 1.95 (m, 1H).

MS (ES+): m/z 368 (M+1).

Analysis: $C_{21}H_{21}NO_5$ 0.5H$_2$O C, 66.95 (67.0); H, 5.81 (5.89); N, 3.67 (3.72).

EXAMPLE 58

(+)-trans-5,7-Dihydroxy-8-(2-hydroxymethyl-1-methyl-pyrrolidin-3-yl)-2-phenyl-chromen-4-one hydrochloride Compound of example 57 (0.053 g, 0.144 mmol) was converted to its hydrochloride salt using procedure as described in example 9.

Yield: 0.052 g (89.5%).

$^1$H NMR (CD$_3$OD): δ 8.07 (d, 2H), 7.55 (m, 3H), 6.76 (s, 1H), 6.35 (s, 1H), 4.50 (q, 1H), 3.92 (m, 2H), 3.81 (m, 1H), 3.53 (m, 2H), 3.04 (s, 3H), 2.62 (m, 1H), 2.38 (m, 1H).

MS (ES−): m/z 366 (M−36.5).

EXAMPLE 59

(+)-trans-4-[8-(2-Hydroxymethyl-1-methyl-pyrrolidin-3-yl)-5,7-dimethoxy-4-oxo-4H-chromen-2-yl]-3-methyl-benzonitrile Compound of example 12A (1.0 g, 3.24 mmol) in dry DMF (15 mL) was reacted with ethyl 2-methyl-4-cyanobenzoate (1.34 g, 7.09 mmol) in the presence of NaH (50%, 0.776 g, 16.16 mmol) as described in example 16, to get the title compound.

Yield: 0.8 g (57%).

$^1$H NMR (CDCl$_3$): δ 7.76 (d, 1H), 7.65 (m, 2H), 6.48 (s, 1H), 6.35 (s, 1H), 4.20 (m, 1H), 4.02 (s, 3H), 3.99 (s, 3H), 3.74 (d, 1H), 3.40 (d, 1H), 3.35 (m, 1H), 2.86 (d, 1H), 2.75 (m, 1H), 2.52 (s, 3H), 2.49 (s, 3H), 2.08 (m, 2H).

MS (CI): m/z 435 (M+1).

EXAMPLE 60

(+)-trans-4-[5,7-Dihydroxy-8-(2-hydroxymethyl-1-methyl-pyrrolidin-3-yl)-4-oxo-4H-chromen-2-yl]-3-methyl-benzonitrile Compound of example 59 (0.6 g, 1.38 mmol) was demethylated using pyridine hydrochloride (6 g, 51.95 mmol) as described in example 17 to obtain the title compound.

Yield: 0.35 g (62%); mp: 145-147° C.

IR cm$^{-1}$: 3400, 2250, 1670.

$^1$H NMR (DMSO d$_6$): δ 12.52 (s, 1H), 7.55 (m, 3H), 6.28 (s, 1H), 6.25 (s, 1H), 4.05 (m, 1H), 3.70 (d, 2H), 3.34 (m, 1H), 3.20 (m, 1H), 3.05 (m, 1H), 2.65 (s, 3H), 2.48 (s, 3H), 2.30 (m, 1H), 2.02 (m, 1H).

MS (ES+): m/z 407 (M+1).

Analysis: C$_{23}$H$_{22}$N$_2$O$_5$.2H$_2$O C, 62.35 (62.43); H, 5.06 (5.0); N, 6.1 (6.63).

EXAMPLE 61

(+)-trans-4-[5,7-Dihydroxy-8-(2-hydroxymethyl-1-methyl-pyrrolidin-3-yl)-4-oxo-4H-chromen-2-yl]-3-methyl-benzonitrile hydrochloride Compound of example 60 (0.053 g, 0.13 mmol) was converted to its hydrochloride salt using procedure described in example 9.

Yield: 0.049 g (84.77%).

$^1$H NMR (CD$_3$OD): δ 7.81 (m, 2H), 7.71 (d, 1H), 6.45 (s, 1H), 6.37 (s, 1H), 4.22 (m, 1H), 3.90 (m, 2H), 3.71 (m, 1H), 3.60 (dd, 1H), 3.45 (q, 1H), 2.99 (s, 3H), 2.55 (s, 3H), 2.50 (m, 1H), 2.27 (m, 1H).

MS (EI): m/z 406 (M−36.5)

EXAMPLE 62

(±)-trans-8-(2-Hydroxymethyl-1-methyl-pyrrolidin-3-yl)-5,7-dimethoxy-2-(4-trifluoromethyl-phenyl)-chromen-4-one Compound of example 6 (1.5 g, 4.84 mmol) in dry DMF (15 mL) was reacted with methyl 4-trifluoromethylbenzoate (3.27 g, 16.02 mmol) in the presence of NaH (50%, 1.2 g, 25 mmol) as described in example 16, to obtain the title compound.

Yield: 0.7 g (31.8%); mp: 114-115° C.

IR cm$^{-1}$: 3450, 1640.

$^1$H NMR (CDCl$_3$): δ 8.17 (d, 2H), 7.78 (d, 2H), 6.75 (s, 1H), 6.48 (s, 1H), 4.38 (m, 1H), 4.00 (s, 3H), 3.98 (s, 3H), 3.70 (dd, 1H), 3.38 (d, 1H), 3.28 (t, 1H), 2.75 (q, 1H), 2.65 (d, 1H), 2.44 (s, 3H), 2.08 (m, 2H).

MS (ES+): m/z 464 (M+1).

Analysis: C$_{24}$H$_{24}$F$_3$NO$_5$. H$_2$O C, 59.13 (59.8); H, 5.51 (5.44); N, 2.34 (2.9).

EXAMPLE 63

(±)-trans-5,7-Dihydroxy-8-(2-hydroxymethyl-1-methyl-pyrrolidin-3-yl)-2-(4-trifluoromethyl-phenyl)-chromen-4-one Compound of example 62 (0.5 g, 1.08 mmol) was demethylated using pyridine hydrochloride (4.5 g, 38.96 mmol) as described in example 17 to obtain the title compound.

Yield: 0.28 g (59%); mp: 238° C.

IR cm$^{-1}$: 3350, 1660.

$^1$H NMR (DMSO d$_6$): δ 12.70 (s, 1H), 8.33 (d, 2H), 7.98 (d, 2H), 7.08 (s, 1H), 6.18 (s, 1H), 4.05 (m, 1H), 3.55 (m, 2H), 3.00 (m, 3H), 2.55 (s, 3H), 2.25 (m, 1H), 1.98 (m, 1H).

MS (ES−): m/z 434 (M−1).

Analysis: C$_{22}$H$_{20}$F$_3$NO$_5$ C, 60.34 (60.69); H, 4.48 (4.63); N, 2.89 (3.42).

EXAMPLE 64

(+)-trans-8-(2-Hydroxymethyl-1-methyl-pyrrolidin-3-yl)-5,7-dimethoxy-2-(4-trifluoromethyl-phenyl)-chromen-4-one Compound of example 12A (0.8 g, 2.6 mmol) in dry DMF (15 mL) was reacted with methyl 4-trifluoromethylbenzoate (1.74 g, 8.53 mmol) in the presence of NaH (50%, 0.63 g, 13.13 mmol) as described in example 16 to obtain the title compound.

Yield: 1.0 g (87%); mp: 114-115° C.

$^1$H NMR (CDCl$_3$): δ 8.15 (d, 2H), 7.78 (d, 2H), 6.75 (s, 1H), 6.48 (s, 1H), 4.48 (m, 1H), 4.02 (s, 3H), 4.00 (s, 3H), 3.80 (d, 1H), 3.42 (m, 2H), 2.85 (m, 2H), 2.55 (s, 3H), 2.18 (m, 2H).

MS (ES+): m/z 464 (M+1).

EXAMPLE 65

(+)-trans-5,7-Dihydroxy-8-(2-hydroxymethyl-1-methyl-pyrrolidin-3-yl)-2-(4-trifluoromethyl-phenyl)-chromen-4-one Compound of example 64 (0.7 g, 1.51 mmol) was demethylated using pyridine hydrochloride (7 g, 60.60 mmol) as described in example 17 to obtain the title compound.
Yield: 0.28 g (42%); mp: 235-237° C.
IR cm$^{-1}$: 3400, 1660.
$^1$H NMR (DMSO d$_6$): δ 12.82 (s, 1H), 8.35 (d, 2H), 7.95 (d, 2H), 7.08 (s, 1H), 6.17 (s, 1H), 4.05 (m, 1H), 3.56 (m, 2H), 2.98 (m, 3H), 2.50 (s, 3H), 2.25 (m, 1H), 1.98 (m, 1H).
MS (CI): m/z 436 (M+1).
Analysis: C$_{22}$H$_{20}$F$_3$NO$_5$.2H$_2$O C, 55.79 (56.04); H, 4.53 (5.1); N, 2.91 (2.97).

EXAMPLE 66

(+)-trans-5,7-Dihydroxy-8-(2-hydroxymethyl-1-methyl-pyrrolidin-3-yl)-2-(4-trifluoromethyl-phenyl)-chromen-4-one hydrochloride Compound of example 65 (0.058 g, 0.13 mmol) was converted to its hydrochloride salt using procedure described in example 9.
Yield: 0.052 g (84.8%).
$^1$H NMR (CD$_3$OD): δ 8.27 (d, 2H), 7.84 (d, 2H), 6.89 (s, 1H), 6.36 (s, 1H), 4.50 (q, 1H), 3.88 (m, 3H), 3.60 (m, 2H), 3.06 (s, 3H), 2.64 (m, 1H), 2.36 (m, 1H).
MS (ES−): m/z 434 (M−36.5).

EXAMPLE 67

(+)-trans-8-(2-Hydroxymethyl-1-methyl-pyrrolidin-3-yl)-5,7-dimethoxy-2-thiophen-2-yl-chromen-4-one Compound of example 12A (0.95 g, 3.07 mmol) in dry DMF (15 mL) was treated with thiophene-2-carboxylic acid ethyl ester (2.25 g, 14.42 mmol) in the presence of NaH (50%, 0.741 g, 15.43 mmol) as described in example 16 to get the title compound.
Yield: 0.5 g (40%).
$^1$H NMR (CDCl$_3$): δ 7.88 (d, 1H), 7.55 (d, 1H), 7.18 (t, 1H), 6.55 (s, 1H), 6.45 (s, 1H), 4.38 (m, 1H), 4.03 (s, 3H), 4.00 (s, 3H), 3.75 (dd, 1H), 3.45 (m, 2H), 2.92 (m, 2H), 2.58 (s, 3H), 2.20 (m, 2H).
MS (ES+): m/z 402 (M+1).

EXAMPLE 68

(+)-trans-5,7-Dihydroxy-8-(2-hydroxymethyl-1-methyl-pyrrolidin-3-yl)-2-thiophen-2-yl-chromen-4-one Compound of example 67 (0.29 g, 0.72 mmol) of was subjected to demethylation using pyridine hydrochloride (2.9 g, 25.11 mmol) as described in example 17 to obtain the title compound.
Yield: 0.149 g (55%); mp: 218-220° C.
IR cm$^{-1}$: 3340, 1650.
$^1$H NMR (DMSO d$_6$): δ 12.90 (s, 1H), 8.08 (d, 1H), 8.00 (d, 1H), 7.32 (t, 1H), 6.85 (s, 1H), 6.20 (s, 1H), 3.95 (m, 1H), 3.58 (m, 2H), 3.30 (m, 2H), 3.18 (m, 1H), 2.65 (s, 3H), 2.25 (m, 1H), 2.15 (m, 1H).
MS (CI): m/z 374 (M+1).
Analysis: C$_{19}$H$_{19}$NO$_5$S.1.5H$_2$O C, 57.11 (56.96); H, 5.03 (5.5); N, 3.44 (3.49).

EXAMPLE 69

(+)-trans-5,7-Dihydroxy-8-(2-hydroxymethyl-1-methyl-pyrrolidin-3-yl)-2-thiophen-2-yl-chromen-4-one hydrochloride Compound of example 68 (0.042 g, 0.112 mmol) was converted to its hydrochloride salt using procedure as described in example 9.
Yield: 0.043 g (93.4%).
$^1$H NMR (CD$_3$OD): δ 7.95 (s, 1H), 7.81 (d, 1H), 7.24 (bs, 1H), 6.60 (s, 1H), 6.32 (s, 1H), 4.38 (m, 1H), 3.85 (m, 3H), 3.59 (m, 2H), 3.06 (s, 3H), 2.60 (m, 1H), 2.39 (m, 1H).
MS (EI): m/z 373 (M−36.5).

EXAMPLE 70

(+)-trans-2-(2-Chloro-5-methoxy-phenyl)-8-(2-hydroxymethyl-1-methyl-pyrrolidin-3-yl)-5,7-dimethoxy-chromen-4-one Compound of example 12A (1.0 g, 3.2 mmol) in dry DMF (25 mL) was reacted with methyl 2-chloro-5-methoxybenzoate (1.3 g, 6.4 mmol) in the presence of NaH (50%, 0.776 g, 16.0 mmol) as described in example 16 to obtain the title compound.
Yield: 0.8 g (54%).
$^1$H NMR (CDCl$_3$): δ 7.40 (d, 1H), 7.18 (m, 1H), 6.95 (m, 1H), 6.46 (s, 1H), 6.42 (s, 1H), 4.20 (m, 1H), 4.05 (s, 3H), 4.00 (s, 3H), 3.85 (s, 3H), 3.60 (d, 1H), 3.45 (d, 1H), 3.20 (m, 1H), 2.78 (m, 1H), 2.60 (m, 1H), 2.38 (s, 3H), 2.20 (m, 2H).
MS (CI): m/z 460 (M+1).

EXAMPLE 71

(+)-trans-2-(2-Chloro-5-methoxy-phenyl)-5,7-dihydroxy-8-(2-hydroxymethyl-1-methyl-pyrrolidin-3-yl)-chromen-4-one (A) and (+)-trans-2-(2-Chloro-5-hydroxy-phenyl)-5,7-dihydroxy-8-(2-hydroxymethyl-1-methyl-pyrrolidin-3-yl)-chromen-4-one (B)

Compound of example 70 (0.75 g, 1.63 mmol) was demethylated using pyridine hydrochloride (8.0 g, 69.0 mmol) as described in example 17 to obtain the title compounds.

Compound (A)
Yield: 0.05 g (7%); mp: 220-221° C.
IR cm$^{-1}$: 3450, 1655.
$^1$H NMR (CDCl$_3$): δ 12.60 (s, 1H), 7.40 (d, 1H), 7.10 (d, 1H), 7.00 (m, 1H), 6.45 (s, 1H), 6.30 (s, 1H), 4.20 (m, 1H), 3.90 (m, 2H), 3.85 (s, 3H), 3.40 (m, 1H), 3.30 (m, 1H), 3.20 (m, 1H), 2.70 (s, 3H), 2.40 (m, 1H), 2.10 (m, 1H).
MS (ES−): m/z 430 (M−1).

Compound (B):
Yield: 0.3 g (44%); mp: 266-267° C.
IR cm$^{-1}$: 3500, 1660.
$^1$H NMR (DMSO d$_6$): δ 12.70 (s, 1H), 7.47 (d, 1H), 7.12 (s, 1H), 7.00 (m, 1H), 6.45 (s, 1H), 6.25 (s, 1H), 3.85 (m, 1H), 3.50 (m, 3H), 3.00 (m, 2H), 2.88 (m, 1H), 2.50 (s, 3H), 2.20 (m, 1H), 1.90 (m, 1H).
MS (ES+): m/z 418 (M+1).
Analysis: C$_{21}$H$_{20}$ClNO$_6$.0.5H$_2$O C, 59.48 (59.09); H, 4.88 (4.95); N, 3.53 (3.28); Cl, 8.0 (8.3).

EXAMPLE 72

(+)-trans-2-(2-Chloro-5-hydroxy-phenyl)-5,7-dihydroxy-8-(2-hydroxymethyl-1-methyl-pyrrolidin-3- yl)-chromen-4-one hydrochloride

Compound (B) of example 71 (0.1 g 0.24 mmol) was converted to its hydrochloride salt using procedure as described in example 9.

Yield: 0.1 g (92%); mp: 189-190° C.
$^1$H NMR (CD$_3$OD): δ 7.40 (d, 1H), 7.15 (d, 1H), 6.95 (dd, 1H), 6.48 (s, 1H), 6.32 (s, 1H), 4.23 (m, 1H), 3.90 (m, 1H), 3.81 (dd, 1H), 3.67 (m, 1H), 3.58 (dd, 1H), 3.38 (m, 1H), 2.98 (s, 3H), 2.48 (m, 1H), 2.30 (m, 1H).
MS (ES+): m/z 418 (M-36.5).

EXAMPLE 73

(+)-trans-2-(3-Chloro-phenyl)-8-(2-hydroxymethyl-1-methyl-pyrrolidin-3-yl)-5,7-dimethoxy-chromen-4-one Compound of example 12A (1 g, 3.24 mmol) in DMF (15 mL), reacted with methyl 3-chlorobenzoate (2.66 g, 15.6 mmol) in the presence of NaH (50%, 0.776 g, 16.16 mmol) as described in example 16, afforded the title compound.

Yield: 0.35 g (25%).
$^1$H NMR (CDCl$_3$): δ 8.08 (d, 1H), 7.90 (d, 1H), 7.45 (m, 2H), 6.65 (s, 1H), 6.45 (s, 1H), 4.40 (m, 1H), 4.00 (s, 3H), 3.98 (s, 3H), 3.75 (dd, 1H), 3.35 (m, 2H), 2.75 (m, 2H), 2.45 (s, 3H), 2.10 (m, 2H).
MS (ES+): m/z 430 (M+1).

EXAMPLE 74

(+)-trans-2-(3-Chloro-phenyl)-5-hydroxy-8-(2-hydroxymethyl-1-methyl-pyrrolidin-3-yl)-7-methoxy-chromen-4-one (A) and (+)-trans-2-(3-Chloro-phenyl)-5,7-dihydroxy-8-(2-hydroxymethyl-1-methyl-pyrrolidin-3-yl)-chromen-4-one (B)

Compound of example 73 (0.25 g, 0.58 mmol) was subjected to demethylation using pyridine hydrochloride (2.5 g, 21.64 mmol) as described in example 17 to afford the title compounds.

Compound (A):
Yield: 0.035 g (14.5%); mp: 146-147° C.
IR cm$^{-1}$: 3300, 1650.
MS (ES+): m/z 416 (M+1).
Analysis: C$_{22}$H$_{22}$ClNO$_5$.2H$_2$O C, 58.76 (58.47); H, 5.19 (5.70); N, 3.34 (3.1); Cl, 7.43 (7.84).

Compound (B)
Yield: 0.085 g (36.5%); mp: 215-217° C.
IR cm$^{-1}$: 3400, 1660.
MS (ES+): m/z 402 (M+1).
Analysis: C$_{21}$H$_{20}$ClNO$_5$.0.5H$_2$O C, 61.18 (61.39); H, 5.03 (5.15); N, 3.46 (3.4); Cl, 8.97 (8.62).

EXAMPLE 75

(+)-trans-2-(3-Fluoro-phenyl)-5,7-dimethoxy-8-(2-hydroxymethyl-1-methyl-pyrrolidin-3-yl)-chromen-4-one Compound of example 12A (0.83 g, 2.69 mmol) in dry DMF (10 mL) reacted with methyl 3-fluorobenzoate (1.82 g, 11.82 mmol) in the presence of NaH (50%, 0.64 g, 13.33 mmol) as described in example 16, afforded the title compound.

Yield: 0.73 g (65.7%).
MS (CI): m/z 414 (M+1).

EXAMPLE 76

(+)-trans-2-(3-Fluoro-phenyl)-5,7-dihydroxy-8-(2-hydroxymethyl-1-methyl-pyrrolidin-3-yl)-chromen-4-one Compound of example 75 (0.51 g, 1.23 mmol) was demethylated using pyridine hydrochloride (5.1 g, 44.15 mmol) as described in example 17, gave the title compound.

Yield: 0.25 g (52.8%); mp: 218-220° C.
IR cm$^{-1}$: 3390, 1660.
$^1$H NMR (DMSO d$_6$): δ 12.85 (s, 1H), 8.00 (m, 2H), 7.65 (m, 1H), 7.45 (m, 1H), 7.05 (s, 1H), 6.18 (s, 1H), 4.05 (m, 1H), 3.58 (m, 2H), 2.95 (m, 3H), 2.50 (s, 3H), 2.25 (m, 1H), 1.98 (m, 1H).
MS (ES+): m/z 386 (M+1).
Analysis: C$_{21}$H$_{20}$FNO$_5$.0.5H$_2$O C, 63.25 (63.96); H, 5.09 (5.36); N, 3.57 (3.55).

EXAMPLE 77

(+)-trans-2-(4-Bromo-phenyl)-8-(2-hydroxymethyl-1-methyl-pyrrolidin-3-yl)-5,7-dimethoxy-chromen-4-one Compound of example 12A (0.83 g, 2.6 mmol) in dry DMF (10 mL) was reacted with methyl 4-bromobenzoate (1.87 g, 8.7 mmol) in the presence of NaH (50%, 0.63 g, 13.18 mmol) as described in example 16 to afford the title compound.

Yield: 0.97 g (78%).
$^1$H NMR (CDCl$_3$): δ 7.90 (d, 2H), 7.60 (d, 2H), 6.65 (s, 1H), 6.45 (s, 1H), 4.35 (m, 1H), 4.02 (s, 3H), 3.99 (s, 3H), 3.75 (dd, 1H), 3.35 (m, 2H), 2.80 (m, 1H), 2.68 (m, 1H), 2.43 (s, 3H), 2.15 (m, 2H).
MS (EI): m/z 474 (M$^+$).

EXAMPLE 78

(+)-trans-2-(4-Bromo-phenyl)-5-hydroxy-8-(2-hydroxymethyl-1-methyl-pyrrolidin-3-yl)-7-methoxy-chromen-4-one (A) and (+)-trans-2-(4-Bromo-phenyl)-5,7-dihydroxy-8-(2-hydroxymethyl-1-methyl-pyrrolidin-3-yl)-chromen-4-one (B)

Compound of example 77 (0.61 g, 1.29 mmol) was subjected to demethylation with pyridine hydrochloride (6.1 g, 52.81 mmol) as described in example 17, afforded the two title compounds which were separated using column chromatography.

Compound A:
Yield: 0.2 g (33.6%); mp: 163-165° C.
IR cm$^{-1}$: 3420, 2970, 1680.
$^1$H NMR (DMSO d$_6$): δ 13.10 (s, 1H), 8.10 (d, 2H), 7.80 (d, 2H), 7.10 (s, 1H), 6.65 (s, 1H), 3.99 (m, 1H), 3.95 (s, 3H), 3.55 (m, 1H), 3.45 (m, 1H), 3.18 (m, 1H), 2.75 (m, 2H), 2.45 (s, 3H), 2.05 (m, 2H).
MS (CI): m/z 461 (M+1).

Analysis: $C_{22}H_{22}BrNO_5.H_2O$ C, 54.95 (55.24); H, 4.66 (5.05); N, 3.39 (2.93); Br, 16.68 (16.70).

Compound B:
Yield: 0.21 g (36.4%); mp: 193-195° C.
IR cm$^{-1}$: 3410, 1710.
$^1$H NMR (DMSO d$_6$): δ 12.85 (s, 1H), 8.09 (d, 2H), 7.80 (d, 2H), 6.95 (s, 1H), 6.15 (s, 1H), 4.00 (m, 1H), 3.55 (m, 2H), 3.06 (m, 3H), 2.50 (s, 3H), 2.25 (m, 1H), 1.97 (m, 1H).
MS (EI): m/z 446 (M+).
Analysis: $C_{21}H_{20}BrNO_5.H_2O$ C, 54.00 (54.23); H, 4.59 (4.76); N, 3.10 (3.01); Br, 17.37 (17.17).

EXAMPLE 79

(+)-trans-2-(2,6-Difluoro-phenyl)-8-(2-hydroxymethyl-1-methyl-pyrrolidin-3-yl)-5,7-dimethoxy-chromen-4-one Compound of example 12A (1.5 g, 4.85 mmol) in dry DMF (20 mL) was reacted with 2,6-difluoro-benzoyl chloride (0.8 mL, 1.13 g, 6.4 mmol) in the presence of NaH (50%, 1.02 g, 21.25 mmol) as described in example 16 to afford the title compound.
Yield: 0.09 g (5%).
$^1$H NMR (CDCl$_3$): δ 7.50 (m, 1H), 7.10 (t, 2H), 6.42 (s, 1H), 6.40 (s, 1H), 4.11 (m, 1H), 4.00 (s, 3H), 3.97 (s, 3H), 3.66 (dd, 1H), 3.52 (d, 1H), 3.25 (m, 1H), 2.95 (m, 1H), 2.65 (m, 1H), 2.45 (s, 3H), 2.00 (m, 2H).
MS (ES+): m/z 432 (M+1).

EXAMPLE 80

(+)-trans-2-(2,6-Difluoro-phenyl)-5,7-dihydroxy-8-(2-hydroxymethyl-1-methyl-pyrrolidin-3-yl)-chromen-4-one Compound of example 79 (0.09 g, 0.208 mmol) subjected to demethylation using pyridine hydrochloride (1 g, 8.66 mmol), as described in example 17, afforded the title compound.
Yield: 0.032 g (38%); mp: 242-244° C.
IR cm$^{-1}$: 3300, 1680, 1650.
MS (ES+): m/z 404 (M+1)

EXAMPLE 81

(±)-trans-4-[8-(2-Hydroxymethyl-1-methyl-pyrrolidin-3-yl)-5,7-dimethoxy-4-oxo-4H-chromen-2-yl]-benzonitrile Compound of example 6 (1.5 g, 4.85 mmol) in dry DMF (15 mL) reacted with methyl 4-cyanobenzoate (2.57 g, 17.2 mmol) in the presence of NaH (50%, 1.2 g, 25 mmol), as described example 16, afforded the title compound.
Yield: 0.65 g (31.8%); mp: 214-216° C.
IR cm$^{-1}$: 3400, 2210, 1640.
$^1$H NMR (CDCl$_3$): δ 8.15 (d, 2H), 7.78 (d, 2H), 6.75 (s, 1H), 6.48 (s, 1H), 4.45 (m, 1H), 4.02 (s, 3H), 4.00 (s, 3H), 3.70 (dd, 1H), 3.30 (m, 2H), 2.78 (m, 1H), 2.60 (d, 1H), 2.42 (s, 3H), 2.08 (m, 2H).
MS (CI): m/z 421 (M+1).
Analysis: $C_{24}H_{24}N_2O_5.0.5H_2O$ C, 67.05 (67.12); H, 5.78 (5.63); N, 6.1 (6.5).

EXAMPLE 82

(±)-trans-4-[5-Hydroxy-8-(2-hydroxymethyl-1-methyl-pyrrolidin-3-yl)-7-methoxy-4-oxo-4H-chromen-2-yl]-benzonitrile (A) and (±)-trans-4-[5,7-Dihydroxy-8-(2-hydroxymethyl-1-methyl-pyrrolidin-3-yl)-4-oxo-4H-chromen-2-yl]-benzonitrile (B)

Compound of example 81 (0.30 g, 0.71 mmol) was reacted with pyridine hydrochloride (3 g, 26 mmol) as described in example 17, afforded the title compounds.

Compound (A):
Yield: 0.033 g (10%).
IR cm$^{-1}$: 3320, 2210, 1640.
$^1$H NMR (CDCl$_3$): δ 12.80 (s, 1H), 8.35 (d, 2H), 8.08 (d, 2H), 7.20 (s, 1H), 6.63 (s, 1H), 4.38 (m, 1H), 3.98 (m, 1H), 3.95 (s, 3H), 3.50 (m, 1H), 3.48 (m, 1H), 3.10 (m, 1H), 2.65 (m, 1H), 2.40 (s, 3H), 2.00 (m, 2H).
MS (CI): m/z 407 (M+1).
Analysis: $C_{23}H_{22}N_2O_5$, 0.5H$_2$O C, 63.96 (63.73); H, 5.46 (5.81); N, 5.63 (5.46).

Compound (B):
Yield: 0.1 g (36%).
IR cm$^{-1}$: 3500, 2220, 1660.
$^1$H NMR (DMSO d$_6$): δ 12.80 (s, 1H), 8.26 (d, 2H), 8.08 (d, 2H), 7.10 (s, 1H), 6.15 (s, 1H), 4.05 (m, 1H), 3.58 (m, 2H), 3.04 (m, 3H), 2.55 (s, 3H), 2.25 (m, 1H), 2.00 (m, 1H).
MS (CI): m/z 393 (M+1).

EXAMPLE 83

(+)-trans-4-[8-(2-Hydroxymethyl-1-methyl-pyrrolidin-3-yl)-5,7-dimethoxy-4-oxo-4H-chromen-2-yl]-benzonitrile Compound of example 12A (0.98 g, 3.17 mmol) in dry DMF (15 mL) reacted with methyl 4-cyanobenzoate (1.02 g, 6.34 mmol) in the presence of NaH (50%, 0.762 g, 15.86 mmol) as described in example 16, afforded the title compound.
Yield: 0.56 g (42%).
IR cm$^{-1}$: 3400, 2210, 1640.
$^1$H NMR (DMSO d$_6$): δ 8.28 (d, 2H), 8.05 (d, 2H), 6.98 (s, 1H), 6.70 (s, 1H), 4.30 (m, 1H), 4.00 (s, 3H), 3.95 (s, 3H), 3.50 (m, 2H), 3.20 (m, 2H), 2.65 (m, 1H), 2.40 (s, 3H), 2.00 (m, 2H).
MS (ES+): m/z 421 (M+1).

EXAMPLE 84

(+)-trans-4-[5-Hydroxy-8-(2-hydroxymethyl-1-methyl-pyrrolidin-3-yl)-7-methoxy-4-oxo-4H-chromen-2-yl]-benzonitrile (A) and (+)-trans-4-[5,7-Dihydroxy-8-(2-hydroxymethyl-1-methyl-pyrrolidin-3-yl)-4-oxo-4H-chromen-2-yl]-benzonitrile (B)

Compound of example 83 (0.50 g, 1.19 mmol) reacted with pyridine hydrochloride (5 g, 43.29 mmol) as described in example 17, afforded the title compounds.

Compound (A):
Yield: 0.1 g (20%).
IR cm$^{-1}$: 3420, 2250, 1660.
$^1$H NMR (DMSO d$_6$): δ 12.98 (s, 1H), 8.35 (d, 2H), 8.08 (d, 2H), 7.20 (s, 1H), 6.65 (s, 1H), 4.30 (m, 1H), 4.00 (m, 1H), 3.95 (s, 3H), 3.50 (m, 1H), 3.48 (m, 1H), 3.08 (m, 1H), 2.60 (m, 1H), 2.35 (s, 3H), 1.98 (m, 2H).

MS (ES+): m/z 407 (M+1).

Analysis: $C_{23}H_{22}N_2O_5.0.5H_2O$ C, 64.44 (64.39); H, 5.11 (5.6); N, 6.31 (6.53).

Compound (B):

Yield: 0.19 g (40%).

IR cm$^{-1}$: 3400, 2240, 1660.

$^1$H NMR (DMSO d$_6$): δ 12.80 (s, 1H), 8.28 (d, 2H), 8.05 (d, 2H), 7.10 (s, 1H), 6.15 (s, 1H), 4.00 (m, 1H), 3.55 (m, 2H), 3.00 (m, 3H), 2.60 (s, 3H), 2.25 (m, 1H), 1.98 (m, 1H).

MS (ES+): m/z 393 (M+1),

Analysis: $C_{22}H_{20}N_2O_5.0.5H_2O$ C, 63.38 (63.0); H, 5.22 (5.52); N, 6.64 (6.67).

EXAMPLE 85

(±)-trans-2-[(3,5-Bis-trifluoromethyl)-phenyl]-8-(2-hydroxymethyl-1-methyl-pyrrolidin-3-yl)-5,7-dimethoxy-chromen-4-one Compound of example 6 (1.26 g, 3.59 mmol) in dry DMF (20 mL) was condensed with 3,5-bis-trifluoromethyl-benzoyl chloride (1 g, 3.62 mmol) in the presence of NaH (50%, 0.72 g, 15 mmol) as described in example 16 to obtain the title compound.

Yield: 0.85 g (44.5%).

$^1$H NMR (CDCl$_3$): δ 8.50 (s, 2H), 7.98 (s, 1H), 6.75 (s, 1H), 6.48 (s, 1H), 4.42 (m, 1H), 4.02 (s, 3H), 4.00 (s, 3H), 3.75 (dd, 1H), 3.30 (m, 2H), 2.78 (m, 1H), 2.65 (m, 1H), 2.45 (s, 3H), 2.10 (m, 2H).

MS (ES+): m/z 532 (M+1).

EXAMPLE 86

(±)-trans-2-[(3,5-Bis-trifluoromethyl)-phenyl]-5,7-dihydroxy-8-(2-hydroxymethyl-1-methyl-pyrrolidin-3-yl)-chromen-4-one Compound of example 85 (0.71 g, 1.34 mmol) was reacted with pyridine hydrochloride (7.1 g, 61.47 mmol) as described in example 17 to obtain the title compound.

Yield: 0.4 g (59%); mp: 228-230° C.

IR cm$^{-1}$: 3400, 1650.

$^1$H NMR (DMSO d$_6$): δ 12.80 (s, 1H), 8.72 (s, 2H), 8.40 (s, 1H), 7.32 (s, 1H), 6.20 (s, 1H), 4.00 (m, 1H), 3.55 (m, 2H), 3.09 (m, 1H) 2.95 (m, 2H), 2.50 (s, 3H), 2.15 (m, 1H), 2.03 (m, 1H).

MS (ES+): m/z 504 (M+1).

Analysis: $C_{23}H_{19}F_6NO_5$ C, 54.1 (54.8); H, 4.13 (3.8); N, 2.82 (2.78).

EXAMPLE 87

(±)-trans-2-(2-Chloro-pyridin-3-yl)-8-(2-hydroxymethyl-1-methyl-pyrrolidin-3-yl)-5,7-dimethoxy-chromen-4-one Compound of example 5 (1.65 g, 4.7 mmol) was reacted with 2-chloro-nicotinic acid (2.44 g, 17.0 mol) in the presence of dry pyridine (25 mL) and POCl$_3$ (2.1 mL, 22.4 mmol) using the conditions described in example 39 to get (±)-trans-2-chloro-nicotinic acid 2-(2-acetoxymethyl-1-methyl-pyrrolidin-3-yl)-6-acetyl-3,5-dimethoxy-phenyl ester. This was converted to the title compound using NaH (50%, 1.29 g, 26.86 mmol) in 1,4-dioxane (25 mL) followed by treatment with HCl as described in example 16.

Yield: 0.38 g (19%).

MS (ES+): m/z 431 (M+1).

EXAMPLE 88

(±)-trans-2-(2-Chloro-pyridin-3-yl)-5,7-dihydroxy-8-(2-hydroxymethyl-1-methyl-pyrrolidin-3-yl)-chromen-4-one Compound of example 87 (0.3 g, 0.69 mmol) was demethylated using pyridine hydrochloride (3 g, 25.97 mmol) as described in example 17 to obtain the title compound.

Yield: 0.072 g (25%).

IR cm$^{-1}$: 3450, 1660, 1400.

MS (ES+): m/z 403 (M+1).

Analysis: $C_{20}H_{19}ClN_2O_5.H_2O$ C, 57.29 (57.17); H, 5.1 (5.01); N, 6.36 (6.66); Cl, 8.94 (8.44).

EXAMPLE 89

(+)-trans-2-(2-Chloro-pyridin-3-yl)-8-(2-hydroxymethyl-1-methyl-pyrrolidin-3-yl)-5,7-dimethoxy-chromen-4-one Compound of example 11A (4.2 g, 11.97 mmol) was reacted with 2-chloro-nicotinic acid (3.78 g, 24 mmol) in presence of dry pyridine (25 mL) and POCl$_3$ (4.4 mL, 7.35 g, 47.88 mmol) using the conditions described in example 39. (+)-trans-2-Chloro-nicotinic acid 2-(2-acetoxymethyl-1-methyl-pyrrolidin-3-yl)-6-acetyl-3,5-dimethoxy-phenyl ester obtained was converted to the title compound using NaH (50%, 2.44 g, 50.83 mmol) in 1,4-dioxane (50 mL) followed by treatment with HCl as described in example 16.

Yield: 0.63 g (12%).

MS (ES+): m/z 431 (M+1).

EXAMPLE 90

(+)-trans-2-(2-Chloro-pyridin-3-yl)-5,7-dihydroxy-8-(2-hydroxymethyl-1-methyl-pyrrolidin-3-yl)-chromen-4-one Compound of example 89 (0.58 g, 1.35 mmol) was demethylated using pyridine hydrochloride (5.8 g, 50.22 mmol) as described in example 17 to obtain the title compound.

Yield: 0.1 g (18%); mp: 125-127° C.

IR cm$^{-1}$: 3380, 1660.

$^1$H NMR (CDCl$_3$+DMSO d$_6$): δ 12.50 (s, 1H), 8.50 (dd, 1H), 8.00 (d, 1H), 7.40 (dd, 1H), 6.45 (s, 1H), 6.28 (s, 1H), 4.10 (m, 1H), 3.70 (m, 2H), 3.25 (m, 3H), 2.65 (s, 3H), 2.35 (m, 1H), 2.00 (m, 1H).

MS (ES+): m/z 403 (M+1).

Analysis: $C_{20}H_{19}ClN_2O_5.H_2O$ C, 57.29 (57.17); H, 5.1 (5.01); N, 6.36 (6.66); Cl, 8.94 (8.44).

EXAMPLE 91

(+)-trans-8-(2-Hydroxymethyl-1-methyl-pyrrolidin-3-yl)-5,7-dimethoxy-2-(4-nitro-phenyl)-chromen-4-one Compound of example 11A (5.19 g, 14.79 mmol) was reacted with 4-nitrobenzoic acid (5.01 g, 30 mmol) in the presence of dry pyridine (35 mL) and POCl$_3$ (5.5 mL, 23.43 mmol) using the conditions described in example 39 to get (+)-trans-4-nitro-benzoic acid 2-(2-acetoxymethyl-1-methyl-pyrrolidin-3-yl)-6-acetyl-3,5-dimethoxy-phenyl ester. This was converted to the title compound using NaH (50%, 3.41 g, 71.04 mmol) in 1,4-dioxane (90 mL) followed by treatment with HCl as described in example 16.

Yield: 1.9 g (30%).

$^1$H NMR (CDCl$_3$+DMSO d$_6$): δ 8.30 (d, 2H), 8.18 (d, 2H), 6.70 (s, 1H), 6.40 (s, 1H), 4.32 (m, 1H), 3.98 (s, 3H), 3.96 (s, 3H), 3.68 (dd, 1H), 3.30 (m, 2H), 2.75 (m, 1H), 2.60 (m, 1H), 2.40 (s, 3H), 2.08 (m, 2H).

MS (ES+): m/z 441 (M+1).

EXAMPLE 92

(+)-trans-5,7-Dihydroxy-8-(2-hydroxymethyl-1-methyl-pyrrolidin-3-yl)-2-(4-nitro-phenyl)-chromen-4-one Compound of example 91 (1.9 g, 4.32 mmol) was demethylated using pyridine hydrochloride (19 g, 164.5 mmol) as described in example 17 to obtain the title compound.

Yield: 1.2 g (75%); mp: 275-277° C.

IR cm$^{-1}$: 3500, 1660, 1540.

$^1$H NMR (DMSO d$_6$): δ 12.70 (s, 1H), 8.35 (s, 4H), 7.10 (s, 1H), 6.15 (s, 1H), 4.15 (m, 1H), 3.60 (m, 2H), 3.05 (m, 3H), 2.55 (s, 3H), 2.25 (m, 1H), 2.00 (m, 1H).

MS (ES+): m/z 413 (M+1).

Analysis: $C_{21}H_{20}N_2O_7$ C, 61.48 (61.16); H, 4.68 (4.89); N, 6.81 (6.79).

EXAMPLE 93

(+)-trans-Acetic acid 3-(7-acetoxy-5-hydroxy-2-(4-nitro-phenyl)-4-oxo-4H-chromen-8-yl]-1-methyl-pyrrolidin-2-yl methyl ester To a solution of compound of example 92 (0.050 g, 0.12 mmol) in dichloromethane (10 mL) were added acetic anhydride (0.030 g, 0.3 mmol) and dimethylaminopyridine (0.003 g). The mixture was stirred for 45 min. at 25° C. Reaction mixture was then adsorbed on 0.5 g silica, concentrated and was purified using silica gel chromatography and 2% MeOH in chloroform+1% liquor NH$_3$ as eluant to obtain the title compound.

Yield: 0.020 g (33%).

$^1$H NMR (CDCl$_3$): δ 12.50 (s, 1H), 8.42 (d, 2H), 8.04 (d, 2H), 6.74 (s, 1H), 6.33 (s, 1H), 4.52 (m, 1H), 4.26 (m, 2H), 3.37 (m, 2H), 2.69 (m, 1H), 2.51 (s, 3H), 2.41 (m, 1H), 2.10 (s, 3H), 2.04 (s, 3H), 1.98 (m, 1H).

MS (ES-): m/z 495 (M-1).

EXAMPLE 94

(+)-trans-2-(4-Amino-phenyl)-5,7-dihydroxy-8-(2-hydroxymethyl-1-methyl-pyrrolidin-3-yl)-chromen-4-one Compound of example 92 (1 g, 2.43 mmol) was dissolved in methanol (20 mL) and subjected to hydrogenation at 35 psi using Pd—C (10%, 0.05 g) as a catalyst for 2 h. Pd—C was then filtered. The filtrate was concentrated and the solid product obtained was purified using a silica gel column and 5% methanol+1% liquor NH$_3$ in CHCl$_3$ as eluant to obtain the title compound.

Yield: 0.72 g (72.2%); mp: 172-174° C.

IR cm$^{-1}$: 3340, 1660.

$^1$H NMR (DMSO d$_6$): δ 13.20 (s, 1H), 7.80 (d, 2H), 6.70 (d, 2H), 6.60 (s, 1H), 6.15 (s, 1H), 6.08 (bs, 2H), 4.00 (m, 1H), 3.50 (m, 2H), 3.00 (m, 3H), 2.50 (s, 3H), 2.20 (m, 1H), 1.98 (m, 1H).

MS (ES+): m/z 383 (M+1).

Analysis: $C_{21}H_{22}N_2O_5$.0.5H$_2$O C, 63.88 (64.4); H, 5.92 (5.88); N, 7.12 (7.16).

EXAMPLE 95

(±)-trans-8-(2-Hydroxymethyl-1-methyl-pyrrolidin-3-yl)-5,7-dimethoxy-2-(2-methoxy-phenyl)-chromen-4-one Compound of example 6 (0.7 g, 2.2 mmol) in dry DMF (10 mL) was reacted with methyl 2-methoxybenzoate (1.13 g, 6.8 mmol) in the presence of NaH (50%, 0.544 g, 11.3 mmol) as described in example 16 to obtain the title compound.

Yield: 0.4 g (43%).

MS (ES+): m/z 426 (M+1).

EXAMPLE 96

(±)-trans-5,7-Dihydroxy-8-(2-hydroxymethyl-1-methyl-pyrrolidin-3-yl)-2-(2-hydroxy-phenyl)-chromen-4-one Compound of example 95 (0.4 g, 0.9 mmol) was demethylated using pyridine hydrochloride (6 g, 52.0 mmol) as described in example 17 to obtain the title compound.

Yield: 0.1 g (29%); mp: 212-213° C.

IR cm$^{-1}$: 3400, 1650.

MS (CI): m/z 384 (M+1).

Analysis: $C_{21}H_{21}NO_6$.2.5H$_2$O C, 59.32 (58.87); H, 5.35 (5.88); N, 3.74 (3.26).

EXAMPLE 97

(+)-trans-3-Chloro-4-[8-(2-hydroxymethyl-1-methyl-pyrrolidin-3-yl)-5,7-dimethoxy-4-oxo-4H-chromen-2-yl]-benzonitrile Compound of example 12A (0.7 g, 2.2 mmol) in dry DMF (15 mL) was reacted with methyl 2-chloro-4-cyanobenzoate (0.885 g, 4.5 mmol) in the presence of NaH (50%, 0.544 g, 11.3 mmol) as described in example 16 to obtain the title compound.

Yield: 0.31 g (31%).

IR cm$^{-1}$: 3450, 2220, 1630, 1600.

$^1$H NMR (CDCl$_3$): δ 8.27 (d, 1H), 7.40 (d, 1H), 7.25 (s, 1H), 7.16 (s, 1H), 6.48 (s, 1H), 4.25 (m, 1H), 4.03 (s, 3H), 4.00 (s, 3H), 3.78 (dd, 1H), 3.35 (d, 1H), 3.22 (m, 1H), 2.80 (m, 1H), 2.62 (d, 1H), 2.38 (s, 3H), 2.15 (m, 2H).

MS (ES+): m/z 455 (M+1).

EXAMPLE 98

(+)-trans-3-Chloro-4-[5,7-dihydroxy-8-(2-hydroxymethyl-1-methyl-pyrrolidin-3-yl)-4-oxo-4H-chromen-2-yl]-benzonitrile Compound of example 97 (0.3 g, 0.6 mmol) was demethylated using pyridine hydrochloride (3 g, 26.0 mmol) as described in example 17 to obtain the title compound.

Yield: 0.12 g (46%); mp: 237-239° C.

IR cm$^{-1}$: 3450, 2210, 1650.

¹H NMR (DMSO d$_6$): δ 13.00 (s, 1H), 7.80 (d, 1H), 7.21 (s, 1H), 7.24 (d, 2H), 6.23 (s, 1H), 4.00 (m, 1H), 3.32 (m, 3H), 3.13 (m, 2H), 2.68 (s, 3H), 2.18 (m, 2H).
MS (EI): m/z 426 (M$^+$).
Analysis: C$_{22}$H$_{19}$ClN$_2$O$_5$.0.5H$_2$O, C, 60.47 (60.60); H, 5.07 (4.62); N, 7.36 (6.42); Cl, 8.88 (8.13).

EXAMPLE 99

(+)-trans-2-(4-Bromo-2-chloro-phenyl)-8-(2-hydroxymethyl-1-methyl-pyrrolidin-3-yl)-5,7-dimethoxy-chromen-4-one Compound of example 12A (0.7 g, 2.2 mmol) in dry DMF (15 mL) was reacted with methyl 4-bromo-2-chlorobenzoate (1.13 g, 4.5 mmol) in the presence of NaH (50%, 0.542 g, 11.3 mmol) as described in example 16 to obtain the title compound.
Yield: 0.3 g (27%).
MS (CI): m/z 509 (M+1).

EXAMPLE 100

(+)-trans-2-(4-Bromo-2-chloro-phenyl)-5,7-dihydroxy-8-(2-hydroxymethyl-1-methyl-pyrrolidin-3-yl)-chromen-4-one Compound of example 99 (0.3 g, 0.59 mmol) was demethylated using pyridine hydrochloride (3 g, 26.0 mmol) as described in example 17 to obtain the title compound.
Yield: 0.1 g (35%); mp: 155-156° C.
IR cm$^{-1}$: 3400, 1660.
MS (ES+): m/z 481 (M+1).
Analysis: C$_{21}$H$_{19}$BrClNO$_5$.H$_2$O, C, 50.81 (50.69); H, 4.27 (4.25); N, 2.98 (2.81); Halogens (Cl+Br), 23.97 (23.18).

EXAMPLE 101

(±)-trans-2-(2-Chloro-5-dimethylamino-phenyl)-8-(2-hydroxymethyl-1-methyl-pyrrolidin-3-yl)-5,7-dimethoxy-chromen-4-one Compound of example 6 (0.8 g, 2.58 mmol) in dry DMF (15 mL) was reacted with methyl-2 chloro-5-dimethylaminobenzoate (1.65 g, 7.7 mmol) in the presence of NaH (50%, 0.62 g, 12.9 mmol) as described in example 16 to obtain the title compound.
Yield: 0.150 g (12%).
MS (ES+): m/z 473 (M+1).

EXAMPLE 102

(±)-trans-2-(2-Chloro-5-methylamino-phenyl)-5,7-dihydroxy-8-(2-hydroxymethyl-1-methyl-pyrrolidin-3-yl)-chromen-4-one Compound of example 101 (0.25 g, 0.53 mmol) was demethylated using pyridine hydrochloride (2.5 g, 21.6 mmol) as described in example 17 to obtain the title compound.
Yield: 0.04 g (17%); mp: 208-210° C.
IR cm$^{-1}$: 3450, 1650, 1600.
¹H NMR (DMSO d$_6$): δ 12.75 (s, 1H), 7.28 (m, 1H), 7.10 (m, 1H), 6.72 (m, 1H), 6.52 (s, 1H), 6.25 (s, 1H), 4.33 (m, 1H), 4.00 (m, 1H), 3.77 (m, 1H), 3.28 (m, 2H), 2.98 (m, 1H), 2.87 (s, 3H), 2.67 (s, 3H), 2.48 (m, 1H), 1.95 (m, 1H).
MS (ES+): m/z 431 (M+1).

EXAMPLE 103

(±)-trans-2-(2-Chloro-4-methoxy-phenyl)-8-(2-hydroxymethyl-1-methyl-pyrrolidin-3-yl)-5,7-dimethoxy-chromen-4-one Compound of example 6 (1.0 g, 3.2 mmol) in dry DMF (25 mL) was reacted with methyl 2-chloro-4-methoxybenzoate (1.29 g, 6.4 mmol) in the presence of NaH (50%, 0.776 g, 16 mmol) as described in example 16 to obtain the title compound.
Yield: 0.28 g (19%).
¹H NMR (CDCl$_3$): δ 7.70 (d, 1H), 7.02 (s, 1H), 6.90 (d, 1H), 6.55 (s, 1H), 6.45 (s, 1H), 4.20 (m, 1H), 4.02 (s, 3H), 3.98 (s, 3H), 3.86 (s, 3H), 3.70 (dd, 1H), 3.45 (d, 1H), 3.20 (m, 1H), 2.80 (d, 1H), 2.70 (d, 1H), 2.40 (s, 3H), 2.00 (m, 2H).
MS (ES+): m/z 460 (M+1).

EXAMPLE 104

(±)-trans-2-(2-Chloro-4-hydroxy-phenyl)-5,7-dihydroxy-8-(2-hydroxymethyl-1-methyl-pyrrolidin-3-yl)-chromen-4-one Compound of example 103 (0.25 g, 0.54 mmol) was demethylated using pyridine hydrochloride (4.0 g, 34.6 mmol) as described in example 17 to obtain the title compound.
Yield: 0.1 g (44%); mp: >300° C.
IR cm$^{-1}$: 3400, 1660.
¹H NMR (DMSO d$_6$): δ 12.70 (s, 1H), 7.40 (d, 1H), 6.90 (d, 1H), 6.80 (dd, 1H), 6.35 (s, 1H), 6.25 (s, 1H), 4.05 (m, 1H), 3.80 (d, 2H), 3.60 (m, 1H), 3.38 (m, 1H), 3.20 (m, 1H), 2.75 (s, 3H), 2.20 (m, 2H).
MS (ES−): m/z 416 (M−1).

EXAMPLE 105

(±)-trans-1-[2-Hydroxy-3-(3-hydroxy-1-methyl-piperidin-4-yl)-4,6-dimethoxy-phenyl]-ethanone Compound of example 2 (15 g, 53.4 mmol) was reacted with acetic anhydride (27.2 g, 269 mmol) in the presence of BF$_3$-etherate (37.9 g, 267 mmol) at 25° C. The reaction mixture was poured over crushed ice, made basic using saturated Na$_2$CO$_3$ solution. It was extracted using CHCl$_3$ (3×200 mL). The organic extract was washed with water, dried (anhydrous Na$_2$SO$_4$), and concentrated. The solid obtained was treated with 5% aqueous NaOH (85 mL) at 55-60° C. for 1 h. It was diluted with ice water (100 mL), acidified with acetic acid (pH 5), and further basified using aqueous Na$_2$CO$_3$ (pH 9). Filtration afforded the compound which was washed with water and dried to get the title compound.
Yield: 9 g (54.5%).
MS (CI): m/z 310 (M+1).

EXAMPLE 106

(±)-trans-2-(2-Chloro-phenyl)-8-(3-hydroxy-1-methyl-piperidin-4-yl)-5,7-dimethoxy-chromen-4-one Compound of example 105 (9 g, 29 mmol) in dry DMF (50 mL) was reacted methyl 2-chlorobenzoate (16.5 g, 96.7 mmol) in the presence of NaH (50%, 6.99 g, 145.6 mmol) as described in example 16 to obtain the title compound.
Yield: 7.5 g (60%).

MS (EI): m/z 429 (M+).

EXAMPLE 107

(±)-trans-8-(2-Azidomethyl-1-methyl-pyrrolidin-3-yl)-2-(2-chloro-phenyl)-5,7-dimethoxy-chromen-4-one Triethylamine (0.705 g, 7 mmol) was added to a solution of compound of example (106) (1.5 g, 3.5 mmol) in dry dichloromethane (25 mL) with stirring at 0-5° C., followed by a dropwise addition of methanesulfonyl chloride (0.479 g, 4.1 mmol). The reaction mixture was stirred for 30 min. in an ice-bath, poured into ice water, extracted with EtOAc (2×100 mL), washed with brine, and saturated aqueous $NaHCO_3$ solution, dried (anhydrous $Na_2SO_4$) and concentrated to obtain a syrup. It was dissolved in DMF (25 mL) treated with sodium azide (0.57 g, 8.7 mmol) and stirred for 2 h at 60-70° C. The reaction mixture was poured onto crushed ice, extracted using $CHCl_3$ (3×100 mL). The organic extract was washed with water, dried (anhydrous $Na_2SO_4$) and concentrated to obtain the title compound which was subjected to purification by column chromatography using EtOAc:petroleum ether (60-80° C.) (1:1) as eluant.

Yield: 0.6 g (37%).
IR $cm^{-1}$: 2180, 1640, 1600.
$^1$H NMR ($CDCl_3$): δ 7.60 (d, 1H), 7.45 (m, 3H), 6.48 (s, 1H), 6.45 (s, 1H), 4.05 (m, 1H), 4.02 (s, 3H), 4.00 (s, 3H), 3.45 (dd, 1H), 3.20 (m, 2H), 2.70 (m, 1H), 2.43 (m, 1H), 2.35 (m, 3H), 2.20 (m, 1H), 2.00 (m, 1H).
MS (ES+): m/z 455 (M+1).

EXAMPLE 108

(±)-trans-8-(2-Aminomethyl-1-methyl-pyrrolidin-3-yl)-2-(2-chloro-phenyl)-5,7-dimethoxy-chromen-4-one Compound of example 107 (0.6 g, 1.32 mmol) and triphenylphosphine (0.414 g, 1.58 mmol) were dissolved in THF (10 mL) containing water (0.1 mL). The resultant solution was stirred for 12 h. It was concentrated and the residue obtained was subjected to flash column chromatography using 5% IPA+1% liquor $NH_3$ in $CHCl_3$ as eluant to obtain the title compound.

Yield: 0.45 g (79.6%).
$^1$H NMR ($CDCl_3$): δ 7.60 (d, 1H), 7.45 (m, 3H), 6.48 (s, 1H), 4.05 (s, 3H), 3.99 (s, 3H), 3.95 (m, 1H), 3.08 (t, 1H), 2.75 (dd, 1H), 2.58 (m, 1H), 2.55 (m, 2H), 2.35 (m, 1H), 2.25 (s, 3H), 2.00 (m, 2H).
MS (ES+): m/z 429 (M+1).

EXAMPLE 109

(±)-trans-8-(2-Aminomethyl-1-methyl-pyrrolidin-3-yl)-2-(2-chloro-phenyl)-5,7-dihydroxy-chromen-4-one Compound of example 108 (0.45 g, 1.0 mmol) was demethylated using pyridine hydrochloride (5.0 g, 43.0 mmol) as described in example 17 to obtain the title compound.

Yield: 0.25 g (62%); mp: 218-219° C.
IR $cm^{-1}$: 3450, 1660.
MS (EI): m/z 400 (M+).
Analysis: $C_{21}H_{21}ClN_2O_4$, C, 62.52 (62.92); H, 5.28 (5.28); N, 7.24 (6.99); Cl, 8.51 (8.84).

EXAMPLE 110

(±)-trans-{3-[2-(2-Chloro-phenyl)-5,7-dimethoxy-4-oxo-4H-chromen-8-yl]-1-methyl-pyrrolidin-2-yl}-acetonitrile Triethylamine (0.352 g, 3.5 mmol) was added to a solution of compound of example (106) (1.0 g, 2.3 mmol) in dry dichloromethane (20 mL) with stirring at (0-5° C.), followed by a dropwise addition of methanesulfonyl chloride (0.319 g, 2.8 mmol). The reaction mixture was then stirred for 30 min, at 0-5° C., diluted with $CHCl_3$ (100 mL), washed with, water, saturated aqueous $NaHCO_3$ solution, dried (anhydrous $Na_2SO_4$) and concentrated. The residue was dissolved in IPA (20 mL) and treated with KCN (0.925 g, 14.2 mmol). The reaction mixture was then stirred at 80° C. for 1 h. Aqueous $FeCl_3$ was added to destroy excess KCN. It was basified with aqueous $Na_2CO_3$, extracted with EtOAc (3×100 mL), washed with water, dried (anhydrous $Na_2SO_4$), and concentrated. The crude obtained was purified using a silica gel column and 30% EtOAc+1% liquor $NH_3$ in $CHCl_3$ as an eluant to obtain the title compound.

Yield: 0.5 g (49.5%).
IR $cm^{-1}$: 2210, 1650, 1600.
$^1$H NMR (CDCl3): δ 7.60 (d, 1H), 7.45 (m, 3H), 6.47 (s, 1H), 6.44 (s, 1H), 4.02 (s, 3H), 4.00 (s, 3H), 3.90 (m, 1H), 3.10 (t, 1H), 2.78 (m, 1H), 2.40 (m, 2H), 2.35 (s, 3H), 2.18 (m, 1H), 2.00 (m, 1H), 1.80 (m, 1H).
MS (EI): m/z 438 (M+).

EXAMPLE 111

(±)-trans-{3-[2-(2-Chloro-phenyl)-5,7-dihydroxy-4-oxo-4H-chromen-8-yl]-1-methyl-pyrrolidin-2-yl}-acetonitrile Compound of example 110 (0.45 g, 1.0 mmol) was demethylated using pyridine hydrochloride (4.5 g, 39.0 mmol) as described in example 17 to obtain the title compound.

Yield: 0.35 g (85%); mp: 107-108° C.
IR $cm^{-1}$: 3300, 2240, 1640.
$^1$H NMR (DMSO $d_6$): δ 12.70 (s, 1H), 7.75 (d, 1H), 7.50 (m, 3H), 6.50 (s, 1H), 6.30 (s, 1H), 4.15 (d, 1H), 3.55 (m, 1H), 3.35 (t, 1H), 2.75 (m, 2H), 2.60 (s, 3H), 2.48 (m, 2H), 2.00 (m, 1H).
MS (ES+): m/z 411 (M+1).
Analysis: $C_{22}H_{21}ClN_2O_4$, C, 64.22 (64.00); H, 4.74 (5.13); N, 6.54 (6.79); Cl, 8.93 (8.59).

EXAMPLE 112

(±)-trans-2-(2-Chloro-phenyl)-8-(2-imidazol-1-ylm-ethyl-1-methyl-pyrrolidin-3-yl)-5,7-dimethoxy-chromen-4-one Compound of example 106 (0.7 g, 1.6 mmol) in $CHCl_3$ (20 mL) was treated with triethylamine (0.3 g, 2.8 mmol) and subsequently with methanesulfonyl chloride (0.28 g, 2.4 mmol) as described in example 110. The sulfonyl ester obtained was reacted with imidazole (0.44 g, 6.5 mmol) to get the title compound.

Yield: 0.35 g (46%).
$^1$H NMR (CDCl3): δ 7.45 (m, 5H), 6.77 (s, 1H), 6.67 (s, 1H), 6.48 (s, 1H), 6.44 (s, 1H) 4.00 (s, 3H), 3.97 (s, 3H), 3.90 (m, 1H), 3.75 (m, 1H), 3.10 (m, 2H), 2.40 (m, 2H), 2.25 (s, 3H), 2.10 (m, 1H), 1.90 (m, 2H).

MS (ES+): m/z 480 (M+1).

EXAMPLE 113

(±)-trans-2-(2-Chloro-phenyl)-5,7-dihydroxy-8-(2-imidazol-1-ylmethyl-1-methyl-pyrrolidin-3-yl)-chromen-4-one A mixture of compound of example 112 (0.3 g, 0.625 mmol) and pyridine hydrochloride (3.0 g, 26.0 mmol) was heated as described in example 17 to get the title compound.
Yield: 0.15 g (53%); mp: 249-250° C.
IR cm$^{-1}$: 3500, 1670.
$^1$H NMR (DMSO d$_6$): δ 12.70 (s, 1H), 7.67 (s, 1H), 7.50 (m, 4H), 6.97 (s, 1H), 6.87 (s, 1H), 6.40 (s, 1H), 6.35 (s, 1H), 4.25 (m, 1H), 4.05 (m, 1H), 3.88 (m, 1H), 3.45 (m, 1H), 2.95 (m, 2H), 2.50 (s, 3H), 2.28 (m, 1H), 2.00 (m, 1H).
MS (ES+): m/z 452 (M+1).
Analysis: C$_{24}$H$_{22}$ClN$_3$O$_4$C, 63.97 (63.79); H, 5.16 (4.91); N, 8.96 (9.30); Cl, 7.99 (7.85).

EXAMPLE 114

(±)-trans-2-[2-Chloro-phenyl-8-(2-mercaptomethyl-1-methyl-pyrrolidin-3-yl)]-5,7-dimethoxy-chromen-4-one Compound of example 106 (1.0 g, 2.3 mmol) in CHCl$_3$ (20 mL) was treated with triethylamine (0.3 g, 2.97 mmol) and subsequently with methanesulfonyl chloride (0.319 g, 2.8 mmol) as described in example 110. The sulfonyl ester obtained was reacted with thiourea (0.7 g, 9.2 mmol) followed by hydrolysis with 2% aqueous sodium hydroxide to get the title compound.
Yield: 0.6 g (58.5%).
MS (ES+): m/z 446 (M+1).

EXAMPLE 115

(±)-trans-2-(2-Chloro-phenyl)-5,7-dihydroxy-8-(2-mercaptomethyl-1-methyl-pyrrolidin-3-yl)-chromen-4-one Compound of example 114 (0.6 g, 1.3 mmol) was demethylated using pyridine hydrochloride (6.0 g, 52.0 mmol) as described in example 17 to obtain the title compound.
Yield: 0.15 g (28%); mp: 205-206° C.
IR cm$^{-1}$: 3400, 1650.
MS (ES+): m/z 418 (M+1).
Analysis: C$_{21}$H$_{20}$ClN$_2$O$_4$S.0.5H$_2$O C, 59.43 (59.08); H, 5.58 (4.95); N, 3.7 (3.28).

EXAMPLE 116

1-Benzyl-1-methyl-4-oxo-piperidinium bromide

To a solution of 1-methyl-4-piperidinone (15 g, 132 mmol) in dry acetone (100 mL) was added 1-bromomethylbenzene (24.9 g, 145 mmol) dropwise. It was stirred for 3 h. The precipitated compound was filtered, washed with dry acetone and dried to get the title compound.
Yield: 35 g (93%).

EXAMPLE 117

1-(4-Methoxyphenyl)-4-piperidone

Anhydrous potassium carbonate was added to a solution of 4-methoxyaniline (1.2 g, 9.8 mmol) in ethanol (10 mL) followed by a dropwise addition of a solution of compound of example 116 (2.77 g, 9.8 mmol) in water (3.0 mL). The reaction mixture was heated at 100° C. for 1 h., allowed to cool to room temperature, poured into ice water (100 mL) and extracted using EtOAc (3×50 mL). The organic extract was washed with water, dried (anhydrous Na$_2$SO$_4$) and concentrated to get the title compound.
Yield: 1.58 g (79%).
$^1$H NMR (CDCl$_3$): δ 6.95 (d, 2H), 6.85 (d, 2H), 3.80 (s, 3H), 3.45 (t, 4H), 2.55 (t, 4H).
MS (EI): m/z 205 (M$^+$).

EXAMPLE 118

1-(4-Methoxy-phenyl)-4-(2,4,6-trimethoxy-phenyl)-1,2,3,6-tetrahydro-pyridine

Compound of example 117 (19.0 g, 92 mmol) was added to a solution of 1,3,5-trimethoxybenzene (21.8 g, 130 mmol) in glacial acetic acid (50 mL) at 25° C. HCl gas was bubbled through the reaction mixture for 1 h, slowly raising the temperature up to 90° C. Acetic acid was removed under reduced pressure and the semisolid residue was poured over crushed ice (300 g). The resulting solution was made basic using an aqueous 50% NaOH solution. The precipitated solid was filtered, washed with water and dried. The solid was added slowly to boiling methanol, stirred for fifteen minutes and filtered to remove traces of trimethoxybenzene and the filtrate was concentrated to get the title compound.
Yield: 30 g (91%).
$^1$H NMR (DMSO d$_6$): δ 6.97 (d, 2H), 6.87 (d, 2H), 6.15 (s, 2H), 5.60 (s, 1H), 3.85 (s, 3H), 3.80 (s, 3H), 3.78 (s, 6H), 3.40 (t, 2H), 2.45 (bs, 2H).
MS (EI): m/z 355 (M$^+$).

EXAMPLE 119

1-(4-Methoxy-phenyl)-4-(2,4,6-trimethoxy-phenyl)-piperidin-3-ol

Compound of example 118 (15 g, 42 mmol) was subjected to hydroboration using NaBH$_4$ (2.7 g, 71.4 mmol) and BF$_3$-etherate (12.6 g, 88.8 mmol) in THF (50 mL). Excess diborane was destroyed by the addition of water. Conc. HCl (15 mL) was added and the reaction mixture was stirred at 50-55° C. for 1 h. It was cooled to room temperature The resulting mixture was made basic (pH 12-14) using an aqueous 50% NaOH solution. 30% H$_2$O$_2$ (9 mL) was added and the reaction mixture was stirred at 50-55° C. for 1 h. The reaction mixture was processed as described in example 2 to obtain the title compound.
Yield: 9.5 g (60.2%).
$^1$H NMR (CDCl$_3$): δ 7.00 (d, 2H), 6.90 (d, 2H), 6.20 (s, 2H), 4.50 (m, 1H), 3.85 (s, 3H), 3.82 (s, 6H), 3.80 (s, 3H), 3.65 (d, 1H), 3.20 (m, 1H), 2.70 (m, 1H), 2.60 (m 2H), 1.60 (m, 2H).
MS (ES+): m/z 374 (M+1).

EXAMPLE 120

(±)-trans-Acetic acid 4-(3-acetyl-2-hydroxy-4,6-dimethoxy-phenyl)-1-(4-methoxy-phenyl)-piperidin-3-yl ester Compound of example 119 (0.5 g, 1.3 mmol) was subjected to acylation using BF$_3$-ethrate (0.82 mL, 0.95 g, 6.7 mmol) and acetic anhydride (0.68 g, 6.7 mmol) according to the procedure described in the example 5 to obtain the title compound.

Yield: 0.15 g (25%).

$^1$H NMR (CDCl$_3$): δ 6.97 (d, 2H), 6.23 (d, 2H), 5.92 (s, 1H), 5.78 (m, 1H), 3.90 (s, 3H), 3.88 (s, 3H), 3.80 (m, 1H), 3.78 (s, 3H), 3.50 (m, 2H), 2.78 (m, 1H), 2.53 (s, 3H), 2.48 (m, 1H), 1.85 (s, 3H), 1.65 (m, 2H).

MS (EI): m/z 443 (M$^+$).

EXAMPLE 121

(±)-trans-1-{2-Hydroxy-3-[3-hydroxy-1-(4-methoxy-phenyl)-piperidin-4-yl]-4,6-dimethoxy-phenyl}-ethanone Compound of example 120 (0.25 g, 0.5 mmol) in MeOH (2 mL) was subjected to hydrolysis using 10% aqueous NaOH (2.0 mL) as given in example 6 to obtain the title compound.

Yield: 0.2 g (88%).

$^1$H NMR (CDCl$_3$): δ 14.30 (s, 1H), 6.95 (d, 2H), 6.80 (d, 2H), 6.00 (s, 1H), 4.50 (m, 1H), 3.95 (s, 3H), 3.92 (s, 3H), 3.85 (m, 1H), 3.80 (s, 3H), 3.55 (d, 1H), 3.20 (m, 1H), 2.70 (m, 1H), 2.65 (s, 3H), 2.55 (m, 1H), 1.70 (m, 2H).

MS (EI): m/z 401 (M$^+$).

EXAMPLE 122

(+)-trans-2-(2-Chloro-phenyl)-8-[3-hydroxy-1-(4-methoxyphenyl)-piperidin-4-yl]-5,7-dimethoxy-chromen-4-one Compound of example 121 (2.0 g, 5.0 mmol) in dry DMF (25 mL) was reacted with methyl 2-chlorobenzoate (2.55 g, 15 mmol) in the presence of NaH (50%, 1.19 g, 25 mmol) as described in example 16 to obtain the title compound.

Yield: 1.8 g (69%).

$^1$H NMR (CDCl$_3$): δ 7.65 (d, 1H), 7.48 (m, 3H), 6.90 (m, 4H), 6.48 (s, 1H), 6.42 (s, 1H), 4.50 (m, 1H), 3.90 (s, 6H), 3.82 (m, 1H), 3.78 (s, 3H), 3.56 (d, 1H), 3.42 (m, 1H), 2.68 (m, 1H) 2.52 (m, 1H), 1.82 (m, 2H).

MS (EI): m/z 521 (M$^+$).

EXAMPLE 123

(±)-trans-Acetic acid 3-[2-(2-chloro-phenyl)-5,7-dimethoxy-4-oxo-4H-chromen-8-yl]-1-(4-methoxy-phenyl)-pyrrolidin-2-ylmethyl ester Compound of example 122 (1.7 g, 3.2 mmol) was subjected to ring contraction as described in example 3, method A using methanesulfonyl chloride (0.448 g, 0.3 mL, 3.9 mmol), triethylamine (0.66 g, 0.95 mL, 6.5 mmol). The sulfonyl ester was treated with anhydrous sodium acetate (1.06 g, 13 mmol) to furnish the title compound.

Yield: 1.2 g (66%).

$^1$H NMR (CDCl$_3$): δ 7.55 (d, 1H), 7.45 (d, 1H), 7.30 (t, 1H), 7.05 (t, 1H), 6.80 (d, 2H), 6.65 (d, 2H), 6.55 (s, 1H), 6.38 (s, 1H), 4.35 (m, 1H), 4.28 (m, 1H), 4.00 (s, 3H), 3.99 (m, 1H), 3.82 (m, 1H), 3.78 (s, 3H), 3.70 (s, 3H), 3.52 (m, 1H), 3.35 (m, 1H), 2.25 (m, 2H), 1.75 (s, 3H).

MS (ES+): m/z 564 (M+1).

EXAMPLE 124

(±)-trans-2-(2-Chloro-phenyl)-8-[2-hydroxymethyl-1-(4-methoxy-phenyl)-pyrrolidin-3-yl]-5,7-dimethoxy-chromen-4-one Compound of example 123 (1.1 g, 1.94 mmol) in MeOH (5 mL) was hydrolyzed using 5% methanolic NaOH (5 mL) at 50° C. as described in example 4 to get the title compound.

Yield: 0.7 g (69%).

MS (ES+): m/z 522 (M+1).

EXAMPLE 125

(±)-trans-2-(2-Chloro-phenyl)-5,7-dihydroxy-8-[2-hydroxymethyl-1-(4-hydroxyphenyl)-pyrrolidin-3-yl]-chromen-4-one Compound of example 124 (0.7 g, 1.3 mmol) was demethylated using pyridine hydrochloride (10.5 g, 90.9 mmol) as described in example 17 to obtain the title compound.

Yield: 0.03 g (5%).

MS (ES+): m/z 480 (M+1).

EXAMPLE 126

(±)-trans-Acetic acid 4-[2-(2-chloro-phenyl)-5,7-dimethoxy-4-oxo-4H-chromen-8-yl]-1-methyl-piperidin-3-yl ester To a solution of compound of example 106 (3.35 g, 7.79 mmol) in dry CHCl$_3$ (25 mL) was added acetic anhydride (1.76 g, 17.43 mmol) at 25° C. with stirring, followed by the addition of dimethylaminopyridine (0.033 g, 1% w/w). The mixture was stirred for 0.5 h. It was poured into ice water (50 mL), basified using a saturated aqueous Na$_2$CO$_3$ solution and extracted using CHCl$_3$ (3×100 mL). The organic extract was washed with water, dried (anhydrous Na$_2$SO$_4$) and concentrated. The oil obtained was purified using a silica gel column and 0.1% MeOH+1% liquor NH$_3$ in CHCl$_3$ as eluant to get the title compound.

Yield: 3.33 g (89.7%).

$^1$H NMR (CDCl$_3$): δ 7.68 (d, 1H), 7.60 (d, 1H), 7.42 (t, 2H), 6.50 (s, 1H), 6.38 (s, 1H), 5.78 (m, 1H), 4.00 (s, 6H), 3.98 (m, 1H), 3.50 (m, 1H), 3.22 (m, 1H), 2.95 (m, 1H), 2.55 (m, 1H), 2.40 (s, 3H), 2.08 (m, 2H), 1.70 (s, 3H).

MS (ES+): m/z 472 (M+1).

EXAMPLE 127

(±)-trans-Acetic acid 4-[2-(2-chloro-phenyl)-5,7-dimethoxy-4-oxo-4H-chromen-8-yl]-1-cyano-piperidin-3-yl ester To compound of example 126 (2.9 g, 6.15 mmol) in dry CHCl$_3$ (40 mL) at 0° C. was added cyanogen bromide (2.1 g, 19.8 mmol). The reaction mixture was stirred at room temperature for 8 h. It was poured into water (100 mL) and extracted with CHCl$_3$ (3×100 mL). The organic extract was washed with water, dried (anhydrous Na$_2$SO$_4$) and concentrated. The solid residue obtained was purified using a silica gel column and 2% IPA+1% liquor NH$_3$ in CHCl$_3$ as eluant to obtain the title compound.

Yield: 2.22 g (75%).

IR cm$^{-1}$: 2220, 1740, 1640.

$^1$H NMR (CDCl$_3$): δ 7.52 (m, 4H), 6.48 (s, 1H), 6.42 (s, 1H), 5.68 (m, 1H), 4.02 (s, 6H), 4.00 (m, 1H), 3.70 (m, 1H), 3.50 (m, 1H), 3.38 (m, 1H), 3.10 (t, 1H), 2.90 (t, 1H), 2.58 (m, 1H), 1.70 (s, 3H).

MS (ES+): m/z 483 (M+1).

EXAMPLE 128

(±)-trans-2-(2-Chloro-phenyl)-8-(3-hydroxy-piperidin-4-yl)-5,7-dimethoxy-chromen-4-one Compound of example 127 (2 g, 4.14 mmol) was stirred with $H_3PO_4$ (6N, 50 mL) at 100° C. for 1.5 h. The solution was cooled to 25° C. and poured onto ice (100 g). It was made basic using a saturated aqueous $Na_2CO_3$ solution and extracted with EtOAc (3×150 mL). The organic extract was washed with water, dried (anhydrous $Na_2SO_4$), and concentrated. The crude obtained was purified using a silica gel column and 10% methanol+1% liquor $NH_3$ in $CHCl_3$ as eluant to furnish the title compound.

Yield: 0.87 g (50.5%).
$^1$H NMR ($CDCl_3$+DMSO $d_6$): δ 7.50 (dd, 1H), 7.25 (m, 3H), 6.28 (d, 2H), 4.15 (m, 1H), 3.80 (s, 3H), 3.78 (s, 3H), 3.20 (m, 3H), 2.90 (m, 1H), 2.35 (m, 2H), 2.05 (m, 1H).
MS (ES+): m/z 416 (M+1).

EXAMPLE 129

(±)-trans-2-(2-Chloro-phenyl)-8-(3-hydroxy-1-propyl-piperidin-4-yl)-5,7-dimethoxy-chromen-4-one A mixture of compound of example 128 (0.871 g, 2.09 mmol), n-propyl bromide (0.335 g, 2.72 mmol) and anhydrous $K_2CO_3$ (1.15 g, 8.33 mmol) in dry DMF (20 mL) was stirred at 25° C. for 2 h. The reaction mixture was treated with water and extracted with EtOAc (2×100 mL). The organic extract was washed with water, dried (anhydrous $Na_2SO_4$) and concentrated. The crude obtained was purified on a silica gel column using a mixture of 1% MeOH+1% liquor $NH_3$ in $CHCl_3$ as eluant to get the title compound.

Yield: 0.53 g (55.4%).
$^1$H NMR ($CDCl_3$): δ 7.62 (d, 1H), 7.45 (m, 3H), 6.42 (s, 1H), 6.40 (s, 1H), 4.65 (m, 1H), 3.98 (s, 3H), 3.97 (s, 3H), 3.35 (m, 2H), 3.05 (m, 1H), 2.50 (m, 3H), 2.10 (m, 3H), 1.62 (m, 2H), 0.92 (t, 3H).
MS (ES+): m/z 458 (M+1).

EXAMPLE 130

(±)-trans-Acetic acid 3-[2-(2-chloro-phenyl)-5,7-dimethoxy-4-oxo-4H-chromen-8-yl]-1-propyl-pyrrolidin-2-ylmethyl ester Methanesulfonyl chloride (0.178 g, 1.55 mmol), compound of example 129 (0.55 g, 1.2 mmol) and triethylamine (1 mL) in $CHCl_3$ (10 mL), were reacted as described in example 3, method A to obtain (±)-trans-methanesulfonic acid 4-[2-(2-chloro-phenyl)-5,7-dimethoxy-4-oxo-4H-chromen-8-yl]-1-propyl-piperidin-3-yl ester. This was dissolved in dry IPA at 80-90° C., anhydrous NaOAc (0.49 g, 5.98 mmol) was added, and the reaction mixture was processed as in example 3, method A to give an oily residue which was purified using a silica gel column and 1% IPA+1% liquor $NH_3$ in $CHCl_3$ as eluant to obtain the title compound.

Yield: 0.2 g (33.8%).
MS (ES+): m/z 500 (M+1).

EXAMPLE 131

(±)-trans-2-(2-Chloro-phenyl)-8-(2-hydroxymethyl-1-propyl-pyrrolidin-3-yl)-5,7-dimethoxy-chromen-4-one Compound of example 130 (0.2 g, 0.04 mmol) in methanol (5 mL) was subjected to hydrolysis using a 10% NaOH solution (5 mL) according to the procedure in example 4 to get the title compound.

Yield: 0.17 g (92.8%).
MS (ES+): m/z 458 (M+1).

EXAMPLE 132

(±)-trans-2-(2-Chloro-phenyl)-5,7-dihydroxy-8-(2-hydroxymethyl-1-propyl-pyrrolidin-3-yl)-chromen-4-one Following the procedure in example 17, compound of example 131 (0.155 g, 0.33 mmol) was demethylated using pyridine hydrochloride (2.0 g, 17.3 mmol) to obtain the title compound.

Yield: 0.046 g (31.6%); mp: 94-96° C.
IR cm$^{-1}$: 3000, 1650.
$^1$H NMR ($CDCl_3$): δ 7.61 (dd, 1H), 7.45 (m, 3H), 6.45 (s, 1H), 6.30 (s, 1H), 4.15 (m, 1H), 3.85 (m, 2H), 3.40 (m, 2H), 2.90 (m, 3H), 2.45 (m, 1H), 2.08 (m, 1H), 1.68 (m, 2H), 0.95 (t, 3H).
MS (ES+): m/z 430 (M+1).

EXAMPLE 133

(+)-trans-2-(2-Chloro-3-fluoro-phenyl)-8-(2-hydroxymethyl-1-methyl-pyrrolidin-3-yl)-5,7-dimethoxy-chromen-4-one Compound of example 12A (0.9 g, 2.9 mmol) in dry DMF (10 mL) was reacted with methyl 2-chloro-3-fluorobenzoate (0.656 g, 3.48 mmol) in the presence of NaH (50%, 0.696 g, 14.5 mmol) as detailed in example 16, to obtain the title compound.

Yield: 0.35 g (26.92%).
$^1$H NMR ($CDCl_3$): δ 7.58 (d, 1H), 7.35 (m, 2H), 6.55 (s, 1H), 6.45 (s, 1H), 4.25 (m, 1H), 4.08 (s, 3H), 3.98 (s, 3H), 3.68 (dd, 1H), 3.40 (m, 1H), 3.20 (m, 1H), 2.75 (m, 1H), 2.60 (m, 1H), 2.35 (s, 3H), 2.05 (m, 2H).
MS (ES+): m/z 448 (M+1).

EXAMPLE 134

(+)-trans-2-(2-Chloro-3-fluoro-phenyl)-5,7-dihydroxy-8-(2-hydroxymethyl-1-methyl-pyrrolidin-3-yl)-chromen-4-one Compound of example 133 (0.31 g, 0.74 mmol) was subjected to demethylation using pyridine hydrochloride (3.1 g, 26.84 mmol) as described in example 17 to obtain the title compound.

Yield: 0.12 g (41.37%); mp: 221-223° C.
IR cm$^{-1}$: 3554, 1665, 1650.
$^1$H NMR (DMSO $d_6$): δ 12.30 (s, 1H), 7.18 (m, 3H), 6.18 (s, 1H), 5.98 (s, 1H), 3.80 (m, 1H), 3.50 (m, 2H), 2.96 (m, 2H), 2.75 (m, 1H), 2.42 (s, 3H), 2.10 (m, 1H), 1.70 (m, 1H).
MS (ES+): m/z 420 (M+1).
Analysis: $C_{21}H_{19}ClFNO_5$ C, 58.77 (58.87); H, 4.61 (4.67); N, 3.27 (3.27), Cl, 7.86 (7.8).

EXAMPLE 135

(+)-trans-2-(2-Bromo-3-fluoro-phenyl)-8-(2-hydroxymethyl-1-methyl-pyrrolidin-3-yl)-5,7- dimethoxy-chromen-4-one

Compound of example 12A (1.1 g, 3.6 mmol) in dry DMF (10 mL) was reacted with methyl 2-bromo-3-fluorobenzoate (2 g, 8.58 mmol) in the presence of NaH (50%, 0.854 g, 17.79 mmol) as detailed in example 16, to obtain the title compound.

Yield: 0.45 g (25.7%).
$^1$H NMR (CDCl$_3$): δ 7.75 (m, 1H), 7.40 (m, 2H), 6.46 (s, 1H), 6.42 (s, 1H), 4.15 (m, 1H), 4.02 (s, 3H), 3.98 (s, 3H), 3.65 (m, 1H), 3.35 (m, 1H), 3.10 (m, 1H), 2.70 (m, 1H), 2.45 (m, 1H), 2.28 (s, 3H), 2.02 (m, 2H).
MS (EI): m/z 492 (M$^+$).

EXAMPLE 136

(+)-trans-2-(2-Bromo-3-fluoro-phenyl)-5,7-dihydroxy-8-(2-hydroxymethyl-1-methyl-pyrrolidin-3-yl)-chromen-4-one Compound of example 135 (0.45 g, 0.914 mmol) was subjected to demethylation using pyridine hydrochloride (4.5 g, 38.96 mmol) as described in example 17 to obtain the title compound.

Yield: 0.2 g (47.8%); mp: 237-239° C.
IR cm$^{-1}$: 3408, 1650.
$^1$H NMR (CDCl$_3$+TFA): δ 7.60 (m, 1H), 7.40 (m, 2H), 6.85 (s, 1H), 6.65 (s, 1H), 4.06 (m, 5H), 3.50 (m, 1H), 3.10 (s, 3H), 2.50 (m, 1H), 2.40 (m, 1H).
MS (ES+): m/z 465 (M+1).
Analysis: C$_{21}$H$_{19}$BrFNO$_5$.0.5H$_2$O, C, 53.47 (53.29); H, 3.53 (4.2); N, 2.51 (2.95); Br, 16.45 (16.88).

EXAMPLE 137

(+)-trans-2-(2-Chloro-5-iodo-phenyl)-8-(2-hydroxymethyl-1-methyl-pyrrolidin-3-yl)-5,7-dimethoxy-chromen-4-one Compound of example 12A (0.6 g, 1.94 mmol) in dry DMF (10 mL) was reacted with methyl 2-chloro-5-iodobenzoate (1.26 g, 4.24 mmol) in the presence of NaH (50%, 0.466 g, 9.7 mmol) as detailed in example 16, to obtain the title compound.

Yield: 0.3 g (28.03%).
$^1$H NMR (CDCl$_3$): δ 8.08 (d, 1H), 7.75 (m, 2H), 6.58 (s, 1H), 6.42 (s, 1H), 4.20 (m, 1H), 4.02 (s, 3H), 3.98 (s, 3H), 3.70 (m, 1H), 3.38 (m, 1H), 3.20 (m, 1H), 2.70 (m, 1H), 2.55 (m, 1H), 2.32 (s, 3H), 2.05 (m, 2H).
MS (ES+): m/z 556 (M+1).

EXAMPLE 138

(+)-trans-2-(2-Chloro-5-iodo-phenyl)-5,7-dihydroxy-8-(2-hydroxymethyl-1-methyl-pyrrolidin-3-yl)-chromen-4-one Compound of example 137 (0.1 g, 0.18 mmol) was subjected to demethylation using pyridine hydrochloride (1 g, 8.65 mmol) as described in example 17, to obtain the title compound.

Yield: 0.06 g (63.8%).
IR cm$^{-1}$: 3421, 1657.
$^1$H NMR (CDCl$_3$): δ 12.40 (s, 1H), 7.90 (s, 1H), 7.80 (d, 1H), 7.10 (d, 1H), 6.20 (s, 1H), 6.10 (s, 1H), 3.98 (m, 1H), 3.80 (m, 2H), 3.10 (m, 2H), 2.70 (m, 1H), 2.50 (s, 3H), 2.20 (m, 1H), 1.90 (m, 1H).
MS (ES+): m/z 528 (M+1).

EXAMPLE 139

(+)-trans-2-(2-Bromo-5-chloro-phenyl)-8-(2-hydroxymethyl-1-methyl-pyrrolidin-3-yl)-5,7-dimethoxy-chromen-4-one Compound of example 12A (1 g, 3.23 mmol) in dry DMF (10 mL) was reacted with methyl 2-bromo-5-chlorobenzoate (1.59 g, 6.25 mmol) in the presence of NaH (50%, 0.768 g, 16 mmol) as detailed in example 16 to obtain the title compound.

Yield: 1.02 g (62%).
$^1$H NMR (CDCl$_3$): δ 7.70 (m, 1H), 7.40 (m, 1H), 6.96 (d, 1H), 6.48 (s, 2H), 4.20 (m, 1H), 3.98 (s, 3H), 3.95 (s, 3H), 3.70 (m, 1H), 3.40 (m, 1H), 3.20 (m, 1H), 2.75 (m, 2H), 2.35 (s, 3H), 2.02 (m, 2H).
MS (ES+): m/z 510 (M+1).

EXAMPLE 140

(+)-trans-2-(2-Bromo-5-chloro-phenyl)-5,7-dihydroxy-8-(2-hydroxymethyl-1-methyl-pyrrolidin-3-yl)-chromen-4-one Compound of example 139 (0.11 g, 0.216 mmol) was subjected to demethylation using pyridine hydrochloride (1.1 g, 9.5 mmol) as described in example 17 to obtain the title compound.

Yield: 0.05 g (48.5%); mp: 233-235° C.
IR cm$^{-1}$: 3422, 1663.
$^1$H NMR (CDCl$_3$+DMSO d$_6$): δ 12.40 (s, 1H), 7.48 (d, 1H), 7.30 (s, 1H), 7.12 (d, 1H), 6.12 (s, 1H), 5.98 (s, 1H), 3.85 (m, 1H), 3.50 (m, 2H), 2.98 (m, 1H), 2.75 (m, 1H), 2.45 (s, 3H), 2.31 (m, 1H), 2.15 (m, 1H), 1.70 (m, 1H).
MS (ES+): m/z 481 (M+1).
Analysis: C$_{21}$H$_{19}$BrClNO$_5$C, 51.27 (51.53); H, 4.26 (4.11); N, 3.07 (2.86).

EXAMPLE 141

(±)-trans-3-[2-(2-Chloro-phenyl)-5,7-dimethoxy-4-oxo-4H-chromen-8-yl]-1-methyl-pyrrolidine-2-carbaldehyde Dimethyl sulfoxide (1.8 mL, 25.3 mmol) in methylene chloride (20 mL) was added to a stirred solution of oxalyl chloride (840 μL, 9.84 mmol) in dry methylene chloride (120 mL) dropwise at −50° C. The reaction mixture was stirred for 30 min. Compound of example 7, (2.0 g, 4.65 mmol) in methylene chloride (20 mL) was added dropwise to the reaction mixture. The resulting mixture was further stirred for 30 min. Triethylamine was added dropwise at −50° C. and the reaction mixture was warmed to room temperature and basified with NaHCO$_3$ solution (10 mL). Reaction mixture was extracted with methylene chloride, organic layer was washed with water, brine and dried (anhydrous Na$_2$SO$_4$) to afford the title compound.

Yield: 0.950 g (47.7%).
$^1$H NMR (CDCl$_3$): δ 9.42 (d, 1H), 7.48 (m, 4H), 6.52 (s, 1H), 6.49 (s, 1H), 4.20 (m, 1H), 3.95 (s, 3H), 3.85 (s, 3H), 3.18 (m, 1H), 3.10 (m, 1H), 2.45 (m, 1H), 2.32 (s, 3H), 2.25 (m, 1H), 2.08 (m, 1H).
MS (ES+): m/z 428 (M+1).

EXAMPLE 142

(±)-trans-3-[2-(2-Chloro-phenyl)-5,7-dimethoxy-4-oxo-4H-chromen-8-yl]-1-methyl-1-oxy-pyrrolidine- 2-carboxylic acid 55% m-Chloroperbenzoic acid (2.193 g, 0.7 mmol) in THF (20 mL) was added dropwise to pre-cooled (0° C.) solution of compound of example 141 (1 g, 2.33 mmol) in THF (50 mL). Reaction mixture was brought to room temperature in 2 h. and concentrated to obtain a solid. Saturated NaHCO$_3$ solution was added to the solid, stirred for 5 min, filtered, washed with water and dried in vacuum to afford the title compound.

Yield: 0.7 g (65.3%).

$^1$H NMR (CDCl$_3$+DMSO d$_6$): δ 7.32 (dd, 1H), 7.10 (m, 3H), 6.15 (s, 1H), 6.05 (s, 1H), 4.20 (m, 1H), 3.90 (d, 1H), 3.65 (s, 3H), 3.60 (s, 3H), 3.45 (m, 1H), 3.02 (s, 3H), 2.25 (m, 2H), 1.90 (m, 1H).

MS (EI): m/z 461 (M$^+$).

EXAMPLE 143

(±)-trans-3-[2-(2-Chloro-phenyl)-5,7-dimethoxy-4-oxo-4H-chromen-8-yl]-1-methyl-pyrrolidine-2-carboxylic acid 10% Pd—C (0.030 g) was added to a solution of compound of example 142 (0.4 g, 0.869 mmol) in methanol (50 mL). The reaction mixture was hydrogenated at 10 psi for 2 h. Reaction mass was then filtered over celite and purified using HP-20 column with water and methanol in the ratio 75:25 as eluant to obtain the title compound.

Yield: 0.230 g (59.6%); mp: 165-167° C.

$^1$H NMR (D$_2$O): δ 7.35 (m, 4H), 6.50 (s, 1H), 6.25 (s, 1H), 4.12 (m, 1H), 3.90 (s, 3H), 3.82 (s, 3H), 3.52 (m, 2H), 3.15 (m, 1H), 2.78 (s, 3H), 2.10 (m, 2H).

MS (ES+): m/z 444 (M+1).

EXAMPLE 144

(±)-trans-3-[2-(2-Chloro-phenyl)-5,7-dihydroxy-4-oxo-4H-chromen-8-yl]-1-methyl-pyrrolidine-2-carboxylic acid Compound of example 143 (0.25 g, 0.563 mmol) was treated with pyridine hydrochloride (2.5 g, 21 mmol) and the reaction mixture was further heated at 180° C. for 2 h. Water (1 mL) was added after completion of the reaction and reaction mixture was purified on HP-20 column using water as eluant, followed by methanol and water in the ratio 70:30 to obtain the title compound.

Yield: 0.102 g (43.6%); mp: 295-297° C.

$^1$H NMR (CDCl$_3$+DMSO d$_6$+TFA): δ 12.40 (s, 1H), 7.30 (m, 4H), 6.10 (s, 1H), 6.05 (s, 1H), 4.10 (m, 1H), 3.90 (m, 1H), 3.46 (m, 1H), 3.10 (m, 1H), 2.65 (s, 3H), 2.05 (m, 2H).

MS (ES+): m/z 416 (M+1).

Analysis: C$_{21}$H$_{18}$ClNO$_6$.0.5H$_2$O C, 59.22 (59.37); H, 4.20 (4.50); N, 2.85 (3.29); Cl, 8.14 (8.34).

EXAMPLE 145

(±)-trans-2-(2-Chloro-phenyl)-5,7-dihydroxy-8-(2-hydroxymethyl-1-methyl-1-oxy-pyrrolidin-3-yl)-chromen-4-one Compound of example 8, (0.1 g, 0.249 mmol) in methylene chloride was added to m-chloroperbenzoic acid (0.078 g, 0.250 mmol). Methanol (30 mL) was added to dissolve the reaction mixture and it was stirred for 30 min. It was concentrated to obtain a solid mixture, basified with saturated NaHCO$_3$ solution and stirred further for 5 mins. Mixture was then filtered, washed with water and dried in vacuum to obtain the title compound.

Yield: 0.035 g (33.4%).

$^1$H NMR (CDCl$_3$+DMSO d$_6$+TFA): δ 7.45 (m, 4H), 6.42 (s, 1H), 6.38 (s, 1H), 4.20 (m, 2H), 3.98 (m, 3H), 3.65 (s, 3H), 3.58 (m, 1H), 2.52 (m, 1H), 2.21 (m, 1H).

MS (ES+): m/z 418 (M+1).

EXAMPLE 146

(+)-trans-2-(4-Amino-2-bromo-phenyl)-8-(2-hydroxymethyl-1-methyl-pyrrolidin-3-yl)-5,7-dimethoxy-chromen-4-one Compound of example 41 (0.3 g, 0.6 mmol) was treated with iron dust (0.3 g) in water (1.2 mL) and glacial acetic acid (1.2 mL). The reaction mixture was stirred vigorously at room temperature for 1 h. It was poured into water (25 mL), basified using saturated aqueous Na$_2$CO$_3$ solution and extracted with EtOAc (3×25 mL). The organic extract was washed, dried (anhydrous Na$_2$SO$_4$) and concentrated to obtain the title compound.

Yield: 0.26 g (88%).

$^1$H NMR (CDCl$_3$): δ 7.45 (d, 1H), 6.95 (d, 1H), 6.70 (dd, 1H), 6.48 (s, 1H), 6.42 (s, 1H), 4.15 (m, 1H), 4.05 (s, 3H), 3.95 (s, 3H), 3.60 (dd, 1H), 3.50 (m, 1H), 3.15 (m, 1H), 2.64 (m, 1H), 2.58 (m, 1H), 2.35 (s, 3H), 2.01 (m, 2H).

MS (ES+): m/z 491 (M+1).

EXAMPLE 147

(+)-trans-2-(4-Amino-2-bromo-phenyl)-5,7-dihydroxy-8-(2-hydroxymethyl-1-methyl-pyrrolidin-3-yl)-chromen-4-one Compound of example 146 (0.150 g, 0.3 mmol) was demethylated using pyridine hydrochloride (1.5 g, 13 mmol) as described in example 17 to obtain the title compound.

Yield: 0.070 g (50%); mp: 208° C.

IR cm$^{-1}$: 3408, 1656, 1619.

$^1$H NMR (CDCl$_3$+DMSO d$_6$): δ 12.28 (s, 1H), 6.85 (d, 1H), 6.50 (d, 1H), 6.20 (dd, 1H), 5.80 (s, 1H), 5.65 (s, 1H), 3.54 (m, 1H), 3.20 (d, 2H), 2.64 (m, 3H), 2.15 (s, 3H), 1.80 (m, 1H), 1.40 (m, 1H).

MS (ES+): m/z 462 (M+1).

EXAMPLE 148

(+)-trans-2-(2-Bromo-4-methoxy-phenyl)-8-(2-hydroxymethyl-1-methyl-pyrrolidin-3-yl)-5,7-dimethoxy-chromen-4-one 2-Bromo-4-methoxybenzoic acid (2.8 g, 12.1 mmol) was reacted with compound of example 11A (2.2 g, 6.3 mmol) in dry pyridine (25 mL) using POCl$_3$ (7 g, 45.8 mmol) as described in example 39 to obtain (+)-trans-2-bromo-4-methoxy benzoic acid 2-(2-acetoxymethyl-1-methyl-pyrrolidin-3-yl)-6-acetyl-3,5-dimethoxy-phenylester (3.2 g, 5.7 mmol) a viscous oil, which was converted to the title compound using NaH (50%, 2.8 g, 50 mmol) in dry 1,4-dioxane (100 mL) followed by treatment with HCl as described in example 16.

Yield: 0.6 g (19%).

MS (ES+): m/z 505 (M+1).

EXAMPLE 149

(+)-trans-2-(2-Bromo-4-methoxy-phenyl)-5,7-dihydroxy-8-(2-hydroxymethyl-1-methyl-pyrrolidin-3-yl)-chromen-4-one (A) and (+)-trans-2-(2-Bromo-4-hydroxy-phenyl)-5,7-dihydroxy-8-(2-hydroxymethyl-1-methyl-pyrrolidin-3-yl)-chromen-4-one (B)

Compound of example 148 (0.155 g, 0.3 mmol) was demethylated using pyridine hydrochloride (1.6 g, 13.9 mmol) as described in example 17 to obtain the title compounds.

Compound (A):
Yield: 0.070 g (49%).
MS (EI): m/z 476 (M$^+$).

Compound (B):
Yield: 0.059 g (42%).
MS (EI): m/z 462 (M$^+$).

EXAMPLE 150

2-Bromo-5-nitrobenzoic acid

2-Bromobenzoic acid (10 g, 49.75 mmol) was added in portions with stirring to an ice cold nitrating mixture of 98% $H_2SO_4$ (25 mL) and 69% $HNO_3$ (12 mL) maintaining the temperature of the mixture below 5° C. The reaction mixture was stirred for 1 h. below 5° C. It was poured into ice water (200 mL). The white crystalline product obtained was filtered, washed with water and dried.

Yield: 7.5 g (66%).
$^1$H NMR (CDCl$_3$): δ 8.68 (d, 1H), 8.15 (dd, 1H), 7.85 (d, 1H).
MS (EI): m/z 246 (M$^+$).

EXAMPLE 151

5-Amino-2-bromo-benzoic acid methyl ester

Glacial acetic acid (75 mL) was added dropwise with stirring, at 40-50° C. to a mixture of compound of example 150 (15 g, 57.62 mmol) and iron dust (15 g, 0.267 mol) in water (120 mL). The reaction mixture was stirred vigorously at 25° C. for 1 h. It was poured into water (200 mL), basified using saturated aqueous Na$_2$CO$_3$ solution and extracted with EtOAc (3×250 mL). The organic extract was washed, dried (anhydrous Na$_2$SO$_4$) and concentrated to obtain 5-amino-2-bromobenzoic acid which was then converted into title compound as follows.

5-Amino-2-bromobenzoic acid (10.8 g, 50 mmol) was dissolved in methanol (100 mL). Conc. H$_2$SO$_4$ (2 mL) was added slowly and the reaction mixture heated to reflux for 4 h. The mixture was concentrated and the residue was allowed to cool to room temperature. It was poured over crushed ice. The organic product was extracted using diethyl ether (2×200 mL). The organic extract was washed with water, 10% aqueous NaHCO$_3$, dried (anhydrous Na$_2$SO$_4$) and concentrated to get the title compound.

Yield: 10.4 g (90%).
$^1$H NMR (CDCl$_3$): δ 7.38 (d, 1H), 7.14 (d, 1H), 6.65 (m, 1H), 3.99 (s, 3H).

MS (EI): m/z 231 (M$^+$).

EXAMPLE 152

2-Bromo-5-hydroxy-benzoic acid methyl ester

Compound of example 151 (12 g, 52.1 mmol) was added to 10% aqueous sulfuric acid (110 mL) at 0° C. An aqueous solution (40 mL) of NaNO$_2$ (4.3 g, 62.32 mmol) was added dropwise, with stirring at 0-5° C. The reaction mixture was stirred for 10 min. and was added to an ice cold aqueous solution of copper sulfate (156 g, 1 L, 625 mmol) containing Cu$_2$O (6.8 g, 47.55 mmol). The resultant mixture was stirred at 0° C. for 10 min. It was diluted with water and extracted using EtOAc (3×500 mL). The organic extract was washed with water, dried (anhydrous Na$_2$SO$_4$), concentrated and purified using a silica gel column and 2% EtOAc in petroleum ether (60-80° C.) as eluant to obtain the title compound.

Yield: 6.5 g (53%).
MS (EI): m/z 231 (M$^+$).

EXAMPLE 153

2-Bromo-5-methoxy-benzoic acid methyl ester

Compound of example 152 (6.5 g, 28.1 mmol) was dissolved in dry 1,4-dioxane (50 mL) under dry N$_2$ atmosphere. To this solution, NaH (50%, 3.37 g, 70.20 mmol) was added in portions at 25° C. and the mixture was stirred for 10 min. Dimethyl sulfate (4 mL, 5.31 g, 40.48 mmol) was added and the reaction mixture was stirred at 50° C. for 1 h. It was poured into ice water, acidified using 6N HCl and extracted using EtOAc (3×100 mL). The organic extract was washed with water, dried (anhydrous Na$_2$SO$_4$), concentrated and purified using a silica gel column and 5% EtOAc in petroleum ether (60-80° C.) as eluant to obtain the title compound.

Yield: 3.9 g (57%).
$^1$H NMR (CDCl$_3$): δ 7.55 (d, 1H), 7.32 (d, 1H), 6.90 (m, 1H), 3.95 (s, 3H), 3.80 (s, 3H).
MS (ES+): m/z 246 (M+1).

EXAMPLE 154

2-Chloro-5-nitro-benzoic acid

2-Chlorobenzoic acid (2 g, 12.7 mmol) was added with stirring at 25° C. to a nitrating mixture (20 mL) prepared from 1:1 HNO$_3$ (70%) and H$_2$SO$_4$ (98%). It was stirred for 1 h. and poured into ice water. The title compound obtained was filtered and dried.

Yield: 2.0 g (95%).
$^1$H NMR (CDCl$_3$): δ 8.60 (s, 1H), 8.20 (d, 1H), 7.60 (d, 1H).
MS (EI): m/z 201 (M$^+$).

EXAMPLE 155

2-Chloro-5-nitro-benzoic acid methyl ester

2-Chloro-5-nitrobenzoic acid (11 g, 54.5 mmol) was dissolved in methanol (100 mL). Conc. H$_2$SO$_4$ (2 mL) was added slowly and the reaction mixture heated to reflux for 4 h. The mixture was concentrated and the residue was allowed to cool to room temperature. It was poured over crushed ice. The organic product was extracted using diethyl ether (2×200 mL). The organic extract was washed with water, 10% aqueous NaHCO$_3$, dried (anhydrous Na$_2$SO$_4$) and concentrated to get the title compound.

Yield: 12 g (100%).

$^1$H NMR (CDCl$_3$): δ 8.60 (s, 1H), 8.20 (d, 1H), 7.60 (d, 1H), 3.90 (s, 3H).

MS (EI): m/z 215 (M$^+$).

EXAMPLE 156

5-Amino-2-chloro-benzoic acid methyl ester

Glacial acetic acid (75 mL) was added dropwise with stirring, at 40-50° C. to a mixture of 2-bromo-4-nitro-benzoic acid (12 g, 55.6 mmol) and iron dust (12 g, 0.214 mmol) in water (120 mL). The reaction mixture was stirred vigorously at 25° C. for 1 h. It was poured into water (200 mL), basified using saturated aqueous Na$_2$CO$_3$ solution and extracted with EtOAc (3×250 mL). The organic extract was washed, dried (anhydrous Na$_2$SO$_4$) and concentrated to obtain title compound.

Yield: 10.1 g (80%).

$^1$H NMR (CDCl$_3$): δ 7.10 (d, 1H), 7.05 (d, 1H), 6.80 (dd, 1H), 3.80 (s, 3H).

MS (EI): m/z 185 (M$^+$).

EXAMPLE 157

2-Chloro-5-fluoro-benzoic acid methyl ester

A solution of NaNO$_2$ (3.69 g, 53.4 mmol in 50 mL water) was added dropwise to a stirred suspension of methyl 5-amino-2-chlorobenzoate (9 g, 48.5 mmol) in HCl (10%, 90 mL), keeping the temperature between 0-5° C. The reaction mixture was stirred for 10 min. and a solution of fluoroboric acid (70%, excess) was added to the mixture. The precipitate of diazonium fluoroborate salt was filtered, washed with water and dried. The pyrolysis of this salt was then carried out at 140° C. for 15-20 min. The residue was purified using a silica gel column and 10% CHCl$_3$ in petroleum ether (60-80° C.) as an eluant to furnish the title compound.

Yield: 2.8 g (30%).

$^1$H NMR (CDCl$_3$): δ 7.55 (dd, 1H), 7.40 (m, 1H), 7.15 (m, 1H), 3.95 (s, 3H).

MS (ES+): m/z 189 (M+1).

EXAMPLE 158

2-Chloro-5-hydroxy-benzoic acid methyl ester

Compound of example 156 (9 g, 48.5 mmol) was subjected to diazotization using NaNO$_2$ (4.5 g 48.5 mmol) in water (50 mL) and H$_2$SO$_4$ (10%, 100 mL). Excess nitrous acid was neutralized with urea. The reaction mixture was poured into a suspension of CuSO$_4$.5H$_2$O (144 g, 577 mmol) and Cu$_2$O (5.22 g, 41.4 mmol) in water (900 mL) at 0° C. The reaction mixture was stirred for 15 min. at 0-5° C. and was then extracted using diethyl ether (3×200 mL). The organic extract was washed, dried (anhydrous Na$_2$SO$_4$), concentrated and purified using a silica gel column and 10% EtOAc in petroleum ether (60-80° C.) as eluant to obtain the title compound.

Yield: 4 g (44%).

$^1$H NMR (CDCl$_3$): δ 7.30 (t, 1H), 7.25 (d, 1H), 6.90 (dd 1H), 3.90 (s, 3H).

MS (ES+): m/z 187 (M+1).

EXAMPLE 159

2-Chloro-5-methoxy-benzoic acid methyl ester

Compound of example 158 (4 g, 21.4 mmol) was subjected to methylation using NaH (50%, 1 g) dry 1,4-dioxane (20 mL) and dimethyl sulfate (5.4 g, 42.8 mmol) as described in example 169. Purification using a silica gel column and 20% EtOAc in petroleum ether (60-80° C.) as eluant afforded the title compound (190).

Yield: 4.1 g (96%).

$^1$H NMR (CDCl$_3$): δ 7.30 (t, 1H), 7.25 (d, 1H), 6.90 (dd, 1H), 3.90 (s, 3H), 3.70 (s, 3H).

MS (EI): m/z 200 (M$^+$).

EXAMPLE 160

2-Chloro-5-dimethylamino-benzoic acid methyl ester

Compound of example 154 (4 g, 19.8 mmol) was subjected to hydrogenation at 40 psi, Pd—C (10%, 0.050 g) under methylating conditions using aqueous HCHO (40%, 8 mL) and HCOOH (100%, 8 mL) for 4 h. The catalyst was filtered off and the filtrate concentrated to get the title compound.

Yield: 4 g (95%).

$^1$H NMR (CDCl$_3$): δ 7.35 (d, 1H), 7.30 (t, 1H), 6.90 (d, 1H), 3.90 (s, 3H), 3.00 (s, 6H).

MS (EI): m/z 213 (M$^+$).

EXAMPLE 161

2-Chloro-4-nitro-benzoic acid methyl ester

2-Chloro-4-nitrobenzoic acid (50 g, 248 mmol) was subjected to esterification using methanol (500 mL) and H$_2$SO$_4$ (98%, 15 mL) according to the procedure described in the example 155 to obtain the title compound.

Yield: 48 g (90%)

EXAMPLE 162

4-Amino-2-chloro-benzoic acid methyl ester

Compound of example 161 (50 g, 232 mmol) was subjected to reduction using iron.

Yield: 40 g (93%).

$^1$H NMR (CDCl$_3$): δ 7.80 (d, 1H), 6.70 (s, 1H), 6.50 (dd, 1H), 3.70 (s, 3H).

MS (ES+): m/z 186 (M+1).

EXAMPLE 163

2-Chloro-4-hydroxy-benzoic acid methyl ester

Compound of example 162 (7.9 g, 42.5 mmol) suspended in 10% aqueous H$_2$SO$_4$ (80 mL) was reacted with NaNO$_2$ (3.5 g, 52.1 mmol in 35 mL water) as described in example 174. It was treated with a solution of CuSO$_4$.5H$_2$O (128 g, 513 mmol) and Cu$_2$O (5.5 g, 38.4 mmol) in water (800 mL) as described in the same procedure to obtain the title compound.

Yield: 2.5 g (31%).

$^1$H NMR (CDCl$_3$): δ 7.89 (d, 1H), 6.95 (s, 1H), 6.75 (d, 1H), 3.90 (s, 3H).

MS (EI): m/z 186 (M+).

EXAMPLE 164

2-Chloro-4-methoxy-benzoic acid methyl ester

To a solution of compound of example 163 (2.8 g, 15 mmol) in dry dioxane (50 mL) was added NaH (50%, 1.44 g, 30 mmol) and dimethyl sulfate (3.78 g, 30 mmol). It was stirred at 60-65° C. for 1 h. It was poured into ice water and extracted with EtOAc (2×100 mL). The organic extract was washed with brine, dried (anhydrous $Na_2SO_4$) and concentrated to obtain the title compound.

Yield: 2.5 g (83%).

$^1$H NMR ($CDCl_3$): δ 7.85 (d, 1H), 6.95 (s, 1H), 6.75 (d, 1H), 3.90 (s, 3H), 3.85 (s, 3H).

MS (EI): m/z 200 (M+).

EXAMPLE 165

2-Chloro-4-cyano-benzoic acid methyl ester

4-Amino-2-chloro-benzoic acid methyl ester (25 g, 72.7 mmol) was dissolved in 10% aqueous $H_2SO_4$ (150 mL) and the solution was cooled to 0° C. A solution of $NaNO_2$ (11.15 g, 16.88 mmol) in water (50 mL) was added dropwise maintaining the temperature between 0-5° C. The mixture was stirred for 10 min., excess nitrous acid was neutralized using a saturated aqueous $NaHCO_3$ solution. The resulting mixture was then added to a precooled (0-5° C.) suspension of CuCN (13.87 g, 155 mmol) and KCN (10.07 g, 155 mmol) in water (200 mL). It was stirred for 10 min., then allowed to attain room temperature. It was stirred for 0.5 h. and finally heated on a steam bath for 0.5 h. Excess saturated $FeCl_3$ solution was then added to the reaction mixture. It was extracted using EtOAc (3×200 mL). The organic extract was washed with water, dried (anhydrous $Na_2SO_4$), concentrated and purified using a silica gel column and $CHCl_3$:petroleum ether (60-80° C.) (1:1) as eluant to obtain the title compound.

Yield: 12 g (84%).

$^1$H NMR ($CDCl_3$): δ 7.90 (d, 1H), 7.75 (s, 1H), 7.60 (d, 1H), 4.00 (s, 3H).

MS (ES+): m/z: 196 (M+1).

EXAMPLE 166

4-Bromo-2-chloro-benzoic acid methyl ester

4-Amino-2-chloro-benzoic acid methyl ester (10 g, 54 mmol) was subjected to diazotization, using HBr (48%, 16 mL, water 150 mL) and $NaNO_2$ (4.1 g, 59.4 mmol in 20 mL water) as described in example 158. The diazonium salt formed was poured into a hot (70-80° C.) solution of CuBr (4.25 g, 29.6 mmol) in HBr (48%, 5 mL, water 100 mL). The reaction mixture was stirred at 25° C. for 15 min. It was extracted using diethyl ether (3×100 mL), processed and purified to obtain the title compound.

Yield: 8.0 g (59%).

$^1$H NMR ($CDCl_3$): δ 7.75 (d, 1H), 7.65 (s, 1H), 7.45 (d, 1H), 3.95 (s, 3H).

MS (EI): m/z 249.8 (M+).

EXAMPLE 167

2-Chloro-5-cyano-benzoic acid methyl ester

5-Amino-2-chloro-benzoic acid methyl ester (10 g, 54 mmol) was diazotized followed by treatment with CuCN and KCN using the procedure described in example 165 to get the title compound.

Yield: 8.0 g (59%).

$^1$HNMR ($CDCl_3$): δ 7.95 (d, 1H). 7.70 (d, 1H), 7.35 (m, 1H), 3.95 (s, 3H).

MS (EI): m/z 195 (M+).

EXAMPLE 168

2-Bromo-4-nitro-aniline

N-Bromosuccinimide (26 g, 146 mmol) was added to a stirred solution of 4-nitro aniline (20 g, 145 mmol) in dry DMF (75 mL) in portions under stirring at temperature 25-30° C. Reaction mixture was stirred for 30 min. It was poured over crushed ice slowly under vigorous stirring, filtered and dried, to afford the title compound.

Yield: 30 g (95%).

$^1$H NMR ($CDCl_3$): δ 8.40 (s, 1H), 8.10 (d, 1H), 6.75 (d, 1H), 4.85 (bs, 2H).

MS (ES+): m/z 218 (M+1).

EXAMPLE 169

2-Bromo-4-nitro-benzonitrile

Compound of example 168 (20 g, 92.2 mmol) was dissolved in 10% aqueous $H_2SO_4$ (100 mL) and the solution was cooled to 0° C. A solution of $NaNO_2$ (7.64 g, 110 mmol) in water (20 mL) was added dropwise maintaining the temperature between 0-5° C. The mixture was stirred for 10 min., excess nitrous acid was neutralized using a saturated aqueous $NaHCO_3$ solution. The resulting mixture was then added to a precooled (0-5° C.) suspension of CuCN (9.46 g, 105 mmol) and NaCN (5.20 g, 106 mmol) in water (200 mL). It was stirred for 10 min., and allowed to attain room temperature. It was stirred for 0.5 h and finally heated on a steam bath for 0.5 h. Excess saturated $FeCl_3$ solution was then added to the reaction mixture. It was extracted using EtOAc (3×200 mL). The organic extract was washed with water, dried (anhydrous $Na_2SO_4$), concentrated and purified using a silica gel column and $CHCl_3$ petroleum ether (60-80° C.) (1:1) as eluant to obtain the title compound.

Yield: 3.6 g (17%).

IR cm$^{-1}$: 3100, 2233, 1600, 1350.

$^1$H NMR ($CDCl_3$): δ 8.58 (s, 1H), 8.30 (d, 1H), 7.90 (d, 1H).

MS (ES+): m/z 228 (M+1).

EXAMPLE 170

2-Bromo-4-nitro-benzoic acid

2-Bromo-4-nitro-benzonitrile (0.5 g, 2.34 mmol) was hydrolysed using $H_2SO_4$ (2.2 mL) in water (2.7 mL) at 80° C. for 8 h. After completion of reaction, the solution was poured over crushed ice, basified with sodium carbonate and extracted with EtOAc. Aqueous layer was separated, acidified with 1:1 HCl and extracted with EtOAc (3×100 mL). The combined organic layers were concentrated to obtained compound.

Yield: 0.30 g (55.0%).
mp: 164-166° C.
$^1$H NMR (DMSO d$_6$): δ 8.40 (s, 1H), 8.10 (d, 1H), 7.85 (d, 1H).
MS (ES+): m/z 248 (M+1).

EXAMPLE 171

2-Bromo-4-methoxy-benzoic acid

2-Bromo-4-nitrobenzoic acid (3 g, 12.2 mmol) was reacted with sodium methoxide (6 g, 111 mmol) in dry DMSO (250 mL) at 80° C. After completion of reaction mixture was poured over crushed ice, acidified with 1:1 HCl and extracted with EtOAc (3×150 mL). The organic layer was concentrated to obtain the title compound.

Yield: 2.28 g (81%).
$^1$H NMR (DMSO d$_6$): δ 13.20 (s, 1H), 8.20 (d, 1H), 8.02 (d, 1H), 7.85 (d, 1H), 3.85 (s, 3H).

MS (ES+): m/z 232 (M+1).

The following table illustrate representative examples of the compounds of the present invention:

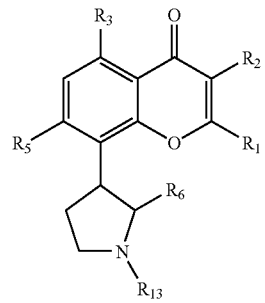

wherein in the compounds of above formula R$_1$, R$_2$, R$_3$, R$_5$, R$_6$ and R$_{13}$ are as defined in the following Table of examples.

| Compound | R$_1$ | R$_2$ | R$_3$ | R$_5$ | R$_6$ | R$_{13}$ |
|---|---|---|---|---|---|---|
| (±)Compound of Example 7 | 2-Chloro-phenyl | H | OCH$_3$ | OCH$_3$ | CH$_2$OH | CH$_3$ |
| (±)Compound of Example 8 | 2-Chloro-phenyl | H | OH | OH | CH$_2$OH | CH$_3$ |
| (+)Compound of Example 13 | 2-Chloro-phenyl | H | OCH$_3$ | OCH$_3$ | CH$_2$OH | CH$_3$ |
| (+)Compound of Example 14 | 2-Chloro-phenyl | H | OH | OH | CH$_2$OH | CH$_3$ |
| (+)Compound of Example 16 | 2-Bromo-phenyl | H | OCH$_3$ | OCH$_3$ | CH$_2$OH | CH$_3$ |
| (+)Compound of Example 17 | 2-Bromo-phenyl | H | OH | OH | CH$_2$OH | CH$_3$ |
| (+)Compound of Example 18 | 2-iodo-phenyl | H | OCH$_3$ | OCH$_3$ | CH$_2$OH | CH$_3$ |
| (+)Compound of Example 19 | 2-iodo-phenyl | H | OH | OH | CH$_2$OH | CH$_3$ |
| (+)Compound of Example 20 | 2-Fluoro-phenyl | H | OCH$_3$ | OCH$_3$ | CH$_2$OH | CH$_3$ |
| (+)Compound of Example 21 | 2-Fluoro-phenyl | H | OH | OH | CH$_2$OH | CH$_3$ |
| (±)Compound of Example 22 | 2-Chloro-5-fluoro-phenyl | H | OCH$_3$ | OCH$_3$ | CH$_2$OH | CH$_3$ |
| (±)Compound of Example 23 | 2-Chloro-5-fluoro-phenyl | H | OH | OH | CH$_2$OH | CH$_3$ |
| (+)Compound of Example 26 | 2-Chloro-5-fluoro-phenyl | H | OCH$_3$ | OCH$_3$ | CH$_2$OH | CH$_3$ |
| (+)Compound of Example 27 | 2-Chloro-5-fluoro-phenyl | H | OH | OH | CH$_2$OH | CH$_3$ |
| (+)Compound of Example 29 | 2-Bromo-5-fluoro-phenyl | H | OCH$_3$ | OCH$_3$ | CH$_2$OH | CH$_3$ |
| (+)Compound of Example 30 | 2-Bromo-5-fluoro-phenyl | H | OH | OH | CH$_2$OH | CH$_3$ |
| (±)Compound of Example 33 | 2-Bromo-5-methoxy-phenyl | H | OCH$_3$ | OCH$_3$ | CH$_2$OH | CH$_3$ |
| (±)Compound of Example 34A | 2-Bromo-5-methoxy-phenyl | H | OH | OH | CH$_2$OH | CH$_3$ |
| (±)Compound of Example 34B | 2-Bromo-5-hydroxy-phenyl | H | OH | OH | CH$_2$OH | CH$_3$ |
| (+)Compound of Example 35 | 2-Bromo-5-methoxy-phenyl | H | OCH$_3$ | OCH$_3$ | CH$_2$OH | CH$_3$ |
| (+)Compound of Example 36A | 2-Bromo-5-methoxy-phenyl | H | OH | OH | CH$_2$OH | CH$_3$ |
| (+)Compound of Example 36B | 2-Bromo-5-hydroxy-phenyl | H | OH | OH | CH$_2$OH | CH$_3$ |
| (+)Compound of Example 37 | 2-Chloro-5-methyl-phenyl | H | OCH$_3$ | OCH$_3$ | CH$_2$OH | CH$_3$ |
| (+)Compound of Example 38 | 2-Chloro-5-methyl-phenyl | H | OH | OH | CH$_2$OH | CH$_3$ |

-continued

| Compound | $R_1$ | $R_2$ | $R_3$ | $R_5$ | $R_6$ | $R_{13}$ |
|---|---|---|---|---|---|---|
| (+)Compound of Example 39 | 2-Bromo-5-nitro-phenyl | H | $OCH_3$ | $OCH_3$ | $CH_2OH$ | $CH_3$ |
| (+) Compound of Example 40 | 2-Bromo-5-nitro-phenyl | H | OH | OH | $CH_2OH$ | $CH_3$ |
| (+)Compound of Example 41 | 2-Bromo-4-nitro-phenyl | H | $OCH_3$ | $OCH_3$ | $CH_2OH$ | $CH_3$ |
| (+)Compound of Example 42 | 2-Bromo-4-nitro-phenyl | H | OH | OH | $CH_2OH$ | $CH_3$ |
| (+)Compound of Example (+) 44 | 2-bromo-4-nitro-phenyl | H | OH | OH | $CH_2OAc$ | $CH_3$ |
| (+)Compound of Example 46 | 2,4-dichloro-5-fluoro-phenyl | H | $OCH_3$ | $OCH_3$ | $CH_2OH$ | $CH_3$ |
| (+)Compound of Example 47 | 2,4-dichloro-5-fluoro-phenyl | H | OH | OH | $CH_2OH$ | $CH_3$ |
| (+)Compound of Example 56 | 2-phenyl | H | $OCH_3$ | $OCH_3$ | $CH_2OH$ | $CH_3$ |
| (+)Compound of Example 57 | 2-phenyl | H | OH | OH | $CH_2OH$ | $CH_3$ |
| (+)Compound of Example 59 | 4-Cyano-phenyl | $CH_3$ | $OCH_3$ | $OCH_3$ | $CH_2OH$ | $CH_3$ |
| (+)Compound of Example 60 | 4-Cyano-phenyl | $CH_3$ | OH | OH | $CH_2OH$ | $CH_3$ |
| (±)Compound of Example 62 | 4-trifluoromethyl-phenyl | H | $OCH_3$ | $OCH_3$ | $CH_2OH$ | $CH_3$ |
| (±)Compound of Example 63 | 4-trifluoromethyl-phenyl | H | OH | OH | $CH_2OH$ | $CH_3$ |
| (+)Compound of Example 64 | 4-trifluoromethyl-phenyl | H | $OCH_3$ | $OCH_3$ | $CH_2OH$ | $CH_3$ |
| (+)Compound of Example 65 | 4-trifluoromethyl-phenyl | H | OH | OH | $CH_2OH$ | $CH_3$ |
| (+)Compound of Example 67 | 2-thiophen-2-yl | H | $OCH_3$ | $OCH_3$ | $CH_2OH$ | $CH_3$ |
| (+)Compound of Example 68 | 2-thiophen-2-yl | H | OH | OH | $CH_2OH$ | $CH_3$ |
| (+)Compound of Example 70 | 2-Chloro-5-methoxy-phenyl | H | $OCH_3$ | $OCH_3$ | $CH_2OH$ | $CH_3$ |
| (+)Compound of Example 71 (Compound A) | 2-Chloro-5-methoxy-phenyl | H | OH | OH | $CH_2OH$ | $CH_3$ |
| (+)Compound of Example 71 (Compound B) | 2-Chloro-5-hydroxy-phenyl | H | OH | OH | $CH_2OH$ | $CH_3$ |
| (+)Compound of Example 73 | 3-Chloro-phenyl | H | $OCH_3$ | $OCH_3$ | $CH_2OH$ | $CH_3$ |
| (+)Compound of Example 74 (Compound A) | 3-Chloro-phenyl | H | OH | $OCH_3$ | $CH_2OH$ | $CH_3$ |
| (+)Compound of Example 74 (Compound B) | 3-Chloro-phenyl | H | OH | OH | $CH_2OH$ | $CH_3$ |
| (+)Compound of Example 75 | 3-Fluoro-phenyl | H | $OCH_3$ | $OCH_3$ | $CH_2OH$ | $CH_3$ |
| (+)Compound of Example 76 | 3-Fluoro-phenyl | H | OH | OH | $CH_2OH$ | $CH_3$ |
| (+) Compound of Example 77 | 4-Bromo-phenyl | H | $OCH_3$ | $OCH_3$ | $CH_2OH$ | $CH_3$ |
| (+) Compound of Example 78 (Compound A) | 4-Bromo-phenyl | H | OH | $OCH_3$ | $CH_2OH$ | $CH_3$ |
| (+) Compound of Example 78 (Compound B) | 4-Bromo-phenyl | H | OH | OH | $CH_2OH$ | $CH_3$ |
| (+)Compound of Example 79 | 2,6-Difluoro-phenyl | H | $OCH_3$ | $OCH_3$ | $CH_2OH$ | $CH_3$ |
| (+) Compound of Example 80 | 2,6-Difluoro-phenyl | H | OH | OH | $CH_2OH$ | $CH_3$ |
| (±)Compound of Example 81 | 4-Cyano-phenyl | H | $OCH_3$ | $OCH_3$ | $CH_2OH$ | $CH_3$ |
| (±)Compound of Example 82 (Compound A) | 4-Cyano-phenyl | H | OH | $OCH_3$ | $CH_2OH$ | $CH_3$ |
| (±) Compound of Example 82 (Compound B) | 4-Cyano-phenyl | H | OH | OH | $CH_2OH$ | $CH_3$ |
| (+) Compound of Example 83 | 4-Cyano-phenyl | H | $OCH_3$ | $OCH_3$ | $CH_2OH$ | $CH_3$ |
| (+)Compound of | 4-Cyano-phenyl | H | OH | $OCH_3$ | $CH_2OH$ | $CH_3$ |

-continued

| Compound | R₁ | R₂ | R₃ | R₅ | R₆ | R₁₃ |
|---|---|---|---|---|---|---|
| Example 84 (Compound A) | | | | | | |
| (+)Compound of Example 84 (Compound B) | 4-Cyano-phenyl | H | OH | OH | CH₂OH | CH₃ |
| (±)Compound of Example 85 | 3,5-Bis-trifluoromethyl-phenyl | H | OCH₃ | OCH₃ | CH₂OH | CH₃ |
| (±)Compound of Example 86 | 3,5-Bis-trifluoromethyl-phenyl | H | OH | OH | CH₂OH | CH₃ |
| (±)Compound of Example 87 | 2-Chloro-pyridin-3-yl | H | OCH₃ | OCH₃ | CH₂OH | CH₃ |
| (±)Compound of Example 88 | 2-Chloro-pyridin-3-yl | H | OH | OH | CH₂OH | CH₃ |
| (+)Compound of Example 89 | 2-Chloro-pyridin-3-yl | H | OCH₃ | OCH₃ | CH₂OH | CH₃ |
| (+) Compound of Example 90 | 2-Chloro-pyridin-3-yl | H | OH | OH | CH₂OH | CH₃ |
| (+) Compound of Example 91 | 4-nitro-phenyl | H | OCH₃ | OCH₃ | CH₂OH | CH₃ |
| (+)Compound of Example 92 | 4-nitro-phenyl | H | OH | OH | CH₂OH | CH₃ |
| (+)Compound of Example 93 | 4-nitro-phenyl | H | OH | OAc | CH₂OAc | CH₃ |
| (+)Compound of Example 94 | 4-Amino-phenyl | H | OH | OH | CH₂OH | CH₃ |
| (±)Compound of Example 95 | 2-methoxy-phenyl | H | OCH₃ | OCH₃ | CH₂OH | CH₃ |
| (±)Compound of Example 96 | 2-hydroxy-phenyl | H | OH | OH | CH₂OH | CH₃ |
| (+)Compound of Example 97 | 4-Cyano-phenyl | Cl | OCH₃ | OCH₃ | CH₂OH | CH₃ |
| (+)Compound of Example 98 | 4-Cyano-phenyl | Cl | OH | OH | CH₂OH | CH₃ |
| (+)Compound of Example 99 | 4-Bromo-2-chloro-phenyl | H | OCH₃ | OCH₃ | CH₂OH | CH₃ |
| (+)Compound of Example 100 | 4-Bromo-2-chloro-phenyl | H | OH | OH | CH₂OH | CH₃ |
| (±)Compound of Example 101 | 2-Chloro-5-dimethylamino-phenyl | H | OCH₃ | OCH₃ | CH₂OH | CH₃ |
| (±)Compound of Example 102 | 2-Chloro-5-methylamino-phenyl | H | OH | OH | CH₂OH | CH₃ |
| (±)Compound of Example 103 | 2-Chloro-4-methoxy-phenyl | H | OCH₃ | OCH₃ | CH₂OH | CH₃ |
| (±)Compound of Example 104 | 2-Chloro-4-hydroxy-phenyl | H | OH | OH | CH₂OH | CH₃ |
| (±)Compound of Example 107 | 2-Chloro-phenyl | H | OCH₃ | OCH₃ | Azidomethyl | CH₃ |
| (±)Compound of Example 108 | 2-Chloro-phenyl | H | OCH₃ | OCH₃ | Aminomethyl | CH₃ |
| (±)Compound of Example 109 | 2-Chloro-phenyl | H | OH | OH | Aminomethyl | CH₃ |
| (±)Compound of Example 110 | 2-Chloro-phenyl | H | OCH₃ | OCH₃ | CH₂CN | CH₃ |
| (±)Compound of Example 111 | 2-Chloro-phenyl | H | OH | OH | CH₂CN | CH₃ |
| (±)Compound of Example 112 | 2-Chloro-phenyl | H | OCH₃ | OCH₃ | 2-imidazol-1-ylmethyl | CH₃ |
| (±)Compound of Example 113 | 2-Chloro-phenyl | H | OH | OH | 2-imidazol-1-ylmethyl | CH₃ |
| (±)Compound of Example 114 | 2-Chloro-phenyl | H | OCH₃ | OCH₃ | 2-mercapto-methyl | CH₃ |
| (±)Compound of Example 115 | 2-Chloro-phenyl | H | OH | OH | 2-mercapto-methyl | CH₃ |
| (±)Compound of Example 123 | 2-Chloro-phenyl | H | OCH₃ | OCH₃ | CH₂OAc | 4-methoxy-phenyl |
| (±)Compound of | 2-Chloro-phenyl | H | OCH₃ | OCH₃ | CH₂OH | 4-methoxy- |

| Compound | R₁ | R₂ | R₃ | R₅ | R₆ | R₁₃ |
|---|---|---|---|---|---|---|
| Example 124 | | | | | | phenyl |
| (±)Compound of Example 125 | 2-Chloro-phenyl | H | OH | OH | CH₂OH | 4-hydroxy-phenyl |
| (±)Compound of Example 131 | 2-Chloro-phenyl | H | OCH₃ | OCH₃ | CH₂OH | propyl |
| (±)Compound of Example 132 | 2-Chloro-phenyl | H | OH | OH | CH₂OH | propyl |
| (+)Compound of Example 133 | 2-Chloro-3-fluoro-phenyl | H | OCH₃ | OCH₃ | CH₂OH | CH₃ |
| (+)Compound of Example 134 | 2-Chloro-3-fluoro-phenyl | H | OH | OH | CH₂OH | CH₃ |
| (+)Compound of Example 135 | 2-Bromo-3-fluoro-phenyl | H | OCH₃ | OCH₃ | CH₂OH | CH₃ |
| (+)Compound of Example 136 | 2-Bromo-3-fluoro-phenyl | H | OH | OH | CH₂OH | CH₃ |
| (+)Compound of Example 137 | 2-Chloro-5-iodo-phenyl | H | OCH₃ | OCH₃ | CH₂OH | CH₃ |
| (+)Compound of Example 138 | 2-Chloro-5-iodo-phenyl | H | OH | OH | CH₂OH | CH₃ |
| (+)Compound of Example 139 | 2-Bromo-5-chloro-phenyl | H | OCH₃ | OCH₃ | CH₂OH | CH₃ |
| (+)Compound of Example 140 | 2-Bromo-5-chloro-phenyl | H | OH | OH | CH₂OH | CH₃ |
| (±)Compound of Example 141 | 2-Chloro-phenyl | H | OCH₃ | OCH₃ | CHO | CH₃ |
| (±)Compound of Example 142 | 2-Chloro-phenyl | H | OCH₃ | OCH₃ | COOH | CH2OH |
| (±)Compound of Example 143 | 2-Chloro-phenyl | H | OCH₃ | OCH₃ | COOH | CH₃ |
| (±)Compound of Example 144 | 2-Chloro-phenyl | H | OH | OH | COOH | CH₃ |
| (±)Compound of Example 145 | 2-Chloro-phenyl | H | OH | OH | COOH | CH2OH |
| (+)Compound of Example 146 | 4-Amino-2-bromo-phenyl | H | OCH₃ | OCH₃ | CH₂OH | CH₃ |
| (+)Compound of Example 147 | 4-Amino-2-bromo-phenyl | H | OH | OH | CH₂OH | CH₃ |
| (+)Compound of Example 148 | 2-Bromo-4-methoxy-phenyl | H | OCH₃ | OCH₃ | CH₂OH | CH₃ |
| (+)Compound of Example 149 | 2-Bromo-4-methoxy-phenyl | H | OH | OH | CH₂OH | CH₃ |

The efficacy of the present compounds in inhibiting the activity of cyclin-dependent kinases can be determined by a number of pharmacological assays well known in the art, such as described below or, for example, in Losiewics, M. D., et al. Biochem. Biophys. Res. Commun., 1994, 201, 589. The kinases, cyclins, and substrates used in the in vitro kinase assay can be proteins isolated from mammalian cells, or alternatively, they can be proteins produced recombinantly. The exemplified pharmacological assays which follow hereinbelow have been carried out with the compounds of the present invention and their salts.

Cdk4/Cyclin D1 Kinase Assay and Cdk2/Cyclin E Kinase Assay

The assays measure phosphorylation of retinoblastoma protein (Rb) by Cdk4 or Cdk2 upon activation by cyclin D1 or cyclin E, respectively, through the transfer of ($\gamma^{32}$P)-phosphate from $\gamma^{32}$P-ATP in a 96-well filter plate assay.

Materials:

Cdk4 or Cdk2 was co-expressed with cyclin D1 or cyclin E, respectively, by a baculovirus expression system in insect cells. For this, 1×10⁷ Sf9 cells were coinfected with baculoviruses containing human Cdk-4 or 2 and cyclin D1 or E genes and after 72 hours cells were lysed in 500 µl of a lysis buffer (50 mM HEPES (pH 7.5), 10 mM MgCl₂, 1 mM DTT, 5 µg/ml of aprotinin, 5 µg/ml of leupeptin, 0.1 mM NaF, 0.2 mM phenylmethylsulfonyl fluoride (PMSF), and sodium orthovanadate). Centrifuged lysate was purified on a GST-sepharose column. Purity of the proteins was checked by SDS-PAGE followed by western blots using specific antibodies (Santacruz Biotec, USA) to Cdk4 or Cdk2.

GST-retinoblastoma (Rb) (aa 776-928) fusion protein is expressed in the bacteria *E. coli* and purified by GSH-Sepharose affinity chromatography. The GST-Rb bound to these beads served as the substrate in the assay.

Readout

Quantitation was by scintillation detection of ($^{32}$P)-GST-Rb in 96-well filter plates using Top Count scintillation 96-well counter (Packard, USA).

Procedure:

The Cdk 4 or Cdk 2 enzyme assay was run in 96-well format using Millipore Multiscreen filtration plates. All assay steps took place in a single filter plate (Unifilter plates, Packard, USA). The filtration wells were pre-wet with kinase buffer (100 µl/well) and the solution was then removed by the application of vacuum, with the filter plate on a vacuum manifold and the vacuum on. 50 µl of GST-Rb bound to GSH-Sepharose beads in kinase buffer (0.5 µg GST-Rb/50 µl) was added to each well and vacuum was applied to removed the buffer. A further 25 µl of a reaction mix containing ATP (cold+hot) and phosphatase inhibitors diluted in kinase buffer were added to each well, followed by the addition of test compound (4× final concentration in kinase buffer) or kinase buffer (control) in an additional 25 μl volume. Finally 50 μl (100 ng) of human Cdk-4/D1 or Cdk-2/E enzyme in kinase buffer was added to each well to initiate the reaction. The reaction was incubated for 30 min at 30° C. After the reaction was complete, vacuum was applied and the plate was washed with the wash buffer (TNEN buffer) three times. The filter plate was air-dried and placed in a Multiscreen adapter plate. To each well, 30 μl Packard Microscint-O cocktail was added and the plate was covered with a Top-Seal A film. The plate was counted in a Packard Top Count Scintillation Counter for 10 min. Flavopiridol was used as a standard inhibitor in all the experiments.

The concentration of compound at which 50% of phosphokinase activity of Cdk4-cyclin D1 and Cdk2-cyclin E was inhibited ($IC_{50}$) was calculated for representative compounds and their pharmaceutically acceptable salts described in the Examples. The results are indicated in Table 1.

TABLE 1

| | $IC_{50}$(μM) | | |
|---|---|---|---|
| Test Compound | Cdk4-CYCLIN D1 | Cdk2-CYCLIN E | Ratio of $IC_{50}$ Cdk2/E:Cdk4/D1 |
| Compound Of Example 36 (Compound A) | 0.08 | 6.00 | 75.0 |
| Compound Of Example 80 | 0.28 | 8.75 | 31.2 |
| Flavopiridol | 0.04 | 0.18 | 4.5 |

The results indicate that the compounds of the present invention have significant inhibitory effects against Cdk4/cyclin D1 and Cdk2/cyclin E with greater selectivity towards Cdk4-D1. The pharmaceutically acceptable salts of the tested compounds show the same activity.

In Vitro Cell Proliferation and Cytotoxicity Assays:

Exponentially growing cultures of ten human cancerous cell lines (HL-60 Promyelocytic Leukemia, PC-3 Prostate, H-460 Lung, MDA-MB-231 Breast, MCF-7 Breast, HeLa Cervix, Colo-205 Colon, H9 Lymphoma (T Cells), U-937 Histiocytic Lymphoma (monocytes) and CaCO-2 Colon) obtained from NCCS, Pune, India were used. The in vitro cell proliferation (NCI, USA protocol) and cytotoxicity assays were carried out using standard procedures viz. $^3$H-Thymidine uptake and MTS assay, respectively (For $^3$H-Thymidine uptake: Cell Biology, A Laboratory Handbook, 1998, Vol 1 Ed Julio E. Celis, and For MTS assay: Promega Protocol, USA, 2000). In the $^3$H-Thymidine uptake assay, cells were harvested after 72 hours onto GF/B unifilter plates (Packard, USA) using a Packard Filtermate Universal harvester and the plates were counted on a Packard TopCount 96-well liquid scintillation counter. The concentration of compound at which 50% of proliferative activity was inhibited ($IC_{50}$) and the degree of toxicity of compound were calculated for representative compounds and their pharmaceutically acceptable salts described in the Examples. It is evident from the following Table 2 that the compounds tested against the following cell lines exhibited anti-proliferative activity but according to the present invention, the inventors considered the compounds with $IC_{50} \geq 10$ μM in proliferation assay as not active or not having significant activity. The results are indicated in Table 2 below.

TABLE 2

| | $IC_{50}$(μM) | | | | | |
|---|---|---|---|---|---|---|
| Test Compound | HeLa Cervix | MCF-7 Breast | PC-3 Prostate | MDAMB-231 Breast | H460 Lung | U-937 Histiocytic lymphoma (monocytes) |
| Compound of Example 14A | 0.1-0.5 ++ | 0.5-1 NT | 0.5-1 ++ | 0.5-1 NT | 5.0-10 NT | 0.1-1 + |
| Compound of Example 17 | 0.1-1 + | 0.5-1 + | 1.0-10 NT | 0.1 NT | >10 NT | 0.1-1 + |
| Flavopiridol | 0.1-0.5 +++ | 0.5 + | 0.05-0.1 ++ | 0.1 ++ | 0.05 + | 0.1 ++ |

NT: not toxic ≦30%;
+: 30-50% toxic;
++: 50-70% toxic;
+++: above 70% toxic.

Having thus described in detail various embodiments of the present invention, it is to be understood that the invention defined by the above paragraphs is not to be limited to particular details set forth in the above description, as many apparent variations thereof are possible without departing from the spirit or scope of the present invention.

We claim:
1. A compound of general formula (Ic), or a stereoisomer, an optical isomer, a pharmaceutically acceptable salt, or a pharmaceutically acceptable solvate;

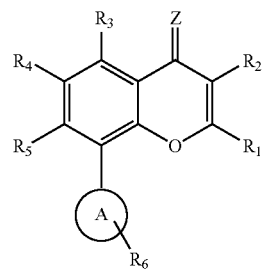

(Ic)

wherein
$R_1$ is phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl, or is a heterocycle, which is a saturated, partially unsaturated or aromatic ring containing 5 or 6 ring atoms of which 1, 2 or 3 are identical or different heteroatoms selected from: nitrogen, oxygen, sulfur, and phosphorus, and where the heterocycle is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$ trifluoromethyl, hydroxyl, cyano, carboxy, $C_1$-$C_4$-alkoxycarbonyl and $C_1$-$C_4$-alkylenehydroxyl;

$R_2$ is hydrogen, $C_1$-$C_6$-alkyl and phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl; $OR_{11}$, halogen, cyano, nitro, $NR_9R_{10}$ or $SR_{11}$;

$R_3$, $R_4$ and $R_5$ are each independently selected from: hydrogen, $C_1$-$C_4$-alkyl, halogen, $OR_{11}$, $C_1$-$C_4$-alkylcarbonyloxy, $NR_9R_{10}$, $SO_2NR_9R_{10}$, carboxyl, cyano and nitro;

Z is O or S;

A is a 5- or 6-membered ring; wherein:

(I) the 5 membered ring is saturated or unsaturated and is represented by any one of the general structures (i) to (v);

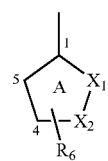

(i)

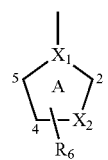

(ii)

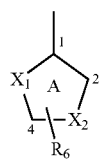

(iii)

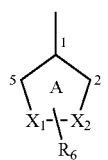

(iv)

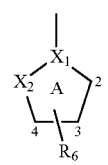

(v)

wherein $X_1$ and $X_2$ each independently represent methylene and a heteroatom selected from: oxygen, sulfur, and nitrogen, provided that at least one of $X_1$ and $X_2$ is a heteroatom, and when $X_1$ or $X_2$ is nitrogen, it is at least monosubstituted by $R_{13}$; wherein $R_{13}$ is selected from: hydrogen, unsubstituted $C_1$-$C_6$-alkyl, $C_1$-$C_6$-alkyl substituted by halogen, hydroxyl or carboxyl, $C_2$-$C_6$-alkenyl, hydroxyl, $C_1$-$C_6$-alkoxy, $C_1$-$C_4$-alkylcarbonyl, toluenesulfonyl, cyano, $SO_2R_{10}$, —$CO(CH_2)_mR_{14}$ and phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl;

$R_6$ is $C_1$-$C_4$-alkyleneOR$_{11}$;

(II) the 6-membered ring is saturated and of the general structure (vi):

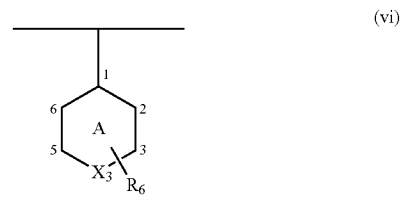

(vi)

wherein $X_3$ is a heteroatom selected from: oxygen, sulfur, and nitrogen and when $X_3$ is nitrogen, it is at least monosubstituted by $R_{13}$, wherein $R_{13}$ is selected from: hydrogen, unsubstituted $C_1$-$C_6$-alkyl, $C_1$-$C_6$-alkyl substituted by halogen, hydroxyl, or carboxyl, $C_2$-$C_6$-alkenyl, hydroxyl, $C_1$-$C_6$-alkoxy, $C_1$-$C_4$-alkylcarbonyl, toluenesulfonyl, cyano, $SO_2R_{10}$, —$CO(CH_2)_mR_{14}$ and phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl;

$R_6$ is —$C_1$-$C_4$-alkyleneOR$_{11}$;

$R_9$ and $R_{10}$ are each independently selected from: hydrogen, $C_1$-$C_4$-alkyl, $C_1$-$C_4$-alkanoyl, $C_1$-$C_4$-alkoxycarbonyl, $C_1$-$C_4$-alkylcarbonyl, carboxamide and sulfonamide; or $R_9$ and $R_{10}$, together with the nitrogen atom to which they are bonded, form a 3-, 4-, 5- or 6-membered heterocyclic ring which can have at least one further heteroatom selected from: nitrogen, oxygen and sulfur, which ring is saturated, partially unsaturated or aromatic, and either unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl;

$R_{11}$ is hydrogen, $C_1$-$C_4$-alkyl, $C_1$-$C_4$-alkanoyl, or $C_1$-$C_4$-alkoxycarbonyl;

$R_{14}$ is hydrogen, $C_1$-$C_4$-alkyl, hydroxyl, $NR_9R_{10}$, halogen, SH, or —S—$C_1$-$C_4$-alkyl; and m is an integer of 0 to 6.

2. The compound, stereoisomer, optical isomer, pharmaceutically acceptable salt, or pharmaceutically acceptable solvate thereof of claim 1;

wherein $R_1$ is phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl, or is a heterocycle, which is a saturated, partially unsaturated or aromatic ring containing 5 or 6 ring atoms of which 1, 2 or 3 are identical or different heteroatoms selected from: nitrogen, oxygen, sulfur, and phosphorus, and where the heterocycle is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl;

$R_2$ is hydrogen, $C_1$-$C_6$-alkyl, phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$ trifluoromethyl, hydroxyl, cyano, carboxy, $C_1$-$C_4$-alkoxycarbonyl and $C_1$-$C_4$-alkylenehydroxyl; $OR_{11}$, halogen, cyano, nitro, $NR_9R_{10}$ or $SR_{11}$;

$R_3$, $R_4$ and $R_5$ are each independently selected from: hydrogen, $C_1$-$C_4$-alkyl, $C_1$-$C_4$-alkoxyl, halogen, $OR_{11}$, $C_1$-$C_4$-alkylcarbonyloxy, $NR_9R_{10}$, $SO_2NR_9R_{10}$, carboxy, cyano and nitro;

Z is O;

A is a 5- or 6-membered ring;

wherein:

(I) the 5-membered ring is saturated or unsaturated and is represented by any one of the general structures (i) to (iv);

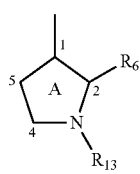

(i)

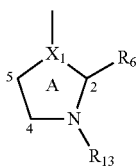

(ii)

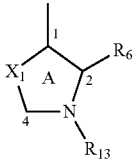

(iii)

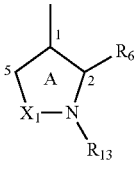

(iv)

wherein $X_1$ is either methylene or a heteroatom selected from: oxygen, sulfur, and nitrogen, except that in structures (ii) and (iv) $X_1$ is either methylene or nitrogen, and wherein $R_{13}$ is selected from: hydrogen, $C_1$-$C_6$-alkyl, which is unsubstituted or substituted by halogen, hydroxyl or carboxyl, $C_2$-$C_6$-alkenyl, hydroxyl, $C_1$-$C_6$-alkoxy, $C_1$-$C_4$-alkylcarbonyl, toluenesulfonyl, cyano, $SO_2R_{10}$, —$CO(CH_2)_mR_{14}$, and phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$ trifluoromethyl, hydroxyl, cyano, carboxy, $C_1$-$C_4$-alkoxycarbonyl and $C_1$-$C_4$-alkylenehydroxyl;

$R_6$ is —$C_1$-$C_4$-alkyleneOR$_{11}$, (II) the 6-membered ring is saturated and represented by the general structure (vi):

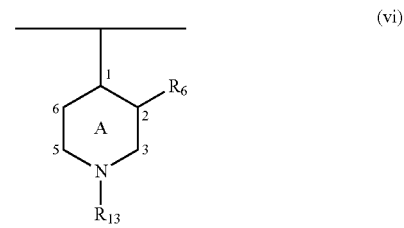

(vi)

wherein $R_{13}$ is selected from: hydrogen, unsubstituted $C_1$-$C_6$-alkyl, $C_1$-$C_6$-alkyl substituted by halogen, hydroxyl or carboxyl, $C_2$-$C_6$-alkenyl, hydroxyl, $C_1$-$C_6$-alkoxy, $C_1$-$C_4$-alkylcarbonyl, toluenesulfonyl, cyano, $SO_2R_{10}$, —$CO(CH_2)_mR_{14}$, and phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl;

$R_9$ and $R_{10}$ are each independently selected from: hydrogen, $C_1$-$C_4$-alkyl, $C_1$-$C_4$-alkanoyl, $C_1$-$C_4$-alkoxycarbonyl, $C_1$-$C_4$-alkylcarbonyl, carboxamide and sulfonamide; or $R_9$ and $R_{10}$, together with the nitrogen atom to which they are bonded, form a 3-, 4-, 5- or 6-membered heterocyclic ring which can have at least one further heteroatom selected from: nitrogen, oxygen and sulfur, which ring is saturated, partially unsaturated or aromatic and either unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$ trifluoromethyl, hydroxyl, cyano, carboxy, carbonyl-$C_1$-$C_4$-alkoxy and —$C_1$-$C_4$-alkylenehydroxyl;

$R_{11}$ is hydrogen, $C_1$-$C_4$-alkyl, $C_1$-$C_4$-alkanoyl, or $C_1$-$C_4$-alkoxycarbonyl;

$R_{14}$ is hydrogen, $C_1$-$C_4$-alkyl, hydroxyl, —$NR_9R_{10}$, halogen, —SH, or —S—$C_1$-$C_4$-alkyl; and m is an integer of 0 to 6.

3. The compound, stereoisomer, optical isomer, pharmaceutically acceptable salt, or pharmaceutically acceptable solvate thereof of claim 1;

wherein $R_1$ is phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl, or is a heterocycle, which is a saturated, partially unsaturated or aromatic ring containing 5 or 6 ring atoms of which 1, 2 or 3 are identical or different heteroatoms selected from: nitrogen, oxygen and sulfur, and where the heterocycle is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl;

$R_2$ and $R_4$ are hydrogen;

$R_3$ and $R_5$ are each independently selected from: $OR_{11}$, $C_1$-$C_4$-alkoxyl and $C_1$-$C_4$-alkylcarbonyloxy; wherein $R_{11}$ is hydrogen;

Z is O;

A is a 5- or 6-membered ring; wherein:

(I) the 5-membered ring is saturated or unsaturated and is represented by any one of the general structures (i) to (iv);

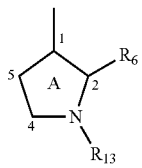

(i)

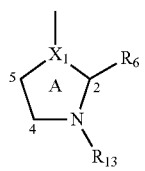

(ii)

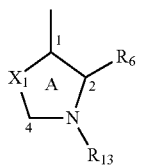

(iii)

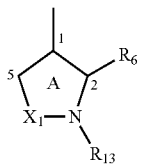

(iv)

wherein $X_1$ is either methylene or a heteroatom selected from: oxygen, sulfur, and nitrogen, except that in structures (ii) and (iv) $X_1$ is either methylene or nitrogen, and wherein $R_{13}$ is selected from: hydrogen, unsubstituted $C_1$-$C_6$-alkyl or $C_1$-$C_6$-alkyl substituted by halogen, hydroxyl or carboxyl, $C_2$-$C_6$-alkenyl, hydroxyl, $C_1$-$C_6$-alkoxy, $C_1$-$C_4$-alkylcarbonyl, toluenesulfonyl, cyano, $SO_2R_{10}$, —$CO(CH_2)_mR_{14}$ and phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$ trifluoromethyl, hydroxyl, cyano, carboxy, $C_1$-$C_4$-alkoxycarbonyl and $C_1$-$C_4$-alkylenehydroxyl;

$R_6$ is —$C_1$-$C_4$-alkyleneOR$_{11}$;

(II) the 6-membered ring is saturated and of the general structure (vi):

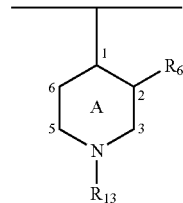

(vi)

wherein $R_{13}$ is selected from: hydrogen, unsubstituted $C_1$-$C_6$-alkyl, $C_1$-$C_6$-alkyl substituted by halogen, hydroxyl or carboxyl, $C_2$-$C_6$-alkenyl, hydroxyl, $C_1$-$C_6$-alkoxy, $C_1$-$C_4$-alkylcarbonyl, toluenesulfonyl, cyano, $SO_2R_{10}$, —$CO(CH_2)_mR_{14}$, and phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and —$C_1$-$C_4$-alkylenehydroxyl;

$R_6$ is —$C_1$-$C_4$-alkyleneOR$_{11}$;

$R_9$ and $R_{10}$ are each independently selected from: hydrogen, $C_1$-$C_4$-alkyl, $C_1$-$C_4$-alkanoyl, $C_1$-$C_4$-alkoxycarbonyl, $C_1$-$C_4$-alkylcarbonyl, carboxamide and sulfonamide; or $R_9$ and $R_{10}$, together with the nitrogen atom to which they are bonded, form a 3-, 4-, 5- or 6-membered heterocyclic ring which can have at least one further heteroatom selected from: nitrogen, oxygen and sulfur, which ring is saturated, partially unsaturated or aromatic and either unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, carbonyl-$C_1$-$C_4$-alkoxy and —$C_1$-$C_4$-alkylenehydroxyl;

$R_{11}$ is hydrogen, $C_1$-$C_4$-alkyl, $C_1$-$C_4$-alkanoyl, or $C_1$-$C_4$-alkoxycarbonyl;

$R_{14}$ is hydrogen, $C_1$-$C_4$-alkyl, hydroxyl, $NR_9R_{10}$, halogen, —SH, or S—$C_1$-$C_4$-alkyl; and m is an integer of 0 to 6.

4. The compound, stereoisomer, optical isomer, pharmaceutically acceptable salt, or pharmaceutically acceptable solvate thereof of claim 1;

wherein

A is a five membered ring represented by formula (i):

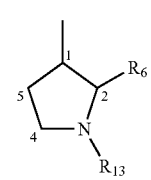

(i)

$R_1$ is phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl, or is a heterocycle, which is a saturated, partially unsaturated or aromatic ring containing 5 or 6 ring atoms of which 1, 2 or 3 are identical or different heteroatoms selected from: nitrogen, oxygen and sulfur, and where the heterocycle is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl;

$R_2$ and $R_4$ are hydrogen;

$R_3$ and $R_5$ are each independently selected from: $OR_{11}$, $C_1$-$C_4$-alkoxyl and $C_1$-$C_4$-alkylcarbonyloxy; wherein $R_{11}$ is hydrogen;

Z is O;

$R_6$ is —$C_1$-$C_4$-alkylene$OR_{11}$;

$R_9$ and $R_{10}$ are each independently selected from: hydrogen, $C_1$-$C_4$-alkyl, $C_1$-$C_4$-alkanoyl, $C_1$-$C_4$-alkoxycarbonyl, $C_1$-$C_4$-alkylcarbonyl, carboxamide and sulfonamide; or $R_9$ and $R_{10}$, together with the nitrogen atom to which they are bonded, form a 3-, 4-, 5- or 6-membered heterocyclic ring which can have at least one further heteroatom selected from: nitrogen, oxygen and sulfur, which ring is saturated, partially unsaturated or aromatic and either unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, carbonyl-$C_1$-$C_4$-alkoxy and —$C_1$-$C_4$-alkylenehydroxyl;

$R_{11}$ is hydrogen, $C_1$-$C_4$-alkyl, $C_1$-$C_4$-alkanoyl, or $C_1$-$C_4$-alkoxycarbonyl; and $R_{13}$ is hydrogen or $C_1$-$C_4$-alkyl.

5. A compound of the general formula (Ig), or a stereoisomer, an optical isomer, a pharmaceutically acceptable salt, or a pharmaceutically acceptable solvate thereof;

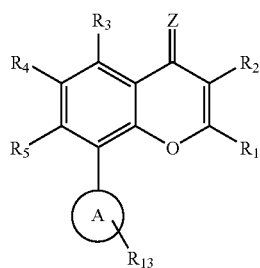

(Ig)

wherein $R_1$ is phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl, or is a heterocycle, which is a saturated, partially unsaturated or aromatic ring containing 5 or 6 ring atoms of which 1, 2 or 3 are identical or different heteroatoms selected from: nitrogen, oxygen, sulfur and phosphorus, and where the heterocycle is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl;

$R_2$ is hydrogen, $C_1$-$C_6$-alkyl, phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl, and $C_1$-$C_4$-alkylenehydroxyl $OR_{11}$, halogen, cyano, nitro, $NR_9R_{10}$ or $SR_{11}$;

$R_3$, $R_4$ and $R_5$ are each independently selected from: hydrogen, $C_1$-$C_4$-alkyl, $C_1$-$C_4$-alkoxyl, halogen, $OR_{11}$, $C_1$-$C_4$-alkylcarbonyloxy, $NR_9R_{10}$, $SO_2NR_9R_{10}$, carboxyl, cyano and nitro;

Z is O or S;

A is a 5-membered saturated ring represented by any one of the general structures (i) to (v);

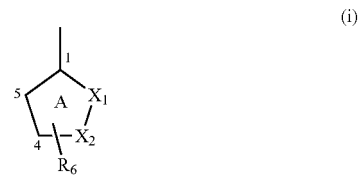

(i)

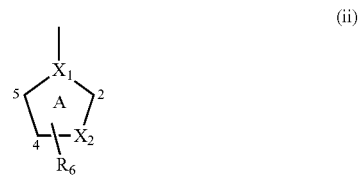

(ii)

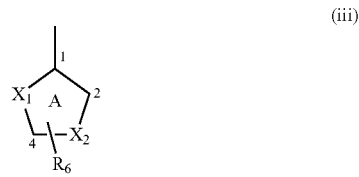

(iii)

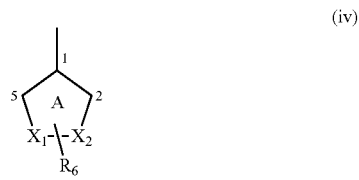

(iv)

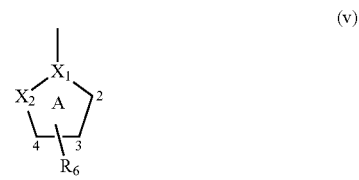

(v)

wherein $X_1$ and $X_2$ independently represent methylene and nitrogen, provided that at least one of $X_1$ and $X_2$ is nitrogen and the nitrogen is at least monosubstituted by $R_{13}$, wherein $R_{13}$ is selected from: hydrogen, unsubstituted $C_1$-$C_6$-alkyl or $C_1$-$C_6$-alkyl substituted by halogen, hydroxyl, or carboxyl, $C_2$-$C_6$-alkenyl, hydroxyl, $C_1$-$C_6$-alkoxy, $C_1$-$C_4$-alkylcarbonyl, toluenesulfonyl, $SO_2R_{10}$, —$CO(CH_2)_mR_{14}$, cyano, and phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$ trifluoromethyl, hydroxyl, cyano, carboxy, $C_1$-$C_4$-alkoxycarbonyl and $C_1$-$C_4$-alkylenehydroxyl; and $R_6$ is $C_1$-$C_4$-alkyl, $C_1$-$C_4$-alkanoyl, hydroxyl, $C_1$-$C_4$-alkoxyl, $C_1$-$C_4$-alkoxycarbonyl, $C_1$-$C_4$-alkylene$OR_{11}$, $C_1$-$C_4$-alkylenehalo, $C_1$-$C_4$-alkylene$NR_9R_{10}$, $C_1$-$C_4$-alkyleneC(O)$OR_9$, phenoxy, —$NR_9R_{10}$, $SR_{12}$, S(O)$_nR_{12}$, —C(O)$R_{12}$ or —C(S)$R_{12}$;

$R_9$ and $R_{10}$ are each independently selected from: hydrogen, $C_1$-$C_4$-alkyl, $C_1$-$C_4$-alkanoyl, $C_1$-$C_4$-alkoxycarbonyl, $C_1$-$C_4$-alkylcarbonyl, carboxamide and sulfonamide; or $R_9$ and $R_{10}$, together with the nitrogen atom to which they are bonded, form a 3-, 4-, 5- or 6-membered heterocyclic ring which can have at least one further heteroatom selected from: nitrogen, oxygen and sulfur, which ring is saturated, partially unsaturated or aromatic and either unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$, trifluoromethyl, hydroxyl, cyano, carboxy, carbonyl-$C_1$-$C_4$-alkoxy and —$C_1$-$C_4$-alkylenehydroxyl;

$R_{11}$ is hydrogen, $C_1$-$C_4$-alkyl, $C_1$-$C_4$-alkanoyl or $C_1$-$C_4$-alkoxycarbonyl;

$R_{12}$ is hydrogen, halogen, $C_1$-$C_4$-alkyl, $NR_9R_{10}$ or $OR_9$;

$R_{14}$ is hydrogen, $C_1$-$C_4$-alkyl, hydroxyl, $NR_9R_{10}$, halogen, SH or —S—$C_1$-$C_4$-alkyl;

m is an integer of 0 to 6; and n is an integer of 1 or 2.

6. A compound of the general formula (Ig) as claimed in claim 5, wherein $X_1$ is methylene and $X_2$ is nitrogen substituted by $R_{13}$, wherein $R_{13}$ is as defined.

7. The compound, stereoisomer, optical isomer, pharmaceutically acceptable salt, or pharmaceutically acceptable solvate thereof of claim 5;

wherein $R_1$ is phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl, or is a heterocycle, which is a saturated, partially unsaturated or aromatic ring containing 5 or 6 ring atoms of which 1, 2 or 3 are identical or different heteroatoms selected from: nitrogen, oxygen and sulfur, and where the heterocycle is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$, trifluoromethyl, hydroxyl, cyano, carboxy, $C_1$-$C_4$-alkoxycarbonyl and $C_1$-$C_4$-alkylenehydroxyl;

$R_2$ and $R_4$ are hydrogen;

$R_3$ and $R_5$ are each independently selected from: $OR_{11}$, $C_1$-$C_4$-alkoxyl and $C_1$-$C_4$-alkylcarbonyloxy; wherein $R_{11}$ is hydrogen;

Z is O;

A is a 5-membered saturated ring represented by any one of the general structures (i) to (v);

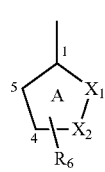

(i)

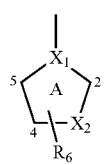

(ii)

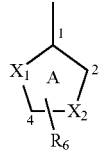

(iii)

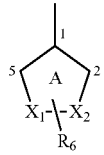

(iv)

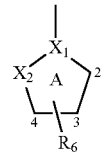

(v)

wherein $X_1$ and $X_2$ each independently represent: methylene and nitrogen, provided that at least one of $X_1$ and $X_2$ is nitrogen and the nitrogen is at least monosubstituted by $R_{13}$, wherein $R_{13}$ is selected from: hydrogen, unsubstituted $C_1$-$C_6$-alkyl, $C_1$-$C_6$-alkyl substituted by halogen, hydroxyl or carboxyl, $C_2$-$C_6$-alkenyl, hydroxyl, $C_1$-$C_6$-alkoxy, $C_1$-$C_4$-alkylcarbonyl, toluenesulfonyl, cyano, $SO_2R_{10}$, —$CO(CH_2)_mR_{14}$ and phenyl, which is unsubstituted or substituted by 1, 2, or 3 identical or different substituents selected from: halogen, $C_1$-$C_4$-alkyl, $C_1$-$C_4$-alkoxy, nitro, $NR_9R_{10}$, $SR_{11}$ trifluoromethyl, hydroxyl, cyano, carboxy, $C_1$-$C_4$-alkoxycarbonyl and $C_1$-$C_4$-alkylenehydroxyl;

$R_6$ is $C_1$-$C_4$-alkyl, $C_1$-$C_4$-alkanoyl, hydroxyl, $C_1$-$C_4$-alkoxyl, $C_1$-$C_4$-alkoxycarbonyl, $C_1$-$C_4$-alkyleneOR$_{11}$, $C_1$-$C_4$-alkylenehalo, $C_1$-$C_4$-alkyleneNR$_9$R$_{10}$, $C_1$-$C_4$-alkyleneC(O)OR$_9$, phenoxy, $NR_9R_{10}$, $SR_{12}$, $S(O)_nR_{12}$, —C(O)R$_{12}$ or —C(S)R$_{12}$;

$R_9$ and $R_{10}$ are each independently selected from: hydrogen, $C_1$-$C_4$-alkyl, $C_1$-$C_4$-alkanoyl, $C_1$-$C_4$-alkoxycarbonyl, $C_1$-$C_4$-alkycarbonyl, carboxamide and sulfonamide; or $R_9$ and $R_{10}$, together with the nitrogen atom to which they are bonded, form a 3-, 4-, 5- or 6-membered heterocyclic ring which can have at least one further heteroatom selected from: nitrogen, oxygen and sulfur, which ring is saturated, partially unsaturated or aromatic and either unsubstituted or substituted by at least one substituent selected from: halogen, $C_1$-$C_4$-alkyl, $C_1$-$C_4$-alkoxy, $C_2$-$C_6$-alkenyl, $C_3$-$C_6$-alkynyl, $C_2$-$C_4$-alkanoyl, nitro, $NR_9R_{10}$, $SR_{11}$ trifluoromethyl, hydroxyl, cyano, carboxy, carbonyl-$C_1$-$C_4$-alkoxy and —$C_1$-$C_4$-alkylenehydroxyl;

$R_{11}$ is hydrogen, $C_1$-$C_4$-alkyl, $C_1$-$C_4$-alkanoyl or $C_1$-$C_4$-alkoxycarbonyl;

$R_{12}$ is hydrogen, halogen, $C_1$-$C_4$-alkyl, $NR_9R_{10}$, or $OR_9$;

$R_{14}$ is hydrogen, $C_1$-$C_4$-alkyl, hydroxyl, $NR_9R_{10}$, halogen, —SH, or —S—$C_1$-$C_4$-alkyl;

m is an integer of 0 to 6; and n is an integer of 1 or 2.

8. The compound, stereoisomer, optical isomer, pharmaceutically acceptable salt, or pharmaceutically acceptable solvate thereof of claim 5;

wherein

R$_1$ is phenyl, which is unsubstituted or substituted by 1, 2, or 3 identical or different substituents selected from: halogen, C$_1$-C$_4$-alkyl, C$_1$-C$_4$-alkoxy, nitro, NR$_9$R$_{10}$, SR$_{11}$, trifluoromethyl, hydroxyl, cyano, carboxy, C$_1$-C$_4$-alkoxycarbonyl and C$_1$-C$_4$-alkylenehydroxyl, or is a heterocycle, which is a saturated, partially unsaturated or aromatic ring containing 5 or 6 ring atoms of which 1, 2 or 3 are identical or different heteroatoms selected from: nitrogen, oxygen and sulfur, and where the heterocycle is unsubstituted or substituted by 1, 2, or 3 identical or different substituents selected from: halogen, C$_1$-C$_4$-alkyl, C$_1$-C$_4$-alkoxy, nitro, NR$_9$R$_{10}$, SR$_{11}$, trifluoromethyl, hydroxyl, cyano, carboxy, C$_1$-C$_4$-alkoxycarbonyl and C$_1$-C$_4$-alkylenehydroxyl;

R$_2$ and R$_4$ are hydrogen;

R$_3$ and R$_5$ are each independently selected from: OR$_{11}$, C$_1$-C$_4$-alkoxyl and C$_1$-C$_4$-alkylcarbonyloxy; wherein R$_{11}$ is hydrogen;

Z is O;

A is a 5-membered saturated ring represented by any one of the general structures (i) to (iv);

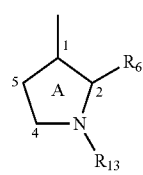

(i)

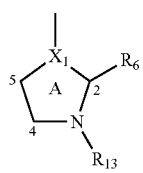

(ii)

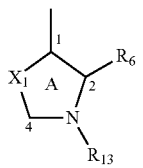

(iii)

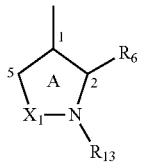

(iv)

wherein X$_1$ is either a methylene or nitrogen; and

R$_{13}$ is selected from: hydrogen, unsubstituted C$_1$-C$_6$-alkyl or C$_1$-C$_6$-alkyl substituted by halogen, hydroxyl or carboxyl, C$_2$-C$_6$-alkenyl, hydroxyl, C$_1$-C$_6$-alkoxy, C$_1$-C$_4$-alkylcarbonyl, toluenesulfonyl, cyano, SO$_2$R$_{10}$, —CO(CH$_2$)$_m$R$_{14}$ and phenyl, which is unsubstituted or substituted by 1, 2, or 3 identical or different substituents selected from: halogen, C$_1$-C$_4$-alkyl, C$_1$-C$_4$-alkoxy, nitro, NR$_9$R$_{10}$, SR$_{11}$, trifluoromethyl, hydroxyl, cyano, carboxy, C$_1$-C$_4$-alkoxycarbonyl and C$_1$-C$_4$-alkylenehydroxyl; and R$_6$ is C$_1$-C$_4$-alkyl, C$_1$-C$_4$-alkanoyl, hydroxyl, C$_1$-C$_4$-alkoxyl, C$_1$-C$_4$-alkoxycarbonyl, C$_1$-C$_4$-alkyleneOR$_{11}$, C$_1$-C$_4$-alkylenehalo, C$_1$-C$_4$-alkyleneNR$_9$R$_{10}$, C$_1$-C$_4$-alkyleneC(O)OR$_9$, phenoxy, NR$_9$R$_{10}$, SR$_{12}$, S(O)$_n$R$_{12}$, —C(O)R$_{12}$ or —C(S)R$_{12}$;

R$_9$ and R$_{10}$ are each independently selected from: hydrogen, C$_1$-C$_4$-alkyl, C$_1$-C$_4$-alkanoyl, C$_1$-C$_4$-alkoxycarbonyl, C$_1$-C$_4$-alkylcarbonyl, carboxamide and sulfonamide; or R$_9$ and R$_{10}$, together with the nitrogen atom to which they are bonded, form a 3-, 4-, 5- or 6-membered heterocyclic ring which can have at least one further heteroatom selected from: nitrogen, oxygen and sulfur, which ring is saturated, partially unsaturated or aromatic and either unsubstituted or substituted by at least one substituent selected from: halogen, C$_1$-C$_4$-alkyl, C$_1$-C$_4$-alkoxy, C$_2$-C$_6$-alkenyl, C$_3$-C$_6$-alkynyl, C$_2$-C$_4$-alkanoyl, nitro, NR$_9$R$_{10}$, SR$_{11}$ trifluoromethyl, hydroxyl, cyano, carboxy, carbonyl-C$_1$-C$_4$-alkoxy and —C$_1$-C$_4$-alkylenehydroxyl;

R$_{11}$ is hydrogen, C$_1$-C$_4$-alkyl, C$_1$-C$_4$-alkanoyl, or C$_1$-C$_4$-alkoxycarbonyl;

R$_{12}$ is hydrogen, halogen, C$_1$-C$_4$-alkyl, —NR$_9$R$_{10}$, or OR$_9$;

R$_{14}$ is hydrogen, C$_1$-C$_4$-alkyl, hydroxyl, —NR$_9$R$_{10}$, halogen, —SH, or —S—C$_1$-C$_4$-alkyl;

m is an integer of 0 to 6; and n is an integer of 1 or 2.

9. A compound as claimed in claim 1, wherein R$_1$ is phenyl or pyridinyl, substituted by 1, 2 or 3 identical or different substituents selected from: halogen, nitro and C$_1$-C$_4$-alkoxy, R$_2$ and R$_4$ are hydrogen, R$_3$ and R$_5$ are OR$_{11}$, A is a saturated 5-membered ring represented by any one of the general structures (i) to (v), wherein R$_{11}$ is hydrogen and X$_1$, X$_2$, R$_6$ and R$_{13}$ are as defined.

10. A compound as claimed in claim 5, wherein R$_1$ is phenyl or pyridinyl, substituted by 1, 2 or 3 identical or different substituents selected from: halogen, nitro and C$_1$-C$_4$-alkoxy, R$_2$ and R$_4$ are hydrogen, and R$_3$ and R$_5$ are OR$_{11}$, A is a saturated 5-membered ring represented by any one of the general structures (i) to (v), wherein R$_{11}$ is hydrogen and X$_1$, X$_2$, R$_6$ and R$_{13}$ are as defined.

11. A compound as claimed in claim 9, wherein R$_1$, R$_2$, R$_3$, R$_4$ and R$_5$ are as defined, A is a saturated 5-membered ring represented by any one of the general structures (i) to (v), wherein X$_1$ is methylene, X$_2$ is nitrogen, R$_6$ is —C$_1$-C$_4$-alkylenehydroxyl, and R$_{13}$ is C$_1$-C$_4$-alkyl.

12. A compound as claimed in claim 10, wherein R$_1$, R$_2$, R$_3$, R$_4$ and R$_5$ are as defined, A is a saturated 5-membered ring represented by any one of the general structures (i) to (v) wherein X$_1$ is methylene, X$_2$ is nitrogen, R$_6$ is selected from: C$_1$-C$_4$-alkyleneOR$_{11}$, C$_1$-C$_4$-alkylenehalo, C$_1$-C$_4$-alkyleneNR$_9$R$_{10}$, and C$_1$-C$_4$-alkyleneC(O)OR$_9$, wherein R$_9$, R$_{10}$ and R$_{11}$ are as defined, and R$_{13}$ is C$_1$-C$_4$-alkyl.

13. A compound of the general formula (Ic) as claimed in claim 1, which is:

(±)-trans-2-(2-chlorophenyl)-8-(2-hydroxymethyl-1-methyl-pyrrolidin-3-yl)-5,7-dimethoxy-chromen-4-one, (±)-trans-2-(2-chlorophenyl)-5,7-dihydroxy-8-(2-hydroxymethyl-1-methyl-pyrrolidin-3-yl)-chromen-4-one, (+)-trans-2-(2-chlorophenyl)-8-(2-hydroxymethyl-1-methyl-pyrrolidin-3-yl)-5,7-dimethoxy-chromen-4-one, (+)-trans-2-(2-chlorophenyl)-5,7-dihydroxy-8-(2-hydroxymethyl-1-methyl-pyrrolidin-3-yl)-chromen-4-one, (−)-trans-2-(2-chlorophenyl)-8-(2-hydroxymethyl-1-methyl-pyrrolidin-3-yl)-5,7-dimethoxy-chromen-4-one, (−)-trans-2-(2-chlorophenyl)-5,7-dihydroxy-8-(2-hydroxymethyl-1-methyl-pyrrolidin-3-yl)-chromen-4-one, (+)-trans-2-(2-bromophenyl)-8-(2-hydroxymethyl-1-methyl-pyrrolidin-3-yl)-5,7-dimethoxy-chromen-4-one, (+)-trans-2-(2-bromophenyl)-5,7-dihydroxy-8-(2-hydroxymethyl-1-methyl-pyrrolidin-3-yl)-chromen-4-one, (+)-trans-8-(2-hydroxymethyl-1-methyl-pyrrolidin-3-yl)-2-(2-iodophenyl)-5,7-dimethoxy-chromen-4-one, (+)-trans-5,7-dihydroxy-8-(2-hydroxymethyl-1-methyl-pyrrolidin-3-yl)-2-(2-iodophenyl)-chromen-4-one, (+)-trans-2-(2-fluorophenyl)-8-(2-hydroxymethyl-1-methyl-pyrrolidin-3-yl)-5,7-dimethoxy-chromen-4-one, (+)-trans-2-(2-fluorophenyl)-5,7-dihydroxy-8-(2-hydroxymethyl-1-methyl-pyrrolidin-3-yl)-chromen-4-one, (±)-trans-2-(2-chloro-5-fluoro-phenyl)-8-(2-hydroxymethyl-1-methyl-pyrrolidin-3-yl)-5,7-dimethoxy-chromen-4-one, (±)-trans-2-(2-chloro-5-fluoro-phenyl)-5,7-dihydroxy-8-(2-hydroxymethyl-1-methyl-pyrrolidin-3-yl)-chromen-4-one, (+)-trans-2-(2-chloro-5-fluoro-phenyl)-8-(2-hydroxymethyl-1-methyl-pyrrolidin-3-yl)-5,7-dimethoxy-chromen-4-one, (+)-trans-2-(2-chloro-5-fluoro-phenyl)-5,7-dihydroxy-8-(2-hydroxymethyl-1-methyl-pyrrolidin-3-yl)-chromen-4-one, (+)-trans-2-(2-bromo-5-fluoro-phenyl)-8-(2-hydroxymethyl-1-methyl-pyrrolidin-3-yl)-5,7-dimethoxy-chromen-4-one, (+)-trans-2-(2-bromo-5-fluoro-phenyl)-5,7-dihydroxy-8-(2-hydroxymethyl-1-methyl-pyrrolidin-3-yl)-chromen-4-one, (±)-trans-2-(2-bromo-5-methoxy-phenyl)-8-(2-hydroxymethyl-1-methyl-pyrrolidin-3-yl)-5,7-dimethoxy-chromen-4-one, (±)-trans-2-(2-bromo-5-methoxy-phenyl)-5,7-dihydroxy-8-(2-hydroxymethyl-1-methyl-pyrrolidin-3-yl)-chromen-4-one, (±)-trans-2-(2-bromo-5-hydroxy-phenyl)-5,7-dihydroxy-8-(2-hydroxymethyl-1-methyl-pyrrolidin-3-yl)-chromen-4-one, (+)-trans-2-(2-bromo-5-methoxy-phenyl)-8-(2-hydroxymethyl-1-methyl-pyrrolidin-3-yl)-5,7-dimethoxy-chromen-4-one, (+)-trans-2-(2-bromo-5-methoxy-phenyl)-5,7-dihydroxy-8-(2-hydroxymethyl-1-methyl-pyrrolidin-3-yl)-chromen-4-one, (+)-trans-2-(2-bromo-5-hydroxy-phenyl)-8-(2-hydroxymethyl-1-methylpyrrolidin-3-yl)-5,7-dihydroxy-chromen-4-one, (+)-trans-2-(2-chloro-5-methyl-phenyl)-8-(2-hydroxymethyl-1-methyl-pyrrolidin-3-yl)-5,7-dimethoxy-chromen-4-one (+)-trans-2-(2-chloro-5-methyl-phenyl)-5,7-dihydroxy-8-(2-hydroxymethyl-1-methyl-pyrrolidin-3-yl)-chromen-4-one, (+)-trans-2-(2-bromo-5-nitro-phenyl)-8-(2-hydroxymethyl-1-methyl-pyrrolidin-3-yl)-5,7-dimethoxy-chromen-4-one, (+)-trans-2-(2-bromo-5-nitro-phenyl)-5,7-dihydroxy-8-(2-hydroxymethyl-1-methyl-pyrrolidin-3-yl)-chromen-4-one, (+)-trans-2-(2-bromo-4-nitro-phenyl)-8-(2-hydroxymethyl-1-methylpyrrolidin-3-yl)-5,7-dimethoxy-chromen-4-one, (+)-trans-2-(2-bromo-4-nitro-phenyl)-5,7-dihydroxy-8-(2-hydroxymethyl-1-methyl-pyrrolidin-3-yl)-chromen-4-one, (+)-trans-2-(2,4-dichloro-5-fluoro-phenyl)-8-(2-hydroxymethyl-1-methyl-pyrrolidin-3-yl)-5,7-dimethoxy-chromen-4-one, (+)-trans-2-(2,4-dichloro-5-fluoro-phenyl)-5,7-dihydroxy-8-(2-hydroxymethyl-1-methyl-pyrrolidin-3-yl)-chromen-4-one, (+)-trans-8-(2-hydroxymethyl-1-methyl-pyrrolidin-3-yl)-5,7-dimethoxy-2-phenyl-chromen-4-one, (+)-trans-5,7-dihydroxy-8-(2-hydroxymethyl-1-methyl-pyrrolidin-3-yl)-2-phenyl-chromen-4-one, (+)-trans-4-[8-(2-hydroxymethyl-1-methyl-pyrrolidin-3-yl)-5,7-dimethoxy-4-oxo-4H-chromen-2-yl]-3-methyl-benzonitrile, (+)-trans-4-[5,7-dihydroxy-8-(2-hydroxymethyl-1-methyl-pyrrolidin-3-yl)-4-oxo-4H-chromen-2-yl]-3-methyl-benzonitrile, (±)-trans-8-(2-hydroxymethyl-1-methyl-pyrrolidin-3-yl)-5,7-dimethoxy-2-(4-trifluoromethyl-phenyl)-chromen-4-one, (±)-trans-5,7-dihydroxy-8-(2-hydroxymethyl-1-methyl-pyrrolidin-3-yl)-2-(4-trifluoromethyl-phenyl)-chromen-4-one, (+)-trans-8-(2-hydroxymethyl-1-methyl-pyrrolidin-3-yl)-5,7-dimethoxy-2-(4-trifluoromethyl-phenyl)-chromen-4-one, (+)-trans-5,7-dihydroxy-8-(2-hydroxymethyl-1-methyl-pyrrolidin-3-yl)-2-(4-trifluoromethyl-phenyl)-chromen-4-one, (−)-trans-8-(2-hydroxymethyl-1-methyl-pyrrolidin-3-yl)-5,7-dimethoxy-2-(4-trifluoromethyl-phenyl)-chromen-4-one, (−)-trans-5,7-dihydroxy-8-(2-hydroxymethyl-1-methyl-pyrrolidin-3-yl)-2-(4-trifluoromethyl-phenyl)-chromen-4-one, (+)-trans-8-(2-hydroxymethyl-1-methyl-pyrrolidin-3-yl)-5,7-dimethoxy-2-thiophen-2-yl-chromen-4-one, (+)-trans-5,7-dihydroxy-8-(2-hydroxymethyl-1-methyl-pyrrolidin-3-yl)-2-thiophen-2-yl-chromen-4-one, (+)-trans-2-(2-chloro-5-methoxy-phenyl)-8-(2-hydroxymethyl-1-methyl-pyrrolidin-3-yl)-5,7-dimethoxy-chromen-4-one, (+)-trans-2-(2-chloro-5-methoxy-phenyl)-5,7-dihydroxy-8-(2-hydroxymethyl-1-methyl-pyrrolidin-3-yl)-chromen-4-one, (+)-trans-2-(2-chloro-5-hydroxy-phenyl)-5,7-dihydroxy-8-(2-hydroxymethyl-1-methyl-pyrrolidin-3-yl)-chromen-4-one, (+)-trans-2-(3-chlorophenyl)-8-(2-hydroxymethyl-1-methyl-pyrrolidin-3-yl)-5,7-dimethoxy-chromen-4-one, (+)-trans-2-(3-chlorophenyl)-5-hydroxy-8-(2-hydroxymethyl-1-methyl-pyrrolidin-3-yl)-7-methoxy-chromen-4-one (+)-trans-2-(3-chlorophenyl)-5,7-dihydroxy-8-(2-hydroxymethyl-1-methyl-pyrrolidin-3-yl)-chromen-4-one, (+)-trans-2-(3-fluorophenyl)-8-(2-hydroxymethyl-1-methyl-pyrrolidin-3-yl)-5,7-dimethoxy-chromen-4-one, (+)-trans-2-(3-fluorophenyl)-5,7-dihydroxy-8-(2-hydroxymethyl-1-methyl-pyrrolidin-3-yl)-chromen-4-one, (+)-trans-2-(4-bromophenyl)-8-(2-hydroxymethyl-1-methyl-pyrrolidin-3-yl)-5,7-dimethoxy-chromen-4-one,
(+)-trans-2-(4-bromophenyl)-5-hydroxy-8-(2-hydroxymethyl-1-methyl-pyrrolidin-3-yl)-7-methoxy-chromen-4-one,
(+)-trans-2-(4-bromophenyl)-5,7-dihydroxy-8-(2-hydroxymethyl-1-methyl-pyrrolidin-3-yl)-chromen-4-one,
(+)-trans-2-(2,6-difluoro-phenyl)-8-(2-hydroxymethyl-1-methyl-pyrrolidin-3-yl)-5,7-dimethoxy-chromen-4-one,
(+)-trans-2-(2,6-difluoro-phenyl)-5,7-dihydroxy-8-(2-hydroxymethyl-1-methyl-pyrrolidin-3-yl)-chromen-4-one,
(±)-trans-4-[8-(2-hydroxymethyl-1-methyl-pyrrolidin-3-yl)-5,7-dimethoxy-4-oxo-4H-chromen-2-yl]-benzonitrile,
(±)-trans-4-[5-hydroxy-8-(2-hydroxymethyl-1-methyl-pyrrolidin-3-yl)-7-methoxy-4-oxo-4H-chromen-2-yl]-benzonitrile,
(±)-trans-4-[5,7-dihydroxy-8-(2-hydroxymethyl-1-methyl-pyrrolidin-3-yl)-4-oxo-4H-chromen-2-yl]-benzonitrile,
(+)-trans-4-[8-(2-hydroxymethyl-1-methyl-pyrrolidin-3-yl)-5,7-dimethoxy-4-oxo-4H-chromen-2-yl]-benzonitrile,
(+)-trans-4-[5-hydroxy-8-(2-hydroxymethyl-1-methyl-pyrrolidin-3-yl)-7-methoxy-4-oxo-4H-chromen-2-yl]-benzonitrile,
(+)-trans-4-[5,7-dihydroxy-8-(2-hydroxymethyl-1-methyl-pyrrolidin-3-yl)-4-oxo-4H-chromen-2-yl]-benzonitrile,
(±)-trans-2-[(3,5-bis-trifluoromethyl)-phenyl]-8-(2-hydroxymethyl-1-methylpyrrolidin-3-yl)-5,7-dimethoxy-chromen-4-one,
(±)-trans-2-[(3,5-bis-trifluoromethyl)-phenyl]-5,7-dihydroxy-8-(2-hydroxymethyl-1-methylpyrrolidin-3-yl)-chromen-4-one,
(±)-trans-2-(2-chloro-pyridin-3-yl)-8-(2-hydroxymethyl-1-methyl-pyrrolidin-3-yl)-5,7-dimethoxy-chromen-4-one,
(±)-trans-2-(2-chloro-pyridin-3-yl)-5,7-dihydroxy-8-(2-hydroxymethyl-1-methyl-pyrrolidin-3-yl)-chromen-4-one,
(+)-trans-2-(2-chloro-pyridin-3-yl)-8-(2-hydroxymethyl-1-methyl-pyrrolidin-3-yl)-5,7-dimethoxy-chromen-4-one,
(+)-trans-2-(2-chloro-pyridin-3-yl)-5,7-dihydroxy-8-(2-hydroxymethyl-1-methyl-pyrrolidin-3-yl)-chromen-4-one,
(+)-trans-8-(2-hydroxymethyl-1-methyl-pyrrolidin-3-yl)-5,7-dimethoxy-2-(4-nitrophenyl)-chromen-4-one,
(+)-trans-5,7-dihydroxy-8-(2-hydroxymethyl-1-methyl-pyrrolidin-3-yl)-2-(4-nitrophenyl)-chromen-4-one,
(+)-trans-2-(4-aminophenyl)-5,7-dihydroxy-8-(2-hydroxymethyl-1-methyl-pyrrolidin-3-yl)-chromen-4-one,
(±)-trans-8-(2-hydroxymethyl-1-methyl-pyrrolidin-3-yl)-5,7-dimethoxy-2-(2-methoxy-phenyl)-chromen-4-one,
(±)-trans-5,7-dihydroxy-8-(2-hydroxymethyl-1-methyl-pyrrolidin-3-yl)-2-(2-hydroxy-phenyl)-chromen-4-one,
(+)-trans-3-chloro-4-[8-(2-hydroxymethyl-1-methyl-pyrrolidin-3-yl)-5,7-dimethoxy-4-oxo-4H-chromen-2-yl]benzonitrile,
(+)-trans-3-chloro-4-[5,7-dihydroxy-8-(2-hydroxymethyl-1-methyl-pyrrolidin-3-yl)-4-oxo-4H-chromen-2-yl]benzonitrile,
(+)-trans-2-(4-bromo-2-chloro-phenyl)-8-(2-hydroxymethyl-1-methyl-pyrrolidin-3-yl)-5,7-dimethoxy-chromen-4-one,
(+)-trans-2-(4-bromo-2-chloro-phenyl)-5,7-dihydroxy-8-(2-hydroxymethyl-1-methyl-pyrrolidin-3-yl)-chromen-4-one,
(±)-trans-2-(2-chloro-5-dimethylamino-phenyl)-8-(2-hydroxymethyl-1-methyl-pyrrolidin-3-yl)-5,7-dimethoxy-chromen-4-one,
(±)-trans-2-(2-chloro-5-methylamino-phenyl)-5,7-dihydroxy-8-(2-hydroxymethyl-1-methyl-pyrrolidin-3-yl)-chromen-4-one,
(±)-trans-2-(2-chloro-4-methoxy-phenyl)-8-(2-hydroxymethyl-1-methyl-pyrrolidin-3-yl)-5,7-dimethoxy-chromen-4-one,
(±)-trans-2-(2-chloro-4-hydroxy-phenyl)-5,7-dihydroxy-8-(2-hydroxymethyl-1-methyl-pyrrolidin-3-yl)-chromen-4-one,
(±)-trans-2-(2-chlorophenyl)-8-(3-hydroxy-1-methyl-piperidin-4-yl)-5,7-dimethoxy-chromen-4-one,
(±)-trans-8-(2-azidomethyl-1-methyl-pyrrolidin-3-yl)-2-(2-chloro-phenyl)-5,7-dimethoxy-chromen-4-one,
(±)-trans-8-(2-aminomethyl-1-methyl-pyrrolidin-3-yl)-2-(2-chloro-phenyl)-5,7-dimethoxy-chromen-4-one,
(±)-trans-8-(2-aminomethyl-1-methyl-pyrrolidin-3-yl)-2-(2-chloro-phenyl)-5,7-dihydroxy-chromen-4-one,
(±)-trans-{3-[2-(2-chlorophenyl)-5,7-dimethoxy-4-oxo-4H-chromen-8-yl]-1-methyl-pyrrolidin-2-yl}-acetonitrile,
(±)-trans-{3-[2-(2-chlorophenyl)-5,7-dihydroxy-4-oxo-4H-chromen-8-yl]-1-methyl-pyrrolidin-2-yl}-acetonitrile,
(±)-trans-2-(2-chlorophenyl)-8-(2-imidazol-1-ylmethyl-1-methyl-pyrrolidin-3-yl)-5,7-dimethoxy-chromen-4-one,
(±)-trans-2-(2-chlorophenyl)-5,7-dihydroxy-8-(2-imidazol-1-ylmethyl-1-methyl-pyrrolidin-3-yl)-chromen-4-one,
(±)-trans-2-[2-chlorophenyl-8-(2-mercaptomethyl-1-methyl-pyrrolidin-3-yl)]-5,7-dimethoxy-chromen-4-one,
(±)-trans-2-(2-chlorophenyl)-5,7-dihydroxy-8-(2-mercaptomethyl-1-methyl-pyrrolidin-3-yl)-chromen-4-one,
(±)-trans-2-(2-chlorophenyl)-8-[2-hydroxymethyl-1-(4-methoxy-phenyl)-pyrrolidin-3-yl]-5,7-dimethoxy-chromen-4-one,
(±)-trans-2-(2-chlorophenyl)-5,7-dihydroxy-8-[2-hydroxymethyl-1-(4-hydroxyphenyl)-pyrrolidin-3-yl]-chromen-4-one,
(±)-trans-2-(2-chlorophenyl)-8-(3-hydroxy-piperidin-4-yl)-5,7-dimethoxy-chromen-4-one,
(±)-trans-2-(2-chlorophenyl)-8-(3-hydroxy-1-propyl-piperidin-4-yl)-5,7-dimethoxy-chromen-4-one,
(±)-trans-2-(2-chlorophenyl)-8-(2-hydroxymethyl-1-propyl-pyrrolidin-3-yl)-5,7-dimethoxy-chromen-4-one,
(±)-trans-2-(2-chlorophenyl)-5,7-dihydroxy-8-(2-hydroxymethyl-1-propyl-pyrrolidin-3-yl)-chromen-4-one,
(+)-trans-2-(2-chloro-3-fluoro-phenyl)-8-(2-hydroxymethyl-1-methyl-pyrrolidin-3-yl)-5,7-dimethoxy-chromen-4-one,
(+)-trans-2-(2-chloro-3-fluoro-phenyl)-5,7-dihydroxy-8-(2-hydroxymethyl-1-methyl-pyrrolidin-3-yl)-chromen-4-one,
(+)-trans-2-(2-bromo-3-fluoro-phenyl)-8-(2-hydroxymethyl-1-methyl-pyrrolidin-3-yl)-5,7-dimethoxy-chromen-4-one, (+)-trans-2-(2-bromo-3-fluoro-phenyl)-5,7-dihydroxy-8-(2-hydroxymethyl-1-methyl-pyrrolidin-3-yl)-chromen-4-one, (+)-trans-2-(2-chloro-5-iodo-phenyl)-8-(2-hydroxymethyl-1-methyl-pyrrolidin-3-yl)-5,7-dimethoxy-chromen-4-one, (+)-trans-2-(2-chloro-5-iodo-phenyl)-5,7-dihydroxy-8-(2-hydroxymethyl-1-methyl-pyrrolidin-3-yl)-chromen-4-one, (+)-trans-2-(2-bromo-5-chloro-phenyl)-8-(2-hydroxymethyl-1-methyl-pyrrolidin-3-yl)-5,7-dimethoxy-chromen-4-one, (+)-trans-2-(2-bromo-5-chloro-phenyl)-5,7-dihydroxy-8-(2-hydroxymethyl-1-methyl-pyrrolidin-3-yl)-chromen-4-one, (±)-trans-3-[2-(2-chlorophenyl)-5,7-dimethoxy-4-oxo-4H-chromen-8-yl]-1-methyl-pyrrolidine-2-carbaldehyde, (±)-trans-3-[2-(2-chlorophenyl)-5,7-dimethoxy-4-oxo-4H-chromen-8-yl]-1-methyl-1-oxy-pyrrolidine-2-carboxylic acid, (±)-trans-3-[2-(2-chlorophenyl)-5,7-dimethoxy-4-oxo-4H-chromen-8-yl]-1-methyl-pyrrolidine-2-carboxylic acid, (±)-trans-3-[2-(2-chlorophenyl)-5,7-dihydroxy-4-oxo-4H-chromen-8-yl]-1-methyl-pyrrolidine-2-carboxylic acid, (±)-trans-2-(2-chlorophenyl)-5,7-dihydroxy-8-(2-hydroxymethyl-1-methyl-1-oxy-pyrrolidin-3-yl)-chromen-4-one, (+)-trans-2-(4-amino-2-bromo-phenyl)-8-(2-hydroxymethyl-1-methyl-pyrrolidin-3-yl)-5,7-dimethoxy-chromen-4-one, (+)-trans-2-(4-amino-2-bromo-phenyl)-5,7-dihydroxy-8-(2-hydroxymethyl-1-methyl-pyrrolidin-3-yl)-chromen-4-one, (+)-trans-2-(2-bromo-4-methoxy-phenyl)-8-(2-hydroxymethyl-1-methyl-pyrrolidin-3-yl)-5,7-dimethoxy-chromen-4-one, (+)-trans-2-(2-bromo-4-methoxy-phenyl)-5,7-dihydroxy-8-(2-hydroxymethyl-1-methyl-pyrrolidin-3-yl)-chromen-4-one, and (+)-trans-2-(2-bromo-4-hydroxy-phenyl)-5,7-dihydroxy-8-(2-hydroxymethyl-1-methyl-pyrrolidin-3-yl)-chromen-4-one.

14. A pharmaceutically acceptable salt of a compound of general formula (1c) as claimed in claim 1, wherein the pharmaceutically acceptable salt is selected from the group consisting of: an inorganic or organic acid salt, where the acid, is boric acid, perchloric acid, hydrochloric acid, hydrobromic acid, sulfuric acid, sulfamic acid, phosphoric acid, nitric acid, acetic acid, propionic acid, succinic acid, glycolic acid, gluconic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxybenzoic acid, fumaric acid, toluenesulfonic acid, methanesulfonic acid, ethane disulfonic acid, oxalic acid, isethionic acid, ketoglutaric acid, benzenesulfonic acid or glycerophosphoric acid; an alkali metal salt, where the alkali metal is Lithium (Li), sodium (Na) or potassium (K).

15. A pharmaceutically acceptable salt of a compound of general formula (1c) as claimed in claim 14, which is an inorganic or organic acid salt where the acid is selected from the group consisting of: hydrochloric acid, citric acid, tartaric acid, maleic acid, acetic acid, sulfuric acid, methane sulfonic acid and nitric acid.

16. A pharmaceutically acceptable salt of a compound of general formula (1c) as claimed in claim 15, which is:

(±)-trans-2-(2-chlorophenyl)-5,7-dihydroxy-8-(2-hydroxymethyl-1-methyl-pyrrolidin-3-yl-chromen-4-one hydrochloride, (+)-trans-2-(2-chlorophenyl)-5,7-dihydroxy-8-(2-hydroxymethyl-1-methyl-pyrrolidin-3-yl)-chromen-4-one hydrochloride, (−)-trans-2-(2-chlorophenyl)-5,7-dihydroxy-8-(2-hydroxymethyl-1-methyl-pyrrolidin-3-yl)-chromen-4-one hydrochloride, (±)-trans-2-(2-chloro-5-fluoro-phenyl)-5,7-dihydroxy-8-(2-hydroxymethyl-1-methyl-pyrrolidin-3-yl)-chromen-4-one hydrochloride, (±)-trans-2-(2-chloro-5-fluoro-phenyl)-5,7-dihydroxy-8-(2-hydroxymethyl-1-methyl-pyrrolidin-3-yl)-chromen-4-one methane sulfonate, (+)-trans-2-(2-chloro-5-fluoro-phenyl)-5,7-dihydroxy-8-(2-hydroxymethyl-1-methyl-pyrrolidin-3-yl)-chromen-4-one hydrochloride, (+)-trans-2-(2-bromo-5-fluoro-phenyl)-5,7-dihydroxy-8-(2-hydroxymethyl-1-methyl-pyrrolidin-3-yl)-chromen-4-one hydrochloride, (+)-trans-2-(2-bromo-5-fluoro-phenyl)-5,7-dihydroxy-8-(2-hydroxymethyl-1-methyl-pyrrolidin-3-yl)-chromen-4-one methane sulfonate, (+)-trans-2-(2-bromo-4-nitro-phenyl)-5,7-dihydroxy-8-(2-hydroxymethyl-1-methyl-pyrrolidin-3-yl)-chromen-4-one hydrochloride, (+) acetic acid 3-[2-(2-bromo-4-nitro-phenyl)-5,7-dihydroxy-4-oxo-4H-chromen-8-yl]-1-methyl-pyrrolidin-2-yl methyl ester hydrochloride, (+)-trans-2-(2,4-dichloro-5-fluoro-phenyl-5,7-dihydroxy-8-(2-hydroxymethyl-1-methyl-pyrrolidin-3-yl)-chromen-4-one hydrochloride, (+)-trans-2-(2,4-dichloro-5-fluoro-phenyl)-5,7-dihydroxy-8-(2-hydroxymethyl-1-methyl-pyrrolidin-3-yl)-chromen-4-one methane sulfonate, (+)-trans-2-(2,4-dichloro-5-fluoro-phenyl)-5,7-dihydroxy-8-(2-hydroxymethyl-1-methyl-pyrrolidin-3-yl)-chromen-4-one citrate, (+)-trans-2-(2,4-dichloro-5-fluoro-phenyl)-5,7-dihydroxy-8-(2-hydroxymethyl-1-methyl-pyrrolidin-3-yl)-chromen-4-one tartrate, (+)-trans-2-(2,4-dichloro-5-fluoro-phenyl)-5,7-dihydroxy-8-(2-hydroxymethyl-1-methyl-pyrrolidin-3-yl)-chromen-4-one maleate, (+)-trans-2-(2,4-dichloro-5-fluoro-phenyl)-5,7-dihydroxy-8-(2-hydroxymethyl-1-methyl-pyrrolidin-3-yl)-chromen-4-one acetate, (+)-trans-2-(2,4-dichloro-5-fluoro-phenyl)-5,7-dihydroxy-8-(2-hydroxymethyl-1-methyl-pyrrolidin-3-yl)-chromen-4-one sulfate, (+)-trans-2-(2,4-dichloro-5-fluoro-phenyl)-5,7-dihydroxy-8-(2-hydroxymethyl-1-methyl-pyrrolidin-3-yl)-chromen-4-one nitrate, (+)-trans-5,7-dihydroxy-8-(2-hydroxymethyl-1-methyl-pyrrolidin-3-yl)-2-phenyl-chromen-4-one hydrochloride, (+)-trans-4-[5,7-dihydroxy-8-(2-hydroxymethyl-1-methyl-pyrrolidin-3-yl)-4-oxo-4H-chromen-2-yl]-3-methyl-benzonitrile hydrochloride, (+)-trans-5,7-dihydroxy-8-(2-hydroxymethyl-1-methyl-pyrrolidin-3-yl)-2-(4-trifluoromethyl-phenyl)-chromen-4-one hydrochloride, (+)-trans-5,7-dihydroxy-8-(2-hydroxymethyl-1-methyl-pyrrolidin-3-yl)-2-thiophen-2-yl-chromen-4-one hydrochloride, and (+)-trans-2-(2-chloro-5-hydroxy-phenyl)-5,7-dihydroxy-8-(2-hydroxymethyl-1-methyl-pyrrolidin-3-yl)-chromen-4-one hydrochloride.

17. A pharmaceutical composition comprising a therapeutically effective amount of a compound of general formula (Ic) as claimed in claim 1, or a stereoisomer, optical isomer, pharmaceutically acceptable salt or a pharmaceutically acceptable solvate thereof, and a pharmaceutically acceptable carrier and, optionally, an additive.

18. A process for the preparation of a compound of general formula (Ic), as claimed in claim 1, or a pharmaceutically acceptable salt thereof:

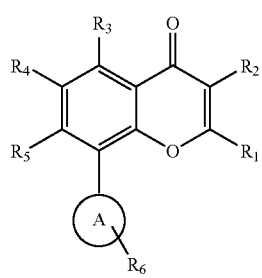
(Ic)

wherein
$R_1$, $R_2$, $R_3$, $R_4$, $R_5$, $R_6$ and A are as defined,
which process comprises reacting a compound of formula (XA):

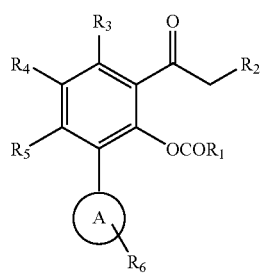
XA wherein in each case $R_1$, $R_2$, $R_3$, $R_4$, $R_5$, $R_6$ and A are as defined, with an organic or inorganic base, subsequently adding an acid to the reaction mixture, followed by adding an organic or inorganic base, and, if appropriate, converting the compound of formula (Ic) into a pharmaceutically acceptable salt, or reacting a compound of formula (XIIA):

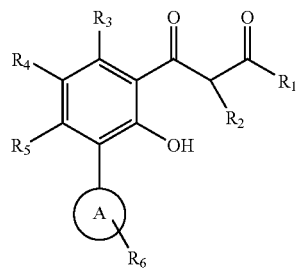
XIIA wherein in each case $R_1$, $R_2$, $R_3$, $R_4$, $R_5$, $R_6$ and A are as defined, with an acid, subsequently adding an organic or inorganic base to the reaction mixture, and optionally, converting the compound of formula (Ic) into a pharmaceutically acceptable salt.

19. The process of claim 18, wherein the compound of formula (XIIA) is obtained by reacting a compound of formula (XIA):

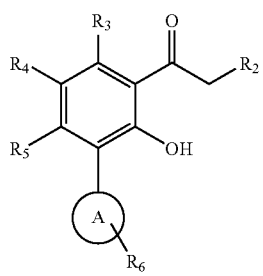
XIA wherein $R_2$, $R_3$, $R_4$, $R_5$, $R_6$ and A are as defined above, with a carboxylic acid ester, an acid halide, or an activated ester in the presence of an organic or inorganic base in an organic or inorganic solvent.

20. A process for the preparation of a compound of formula (XIIIA) or a pharmaceutically acceptable salt thereof:

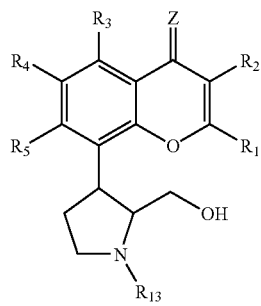
XIIIA wherein $R_1$, $R_2$, $R_3$, $R_4$, $R_5$ and $R_{13}$ are as defined in claim 1, comprising reacting a compound of formula (VIIA):

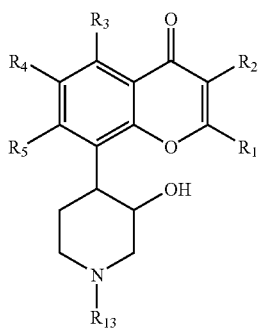

wherein $R_1$, $R_2$, $R_3$, $R_4$, $R_5$ and $R_{13}$ are as defined in claim 1, with a reagent suitable to effect replacement of the OH group on the piperidino ring by a leaving group, in the presence of an organic or inorganic base, followed by adding an organic base in the presence of an organic solvent to effect contraction of the piperidino ring, and optionally, converting the resulting compound of formula (XIIIA) into a pharmaceutically acceptable salt.

21. A process for the preparation of a compound of the formula (1f) as claimed in claim 4, or a pharmaceutically acceptable salt thereof:

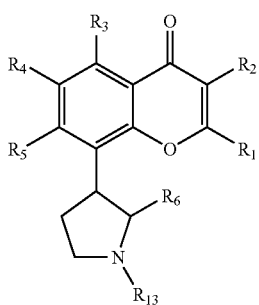

wherein
$R_1$, $R_2$, $R_3$, $R_4$, $R_5$, $R_6$ and $R_{13}$ are as defined, comprising reacting a racemic compound of the formula (VIII):

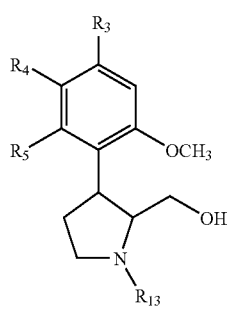

wherein $R_3$, $R_4$, $R_5$ and $R_{13}$ are as defined, with a chiral auxiliary in the presence of a solvent to form a diastereomeric salt of the compound of formula (VIII), crystallising out the required diastereomeric salt and subsequently treating it with a base to obtain the desired enantiomer of the compound of formula (VIII), treating the compound of formula (VIII) with an acylating agent or an activated form of an acid in the presence of a Lewis acid catalyst to obtain the acylated compound of formula (IX):

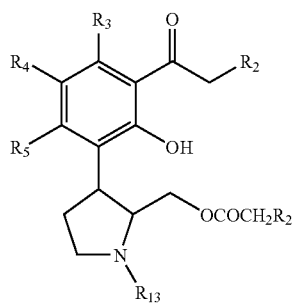

wherein $R_2$, $R_3$, $R_4$, $R_5$ and $R_{13}$ are as defined, treating the compound of formula (IX) with either:
(a) an acid chloride of formula $R_1COCl$, an anhydride of formula $(R_1CO)_2O$ or an ester of formula $R_1COOCH_3$, where $R_1$ is as defined,
(b) an acid of formula $R_1COOH$, where $R_1$ is as defined, and phosphorus oxychloride, in the presence of an acid scavenger to obtain an acid chloride in situ, or
(c) a combination of $R_1COOH$ (where $R_1$ is as defined), and polyphoshoric acid, to form the compound of formula (X):

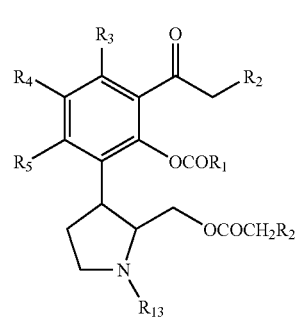

wherein $R_1$, $R_2$, $R_3$, $R_4$, $R_5$ and $R_{13}$ are as defined in claim 4, treating the compound of formula (X) with a base, followed by treating with an acid and subsequently with a base to form the subject compound of formula (If), and optionally, converting the subject compound into a pharmaceutically acceptable salt; alternatively, subjecting the compound of formula (IX) above to ester hydrolysis by treating with a base in aqueous ethanol or methanol to form a compound of formula (XI):

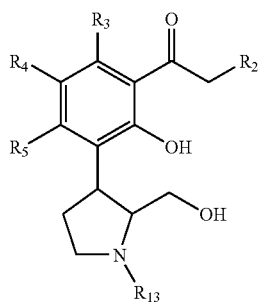

XI wherein $R_2$, $R_3$, $R_4$, $R_5$ and $R_{13}$ are as defined, treating the compound of formula (XI) with a carboxylic acid ester, an acid chloride or an activated ester, in the presence of a base in a solvent to form a compound of the formula (XII):

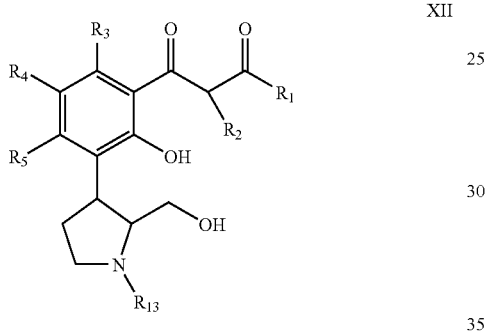

XII wherein $R_1$, $R_2$, $R_3$, $R_4$, $R_5$ and $R_{13}$ are as defined, and treating the compound of formula (XII) with an acid and subsequently treating with a base to form the subject compound of formula (1f), and optionally, converting the subject compound into a pharmaceutically acceptable salt.

\* \* \* \* \*